United States Patent
Routier et al.

(10) Patent No.: US 10,059,704 B2
(45) Date of Patent: Aug. 28, 2018

(54) 1,4-DISUBSTITUTED 1,2,3-TRIAZOLES, METHODS FOR PREPARING SAME, AND DIAGNOSTIC AND THERAPEUTIC USES THEREOF

(75) Inventors: Sylvain Routier, Tigy (FR); Franck Suzenet, La Chapelle Saint Mesmin (FR); Frederic Pin, Saint-Jean-de-Braye (FR); Sylvie Chalon, Saint Cyr sur Loire (FR); Johnny Vercouillie, Amboise (FR); Denis Guilloteau, Saint Cyr sur Loire (FR)

(73) Assignees: CENTRE NATIONAL DE LA RECHERCHE SCIENTIFIQUE (C.N.R.S.), Paris (FR); INSTITUT NATIONAL DE LA SANTA ET DE LA RECHERCHE MEDICALE (INSERM), Paris (FR)

( * ) Notice: Subject to any disclaimer, the term of this patent is extended or adjusted under 35 U.S.C. 154(b) by 1079 days.

(21) Appl. No.: 14/112,864

(22) PCT Filed: Apr. 20, 2012

(86) PCT No.: PCT/EP2012/057309
§ 371 (c)(1),
(2), (4) Date: Oct. 18, 2013

(87) PCT Pub. No.: WO2012/143526
PCT Pub. Date: Oct. 26, 2012

(65) Prior Publication Data
US 2014/0030191 A1    Jan. 30, 2014

(30) Foreign Application Priority Data
Apr. 20, 2011 (FR) .................. 11 53420

(51) Int. Cl.
| | | |
|---|---|---|
| C07D 451/04 | (2006.01) | |
| A61K 51/04 | (2006.01) | |
| C07D 453/02 | (2006.01) | |
| C07D 455/02 | (2006.01) | |

(52) U.S. Cl.
CPC ........ *C07D 451/04* (2013.01); *A61K 51/0453* (2013.01); *A61K 51/0455* (2013.01); *A61K 51/0459* (2013.01); *A61K 51/0463* (2013.01); *C07D 453/02* (2013.01); *C07D 455/02* (2013.01); *G01N 2333/70571* (2013.01); *G01N 2800/28* (2013.01); *G01N 2800/2821* (2013.01)

(58) Field of Classification Search
CPC ............... C07D 451/04; C07D 453/02; A61K 51/0459; A61K 51/0455; A61K 51/0463; A61K 51/0453; A61K 51/0461; G01N 2800/28; G01N 2800/2821; G01N 2333/70571
See application file for complete search history.

(56) References Cited

U.S. PATENT DOCUMENTS

2011/0201656 A1* 8/2011 Nardi .................. C07D 249/06
514/359

FOREIGN PATENT DOCUMENTS

| EP | 1 764 362 | 3/2007 |
|---|---|---|
| EP | 2 308 869 | 4/2011 |
| WO | 96/21660 | 7/1996 |
| WO | 2005/049612 | 6/2005 |
| WO | 2006/065217 | 6/2006 |
| WO | 2006/065601 | 6/2006 |
| WO | 2007/021574 | 2/2007 |
| WO | 2009/092293 | 7/2009 |
| WO | 2011/025690 | 3/2011 |

OTHER PUBLICATIONS

Jaiprakash N. Sangshetti and Devanand B. Shinde: "One pot synthesis and SAR of some novel 3-substituted 5.6-diphenyl-1.2. 4-triazines as antifungal agents". Bioorganic & Medicinal Chemistry Letters. vol. 20. No. 2. 2010. pp. 742-745. XP026812571. abstract—table 4—compounds 4a 4c-4i 41.

International Search Report dated May 30, 2012 in corresponding PCT application.

* cited by examiner

Primary Examiner — Michael G Hartley
Assistant Examiner — Leah H Schlientz
(74) Attorney, Agent, or Firm — Young & Thompson

(57) ABSTRACT

A compound having the following general formula (I):

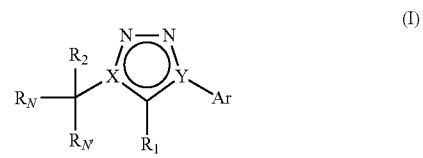

wherein:
- X is a nitrogen atom and Y is a carbon atom; or
- X is a carbon atom and Y is a nitrogen atom;
- the Ar group is an aryl or heteroaryl group; and
- the $R_N$ and $R_{N'}$ groups, together with the carbon atoms to which they are bound, form a monocyclic or bicyclic azacycloalkane group. The pharmaceutically acceptable salts thereof, the hydrates or polymorphic crystalline structures thereof, and to the racemates, diastereoisomers, or enantiomers thereof are also described.

17 Claims, No Drawings

1,4-DISUBSTITUTED 1,2,3-TRIAZOLES, METHODS FOR PREPARING SAME, AND DIAGNOSTIC AND THERAPEUTIC USES THEREOF

The present invention relates to 1,4-disubstituted 1,2,3-triazole type compounds and to the methods of preparation thereof. It also relates to the therapeutic and diagnostic uses of said compounds as an agonist, antagonist and/or ligand of alpha 7 nicotinic receptor.

The central cholinergic systems regulate a large number of physiological and cognitive functions. These effects are regulated by various different types of receptors including nicotinic receptors, which belong to the family of channel receptors and include multiple subtypes that modulate various biological effects. Compounds that selectively target certain types of receptors may prove to be useful for diagnosing or treating diseases associated with them, like for instance, cognitive impairment, pain, addiction to tobacco, etc.

Amongst the various subtypes, the alpha 7 nicotinic receptor (Rα7) are particularly involved in cognitive processes and in a large number of diseases of the central nervous system such as addiction, psychiatric disorders (schizophrenia, attention deficit disorder, etc) and neurodegenerative diseases, particularly Alzheimer's disease.

The study of these receptors, which play an important and early role in the pathogenesis of diseases of the central nervous system (CNS) and the peripheral nervous system (PNS), make it possible to monitor the evolution of these diseases.

In fact, the Rα7s are widely expressed in the cerebral regions that are affected over the course of Alzheimer's disease and variations in the density of these receptors are observed and occur preceding neuronal death in several regions of the brain such as the hippocampus, the cortex or the basal ganglia.

Moreover, agonists and/or antagonists for Rα7 represent an alternative for the treatment of these diseases.

To date, no radiopharmaceutical marker comprising an $^{18}F$ has heretofore been demonstrated in clinical use for the diagnosis and monitoring of Alzheimer's disease.

Moreover, no ligands of the Rα7 agonist type are currently prescribed for the treatment of this disease.

The present invention aims to provide novel types of Rα7 ligands that are either agonists or antagonists.

The present invention also aims to provide novel Rα7 ligands that make it possible to obtain radiopharmaceutical markers which may be used in molecular imaging for the early diagnosis and monitoring of diseases of the CNS, in particular Alzheimer's disease, and diseases of the PNS.

The present invention also aims to provide novel Rα7 ligands for the therapeutic treatment of diseases of the CNS, in particular Alzheimer's disease, and diseases of the PNS.

Among the 1,4-disubstituted 1,2,3-triazole type compounds mention may be made in particular of the compounds having the following general formula (I):

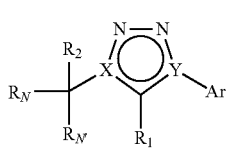

(I)

wherein:
X represents C and Y represents N; or
X represents N and Y represents C; and
the Ar group is selected from among the aryl and heteroaryl groups comprising from 1 to 30 carbon atoms, possibly substituted by one or more groups selected from among:
  the halogen atoms,
  the —OH group,
  the linear or branched alkyl and alkoxy groups comprising from 1 to 10 carbon atoms, possibly substituted,
  the aryl or heteroaryl groups comprising from 1 to 30 carbon atoms, possibly substituted,
the $R_N$ and $R_{N'}$ groups, together with the carbon atoms to which they are bound, form a monocyclic or bicyclic azacycloalkane group comprising from 3 to 30 carbon atoms and at least one trisubstituted endocyclic nitrogen atom, possibly in quaternary ammonium form, the said azacycloalkane group being possibly substituted by one or more groups selected from among:
  the halogen atoms,
  the —OH group,
  the linear or branched alkyl and alkoxy groups comprising from 1 to 10 carbon atoms, possibly substituted,
$R_1$ is a group selected from among:
  the halogen atoms,
  the aryl or heteroaryl groups comprising from 1 to 30 carbon atoms, possibly substituted,
  the —R, —OR or —SiRR'R", R, R' and R" groups being independently selected from the group consisting of the hydrogen atom and linear or branched alkyl groups comprising from 1 to 10 carbon atoms, possibly substituted,
  the —NR$_a$R$_b$, R$_a$ and R$_b$ groups being independently selected from the group consisting of the hydrogen atom and the alkyl and acyl groups comprising from 1 to 10 carbon atoms, possibly substituted,
  the —NHR$_c$, R$_c$ groups being selected from among the aryl and heteroaryl groups comprising from 1 to 30 carbon atoms,
$R_2$ is a group selected from among:
  the halogen atoms, preferably F,
  the —R, —OR, —C(O)Oalkyl, —OC(O)R, —OC(O)NHR, —O—(SO$_2$)—R and —O—(SO$_2$)—NHR groups wherein R is as defined here above,
  $R_2$ represents H when X is N;
as well as the pharmaceutically acceptable salts thereof, the hydrates or polymorphic crystalline structures, racemates, diastereoisomers (diastereomers) or enantiomers thereof, with the following compounds being excluded:
3-(1-(2,3-difluorophenyl)-1H-tetrazol-5-yl)-5-(1-(1-propylpiperidin-4-yl)-1H-1,2,3-triazol-4-yl)pyridin-2-amine;
3-(1-(2,3-difluorophenyl)-1H-tetrazol-5-yl)-5-(1-(piperidin-4-yl)-1H-1,2,3-triazol-4-yl)pyridin-2-amine;
3-(1-(2,3-difluorophenyl)-1H-tetrazol-5-yl)-5-(1-(8-methyl-8-azabicyclo[3.2.1]octan-3-yl)-1H-1,2,3-triazol-4-yl)pyridin-2-amine;
3-(1-(2,3-difluorophenyl)-1H-tetrazol-5-yl)-5-(1-(quinuclidin-3-yl)pyridin-2-amine;
5-(1-(6-azaspiro[2.5]octan-4-yl)-1H-1,2,3-triazol-4-yl)-3-(1-(2,3-difluorophenyl)-1H-tetrazol-5-yl)pyridin-2-amine;
(R)-3-(4-(6-amino-5-(1-(2,3-difluorophenyl)-1H-tetrazol-5-yl)pyridin-3-yl)-1H-1,2,3-triazol-1-yl)azepan-2-one; and 3-(1-(2,3-difluorophenyl)-1H-tetrazol-5-yl)-5-(1-(2,2,6,6-tetramethylpiperidin-4-yl)-1H-1,2,3-triazol-4-yl)pyridin-2-amine.

In particular, the present invention relates to compounds having the following general formula (I):

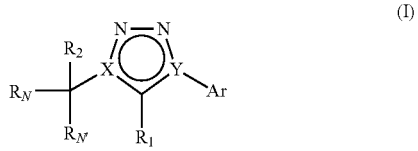

wherein:
X represents C and Y represents N; or
X represents N and Y represents C; and
the Ar group is selected from among the aryl groups comprising from 6 to 30 carbon atoms and the heteroaryl groups comprising from 1 to 30 carbon atoms, possibly substituted by one or more groups selected from among:
the halogen atoms,
the —OH group,
the linear or branched alkyl and alkoxy groups comprising from 1 to 10 carbon atoms, possibly substituted, and
the aryl groups comprising from 6 to 30 carbon atoms and the heteroaryl groups comprising from 1 to 30 carbon atoms, possibly substituted,
the $R_N$ and $R_{N'}$ groups, together with the carbon atoms to which they are bound, form a monocyclic or bicyclic azacycloalkane group comprising from at least one trisubstituted endocyclic nitrogen atom, possibly in quaternary ammonium form, selected from among the following:

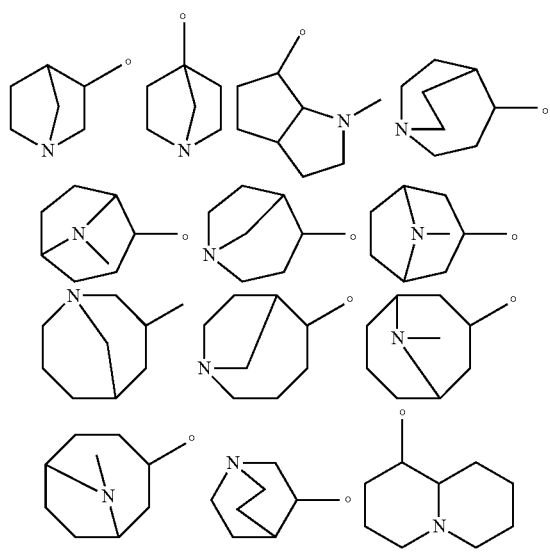

the said azacycloalkane group being possibly substituted by one or more groups selected from among:
the halogen atoms,
the —OH group, and
the linear or branched alkyl and alkoxy groups comprising from 1 to 10 carbon atoms, possibly substituted, $R_1$ is a group selected from among:
the halogen atoms,
the aryl groups comprising from 6 to 30 carbon atoms and the heteroaryl groups comprising from 1 to 30 carbon atoms, possibly substituted
the —R, —OR or —SiRR'R", R, R' and R" groups being independently selected from the group consisting of the hydrogen atom and the linear or branched alkyl groups comprising from 1 to 10 carbon atoms, possibly substituted,
the —$NR_aR_b$, $R_a$ and $R_b$ groups being independently selected from the group consisting of the hydrogen atom and the alkyl and acyl groups comprising from 1 to 10 carbon atoms, possibly substituted, and
the —$NHR_c$, $R_c$ groups being selected from among the aryl groups comprising from 6 to 30 carbon atoms and the heteroaryl groups comprising from 1 to 30 carbon atoms; and $R_2$ is a group selected from among:
the halogen atoms, preferably F,
the —R, —OR, —C(O)Oalkyl, —OC(O)R, —OC(O)NHR, —O—($SO_2$)—R and —O—($SO_2$)—NHR groups wherein R is as defined here above,
$R_2$ representing H when X is N;
as well as the pharmaceutically acceptable salts thereof, the hydrates or polymorphic crystalline structures, racemates, diastereoisomers or enantiomers thereof, with the following compounds being excluded:
3-(1-(2,3-difluorophenyl)-1H-tetrazol-5-yl)-5-(1-(8-methyl-8-azabicyclo[3.2.1]octan-3-yl)-1H-1,2,3-triazol-4-yl)pyridin-2-amine; and
3-(1-(2,3-difluorophenyl)-1H-tetrazol-5-yl)-5-(1-(quinuclidin-3-yl)-1H-1,2,3-triazol-4-yl)pyridin-2-amine;

The compounds excluded from the invention have the following chemical structure:

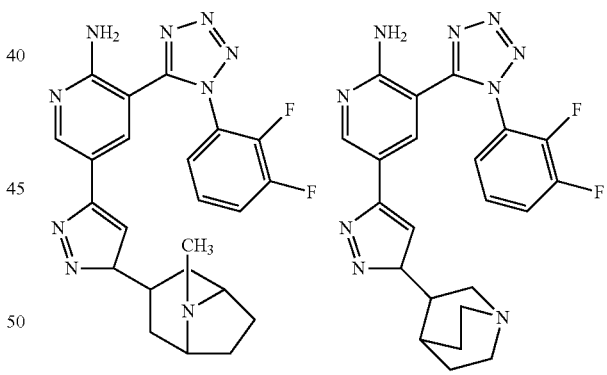

As well, the compounds according to the invention are not the following compounds:
3-(1-(2,3-difluorophenyl)-1H-tetrazol-5-yl)-5-(1-(1-propylpiperidin-4-yl)-1H-1,2,3-triazol-4-yl)pyridin-2-amine;
3-(1-(2,3-difluorophenyl)-1H-tetrazol-5-yl)-5-(1-(piperidin-4-yl)-1H-1,2,3-triazol-4-yl)pyridin-2-amine;
5-(1-(6-azaspiro[2.5]octan-4-yl)-1H-1,2,3-triazol-4-yl)-3-(1-(2,3-difluorophenyl)-1H-tetrazol-5-yl)pyridin-2-amine;
(R)-3-(4-(6-amino-5-(1-(2,3-difluorophenyl)-1H-tetrazol-5-yl)pyridin-3-yl)-1H-1,2,3-triazol-1-yl)azepan-2-one; and
3-(1-(2,3-difluorophenyl)-1H-tetrazol-5-yl)-5-(1-(2,2,6,6-tetramethylpiperidin-4-yl)-1H-1,2,3-triazol-4-yl)pyridin-2-amine;

the said compounds having the following chemical structure:

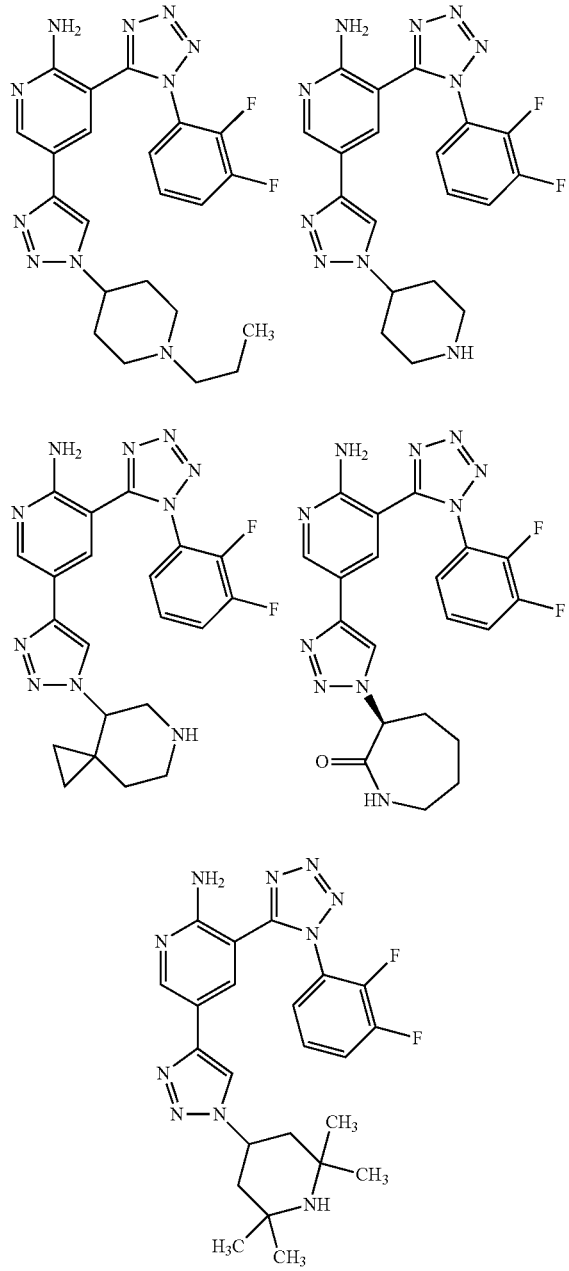

According to a particular embodiment, the above mentioned azacycloalkane is not substituted.

In another particular embodiment, the above mentioned azacycloalkane is substituted by a substituent selected from the group consisting of: halogen, —OH and a linear or branched alkyl group comprising from 1 to 10 carbon atoms, possibly substituted.

In particular, the above mentioned azacycloalkane is substituted by a methyl group, the said methyl group being substituted by a heteroaryl, and in particular by a pyridine. Preferably, the above mentioned azacycloalkane is substituted by:

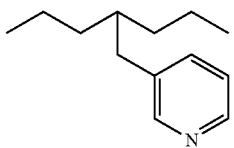

According to one embodiment, $R_2$ represents an —OH groups or a halogen, in particular F.

According to one embodiment, $R_1$ represents H or —$NH_2$.

In the compounds of the invention, the $R_N$, $R_{N'}$ and $R_2$ groups are bound to the same carbon atom. The said carbon atom is also bound to the atom represented by the X of the triazole ring of the compounds having the formula (I).

In the compounds of the invention, X and Y are different from each other and represent a nitrogen atom or a carbon atom, it being known that X and Y, together with the two nitrogen atoms and the carbon atom (carrying the $R_1$ group) to which they are bound, form an aromatic 1,2,3-triazole ring.

According to one embodiment, in the compounds having the formula (I), the Ar group does not represent the following group:

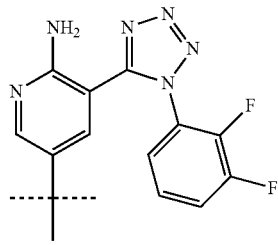

According to one embodiment, in compounds having the formula (I), the Ar group is not a 4-amino-3-pyridinyl group and the $R_N$ and $R_{N'}$ groups cannot, together with the carbon atom to which they are bound, form the following groups:

Typically, the invention does not include compounds having the formula (I) wherein the Ar group is not a 4-amino-3-pyridinyl group and the $R_N$ and $R_{N'}$ groups cannot, together with the carbon atom to which they are bound, form the following groups:

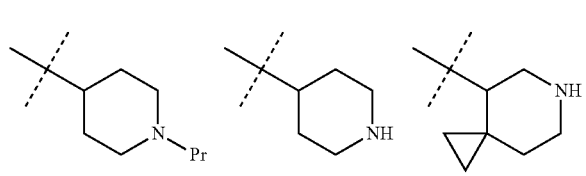

-continued

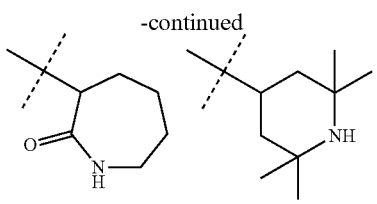

According to one embodiment, the compounds having the general formula (I) are such that:
X represents C and Y represents N, or
X represents N and Y represents C;
the Ar group is selected from among the aryl groups comprising from 6 to 30 carbon atoms and the heteroaryl groups comprising from 1 to 30 carbon atoms, possibly substituted by one or more groups selected from among:
the halogen atoms,
the —OH group,
the linear or branched alkyl and alkoxy groups comprising from 1 to 10 carbon atoms, possibly substituted, and
the aryl groups comprising from 6 to 30 carbon atoms and the heteroaryl groups comprising from 1 to 30 carbon atoms, possibly substituted,
the $R_N$ and $R_{N'}$ groups, together with the carbon atoms to which they are bound, form an azacycloalkane group selected from among the tropane, quinuclidine and octahydro-quinolizine groups, the said azacycloalkane group being possibly substituted by one or more groups selected from among:
the halogen atoms,
the —OH group, and
the linear or branched alkyl and alkoxy groups comprising from 1 to 10 carbon atoms, possibly substituted,
$R_1$ is a group selected from among:
the halogen atoms,
the aryl groups comprising from 6 to 30 carbon atoms and the heteroaryl groups comprising from 1 to 30 carbon atoms, possibly substituted
the —R, —OR or —SiRR'R", R, R' and R" groups being independently selected from the group consisting of the hydrogen atom and linear or branched alkyl groups comprising from 1 to 10 carbon atoms, possibly substituted,
the —$NR_aR_b$, $R_a$ and $R_b$ groups being independently selected from the group consisting of the hydrogen atom and the alkyl and acyl groups comprising from 1 to 10 carbon atoms, possibly substituted, and
the —$NHR_c$, $R_c$ groups being selected from among the aryl groups comprising from 6 to 30 carbon atoms and the heteroaryl groups comprising from 1 to 30 carbon atoms; and
$R_2$ is a group selected from among:
the halogen atoms, preferably F,
the —R, —OR, —C(O)Oalkyl, —OC(O)R, —OC(O)NHR, —O—($SO_2$)—R and —O—($SO_2$)—NHR groups wherein R is as defined here above,
$R_2$ represents H when X is N;
as well as the pharmaceutically acceptable salts thereof, the hydrates or polymorphic crystalline structures, racemates, diastereoisomers or enantiomers thereof,
with the following compounds being excluded:
3-(1-(2,3-difluorophenyl)-1H-tetrazol-5-yl)-5-(1-(8-methyl-8-azabicyclo[3.2.1]octan-3-yl)-1H-1,2,3-triazol-4-yl)pyridin-2-amine; and
3-(1-(2,3-difluorophenyl)-1H-tetrazol-5-yl)-5-(1-(quinuclidin-3-yl)-1H-1,2,3-triazol-4-yl)pyridin-2-amine.
According to one embodiment, the $R_N$ and $R_{N'}$ groups, together with the carbon atoms to which they are bound, form a group selected from among the tropane, quinuclidine and octahydro-quinolizine groups.
Preferably, the azacycloalkane is selected from one of the following groups:

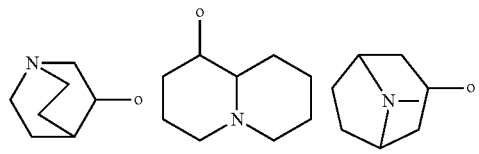

According to one embodiment, the compounds having the formula (I) are such that:
X represents a nitrogen atom and Y represents a carbon atom, and/or
the Ar group represents an aryl group comprising from 6 to 30 carbon atoms, substituted or unsubstituted, and/or
the $R_N$ and $R_{N'}$ groups, together with the carbon atoms to which they are bound, form a group selected from among the tropane, quinuclidine and octahydro-quinolizine groups.
The Ar group may be chosen from the phenyl or naphthyl groups, possibly substituted by one or more groups selected from among: —F, —Br, —Cl, —$OCH_3$, —OH, —$CH_2F$, —$CH_2Br$, —$CH_2OH$, —$CF_3$, the alkyl groups comprising from 1 to 10 carbon atoms (preferably a methyl group), possibly substituted and an aryl or a heteroaryl group, possibly substituted.
Preferably, the Ar group represents an aryl group having 6 to 30 carbon atoms, in particular a phenyl group, substituted by an aryl group having 6 to 30 carbon atoms, and/or by a heteroaryl group comprising from 1 to 30 carbon atoms, possibly substituted.
In particular, when the Ar group, representing an aryl group, is substituted by an aryl group comprising from 6 to 30 carbon atoms, such as a phenyl group, the said aryl group is possibly substituted by at least one —$CH_2OH$ group.
In particular, when the Ar group, representing an aryl group, is substituted by a heteroaryl group comprising from 1 to 30 carbon atoms, the said heteroaryl group is possibly substituted by at least one substituent selected from the group consisting of: halogen, especially F, —C(=O)H, —$CH_2OH$ and $NO_2$.
According to one embodiment, the compounds having the formula (I) are such that:
X represents a nitrogen atom and Y represents a carbon atom, and/or
the Ar group represents a heteroaryl group comprising from 1 to 30 carbon atoms, substituted or unsubstituted, and/or
the $R_N$ and $R_{N'}$ groups, together with the carbon atoms to which they are bound, form a group selected from among the tropane, quinuclidine and octahydro quinolizine groups.
The Ar group may in particular be chosen from among the pyridine, thiophene, benzothiophene and benzofuran groups, possibly substituted by one or more groups selected from among —Br, —Cl, —F, —OMe, the alkyl groups comprising from 1 to 10 carbon atoms (preferably a methyl group) possibly substituted, and the aryl groups comprising from 6 to 30 carbon atoms (for example a phenyl group) or the heteroaryl groups comprising from 1 to 30 carbon atoms (for example a thiophene, furan or pyridine group), possibly substituted.

According to one embodiment, the Ar group represents a heteroaryl group comprising from 1 to 30 carbon atoms, substituted by an aryl group comprising from 6 to 30 carbon atoms, and/or a heteroaryl group comprising from 1 to 30 carbon atoms, possibly substituted.

In particular, when the Ar group, representing a heteroaryl group is substituted by an aryl group comprising from 6 to 30 carbon atoms, such as a phenyl group, the said aryl group is possibly substituted by at least one substituent selected from the group consisting of:
—CH$_2$OH;
halogen and in particular F or Cl;
—CH$_2$F, —CH$_2$Cl;
COOCH$_3$;

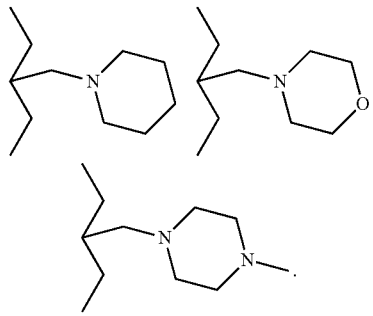

In particular, when the Ar group, representing a heteroaryl group, is substituted by a heteroaryl group comprising from 1 to 30 carbon atoms, the said heteroaryl group is possibly substituted by at least one substituent selected from the group consisting of: halogen, and in particular F or Cl, and NO$_2$.

According to one embodiment, the compounds having the formula (I) are such that:
X represents a nitrogen atom and Y represents a carbon atom, and
the Ar group represents an aryl group comprising from 6 to 30 carbon atoms, substituted or unsubstituted.

Preferably, the compounds having the formula (I) are such that:
X represents a nitrogen atom and Y represents a carbon atom, and
the Ar group represents a heteroaryl group comprising from 1 to 30 carbon atoms, substituted or unsubstituted.

Preferably, the compounds having the formula (I) are such that:
X represents a carbon atom and Y represents a nitrogen atom, and
the Ar group represents an aryl group comprising from 6 to 30 carbon atoms, substituted or unsubstituted Preferably, the compounds having the formula (I) are such that:
X represents a carbon atom and Y represents a nitrogen atom, and
the Ar group represents a heteroaryl group comprising from 1 to 30 carbon atoms, substituted or unsubstituted.

According to the present invention, the "alkyl" radicals represent saturated hydrocarbon radicals, in straight or branched chain comprising from 1 to 10 carbon atoms, preferably 1 to 5 carbon atoms (they may typically be represented by the formula $C_nH_{2n+1}$, n representing the number of carbon atoms). As examples, when they are linear, mention may be made of methyl, ethyl, propyl, butyl, pentyl, hexyl, octyl, nonyl and decyl radicals. In particular, when they are branched or substituted by one or more alkyl radicals, isopropyl, tert-butyl, 2-ethylhexyl, 2-methylbutyl, 2-methylpentyl, 1-methylpentyl and 3-methylheptyl may be mentioned.

According to the present invention, the "alkyl" radicals also refer to the linear or branched $C_1$-$C_{10}$ alkyl chains, substituted by one or more groups selected from among:
the halogen atoms, and in particular F, Cl or Br,
the aryl groups comprising from 6 to 30 carbon atoms,
the heteroaryl groups comprising from 1 to 30 carbon atoms, and in particular a pyridine,
the —R, —OR groups, and in particular —OH, —SR or —SiRR'R", R, R' and R" being independently selected from the group consisting of the hydrogen atom and the linear or branched alkyl groups comprising from 1 to 10 carbon atoms, possibly substituted,
the —NR$_a$R$_b$, R$_a$ and R$_b$ groups being independently selected from the group consisting of the hydrogen atom and the alkyl and acyl groups comprising from 1 to 10 carbon atoms, possibly substituted,
the —NHR$_c$, R$_c$ groups being selected from among the aryl and heteroaryl groups comprising from 1 to 30 carbon atoms, possibly substituted.

The "azacycloalkane" radical is a non-aromatic, saturated or partially unsaturated, monocyclic or bicyclic hydrocarbon radical that includes at least one trisubstituted endocyclic nitrogen atom, comprising from 3 to 30 carbon atoms, and preferably from 3 to 10 carbon atoms, possibly substituted by a $C_1$-$C_{10}$ alkyl or alkoxy group, a halogen atom like for instance Br, F or Cl, an —OH group or a —CH$_2$pyridine group.

The term "endocyclic nitrogen atom" is understood to refer to a nitrogen atom engaged in one or more carbon rings.

The azacycloalkanes are preferably selected from among the following radicals, possibly substituted by one or more halogen atoms, one or more linear or branched alkyl or alkoxy groups, possibly substituted:

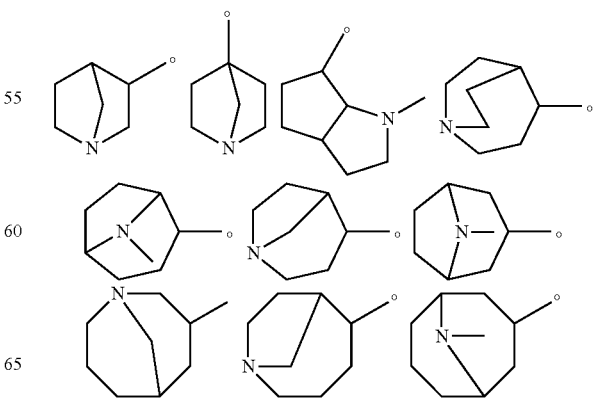

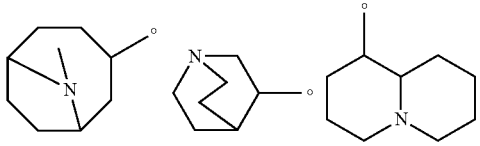

The symbol "o" represents the point of attachment to the side chain of the compound having the formula (I).

The azacycloalkanes may also contain one or more heteroatoms selected from among O or S.

The term "aryl" is understood to refer to an aromatic hydrocarbon system that is mono or bicyclic or polycyclic, containing from 6 to 30, preferably from 6 to 10 carbon atoms. Among the aryl radicals, mention may be made of the phenyl or naphthyl radical, more particularly substituted by at least one halogen atom.

When the aryl radical comprises at least one heteroatom, it is a "heteroaryl" radical that is being discussed. Thus, the term "heteroaryl" denotes an aromatic system comprising one or more (typically from 1 to 6, preferably from 1 to 4) heteroatoms, selected from among the monocyclic or bicyclic or polycyclic nitrogen, oxygen or sulfur, comprising from 1 to 30, preferably from 2 to 20, more preferably from 3 to 15 and advantageously from 4 to 10 carbon atoms.

Among the heteroaryl radicals, mention may be made of pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]pyridine, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzoazaindole, 1,2,4-triazinyl, benzothiazolyl, furanyl, benzofuranyl, imidazolyl, indolyl, triazolyl, tetrazolyl, indolizinyl, isoxazolyl, isoquinolinyl, isothiazolyl, oxadiazolyl, pyrazinyl, pyridazinyl, pyrazolyl, pyridyl, pyrimidinyl, purinyl, quinazolinyl, quinolinyl, isoquinolyl, 1,3,4-thiadiazolyl, thiazolyl, triazinyl, isothiazolyl, carbazolyl, thiophenyl, benzothiophenyl, as well as the corresponding groups derived from the fusion thereof or from the fusion with the phenyl nucleus.

The "alkyl", "aryl", "heteroaryl" and "cycloalkyl" radicals mentioned above may be substituted by one or more (typically from 1 to 5, preferably from 1 to 3) substituents. Among these substituents, mention may be made of the following groups: CHO, amino, amine, hydroxy, thio, halogen, and in particular F, Br or Cl, haloalkyl, carboxyl, alkyl (substituted or unsubstituted), (hetero)aryl, cycloalkyl, heterocycloalkyl, alkaryl, alkoxy, and in particular —OMe, alkylthio, alkylcarbonyl, aminocarbonyl, alkylcarboxyl, and notably —COOMe, alkylamino, aryloxy, arylalkoxy, cyano, trifluoromethyl, alkylsulfonyl, nitro, carboxy or carboxyalkyl.

Among the heterocycloalkyls, mention may be made of morpholine, N-methylpiperazine and piperidine.

According to one embodiment, the "alkyl", "aryl", "heteroaryl" and "cycloalkyl" groups are substituted by one or more halogen atoms, preferably F or I.

According to another embodiment, the "alkyl" group is substituted by one or more heterocycloalkyls, including morpholine, N-methylpiperazine or piperidine.

According to another embodiment, the "alkyl" group is substituted by one or more —OH groups.

According to another embodiment, the term "alkyl" group is substituted with one or more heteroaryl groups, and in particular a pyridine.

Among the alkyl groups, mention may be made of the perfluorinated alkyl groups.

Among the aryl or heteroaryl groups, either substituted or not, mention may be made more particularly of the following:

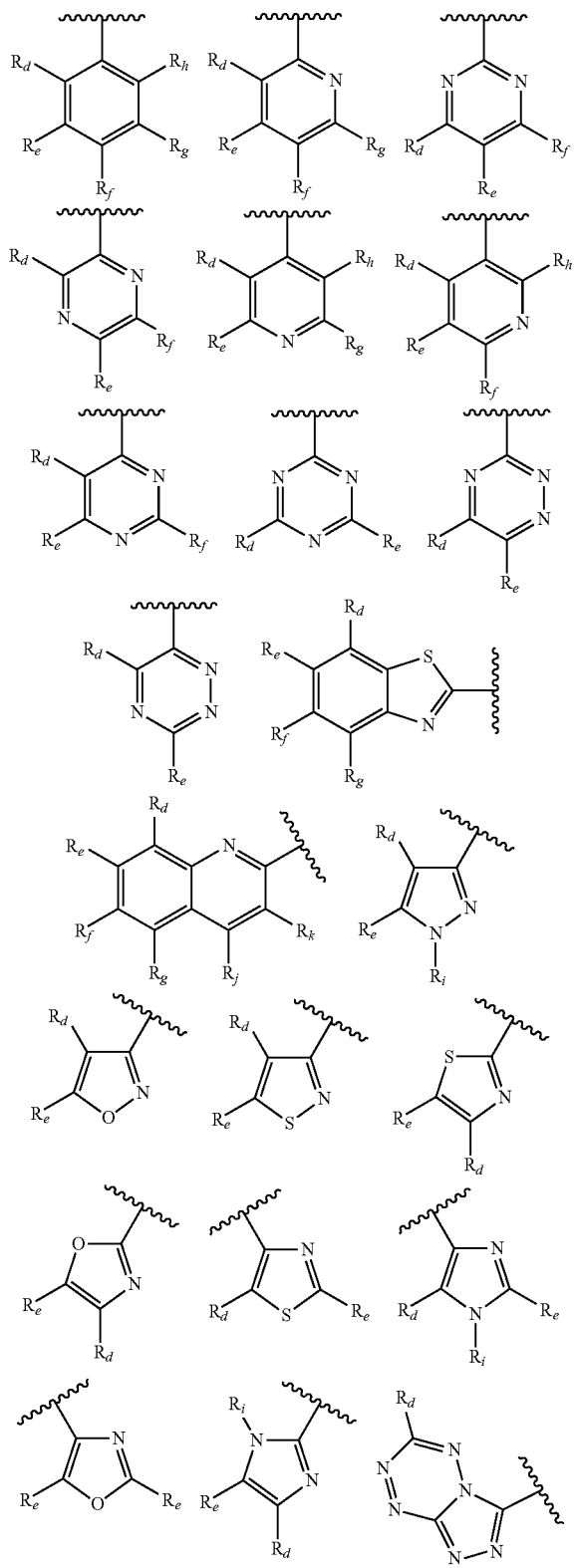

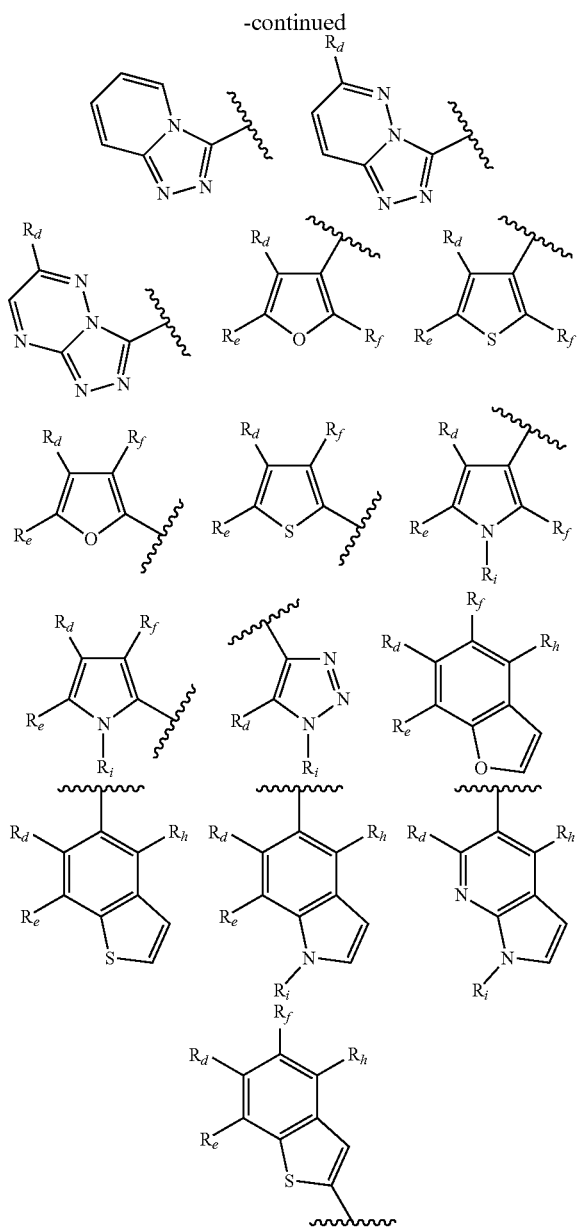

the $R_d$, $R_e$, $R_f$, $R_g$, $R_h$, $R_j$ and $R_k$ groups being selected, independently of one another, from the group consisting of the following substituents:

a hydrogen atom, a halogen atom, in particular Br, Cl or F, a (hetero)aryl group as defined here above, an alkyl group comprising from 1 to 10 carbon atoms, and preferably being a methyl group, the said alkyl group being possibly substituted in particular by one or more substituents selected from the group consisting of the following substituents:

halogen atoms, alkenyl or alkynyl groups comprising from 2 to 10 carbon atoms, aryl groups comprising from 6 to 30 carbon atoms, heteroaryl groups comprising from 1 to 30 carbon atoms, $COR'_\alpha$, $COOR'_\alpha$, $SR'_\alpha$, $OR'_\alpha$ ou $NR'_\alpha R_\beta$, $R'_\alpha$ and $R_\beta$ groups representing independently of one another a hydrogen atom, an alkyl group comprising from 1 to 10 carbon atoms, or an aryl group comprising from 6 to 30 carbon atoms, or a heteroaryl group comprising from 1 to 30 carbon atoms, a —CHO group, a —CN group, a —NO$_2$ group, a —CF$_3$ group, a phenyl group, a —SO$_2$R'$_\alpha$, R'$_\alpha$ group being as defined here above, in particular a —SO$_2$CH$_3$ group, an —O—(CH$_2$)$_n$—O—R'$_\alpha$, R'$_\alpha$ group being as defined here above, preferably representing an alkyl group, and n representing an integer from 1 to 10, preferably equal to 1, in particular —OCH$_2$OCH$_3$, a —CO$_2$R'$_\alpha$, R'$_\alpha$ group being as defined here above, in particular a —CO$_2$H group, a —COR'$_\alpha$, R'$_\alpha$ group being as defined here above, in particular a —COCH$_3$ group, a —SR'$_\alpha$ or OR'$_\alpha$, R'$_\alpha$ group being as defined here above, in particular an —OH, —OCH$_3$, —SH, —SCH$_3$, —O—CH(CH$_3$)$_2$, —O—CH$_2$—CH$_2$—CH$_3$ group, a —NR'$_\alpha$ R$_\beta$, R'$_\alpha$ and R$_\beta$ group being as defined here above, in particular a NH$_2$ group, a —CONR'$_\alpha$R$_\beta$, R'$_\alpha$ and R$_\beta$ group being as defined here above, in particular a —CONH$_2$ group, a —NHCOR'$_\alpha$, R'$_\alpha$ group being as defined here above, and a 2-pyridinyl group;

the R$_i$ group being a hydrogen atom or an alkyl group comprising from 1-10 carbon atoms.

According to one embodiment, the "aryl" groups are substituted by one or more groups selected from the group consisting of: —COOMe; —OMe; a halogen, and in particular F, Cl or Br; an alkyl group comprising from 1 to 10 carbon atoms, possibly substituted by —OH, a halogen, or a heterocycloalkyl, such as —CH$_2$OH, —CH$_2$F, —CH$_2$Cl,

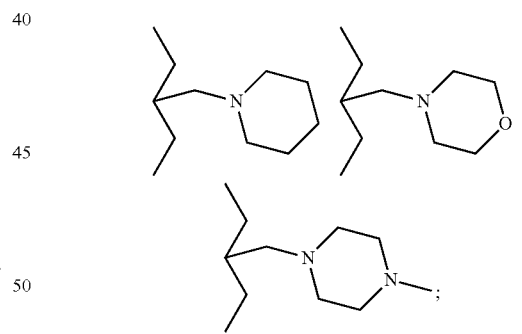

a heteroaryl group comprising from 1 to 30 carbon atoms, possibly substituted.

In one embodiment, the "heteroaryl" groups are substituted by one or more groups selected from the group consisting of: a halogen, in particular F, Cl or Br, —NO$_2$; —C(=O)H;

—CH$_2$OH; an aryl group comprising from 6 to 30 carbon atoms, in particular a phenyl, possibly substituted; a heteroaryl group comprising from 1 to 30 carbon atoms, possibly substituted.

The "alkenyl" radicals represent hydrocarbon radicals, in straight or linear chain, and comprise one or more ethylenic unsaturations. When they comprise only one double bond they can typically be represented by the formula C$_n$H$_{2n}$, n representing the number of carbon atoms. Among the alkenyl radicals, mention may be made of the allyl or vinyl radicals.

The "alkynyl" radicals represent hydrocarbon radicals, in straight or linear chain, and comprise one or more acetylenic unsaturations. When they comprise only one triple bond they can typically be represented by the formula $C_nH_{2n-2}$, n representing the number of carbon atoms. Among the alkynyl radicals, mention may be made of acetylene.

Among the aryl groups mention may be made of:

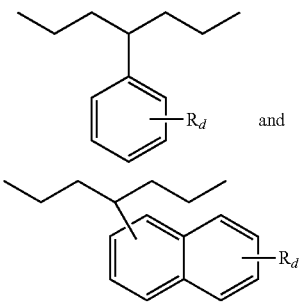

and $R_d$ being as defined here above, and preferably being selected from the group consisting of: H, F, Br, $OCH_3$, OH, $CH_2F$, $COOCH_3$, $CH_2Br$, $CH_2OH$ and the alkyl groups comprising from 1 to 10 carbon atoms, possibly substituted.

Among the aryl groups, mention may also be made of:

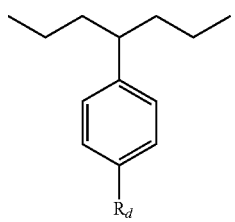

$R_d$ being as defined here above.

Among the heteroaryl groups, mention may be made of:

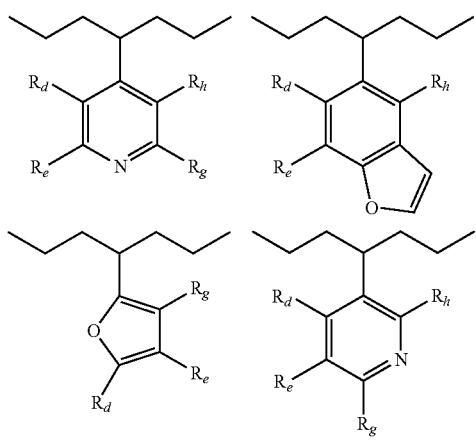

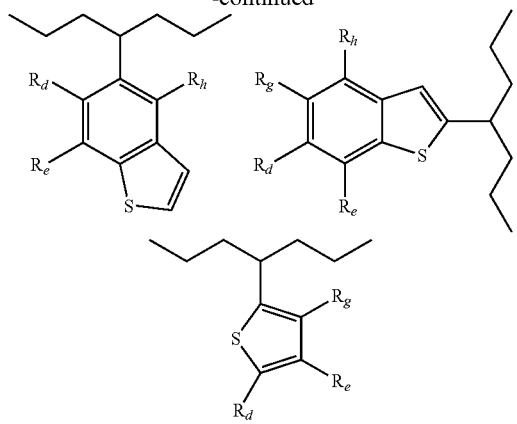

$R_d$, $R_e$, $R_g$ and $R_h$ are selected independently of one another, from the group consisting of the following substituents: a hydrogen atom, a halogen atom, in particular Br, Cl or F, and an alkyl group comprising from 1 to 10 carbon atoms, and preferably being a methyl group, an aryl group comprising from 6 to 30 carbon atoms possibly substituted or a heteroaryl group comprising from 1 to 30 carbon atoms, possibly substituted. In particular, $R_d$, $R_e$, $R_g$ and $R_h$ are selected independently of one another, from the group consisting of:
  a hydrogen atom;
  an aryl group comprising from 6 to 30 carbon atoms, substituted by at least one substituent selected from the group consisting of:
  $CH_2OH$;
  $CH_2Cl$;
  an aryl group comprising from 6 to 30 carbon atoms, in particular a phenyl, possibly substituted by at least one —$CH_2OH$ group;
  a heteroaryl group comprising from 1 to 30 carbon atoms, possibly substituted by at least one substituent selected from the group consisting of: F, Cl, C(=O)H, $CH_2OH$, and $NO_2$.
a heteroaryl group comprising from 1 to 30 carbon atoms, possibly substituted with a substituent selected from the group consisting of:
  a halogen, and in particular F,
  an aryl group comprising from 6 to 30 carbon atoms, in particular a phenyl, possibly substituted by at least one F, Cl, $CO_2CH_3$, $CH_2F$, $CH_2Cl$ group,

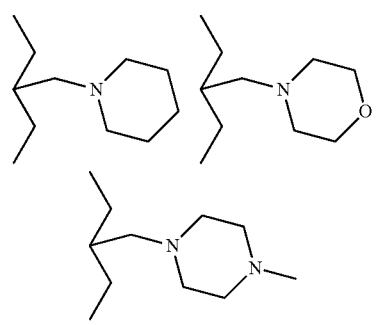

a heteroaryl group comprising from 1 to 30 carbon atoms, possibly substituted by at least one $NO_2$ group.

The "alkoxy" radicals according to the present invention are radicals having the formula —O-alkyl, the alkyl group being as previously defined here above.

The term "alkylthio" refers to an —S-alkyl group, the alkyl group being as defined here above.

The term "alkylamino" refers to a —NH-alkyl group, the alkyl group being as defined here above.

The term "alkylcarbonyl" refers to a —CO-alkyl group, the alkyl group being as defined here above.

The term "alkylcarboxyl" refers to a —COO-alkyl group, the alkyl group being as defined here above.

The term "alkylsulfonyl" refers to a —SO$_2$-alkyl group, the alkyl group being as defined here above.

Among the halogen atoms, in particular mention may be made of fluorine, chlorine, bromine and iodine.

The term "aryloxy" refers to an —O-aryl group, the aryl group being as defined here above.

The term "arylalkoxy" refers to an aryl-alkoxy-group, the aryl and alkoxy groups being as defined here above.

The term "carboxyalkyl" refers to an HOOC-alkyl-group, the alkyl group being as defined here above. As an example of the carboxyalkyl groups mention may be made in particular of carboxymethyl or carboxyethyl.

When an alkyl radical is substituted by an aryl group, it is an "arylalkyl" or "aralkyl" radical that is being discussed. The "arylalkyl" or "aralkyl" radicals are aryl-alkyl-radicals, the aryl and alkyl groups being as defined here above. Among the arylalkyl radicals, in particular mention may be made of benzyl or phenethyl. The arylalkyl groups may be substituted by one or more substituents. Among these substituents, mention may be made of the following groups: amino, hydroxy, thio, halogen, carboxyl, alkyl, alkoxy, alkylthio, alkylcarbonyl, alkylcarboxyl, alkylamino, aryloxy, arylalkoxy, cyano, trifluoromethyl, alkylsulfonyl, carboxy or carboxyalkyl.

The term "pharmaceutically acceptable salts" makes reference to inorganic and organic, relatively nontoxic acid addition salts, and base addition salts, of the compounds of the present invention. These salts can be prepared in situ during the final isolation and purification of the compounds. In particular, the acid addition salts may be prepared by making the purified compound in its pure form react separately with an organic or inorganic acid and isolating the salt thus formed. Included among the examples of acid addition salts are the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptanate, and lactobionate salts, sulfamates, malonates, salicylates, propionates, methylenebis-b-hydroxynaphthoates, gentisic acid, isethionates, di-p-toluoyltartrates, methanesulfonates, ethanesulfonates, benzenesulfonates, p-toluenesulfonates, cyclohexylsulfamates and quinateslaurylsulfonate, and the like (see, for example, S M Berge et al "Pharmaceutical Salts" *J. Pharm. Sci,* 66: p. 1-19 (1977)). The acid addition salts may also be prepared by making the purified compound in its acid form react separately with an organic or inorganic base and isolating the salt thus formed. The acid addition salts include the amine and metal salts. Suitable metal salts include sodium, potassium, calcium, barium, zinc, magnesium and aluminum. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, and zinc hydroxide. Suitable amine base addition salts are prepared from amines which have sufficient alkalinity in order to form a stable salt, and preferably include amines which are often used in medicinal chemistry on account of their low toxicity and the acceptability thereof for medical use: ammonia, ethylenediamine, N-methyl glucamine, lysine, arginine, ornithine, choline, N,N'-dibenzylethylenediamine, chloroprocaine, diethanolamine, procaine, N-benzyl-phenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethyl ammonium, tetraethyl ammonium, methylamine, dimethylamine, trimethylamine, ethylamine, basic amino acids, for example lysine and arginine and dicyclohexyl amine, and the like.

The invention also relates to the tautomer forms, to the enantiomers, diastereoisomers, epimers and the organic or inorganic salts of the compounds having the general formula (I).

According to one embodiment, the present invention relates to compounds having the formula (II):

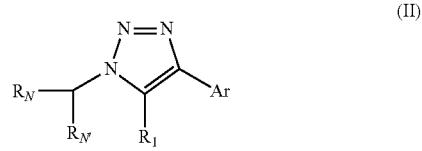

(II)

wherein the $R_1$, $R_N$, $R_{N'}$ and Ar groups are as defined here above (II).

In another embodiment, the present invention relates to compounds having the formula (II):

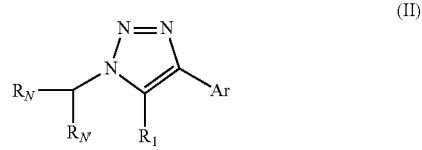

(II)

wherein:
the $R_1$, $R_N$, and $R_{N'}$ groups are as defined here above, and
and the Ar group represents a phenyl grouping, possibly substituted by one or more groups selected from among:
the halogen atoms, in particular a chlorine, bromine or fluorine atom,
the —OH group,
the linear or branched alkyl groups and alkoxy comprising from 1 to 10 carbon atoms, possibly substituted and
the aryl groups comprising from 6 to 30 carbon atoms and the heteroaryl groups comprising from 1 to 30 carbon atoms, possibly substituted.

In particular, the alkyl groups in the compounds having the formula (II) are substituted by at least one —OH group or a halogen, and in particular chlorine or fluorine. Preferably, the said substituted alkyl groups are selected from among $CH_2OH$, $CH_2Cl$, $CH_2F$.

In particular, the aryl groups in the compounds having the formula (II) are substituted by at least one halogen, and in particular a fluorine, or by a $CH_2OH$ group.

In particular, the heteroaryl groups are unsubstituted.

In particular, the heteroaryl groups in the compounds having the formula (II) are substituted by at least one substituent selected from the group consisting of: —C(=O)H, NO₂, CH₂OH, halogen, such as fluorine.

According to another embodiment, the present invention relates to compounds having the formula (II):

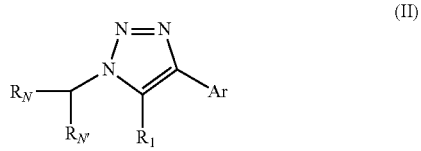

wherein
the Ar group is selected from among the phenyl, pyridyl, thiophenyl, furanyl, benzothiophenyl, benzofuranyl and naphthalenyl groups, possibly substituted by one or more substituents selected from among:
  the halogen atoms,
  the —OH group,
  the linear or branched alkyl and alkoxy groups comprising from 1 to 10 carbon atoms, possibly substituted, and
  the aryl groups comprising from 6 to 30 carbon atoms and the heteroaryl groups comprising from 1 to 30 carbon atoms, possibly substituted;
the $R_N$ and $R_{N'}$ groups, together with the carbon atoms to which they are bound, form a group selected from among the tropane, quinuclidine and octahydro quinolizine groups;
$R_1$ is a group selected from among
  the hydrogen atom,
  the halogen atoms,
  the aryl groups comprising from 6 to 30 carbon atoms and the heteroaryl groups comprising from 1 to 30 carbon atoms, possibly substituted,
  the —$NR_aR_b$ groups, wherein $R_a$ and $R_b$ are as defined here above, such as NH₂, and
  the —$NHR_c$ groups, wherein $R_c$ is as defined here above.

In particular, the alkyl groups in the compounds having the formula (II) are substituted by at least one —OH group or a halogen, and specifically a chlorine, a bromine or a fluorine. Preferably, the said substituted alkyl groups are selected from among CH₂OH, CH₂Cl, CH₂F.

In particular, the aryl groups in the compounds having the formula (II) are substituted by at least one substituent selected from the group consisting of: halogen, and in particular a fluorine or a chlorine; COOCH₃; CH₂OH; CH₂F; CH₂Cl;

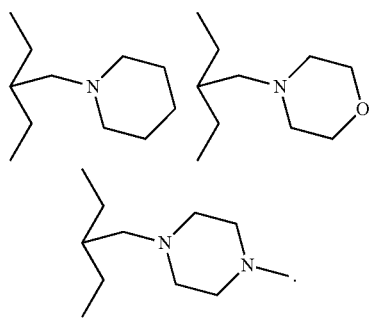

In particular, the heteroaryl groups in the compounds having the formula (II) are unsubstituted.

In particular, the heteroaryl groups in the compounds having the formula (II) are substituted by at least one substituent selected from the group consisting of: —C(=O)H, NO₂, CH₂OH, halogen, such as Cl or F According to one embodiment, in the compounds having the formula (II), $R_1$ represents a hydrogen atom.

Among the compounds of the invention mention in particular may be made of the compounds having the following formula (II-1):

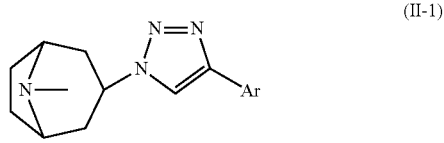

in which the $R_2$ and Ar groups are as defined here above.

The compounds having the formula (II-1) are compounds having the formula (II) as defined here above, wherein the $R_N$ and $R_{N'}$ groups, together with the carbon atoms to which they are bound, form a tropane group, possibly substituted.

According to one embodiment, for the compounds having the formula (II-1), the Ar group represents a phenyl grouping, possibly substituted by one or more groups selected from among:
  the halogen atoms,
  the —OH group,
  the linear or branched alkyl and alkoxy groups comprising from 1 to 10 carbon atoms, possibly substituted, and
  the aryl groups comprising from 6 to 30 carbon atoms and the heteroaryl groups comprising from 1 to 30 carbon atoms, possibly substituted.

Among these compounds having the formula (II-1), mention may thus be made of the compounds having the following formula (II-1-1):

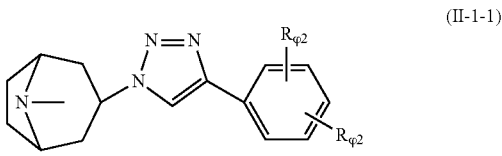

wherein $R_{φ1}$ and $R_{φ2}$ are selected from among H, the halogen atoms, alkyl groups and the linear or branched alkyl and alkoxy groups comprising from 1 to 10 carbon atoms, possibly substituted.

In particular when $R_{φ1}$ and/or $R_{φ2}$ represent(s) an alkyl group, the said alkyl group is possibly substituted by at least one substituent selected from the group consisting of: —OH and a halogen atom such as a fluorine.

According to one embodiment, the present invention also relates to compounds having the following formula (II-1-1-1):

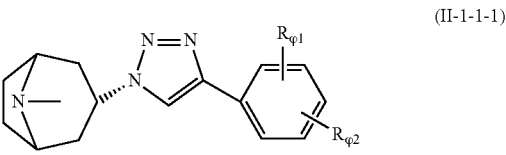

wherein $R_{φ1}$ and $R_{φ2}$ are as defined here above in the formula (II-1-1).

Thus, the present invention relates to the following compounds:

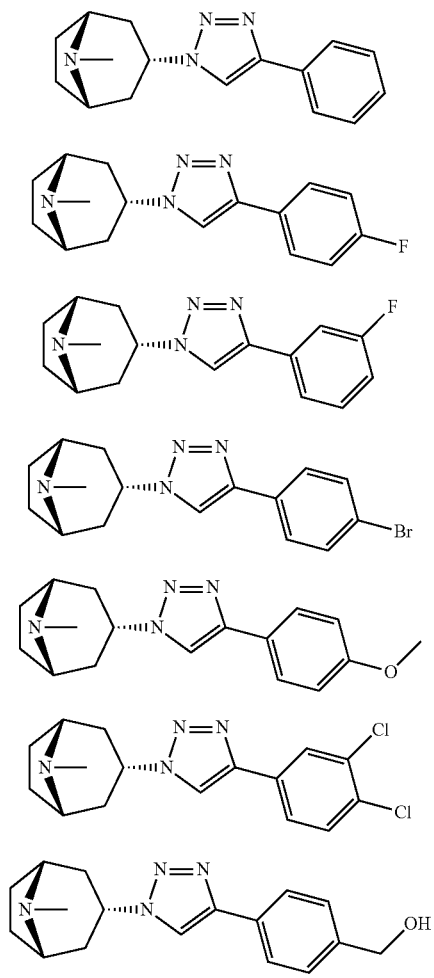

According to one embodiment, for the compounds having the formula (II-1), the Ar group represents a monocyclic or bicyclic aryl or heteroaryl grouping, possibly substituted by one or more groups selected from among the halogen, the linear or branched alkyl or alkoxy groups comprising from 1 to 10 carbon atoms, the aryl groups comprising from 6 to 30 carbon atoms and the heteroaryl groups comprising from 1 to 30 carbon atoms, possibly substituted.

In particular, when the Ar group represents a monocyclic or bicyclic aryl or heteroaryl grouping substituted by a heteroaryl group, the said heteroaryl group is not substituted.

Thus, the present invention relates to the following compounds:

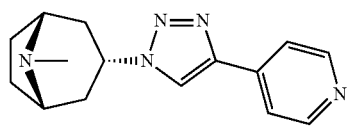

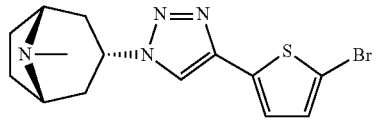

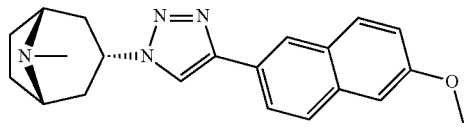

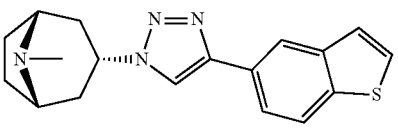

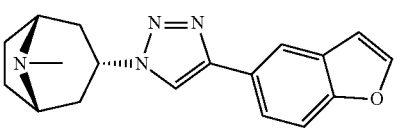

Among the compounds of the invention mention may be made of the compounds having the formula (II-2):

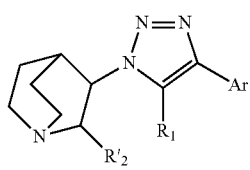

(II-2)

wherein
the $R_1$ and Ar groups are as defined here above, and
the $R_2$ group represents a linear or branched alkyl group comprising from 1 to 10 carbon atoms, possibly substituted by an aryl group comprising from 6 to 30 carbon atoms and a heteroaryl group comprising from 1 to 30 carbon atoms, possibly substituted.

The compounds having the formula (II-2) are compounds having the formula (II) as defined here above, wherein the $R_N$ and $R_{N'}$ groups, together with the carbon atoms to which they are bound, form a quinuclidine group, possibly substituted.

According to one embodiment, for compounds having the formula (II-2), the Ar group represents a phenyl grouping, possibly substituted by one or more groups selected from among:
the halogen atoms, in particular F, Cl or Br,
the —OH group,
the linear or branched alkyl and alkoxy groups comprising from 1 to 10 carbon atoms, possibly substituted, and the aryl groups comprising from 6 to 30 carbon atoms and the heteroaryl groups comprising from 1 to 30 carbon atoms, possibly substituted.

In particular, in the formula (II-2), the said alkyl groups are substituted by at least one —OH group or a halogen atom, such as F or Cl.

In particular, in the formula (II-2), the said aryl groups are unsubstituted.

In particular, in the formula (II-2), the said aryl groups are substituted by at least one CH$_2$OH group or a halogen atom, such as F, Cl or Br.

In particular, in the formula (II-2), the said heteroaryl groups are unsubstituted.

In particular, in the formula (II-2), the said heteroaryl groups are substituted by at least one substituent selected from the group consisting of: —C(=O)H, NO$_2$, CH$_2$OH and a halogen such as F.

Among the compounds having the formula (II-2), mention may be made of the compounds having the following formula (II-2-a) or (II-2-b):

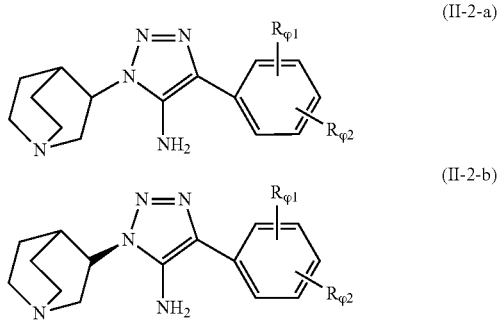

wherein R$_{\varphi 1}$ and R$_{\varphi 2}$ are selected from among H, the halogen atoms, the linear or branched alkyl and alkoxy groups comprising from 1 to 10 carbon atoms, possibly substituted.

Among these compounds, mention may also be made, for example, of the following compound:

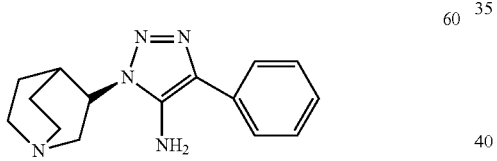

For the compounds having the formula (II-2), R$_1$ may represent H.

For the compounds having the formula (II-2), R'$_2$ may represent H.

Among the compounds having the formula (II-2), mention may thus be made of the compounds having the following formula (II-2-1):

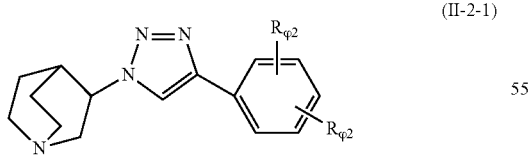

wherein R$_{\varphi 1}$ and R$_{\varphi 2}$ are selected from among H, the halogen atoms, the linear or branched alkyl and alkoxy groups comprising from 1 to 10 carbon atoms, possibly substituted.

According to one embodiment, in the formula (II-2-1), at least one of R$_{\varphi 1}$ and R$_{\varphi 2}$ represents an alkyl group substituted by an —OH group. In particular, at least one of R$_{\varphi 1}$ and R$_{\varphi 2}$ represents CH$_2$OH.

According to one embodiment, in the formula (II-2-1) at least one of R$_{\varphi 1}$ and R$_{\varphi 2}$ represents an alkyl group substituted by halogen. In particular, at least one of R$_{\varphi 1}$ and R$_{\varphi 2}$ represents CH$_2$CH or F$_2$Cl.

According to one embodiment, in the formula (II-2-1) at least one of R$_{\varphi 1}$ and R$_{\varphi 2}$ represents a halogen, and in particular F, Cl or Br. In particular, at least one of R$_{\varphi 1}$ and R$_{\varphi 2}$ represents F, Cl or Br.

In one embodiment, in the formula (II-2-1), at least one of R$_{\varphi 1}$ and R$_{\varphi 2}$ represents an alkoxy group, and in particular a methoxy.

According to one embodiment, the present invention relates to compounds having the following formula (II-2-1-1):

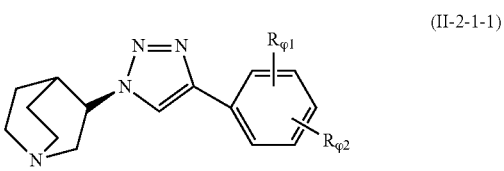

wherein R$_{\varphi 1}$ and R$_{\varphi 2}$ are as defined here above in the formula (II-2-1).

According to one embodiment, the present invention relates to compounds having the formula (II-2-1-2) as follows:

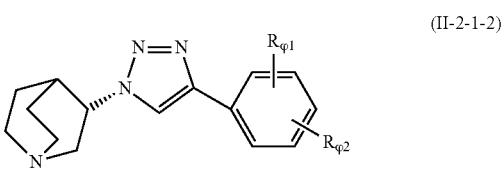

wherein R$_{\varphi 1}$ and R$_{\varphi 2}$ are as defined here above in the formula (II-2-1).

Thus, the present invention relates to the following compounds:

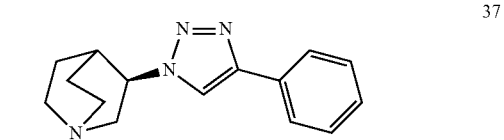

37

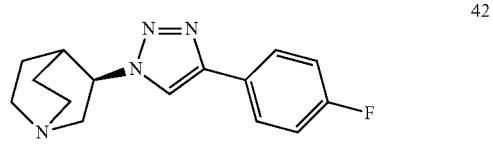

42

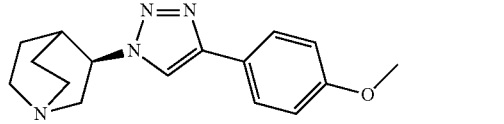

46

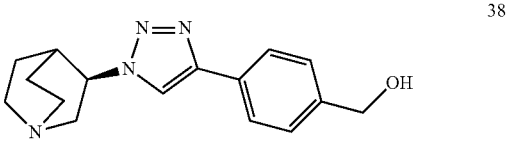

38

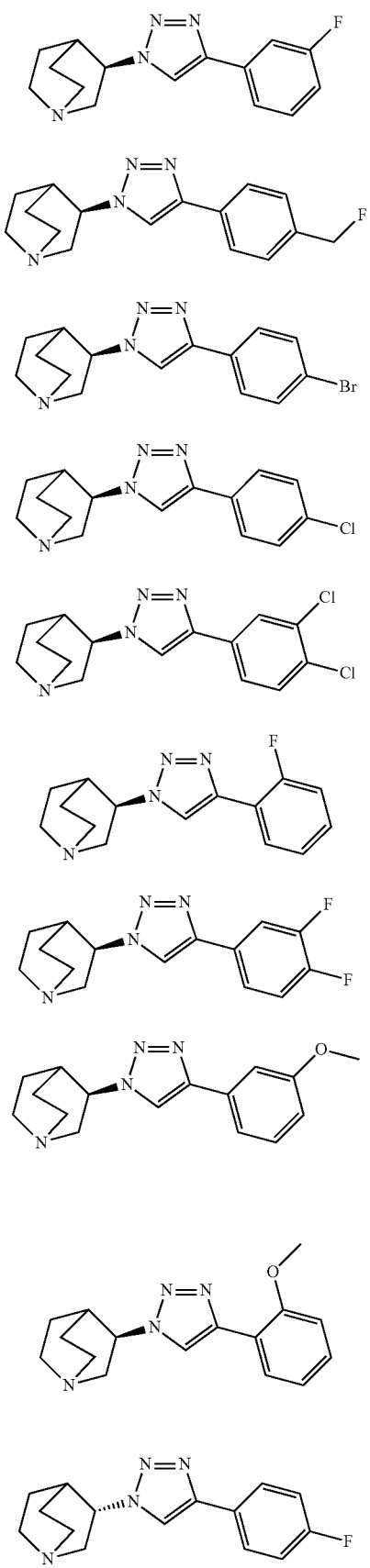

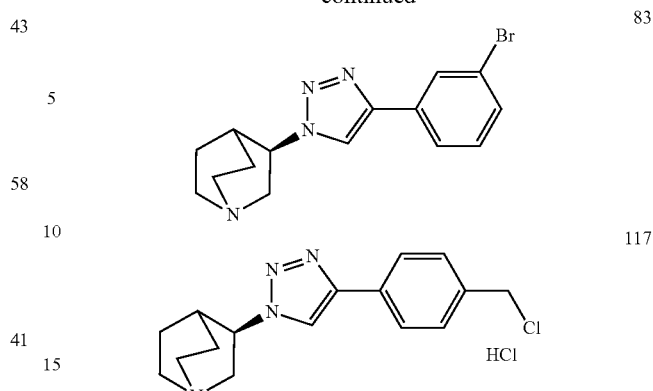

According to one embodiment, for the compounds having the formula (II-2), the Ar group represents a monocyclic or bicyclic aryl or heteroaryl grouping, possibly substituted by one or more groups selected from among the halogen atoms, the linear or branched alkyl or alkoxy groups comprising from 1 to 10 carbon atoms, and the aryl groups comprising from 1 to 30 carbon atoms and the heteroaryl groups comprising from 1 to 30 carbon atoms, the said aryl and heteroaryl groups being possibly substituted.

According to one embodiment, in the formula (II-2), the Ar group representing a monocyclic or bicyclic heteroaryl group, is substituted by at least one halogen, and especially F or Br.

According to another embodiment, in the formula (II-2), the Ar group representing a monocyclic or bicyclic heteroaryl group, is substituted by at least one unsubstituted alkoxy group, such as a methoxy group.

According to one embodiment, in the formula (II-2), the Ar group representing a monocyclic or bicyclic heteroaryl group is not substituted.

According to one embodiment, in the formula (II-2), the Ar group representing a monocyclic or bicyclic heteroaryl group is substituted by at least one aryl group comprising from 1 to 30 carbon atoms, and in particular a phenyl group, the said aryl group being substituted by at least one substituent selected from the group consisting of: F, Cl, COOMe, $CH_2OH$, $CH_2F$, $CH_2C_1$ and $CH_2NR_uR_v$, wherein $R_u$ and $R_v$, together with the nitrogen atoms to which they are bound, form a heterocycle comprising from 5 to 10 atoms, the said heterocycle possibly containing another heteroatom selected from among O, S and N, and being possibly substituted by an alkyl group comprising from 1 to 10 carbon atoms.

According one embodiment, in the formula (II-2), the Ar group representing a monocyclic or bicyclic heteroaryl group is substituted by at least one heteroaryl group comprising from 1 to 30 carbon atoms, possibly substituted by at least one substituent selected from the group consisting of: $NO_2$ or a halogen, and in particular F.

Thus, the present invention relates to the following compounds:

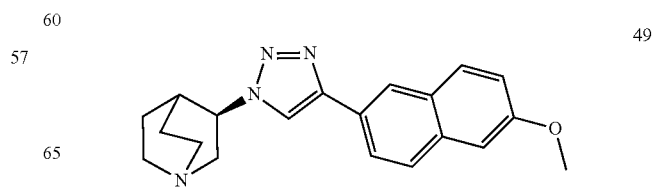

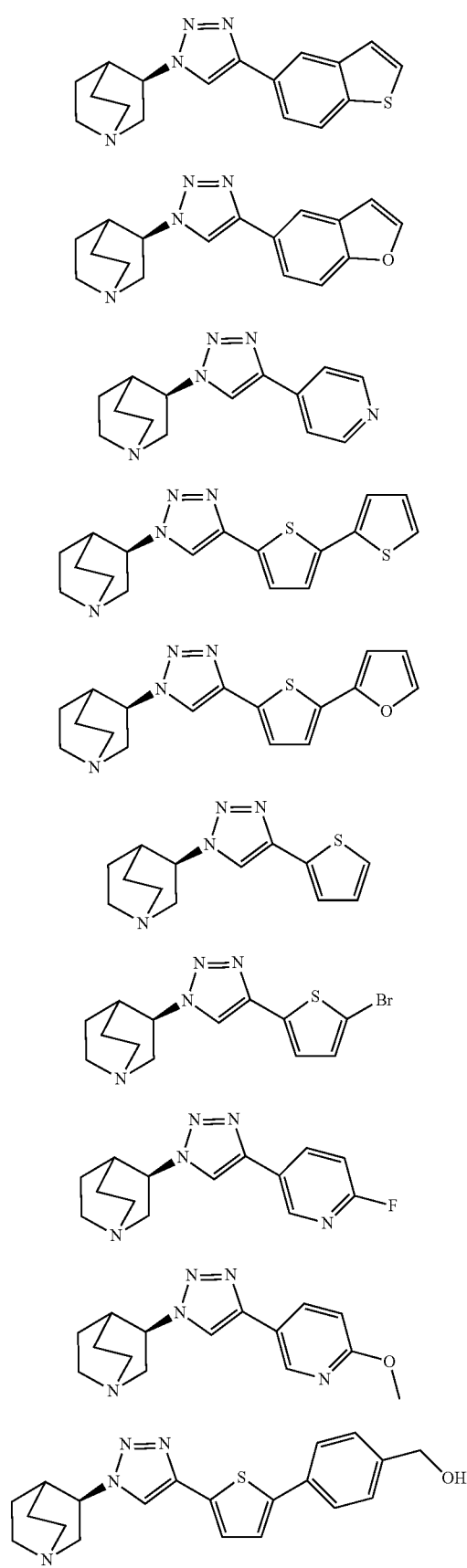
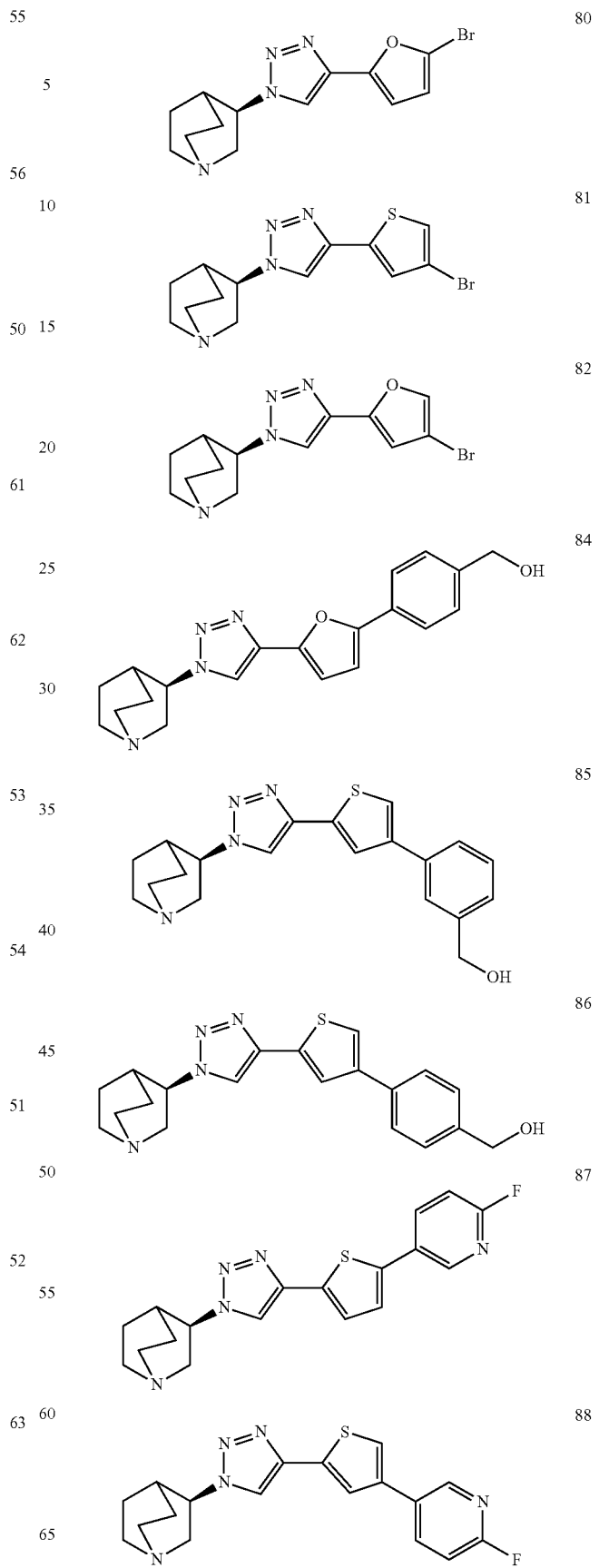

89
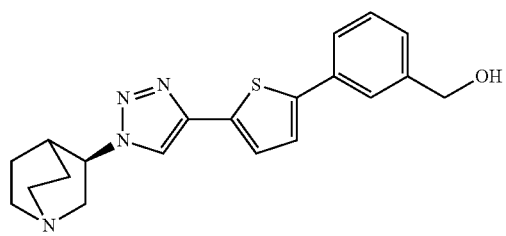
90
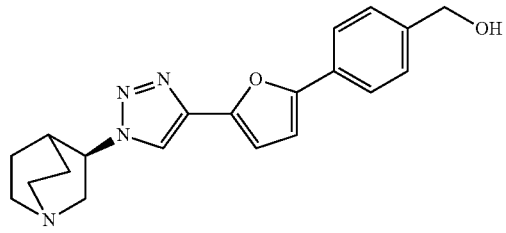
91
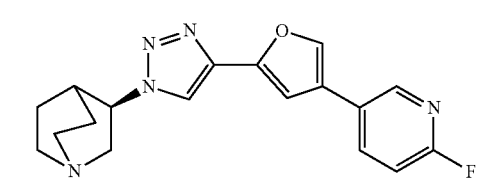
92
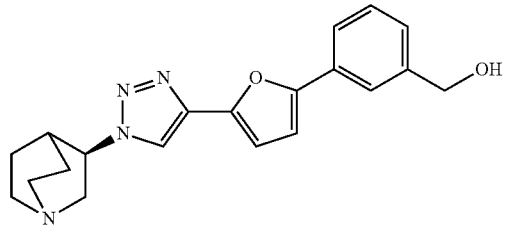
102
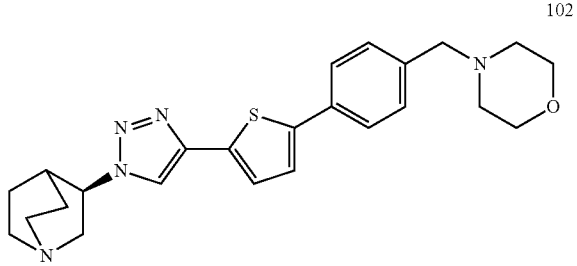
103
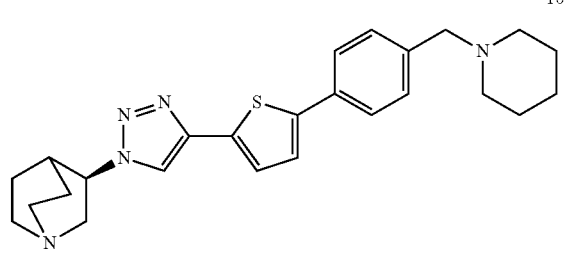
104
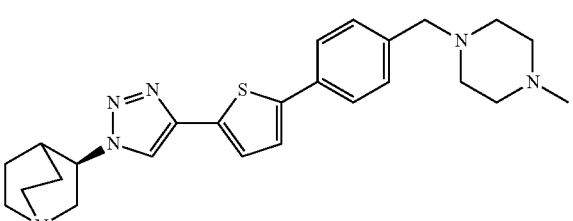
105
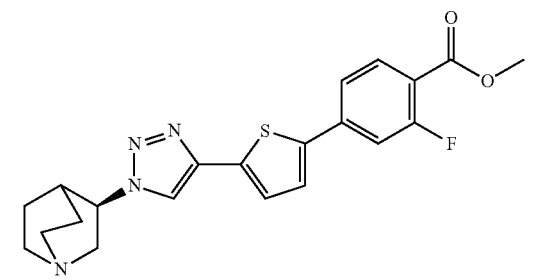
106
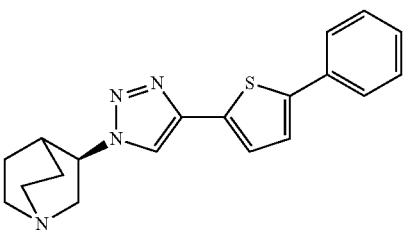
107
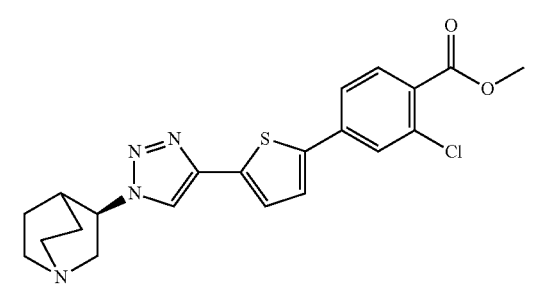
109
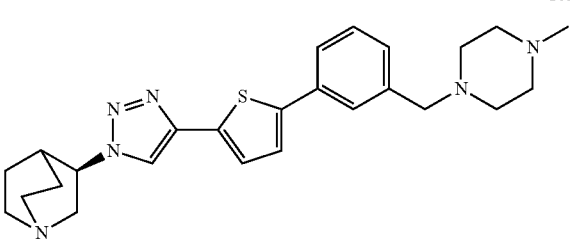
110
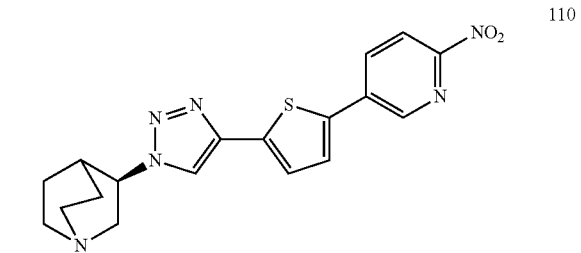

-continued

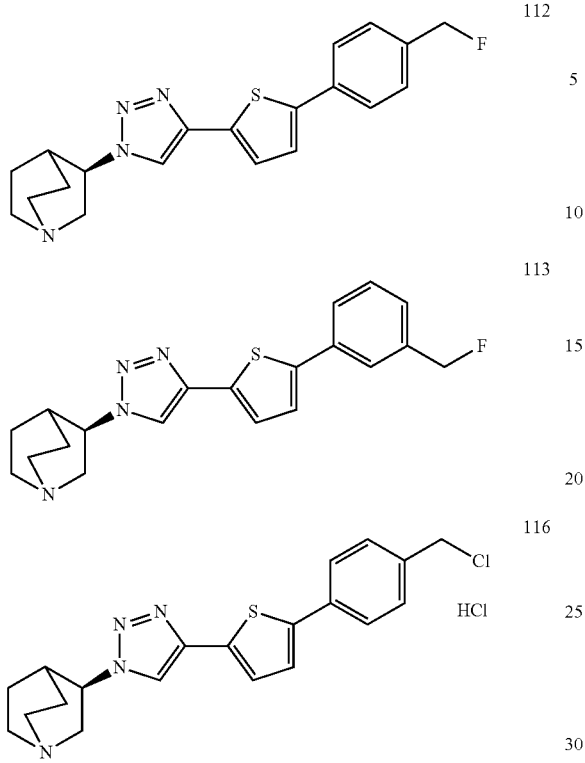

Among the compounds having the formula (II-2), mention may also be made of the compounds having the formula (II-2-3) as follows:

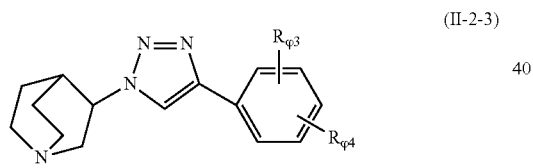

(II-2-3)

wherein $R_{φ3}$ and $R_{φ4}$ are selected from among the aryl groups comprising from 6 to 30 carbon atoms or the heteroaryl groups comprising from 1 to 30 carbon atoms, the said aryl and heteroaryl groups being possibly substituted.

According to one embodiment, in the formula (II-2-3), at least one of $R_{φ3}$ and $R_{φ4}$ represents an unsubstituted heteroaryl group.

According to one embodiment, in the formula (II-2-3), at least one of $R_{φ3}$ and $R_{φ4}$ represents a heteroaryl group substituted by a substituent selected from the group consisting of: —C(=O)H, CH$_2$OH, NO$_2$ and a halogen, particularly F.

According to one embodiment, in the formula (II-2-3), at least one of $R_{φ3}$ and $R_{φ4}$ represents an aryl group substituted by at least one alkyl group comprising from 1 to 10 carbon atoms, the said alkyl group being substituted by an —OH group or a halogen. In particular, at least one of $R_{φ3}$ and $R_{φ4}$ represents a phenyl substituted by CH$_2$OH. In particular, at least one of $R_{φ3}$ and $R_{φ4}$ represents a phenyl substituted by CH$_2$F or CH$_2$Cl.

Thus, the present invention relates to the following compounds:

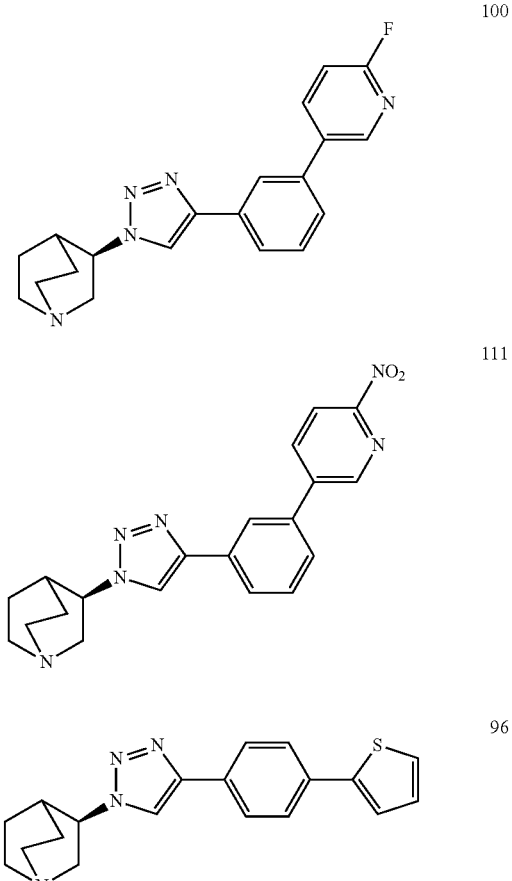

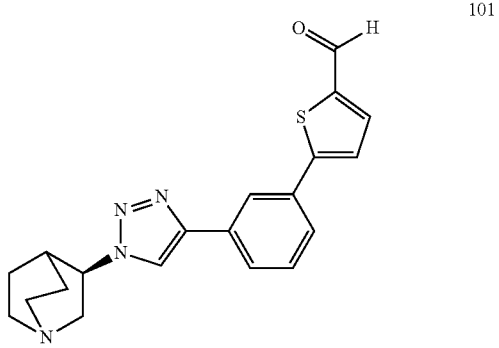

-continued

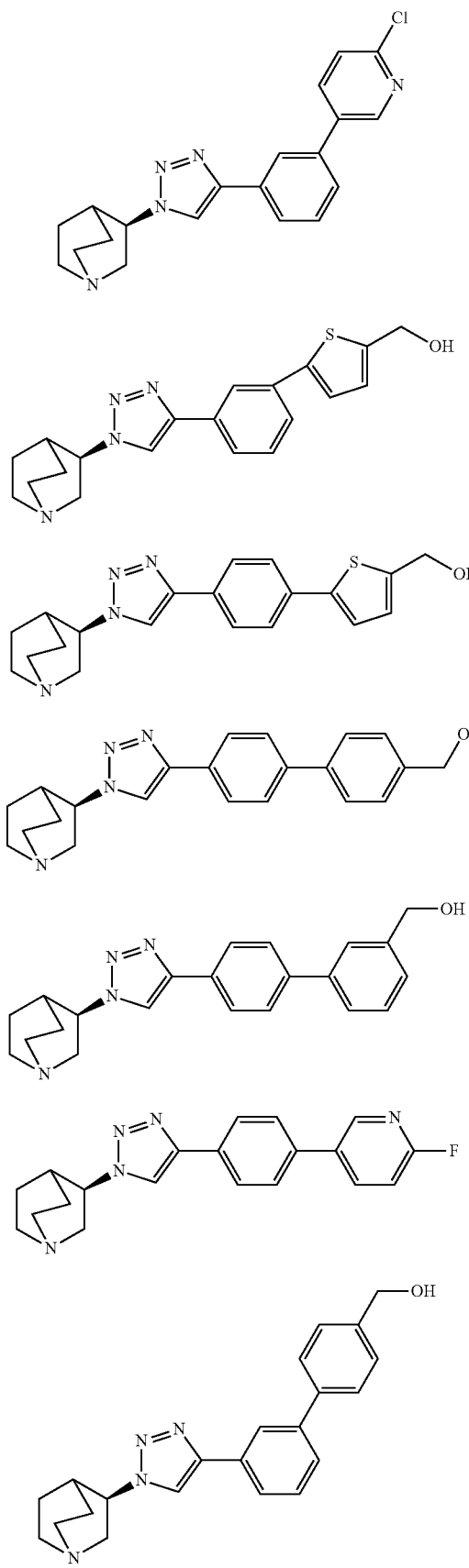

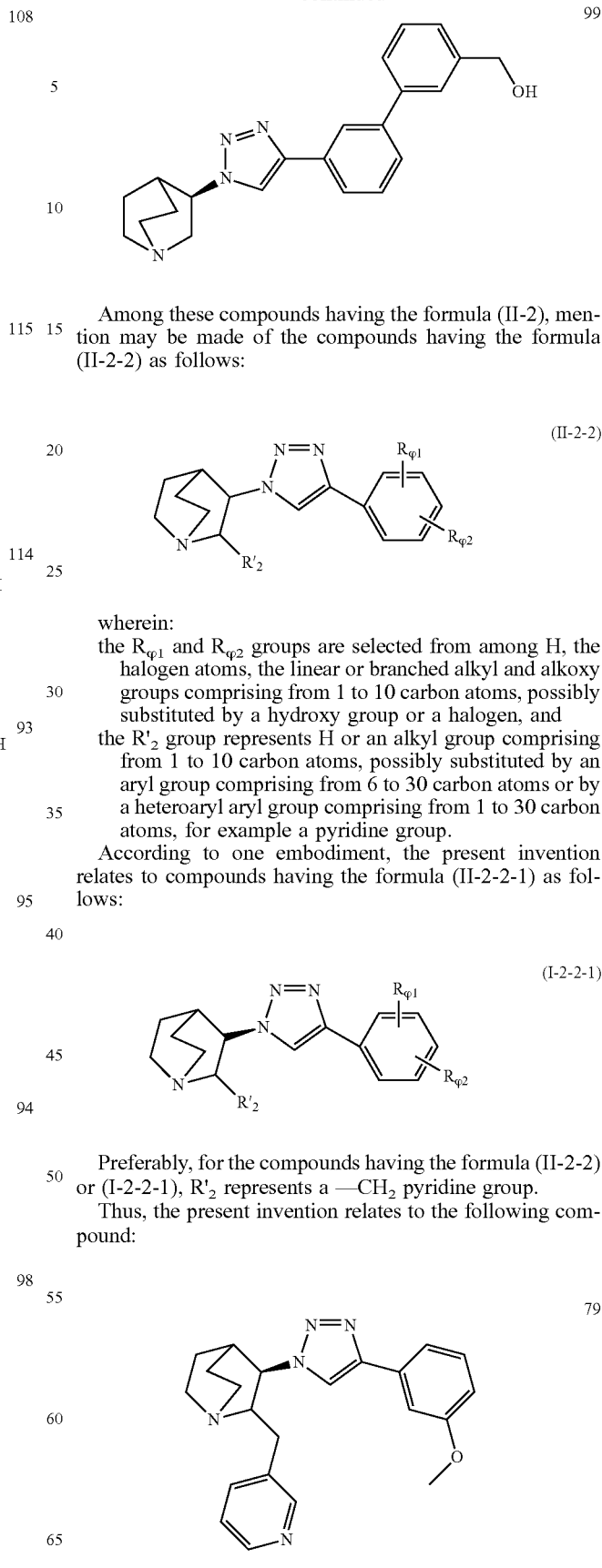

Among these compounds having the formula (II-2), mention may be made of the compounds having the formula (II-2-2) as follows:

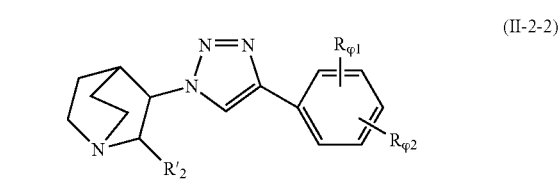

(II-2-2)

wherein:
the $R_{\varphi 1}$ and $R_{\varphi 2}$ groups are selected from among H, the halogen atoms, the linear or branched alkyl and alkoxy groups comprising from 1 to 10 carbon atoms, possibly substituted by a hydroxy group or a halogen, and
the $R'_2$ group represents H or an alkyl group comprising from 1 to 10 carbon atoms, possibly substituted by an aryl group comprising from 6 to 30 carbon atoms or by a heteroaryl aryl group comprising from 1 to 30 carbon atoms, for example a pyridine group.

According to one embodiment, the present invention relates to compounds having the formula (II-2-2-1) as follows:

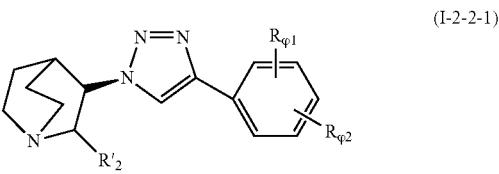

(I-2-2-1)

Preferably, for the compounds having the formula (II-2-2) or (I-2-2-1), $R'_2$ represents a —$CH_2$ pyridine group.

Thus, the present invention relates to the following compound:

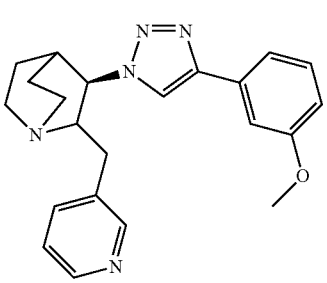

Among the compounds of the invention mention may in particular be made of the compounds having the formula (II-3) as follows:

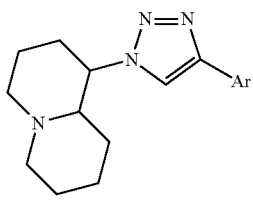

(II-3)

wherein Ar is as defined here above.

Among the compounds of the invention mention may in particular be made of the compounds having the formula (II-3-1) as follows:

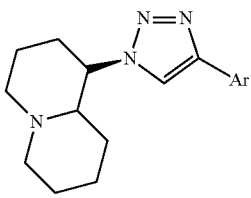

(II-3-1)

wherein Ar is as defined here above.

The compounds having the formula (II-3) are compounds having the formula (II) as defined here above, wherein the $R_N$ and $R_{N'}$ groups, together with the carbon atoms to which they are bound, form an octahydro quinolizine group, possibly substituted.

Thus, the present invention relates to the following compounds:

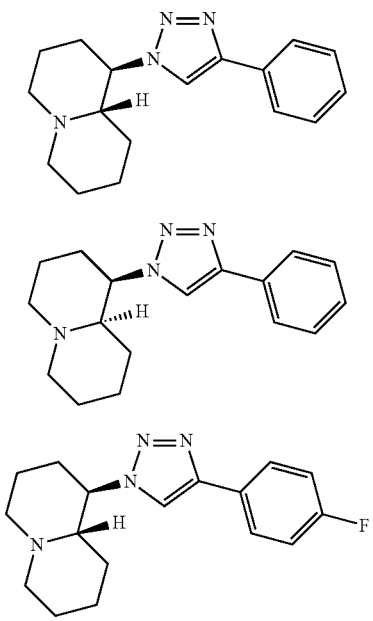

34

34

35

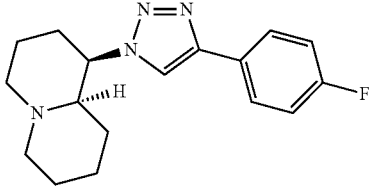

35

According to another embodiment, the present invention relates to compounds having the formula (III):

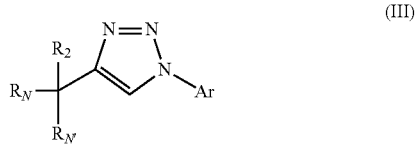

(III)

wherein the $R_1$, $R_2$, $R_N$, $R_{N'}$ and Ar groups are as defined here above.

According to one embodiment, in the formula (III), $R_2$ is —H, —F or —OH.

According to another embodiment, the present invention relates to compounds having the formula (III) wherein:

the $R_1$, $R_2$, $R_N$ and $R_{N'}$ groups are as defined here above, and the Ar group represents a phenyl grouping, possibly substituted by one or more groups selected from among:

the halogen atoms, the —OH group, the linear or branched alkyl and alkoxy groups comprising from 1 to 10 carbon atoms, possibly substituted, and the aryl groups comprising from 6 to 30 carbon atoms or the heteroaryl groups comprising from 1 to 30 carbon atoms, possibly substituted.

According to another embodiment, the present invention relates to compounds having the formula (III) wherein:

the Ar group is selected from among the phenyl, pyridyl, thiophenyl, furanyl, benzothiophenyl, benzofuranyl and naphtalenyl groups, possibly substituted by one or more substituents selected from among:

the halogen atoms, the —R and —OR groups, wherein R is as defined here above, and the aryl groups comprising from 6 to 30 carbon atoms or the heteroaryl groups comprising from 1 to 30 carbon atoms, possibly substituted;

and the $R_N$ and $R_{N'}$ groups, together with the carbon atoms to which they are bound, form a group selected from among the tropane, quinuclidine and octahydro quinolizine groups; and $R_2$ is —H, —F or —OH.

Among the compounds of the invention, mention may be made of the compounds having the formula (III-1) as follows:

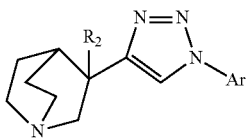

(III-1)

wherein the $R_2$ and Ar groups are as defined here above.

The compounds having the formula (III-1) are compounds having the formula (III) as defined here above, wherein the $R_N$ and $R_{N'}$ groups, together with the carbon atoms to which they are bound, form a quinuclidine group, possibly substituted.

According to one embodiment, for the compounds having the formula (III-1), the Ar group represents a phenyl grouping, possibly substituted by one or more groups selected from among:
- the halogen atoms,
- the —OH group,
- the linear or branched alkyl and alkoxy groups comprising from 1 to 10 carbon atoms, possibly substituted, and
- the aryl groups comprising from 6 to 30 carbon atoms or the heteroaryl groups comprising from 1 to 30 carbon atoms, possibly substituted.

Among these compounds having the formula (III-1), mention may be made of the compounds having the formula (III-1-1) as follows:

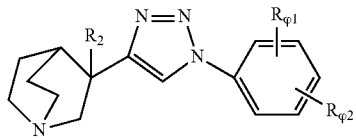

(III-1-1)

wherein:
the $R_{\varphi 1}$ and $R_{\varphi 2}$ groups are selected from among H, the halogen atoms, the linear or branched alkyl and alkoxy groups comprising from 1 to 10 carbon atoms, possibly substituted by a hydroxy group or a halogen, and
$R_2$ is —H, —F or —OH.

Thus, the present invention relates to the following compounds:

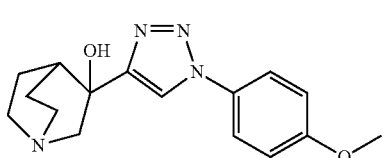

68

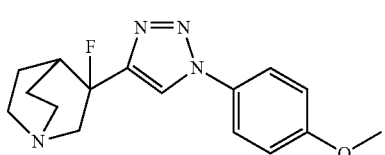

70

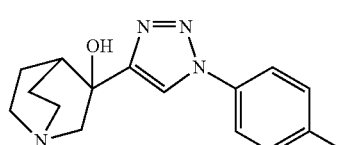

69

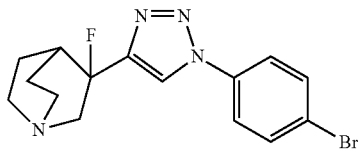

71

According to a particular embodiment, the compounds of the invention comprise at least one radioactive isotope selected from the group consisting of D, $^{18}F$, and $^{11}C$ or $^{123}I$.

According to one embodiment, the compounds of the invention include at least one radioactive isotope selected from the group consisting of $^{18}F$ or $^{123}I$.

According to one embodiment, the $R_2$ group of the compounds of the invention is selected from the group consisting of $^{18}F$, $^{11}C$, or $^{123}I$.

According to one embodiment, the $R_2$ group of the compounds of the invention is selected from the group consisting of $^{18}F$ or $^{123}I$.

Thus, the present invention relates in particular to the following compounds:

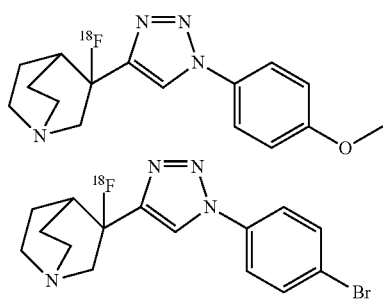

The present invention also relates to compounds having the formula (I) wherein the Ar group represents an aryl or heteroaryl group comprising from 1 to 30 carbon atoms, for example a phenyl, thiophene, pyridine, or furan group, substituted by at least one alkyl group comprising from 1 to 10 carbon atoms substituted by at least one radioactive isotope selected from the group consisting of $^{18}F$, $^{11}C$ and $^{123}I$, preferably $^{18}F$ and $^{123}I$.

Thus, the present invention relates in particular to the following compound:

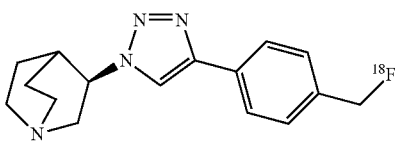 [SMILES: [18F]Cc1ccc(-c2cn([C@H]3CN4CCC3CC4)nn2)cc1]

The present invention also relates to the compounds having the formula (I) wherein the Ar group represents an aryl or heteroaryl group comprising from 1 to 30 carbon atoms, for example a phenyl, thiophene, pyridine, or furan group, substituted by an aryl or heteroaryl group comprising from 1 to 30 carbon atoms, for example a phenyl, thiophene, pyridine, or furan group, substituted by at least one alkyl group comprising from 1 to 10 carbon atoms substituted by at least one radioactive isotope selected from the group consisting of $^{18}F$, $^{11}C$, and $^{123}I$, preferably $^{18}F$ and $^{123}I$.

The invention also relates the compounds I to 117 per se.

The present invention also relates to a pharmaceutical composition comprising a compound having the formula (I) as defined here above, or any compound as mentioned here above, in association with a pharmaceutically acceptable carrier.

The present invention relates to a compound as defined here above having the formula (I) for the use thereof as a medicament.

The present invention also relates to a medicament comprising a compound having the formula (I), possibly in the form of a pharmaceutically acceptable salt, hydrate or polymorphic crystalline structure, racemate, diastereoisomer or enantiomer.

The present invention also relates to a pharmaceutical composition comprising a compound having the formula (I), possibly in the form of a pharmaceutically acceptable salt, hydrate or polymorphic crystalline structure, racemate, diastereoisomer or enantiomer, and a pharmaceutically acceptable excipient.

The pharmaceutical compositions according to the invention may be presented in appropriate forms intended for administration via parenteral, oral, rectal, transdermal or permucosal modes.

The pharmaceutical compositions including these compounds having the general formula (I) will therefore be presented in the form of injectable suspensions or fluids and solutions or multi-dose vials or bottles, in the form of plain or coated tablets, sugar coated tablets (dragees), capsules, gelatine capsules, pills, cachets (wafer capsules), powders, suppositories or rectal capsules, solutions or suspensions, for percutaneous use in a polar solvent, for permucosal use.

Excipients considered to be suitable for use in such administrations are derivatives of cellulose or microcrystalline cellulose, the alkaline earth carbonates, magnesium phosphate, starches, modified starches, and lactose for the solid forms.

For rectal use, cocoa butter or polyethylene glycol stearates are the preferred excipients.

For parenteral use, water, aqueous solutions, physiological serum (normal saline solution), isotonic solutions are the carriers most conveniently used.

The dosage may vary within fairly wide limits (0.5 mg to 1000 mg) based on the therapeutic indication and the route of administration, as well as the age and weight of the subject.

The present invention also relates to a compound having the formula (I) as defined here above, or any compound as mentioned here above, for use thereof as an agonist for the alpha 7 nicotinic receptor (R$\alpha$7).

The present invention also relates to a compound having the formula (I) as defined here above, or any compound as mentioned here above, for use thereof as an antagonist for the alpha 7 nicotinic receptor (R$\alpha$7).

The present invention also relates to a compound having the formula (I) as defined here above, or any compound as mentioned here above, for use thereof in the context of the treatment or prevention of diseases related to the disruption of the cholinergic systems and involving the alpha 7 nicotinic receptor (R$\alpha$7).

More specifically, the said diseases are selected from the group consisting of diseases of the central nervous system, such as addiction, psychiatric disorders like for example schizophrenia and attention deficit disorders, neurodegenerative diseases such as Alzheimer's disease.

The said diseases are also selected from the group consisting of cholinergic disorders of the central nervous system (CNS) or the peripheral nervous system (PNS), diseases or disorders related to smooth muscle contraction, endocrine diseases, diseases or disorders related to neurodegenerative diseases, diseases or disorders related to inflammation, pain and symptoms linked to the withdrawal syndrome occurring during the phase of weaning off the chemical substances being abused.

The diseases of the CNS of interest are many and varied. With regard to neurodegenerative diseases, examples to be cited include Alzheimer's and Parkinson's diseases that are associated with cognitive disorders linked to a deficit of cholinergic functions. Psychiatric disorders associated with an alteration in the central nicotinic receptors include schizophrenia, as well as depression and anxiety. It may be noted that recently a beneficial effect of cholinergic antagonists has been proposed as a new therapeutic approach in autism. One of the most promising therapeutic applications for cholinergic agonists pertains to pain treatment. Moreover nicotine or partial agonists may help in the weaning of process in addiction treatment (in particular for tobacco/smoking cessation). Finally, mention may be made of potential applications for the treatment of epilepsy or for Gilles de la Tourette syndrome (also called Tourette's syndrome).

With respect to the disorders associated with the PNS, the potential applications for R$\alpha$7 ligands are also very varied. Examples to be cited include diseases linked to the contraction of the smooth muscles or of the myocardium, endocrine diseases, diseases related to inflammation.

The compounds of the invention may be used as a diagnostic agent, for preventative or curative ends, or may serve as diagnostic or treatment method elements for certain diseases or disorders, among which examples to be cited include anxiety, cognitive disorders, learning and memory deficits, dysfunctions or disorders, attention deficits, hyperactivity, Alzheimer's disease, Parkinson's disease, Huntington's disease, amyotrophic lateral sclerosis, Gilles de la Tourette's syndrome, depression, mania, manic depression, psychosis, schizophrenia, obsessive compulsive disorders, panic disorder, eating disorders, including necrotic anorexia, bulimia and obesity, narcolepsy, nociception, AIDS dementia, senile dementia, cognitive impairments, mild deficiencies in cognition, memory impairment linked to aging, Pick's disease, dementia associated with Lewy bodies, Down syndrome, amyotrophic lateral sclerosis, Huntington's disease, the reduction of brain function associated with traumatic brain injury, peripheral neuropathy, autism, dyslexia, late onset dyskinesia (also known as tardive dyskinesia), hyperkinesia, epilepsy, post traumatic syndromes, social phobias, sleep disorders, pseudodementia, Ganser syndrome, premenstrual syndrome, late luteal phase dysphoric disorder (LLPDD), chronic fatigue, muteness, tricotillomania, jet lag, high blood pressure, cardiac arrhythmia, smooth muscle contraction disorders including convulsive disorders, angina pectoris, convulsions, diarrhoea, asthma, epilepsy, late onset dyskinesia, hyperkinesia, premature ejaculation and erectile difficulties, disorders of the endocrine system including thyrotoxicity and pheochromocytosis, neurodegenerative disorders, including transient anoxia and neurodegeneration, pain that may be medium, severe, moderate, acute, chronic or recurrent, neuropathic pain, migraine pain, postoperative pain, phantom pain, headaches, central pain, pain associated with diabetic neuropathy, complications related to diabetes and other systemic and neuroimmunomodulatory activities, post therapeutic neuralgia or peripheral nerve injuries, inflammatory disorders including skin inflammation, acne, and rosacea, Crohn's disease, intestinal inflammation, ulcerative colitis and diarrhoea, smoking cessation, ischemia, sepsis, healing of wounds, syndromes associated with the withdrawal or terminating the use of addictive chemical substances including nicotine, heroin, cocaine, morphine, benzodiazepines, substances that are analogous to alcohol and benzodiazepine.

The compounds of the invention may be used as diagnostic tools, monitoring agents for use in diagnostic methods and in particular for imaging of receptors in vivo (neuroimaging) in their labelled or unlabelled form.

The compounds of the invention may be used for the treatment of addiction related diseases linked to stopping the use of addictive substances. These substances include compounds containing nicotine such as tobacco, opiates like heroin, cocaine, morphine, cannabis, benzodiazepines and benzodiazepine derivatives and alcohol. The process of withdrawal from these addictive substances is generally a traumatic experience characterised by anxiety, frustration, difficulties with concentration, anger, agitation, decrease in heart rate, an increase in appetite and weight gain. In this context "treatment" covers the treatment, prevention, prophylaxis and relief of these effects of withdrawal and therefore abstinence as well as treatment results in reduced consumption of the addictive substance.

The present invention also relates to the use of the compounds of the invention comprising at least one radioactive isotope selected from among D, $^{18}F$, $^{11}C$ or $^{123}I$ as defined here above, for use thereof as a radiopharmaceutical marker.

The present invention also relates to the use of the compounds of the invention comprising at least one radioactive isotope selected from among D, $^{18}F$, $^{11}C$ or $^{123}I$ as defined here above, for use thereof as a radiopharmaceutical marker in the early diagnosis and monitoring of diseases of the central nervous system, in particular Alzheimer's disease.

The present invention also relates to the use of the compounds of the invention comprising at least one radioactive isotope selected from among D, $^{18}F$, $^{11}C$ or $^{123}I$ as defined here above, for use thereof as a radiopharmaceutical marker for Rα7.

Such radiopharmaceutical compounds are particularly interesting as radiolabelled ligands, also called radiotracers or radiolabels for the monitoring of diseases involving the Rα7, such as diseases of the central nervous system, in particular Alzheimer's disease.

Such compounds, in particular those having an isotope $^{18}F$ or $^{11}C$, are suitable for use in PET imaging (positron emission tomography) for the early diagnosis of Alzheimer's disease.

Such compounds, particularly those having an isotope $^{123}I$, are suitable for use in SPECT imaging (Single Photon Emission Computed Tomography) for the early diagnosis of Alzheimer's disease.

PET is based on the use of radiopharmaceutical compounds and enables the exploration of biological functions in vivo in an atraumatic manner as well as providing the means for detection and identification of brain damage occurring in the course of neurodegenerative diseases such as Alzheimer's disease. PET is a technique that is particularly suitable for performing early diagnosis and for monitoring the effectiveness of new treatment therapies.

PET enables the exploration and monitoring in vivo in an atraumatic manner, of physiological changes happening at the molecular level. This imaging technique uses radiopharmaceutical medicinal products specific to a molecular target, such as receptor ligands, labelled with a radioisotope that emits positrons such as $^{18}F$.

The diagnosis of Alzheimer's disease is currently based on clinical criteria that only offer a probability based diagnosis.

The in vivo visualisation of lesions caused by Alzheimer's disease, by means of molecular imaging techniques constitutes a diagnostic tool that is sensitive and specific for this disease.

Molecular Imaging techniques (PET or SPECT) make it possible to obtain information about the status of a function at the molecular level even in the absence of anatomical changes.

The use of the compounds of the invention labelled with a radioactive isotope in molecular imaging thus makes it possible to carry out the early and differential diagnostics with respect to diseases such as Alzheimer's disease and to monitor the effectiveness of various therapies.

The present invention also relates to a method for the preparation of a compound having the formula (II) as defined here above, the said method comprising from a step of formation of a 1,2,3-triazole ring by the bringing together in each other's presence of a compound having the following formula (II-a) and a compound having the formula (II-b) as follows:

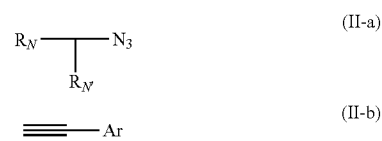

This step of formation of a 1,2,3-triazole ring is preferably carried out in the presence of copper salts (II), for example $CuSO_4.5H_2O$. It is also preferably carried out in the presence of sodium ascorbate. It is preferably carried out at ambient temperature and over a period of about 20 hours.

Preferably, in the compounds having the formula (II), $R_1=H$.

In the case where $R_1$ is other than H, this step is possibly followed by a step of functionalisation of the 5-position of the 1,2,3-triazole ring, whereby the $R_1$ grouping of the compounds (II) is obtained.

The present invention also relates to another method for the preparation of an intermediate compound of synthesis having the formula (II-a) as defined here above, the said method comprising from a step of azidation in situ, in particular in the presence of an azidation reagent such as sulfo-imidazole azide, for example in the presence of hydrated copper sulphate, sodium ascorbate and sodium carbonate in methanol, of a compound (II-a-1) having the following formula:

in free form or in the form of salt, for example hydrochloride salt.

The abovementioned step of azidation is preferably carried out at ambient temperature over a period of about 20 hours, and may be carried out in situ.

The present invention also relates to another method for the preparation of an intermediate compound of synthesis having the formula (II-a) as defined here above, the said method comprising from a step of azidation, in particular in the presence of an azidation reagent such as sodium azide in DMF (dimethyl formamide) at 140° C., of a compound (II-a-2) having the following formula:

wherein the -GP group represents a leaving group (LG), such as an —OMs (mesylate) or —OTs (tosylate) group.

The abovementioned step of azidation is preferably carried out at 75° C. for a period of about 18 hours.

The present invention also relates to another method for the preparation of a compound having the formula (II) as defined here above
wherein
$R_1$ represents a —$NR_aR_b$, $R_a$, $R_b$ and $R_c$ group being as defined here above,
the said method comprising from a step of formation of a 1,2,3-triazole ring by the bringing together in each other's presence of a compound having the formula (II-a) as defined here above and a compound having the formula (II-c) as follows:

This step of formation of a 1,2,3-triazole ring is preferably carried out in the presence of copper salts (II), for example $CuSO_4.5H_2O$. It is also preferably carried out in the presence of sodium ascorbate. It is preferably carried out at ambient temperature and over a period of about 20 hours.

Preferably, in the compounds having the formula (II), $R_1$=—$NH_2$.

In the case where $R_1$ is other than *$NH_2$, this step is possibly followed by a step of alkylation, acylation or arylation of the —$NH_2$ group in the 5-position of the 1,2,3-triazole ring, whereby the $R_1$ grouping of the compounds (II) is obtained.

The present invention also relates to a method for the preparation of a compound having the formula (III) as defined here above,
the said method comprising from a step of formation of a 1,2,3-triazole ring by the bringing together in each other's presence of a compound having the following formula (III-a) and a compound having the formula (III-b) as follows:

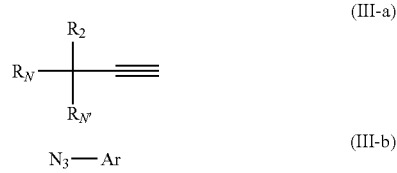

This step of formation of a 1,2,3-triazole ring is preferably carried out in the presence of copper salts (II), for example $CuSO_4.5H_2O$. It is also preferably carried out in the presence of sodium ascorbate. It is preferably carried out at ambient temperature and over a period of about 20 hours.

The present invention also relates to another method for the preparation of an intermediate compound of synthesis having the formula (III-a-1) as follows:

the said method comprising from a step of alkynylation, in particular in the presence of an alkynylation reagent such as trimethylsilyl ethyne in the presence of n-BuLi at −78° C., of a compound (III-a-2) having the following formula:

In the event that the alkynylation reagent is trimethylsilyl ethyne, the trimethylsilyl grouping may be reduced in the presence of $K_2CO_3$ at ambient temperature.

The present invention also relates to a method for the preparation of a compound having the formula (IF-1) as follows:

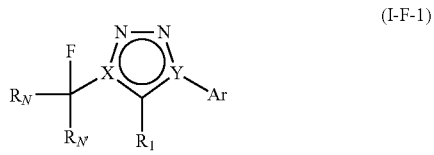

wherein the X, Y, Ar, $R_1$, $R_N$ and $R_{N'}$ groups are as defined here above,
the said method comprising from a step of fluorination, in particular in the presence of a fluorination reagent, of a compound having the formula (I-OH-1) as follows:

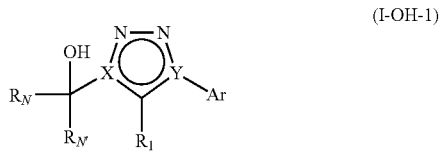

The step of fluorination is preferably carried out in the presence of a fluorinating reagent selected from among sulfur tetrafluoride $SF_4$, bis(2-methoxyethyl)aminosulfur trifluoride (Deoxo-Fluor) and diethylaminosulfur trifluoride (DAST, $Et_2NSF_3$), preferably at 0° C. for a period of about one hour.

Preferably, this step of fluorination is carried out in the presence of a fluorinating reagent comprising radioelements $^{18}F$.

Preferably, in the compounds having the formula (I-F-1) and (I-OH-1):

$R_1$ represents H, and/or the $R_N$ and $R_{N'}$ groups, together with the carbon atoms to which they are bound, form a quinuclidine group, and/or the Ar group represents a phenyl group, possibly substituted with a bromine or a methoxy, and/or X represents C and Y represents N.

The present invention also relates to a method for the preparation of a compound having the formula (IF-2) as follows:

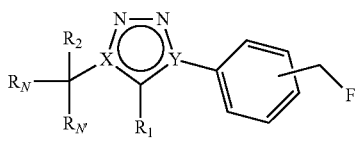

(I-F-2)

wherein the X, Y, $R_1$, $R_2$, $R_N$ and $R_{N'}$ groups are as defined here above, the said method comprising from a step of fluorination, in particular in the presence of a fluorinating reagent, of a compound having the formula (I-OH-2) as follows:

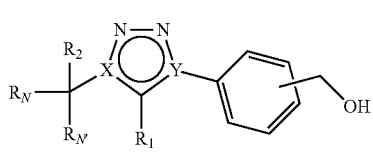

(I-F-2)

The step of fluorination is preferably carried out in the presence of a fluorinating reagent selected from among sulfur tetrafluoride $SF_4$, bis(2-methoxyethyl)aminosulfur trifluoride (Deoxo-Fluor) and diethylaminosulfur trifluoride (DAST, $Et_2NSF_3$), preferably at 0° C. for a period of about one hour.

Preferably, this step of fluorination is carried out in a direct or indirect manner in the presence of a fluorinating reagent comprising radioelements $^{18}F$.

Preferably, in compounds having the formula (I-F-2) and (I-OH-2):

$R_1$ represents H, and/or $R_2$ represents H, and/or the $R_N$ and $R_{N'}$ groups, together with the carbon atoms to which they are bound, form a quinuclidine group, and/or X represents N and Y represents C.

EXAMPLES

Preparation of the Compounds of the Invention

Preparation of Precursors of Tropane Type Compounds (Formula (II-1))

Preparation of 3-endo-tropanamine (2)

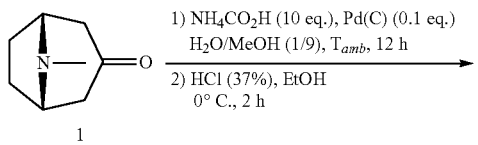

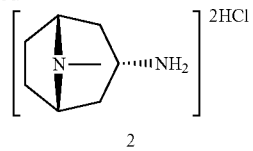

3-Endo-tropanamine (2)

A solution of ammonium formate (25.0 g, 0.40 mol) in 12.5 mL of water was added to a solution of tropanone 1 (6.00 g, 43.0 mmol) in 110 mL of methanol. After complete dissolution of the reaction medium, Palladium on carbon Pd/C (4.60 g, 4.30 mmol) was added and the reaction mixture was stirred at ambient temperature for a period of 12 hours, with care being taken to let out the hydrogen formed. Thereafter, the reaction medium was filtered through Celite and then the filtrate was evaporated under reduced pressure. The resulting oil obtained was diluted in 100 mL of ethanol and then at 0° C., 7.5 mL of a solution of concentrated HCl (37%) was added drop by drop. Finally, the solution was stirred for 2 hours until complete precipitation of the 3-endo-tropanamine 2. The product was recovered by means of vacuum filtration in the form of a white solid with a yield of 98%. Mp: >250° C.; IR (ATR, Diamond): ν (cm$^{-1}$): 1032, 1068, 1104, 1175, 1230, 1356, 1385, 1448, 1517, 1532, 1606, 2047, 2551, 2587, 2627, 2649, 2764, 2876; $^1$H NMR (250 MHz, DMSO-d$_6$): δ (ppm) 2.05-2.40 (m, 6H), 2.62-2.80 (m, 5H), 3.40-3.60 (m, 1H), 3.70-3.92 (m, 2H), 8.32-8.75 (m, 3H), 10.98-11.34 (m, 1H); $^{13}$C NMR (100 MHz, DMSO-d$_6$): δ (ppm) 23.2 (2CH$_2$), 31.9 (2CH$_2$), 37.9 (CH$_3$), 39.2 (CH), 60.2 (2CH); MS (IS): m/z=141.0 [MH]$^+$.

Preparation of True Alkynes (7-9) from Aldehydes (3-5)

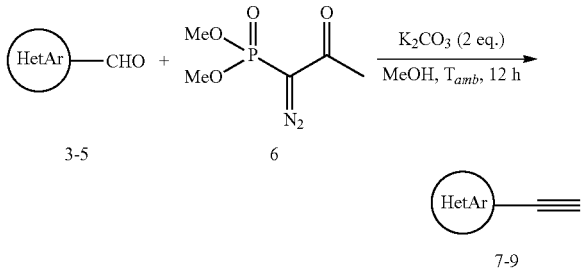

General Procedure A:

To a solution of dimethyl 1-diazo-2-oxopropylphosphonate 6 (1.15 g, 6.00 mmol) in 60 mL of anhydrous methanol, the following were added successively: aldehyde 3-5 (5.00 mmol) and K$_2$CO$_3$ (1.38 g, 10.0 mmol). The reaction mixture was stirred at ambient temperature for a period of 12 hours. After gentle evaporation of the solvent under reduced pressure, the alkynes 7-9 were purified by column chromatography on silica gel with the eluent used being a mixture of petroleum ether/ethyl acetate that enables good separation.

5-Ethynylbenzo[b]thiophene (7)

The product was isolated in the form of a white solid with a yield of 84% by following the general procedure A. $R_f$:

0.40 (PE/EtOAc: 99/1); Mp: 55° C.; IR (ATR, Diamond): ν (cm$^{-1}$): 1050, 1088, 1222, 1258, 1324, 1411, 1431, 3082, 3101, 3277; $^1$H NMR (250 MHz, CDCl$_3$): δ (ppm) 3.11 (s, 1H), 7.31 (d, 1H, J=5.5 Hz), 7.43-7.51 (m, 2H), 7.83 (d, 1H, J=8.4 Hz), 7.99 (s, 1H); $^{13}$C NMR (100 MHz, CDCl$_3$): δ (ppm) 76.9 (CH), 84.1 (C$_q$), 118.1 (C$_q$), 122.6 ($_{aromatic}$CH), 123.8 ($_{aromatic}$CH), 127.6 ($_{aromatic}$CH), 127.7 ($_{aromatic}$ 2CH), 139.6 (C$_q$), 140.3 (C$_q$); MS (IS): m/z=159.1 [MH]$^+$.

5-Ethynylbenzo[b]furan (8)

The product is isolated in the form of a yellow oil with a yield of 90% by following the general procedure A. R$_f$: 0.52 (PE/EtOAc: 95/5); IR (ATR, Diamond): ν (cm$^{-1}$): 882, 1029, 1107, 1118, 1195, 1265, 1329, 1436, 1460, 3290; $^1$H NMR (250 MHz, CDCl$_3$): δ (ppm) 3.03 (s, 1H), 6.75 (d, 1H, J=2.2 Hz), 7.43-7.46 (m, 2H), 7.64 (d, 1H, J=2.2 Hz), 7.77 (s, 1H); $^{13}$C NMR (100 MHz, CDCl$_3$): δ (ppm) 76.0 (CH), 84.2 (C$_q$), 106.7 ($_{aromatic}$CH), 111.7 ($_{aromatic}$CH), 116.8 (C$_q$), 125.6 ($_{aromatic}$CH), 127.7 (C$_q$), 128.6 ($_{aromatic}$CH), 146.1 ($_{aromatic}$CH), 155.0 (C$_q$); MS (IS): m/z=143.1 [MH]$^+$.

2-Bromo-5-ethynyl thiophene (9)

The product was isolated in the form of a yellow oil with a yield of 92% by following the general procedure A. R$_f$: 0.50 (PE/EtOAc: 99/1); IR (ATR, Diamond): ν (cm$^{-1}$): 966, 1048, 1137, 1209, 1419, 1519, 1669, 2102, 3294; $^1$H NMR (250 MHz, CDCl$_3$): δ (ppm) 3.37 (s, 1H), 6.92 (d, 1H, J=3.9 Hz), 7.02 (d, 1H, J=3.9 Hz); $^{13}$C NMR (100 MHz, CDCl$_3$): δ (ppm) 76.2 (CH), 82.5 (C$_q$), 113.7 (C$_q$), 124.0 (C$_q$), 130.1 ($_{aromatic}$CH), 133.6 ($_{aromatic}$CH); MS (IS): m/z=188.1 [MH]$^+$.

Preparation of Alkynes (13-14) by the Sonogashira Coupling Reaction

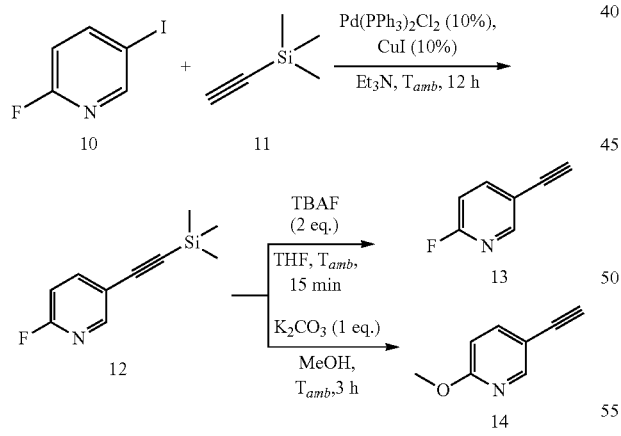

To a solution of 2-fluoro-5-iodopyridine 10 (4.00 g, 17.9 mmol) in 30 mL of previously degassed triethylamine, the following were added successively: ethynyl(trimethyl)silane 11 (2.78 mL, 19.7 mmol), copper iodide (340 mg, 1.79 mmol) and Pd(PPh$_3$) 2Cl$_2$ (1.25 g, 1.79 mmol). The reaction mixture was stirred at ambient temperature for a period of 12 hours. Upon completion of the reaction, the reaction medium was diluted with 100 mL of water and then extracted with ethyl ether. The organic phase was dried over anhydrous MgSO$_4$, filtered and then concentrated under reduced pressure. The product of coupling 12 was engaged in subsequent reactions without further purification.

5-Ethynyl-2-fluoropyridine (13)

The silyl derivative 12 (8.97 mmol) was stirred in 50 mL of THF for 15 minutes in the presence of 9.00 mL of a solution of tetra-n-butylammonium fluoride (1 M in THF—tetrahydrofuran) added drop by drop. Upon completion of the reaction, the solvent was evaporated and the alkyne 13 was purified by column chromatography on silica gel with the eluent used being a mixture of petroleum ether/ethyl acetate (95/5). The product was isolated in the form of a red liquid with a yield of 82%. R$_f$: 0.49 (PE/EtOAc: 95/5); IR (ATR, Diamond): ν (cm$^{-1}$): 927, 1020, 1130, 1240, 1365, 1477, 1575, 3074; $^1$H NMR (250 MHz, CDCl$_3$): δ (ppm) 3.19 (s, 1H), 6.90 (dd, 1H, J=8.5 Hz and 3.0 Hz), 7.85 (ddd, 1H, J=8.5 Hz, 7.6 Hz and 2.3 Hz), 8.34 (d, 1H, J=2.3 Hz); $^{13}$C NMR (100 MHz, CDCl$_3$): δ (ppm) 79.2 (CH), 80.7 (d, C$_q$, J=1 Hz), 109.6 (d, $_{aromatic}$CH, J=38 Hz), 117.3 (d, C$_q$, J=5 Hz), 144.4 (d, $_{aromatic}$CH, J=8 Hz), 151.4 (d, $_{aromatic}$CH, J=15 Hz), 163.1 (d, C$_q$, J=243 Hz); MS (IS): m/z=122.2 [MH]$^+$.

5-Ethynyl-2-methoxy pyridine (14)

The silyl derivative 12 (17.9 mmol) was stirred in 60 mL of methanol for a period of 3 hours in the presence of K$_2$CO$_3$ (2.47 g, 17.9 mmol). The reaction medium was evaporated under reduced pressure and the alkyne 14 was purified by column chromatography on silica gel with the eluent used being a mixture of petroleum ether/ethyl acetate (95/5). The product was isolated in the form of a yellow liquid with a yield of 75%. R$_f$: 96/4). R$_f$: 0.72 (PE/EtOAc: IR (ATR, Diamond): ν (cm$^{-1}$): 1021, 1126, 1251, 1284, 1305, 1367, 1488, 1559, 1600, 3290; $^1$H NMR (250 MHz, CDCl$_3$): δ (ppm) 3.10 (s, 1H), 3.94 (s, 3H), 6.69 (d, 1H, J=8.6 Hz), 7.63 (dd, 1H, J=8.6 Hz and 2.3 Hz), 8.30 (d, 1H, J=2.3 Hz); $^{13}$C NMR (100 MHz, CDCl$_3$): δ (ppm) 53.9 (CH$_3$), 78.8 (CH), 80.9 (C$_q$), 110.9 ($_{aromatic}$CH), 112.1 (CO$_3$141.8 ($_{aromatic}$CH), 151.0 ($_{aromatic}$ CH), 163.9 (C$_q$); MS (IS): m/z=134.0 [MH]$^+$.

Preparation of Tropane Type Compounds 16-27 (Formula (II-1))

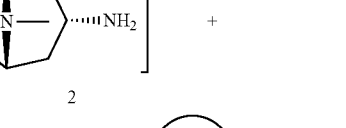

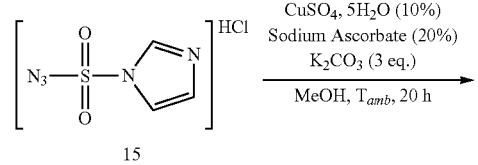

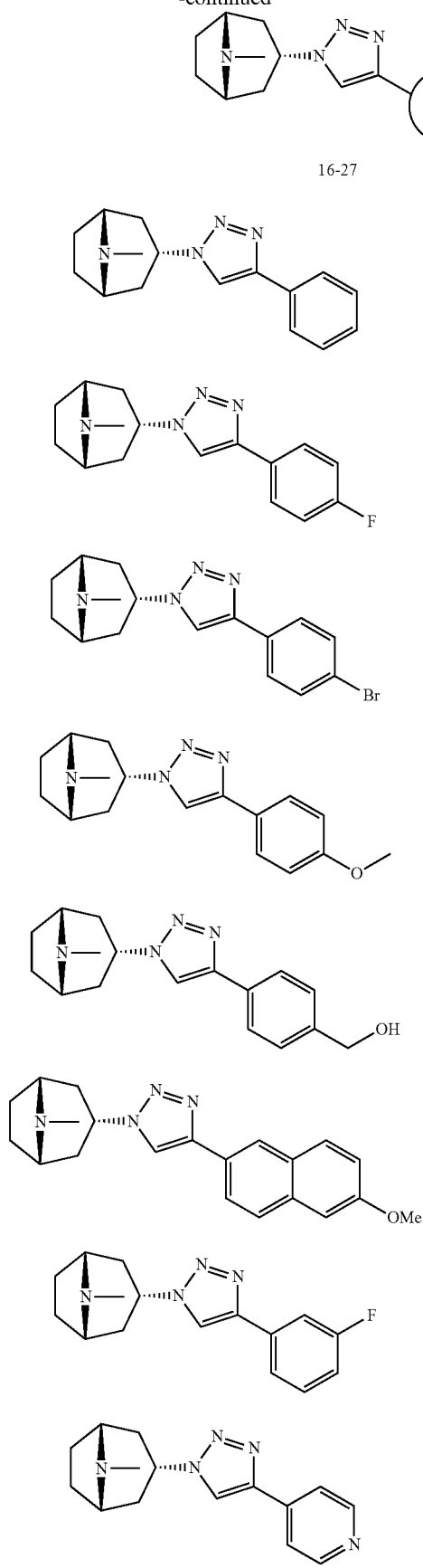

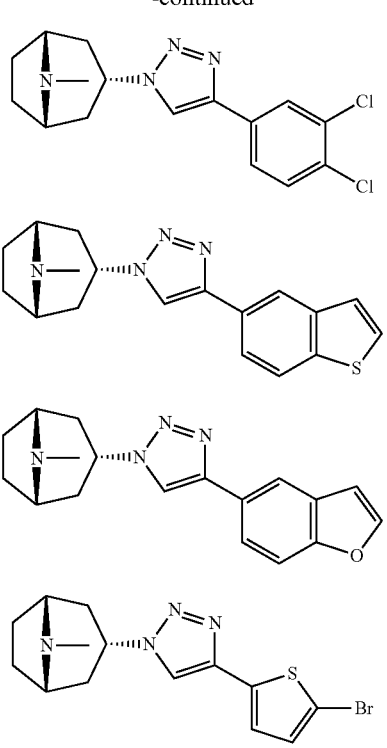

General Procedure B:

Under argon atmosphere, 3-endo-tropanamine 2 (212 mg, 1.00 mmol) and the 1H-imidazole-1-sulfonyl azide 15 (232 mg, 1.10 mmol) were dissolved in 6 mL of methanol to which the following were then added successively: $K_2CO_3$ (415 mg, 3.00 mmol) and a catalytic amount of $CuSO_4 5H_2O$ (25 mg, 0.100 mmol). The reaction medium was stirred at ambient temperature for a period of 2 hours and then concentrated under reduced pressure. The resulting solid obtained was then taken up again in 10 mL of ethyl ether, vacuum filtered and thereafter washed twice with 10 mL of ethyl ether. Finally, the filtrate was evaporated under reduced pressure and the resulting azide thus obtained was engaged in the subsequent step without any further purification.

The latter was dissolved in 6 mL of methanol to which the following were then added successively: the desired alkyne (1.00 mmol), $CuSO_4 5H_2O$ (25 mg, 0.100 mmol) and the sodium ascorbate (40 mg, 0.200 mmol). The reaction mixture was stirred at ambient temperature for a period of 12 hours. At the end of the reaction time, the methanol was evaporated under reduced pressure and the residue was chromatographed by column chromatography on silica gel with the eluent used being a mixture of $CH_2Cl_2$/MeOH/ $NH_4OH$ that enables good separation. In order to remove the traces of imidazole that are often present in the chromatographed triazole products, the mixture was dissolved in ethyl acetate, washed two times with water, dried over anhydrous $MgSO_4$ and evaporated to dryness.

Endo-3-(4-phenyl-1H-1,2,3-triazol-1-yl)tropane (16)

The product was isolated in the form of a white solid with a yield of 40% by following the general procedure B. $R_f$: 0.30 ($CH_2Cl_2$/MeOH/$NH_4OH$: 90/10/0.1); Mp: 135° C. IR (ATR, Diamond): ν $(cm^{-1})$: 1015, 1078, 1116, 1142, 1217, 1335, 1411, 1451, 1481, 2441, 2934; $^1$H NMR (250 MHz, CDCl$_3$): δ (ppm) 1.72-1.80 (m, 2H), 1.99-2.10 (m, 2H), 2.46 (s, 3H), 2.66 (d, 2H, J=15.0 Hz), 2.80-2.89 (m, 2H), 3.40-3.46 (m, 2H), 4.70 (dt, 1H, J=6.8 Hz and 3.6 Hz), 7.31-7.36 (m, 1H), 7.40-7.46 (m, 2H), 7.84 (d, 2H, J=8.1 Hz), 7.87 (s, 1H); $^{13}$C NMR (100 MHz, CDCl$_3$): δ (ppm) 25.2 (2CH$_2$), 35.0 (2CH$_2$), 40.1 (CH$_3$), 51.5 (CH), 60.4 (2CH), 119.1 ($_{aromatic}$CH), 125.9 (2CH$_{aromatic}$), 128.5 ($_{aromatic}$CH), 129.1 (2CH$_{aromatic}$), 130.7 (C$_q$), 148.2 (C$_q$); HRMS (EI-MS): calculated for C$_{16}$H$_{21}$N$_4$ m/z=269.1766. found m/z=269.1757.

Endo-3(4-(4-fluorophenyl)-1H-1,2,3-triazol-1-yl) tropane (17)

The product was isolated in the form of a white solid with a yield of 31% by following the general procedure B. R$_f$: 0.28 (CH$_2$Cl$_2$/MeOH/NH$_4$OH: 90/10/0.1); Mp: 254° C. IR (ATR, Diamond): ν (cm$^{-1}$): 1014, 1081, 1141, 1161, 1224, 1402, 1429, 1452, 1496, 2446, 2470; $^1$H NMR (250 MHz, CDCl$_3$): δ (ppm) 1.89-2.19 (m, 4H), 2.63 (s, 3H), 2.75 (d, 2H, J=15.8 Hz), 3.17-3.30 (m, 2H), 3.62-3.70 (m, 2H), 4.79 (t, 1H, J=7.2 Hz), 7.12 (t, 2H, J=8.6 Hz), 7.81 (dd, 2H, J=8.6 Hz and 5.3 Hz), 7.88 (s, 1H); $^{13}$C NMR (100 MHz, CDCl$_3$): δ (ppm) 24.5 (2CH$_2$), 34.1 (2CH$_2$), 39.5 (CH$_3$), 50.6 (CH), 61.3 (2CH), 116.2 (d, 2CH$_{aromatic}$, J=22 Hz), 119.1 ($_{aromatic}$CH), 126.7 (d, C$_q$, J=3 Hz), 127.6 (d, 2CH$_{aromatic}$, J=8 Hz), 147.8 (C$_q$), 163.0 (d, C$_q$, J=248 Hz); HRMS (EI-MS): calculated for C$_{16}$H$_{20}$FN$_4$ m/z=287.1672. found m/z=287.1669.

Endo-3-(4-(4-bromophenyl)-1H-1,2,3-triazol-1-yl) tropane (18)

The product was isolated in the form of a white solid with a yield of 42% by following the general procedure B. R$_f$: 0.22 (CH$_2$Cl$_2$/MeOH/NH$_4$OH: 90/10/0.1); Mp: 226° C. IR (ATR, Diamond): ν (cm$^{-1}$): 973, 1009, 1068, 1116, 1148, 1214, 1232, 1334, 1396, 1422, 1450, 1478, 2932; $^1$H NMR (250 MHz, CDCl$_3$): δ (ppm) 1.48-1.57 (m, 2H), 1.90-2.00 (m, 2H), 2.28 (s, 3H), 2.51-2.57 (m, 4H), 3.19-3.27 (m, 2H), 4.58-4.66 (m, 1H), 7.54 (d, 2H, J=8.6 Hz), 7.72 (d, 2H, J=8.6 Hz), 7.85 (s, 1H); $^{13}$C NMR (100 MHz, CDCl$_3$): δ (ppm) 25.9 (2CH$_2$), 35.9 (2CH$_2$), 40.6 (CH$_3$), 52.4 (CH), 59.5 (2CH), 119.1 ($_{aromatic}$CH), 122.1 (C$_q$), 127.4 (2CH$_{aromatic}$), 130.0 (C$_q$), 132.2 (2CH$_{aromatic}$), 146.7 (C$_q$); HRMS (EI-MS): calculated for C$_{16}$H$_{20}$BrN$_4$ m/z=347.0871. found m/z=347.0879.

Endo-3-(4-(4-methoxyphenyl)-1H-1,2,3-triazol-1-yl) tropane (19)

The product was isolated in the form of a white solid with a yield of 21% by following the general procedure B. R$_f$: 0.27 (CH$_2$Cl$_2$/MeOH/NH$_4$OH: 90/10/0.1); Mp: 118° C. IR (ATR, Diamond): ν (cm$^{-1}$): 972, 1018, 1036, 1078, 1177, 1219, 1245, 1333, 1397, 1497, 1616, 2943; $^1$H NMR (250 MHz, CDCl$_3$): δ (ppm) 1.65 (d, 2H, J=8.2 Hz), 1.93-2.03 (m, 2H), 2.36 (s, 3H), 2.55-2.75 (m, 4H), 3.29-3.36 (m, 2H), 3.84 (s, 3H), 4.64 (dt, 1H, J=6.2 Hz and 3.3 Hz), 6.96 (d, 2H, J=8.8 Hz), 7.76 (d, 2H, J=8.8 Hz), 7.77 (s, 1H); $^{13}$C NMR (100 MHz, CDCl$_3$): δ (ppm) 25.5 (2CH$_2$), 35.4 (2CH$_2$), 40.3 (CH$_3$), 51.8 (CH), 55.6 (CH$_3$), 59.9 (2CH), 114.5 ($_{aromatic}$2CH), 118.3 (C$_q$), 123.6 (C$_q$), 127.2 (2CH$_{aromatic}$), 147.8 (C$_q$), 159.8 (C$_q$); HRMS (EI-MS): calculated for C$_{17}$H$_{23}$N$_4$O m/z=299.1872. found m/z=299.1881.

(4-(1-(Endo-tropan-3-yl)-1H-1,2,3-triazol-4-yl) phenyl) methanol (20)

The product was isolated in the form of a white solid with a yield of 45% by following the general procedure B. R$_f$: 0.19 (CH$_2$Cl$_2$/MeOH/NH$_4$OH: 90/10/0.1); Mp: >250° C. IR (ATR, Diamond): ν (cm$^{-1}$): 1013, 1060, 1082, 1401, 1431, 1452, 1493, 1650, 2506, 2556, 2587, 3352; $^1$H NMR (250 MHz, DMSO-d$_6$): δ (ppm) 1.47 (d, 2H, J=8.2 Hz), 1.88-2.07 (m, 2H), 2.44 (s, 3H), 2.60-2.82 (m, 4H), 3.50-3.58 (m, 2H), 4.56 (s, 2H), 4.64-4.75 (m, 1H), 5.28 (s large, 1H, OH), 7.43 (d, 2H, J=8.1 Hz), 7.87 (d, 2H, J=8.1 Hz), 8.88 (s, 1H); $^{13}$C NMR (100 MHz, DMSO-d$_6$): δ (ppm) 24.4 (2CH$_2$), 32.9 (2CH$_2$), 39.8 (CH$_3$), 50.7 (CH), 59.4 (2CH), 62.6 (CH$_2$), 120.8 ($_{aromatic}$CH), 124.8 (2CH$_{aromatic}$), 126.9 (2CH$_{aromatic}$), 129.2 (C$_q$), 142.2 (C$_q$), 146.4 (C$_q$); HRMS (EI-MS): calculated for C$_{17}$H$_{23}$N$_4$O m/z=299.1872. found m/z=299.1859.

Endo-3-(4-(6-methoxynaphthalen-2-yl)-1H-1,2,3-triazol-1-yl) tropane (21)

The product was isolated in the form of a white solid with a yield of 33% by following the general procedure B. R$_f$: 0.24 (CH$_2$Cl$_2$/MeOH/NH$_4$OH: 90/10/0.1); Mp: >250° C.; IR (ATR, Diamond): ν (cm$^{-1}$): 908, 1021, 1123, 1163, 1212, 1262, 1345, 1393, 1453, 1612, 2932; $^1$H NMR (250 MHz, CDCl$_3$): δ (ppm) 1.76 (d, 2H, J=8.0 Hz), 1.97-2.07 (m, 2H), 2.43 (s, 3H), 2.61-2.72 (m, 2H), 2.76-2.90 (m, 2H), 3.35-3.45 (m, 2H), 3.93 (s, 3H), 4.65-4.75 (m, 1H), 7.13-7.20 (m, 2H), 7.75-7.82 (m, 2H), 7.87-7.94 (m, 1H), 7.94 (s, 1H), 8.26 (s, 1H); $^{13}$C NMR (100 MHz, CDCl$_3$): δ (ppm) 25.4 (2CH$_2$), 35.3 (2CH$_2$), 40.3 (CH$_3$), 51.8 (CH), 55.6 (CH$_3$), 60.2 (2CH), 106.0 ($_{aromatic}$CH), 119.0 ($_{aromatic}$CH), 119.5 ($_{aromatic}$CH), 124.5 (2CH$_{aromatic}$), 126.0 (C$_q$), 217.6 ($_{aromatic}$CH), 129.2 (C$_q$), 129.9 ($_{aromatic}$CH), 134.6 (C$_q$), 148.2 (C$_q$), 158.2 (C$_q$); HRMS (EI-MS): calculated for C$_{21}$H$_{25}$N$_4$O m/z=349.2028. found m/z=349.2029.

Endo-3-(4-(3-fluorophenyl)-1H-1,2,3-triazol-1-yl) tropane (22)

The product was isolated in the form of a white solid with a yield of 34% by following the general procedure B. R$_f$: 0.23 (CH$_2$Cl$_2$/MeOH/NH$_4$OH: 90/10/0.1); Mp: 124° C. IR (ATR, Diamond): ν (cm$^{-1}$): 1017, 1087, 1156, 1198, 1227, 1336, 1416, 1450, 1477, 1584, 1620, 2937, 2963, 3094; $^1$H NMR (250 MHz, CDCl$_3$): δ (ppm) 1.47-1.57 (m, 2H), 1.92-2.00 (m, 2H), 2.28 (s, 3H), 2.51-2.57 (m, 4H), 3.18-3.26 (m, 2H), 4.62 (quint, 1H, J=5.2 Hz), 6.94-7.09 (m, 1H), 7.32-7.42 (m, 1H), 7.52-7.65 (m, 1H), 7.58 (s, 1H), 7.86 (s, 1H); $^{13}$C NMR (100 MHz, CDCl$_3$): δ (ppm) 25.9 (2CH$_2$), 35.9 (2CH$_2$), 40.6 (CH$_3$), 52.5 (CH), 59.5 (2CH), 112.8 (d, $_{aromatic}$CH, J=22 Hz), 115.1 (d, $_{aromatic}$CH, J=22 Hz), 119.4 ($_{aromatic}$CH), 121.4 (d, $_{aromatic}$CH, J=3 Hz), 130.6 (d, aromatic CH, J=8 Hz), 133.2 (d, C$_q$, J=8 Hz), 146.6 (d, C$_q$, J=3 Hz), 163.4 (d, C$_q$, J=246 Hz); HRMS (EI-MS): calculated for C$_{16}$H$_{20}$FN$_4$ m/z=287.1672. found m/z=287.1671.

Endo-3-(4-(pyridin-4-yl)-1H-1,2,3-triazol-1-yl)tropane (23)

The product was isolated in the form of a brown solid with a yield of 43% by following the general procedure B. R$_f$: 0.12 (CH$_2$Cl$_2$/MeOH/NH$_4$OH: 90/10/0.1); Mp: 146° C. IR (ATR, Diamond): ν (cm$^{-1}$): 817, 1016, 1060, 1082, 1217, 1340, 1426, 1610, 2936; $^1$H NMR (400 MHz, CDCl$_3$): δ

(ppm) 1.48-1.57 (m, 2H), 1.89-2.03 (m, 2H), 2.30 (s, 3H), 2.48-2.66 (m, 4H), 3.21-3.30 (m, 2H), 4.63 (dt, 1H, J=6.8 Hz and 3.3 Hz), 7.72 (d, 2H, J=6.0 Hz), 7.99 (s, 1H), 8.64 (d, 2H, J=6.0 Hz); $^{13}$C NMR (100 MHz, CDCl$_3$): δ (ppm) 25.9 (2CH$_2$), 35.9 (2CH$_2$), 40.6 (CH$_3$), 52.6 (CH), 59.5 (2CH), 120.1 (2CH$_{aromatic}$), 120.6 ($_{aromatic}$CH), 138.3 (C$_q$), 145.2 (C$_q$), 150.6 (2CH$_{aromatic}$); HRMS (EI-MS): calculated for C$_{15}$H$_{20}$N$_5$ m/z=270.1719. found m/z=270.1711.

Endo-3-(4-(3,4-dichlorophenyl)-1H-1,2,3-triazol-1-yl)tropane (24)

The product was isolated in the form of a white solid with a yield of 22% by following the general procedure B. R$_f$: 0.32 (CH$_2$Cl$_2$/MeOH/NH$_4$OH 90/10/0.1); Mp: 136° C. IR (ATR, Diamond): ν (cm$^{-1}$): 825, 1021, 1082, 1117, 1131, 1231, 1336, 1423, 1459, 1473, 2934; $^1$H NMR (400 MHz, CDCl$_3$): δ (ppm) 1.49-1.54 (m, 2H), 1.89-2.03 (m, 2H), 2.29 (s, 3H), 2.48-2.62 (m, 4H), 3.21-3.27 (m, 2H), 4.63 (dt, 1H, J=6.6 Hz and 3.3 Hz), 7.48 (d, 1H, J=8.3 Hz), 7.68 (dd, 1H, J=8.3 Hz and 1.9 Hz), 7.86 (s, 1H), 7.92 (d, 1H, J=1.9 Hz); $^{13}$C NMR (100 MHz, CDCl$_3$): δ (ppm) 25.9 (2CH$_2$), 35.9 (2CH$_2$), 40.6 (CH$_3$), 52.6 (CH), 59.5 (2CH), 119.2 ($_{aromatic}$CH), 125.0 ($_{aromatic}$CH), 127.6 ($_{aromatic}$CH), 131.0 ($_{aromatic}$CH and C$_q$), 132.0 (C$_q$), 133.2 (C$_q$), 145.6 (C$_q$); HRMS (EI-MS): calculated for C$_{16}$H$_{19}$N$_4$Cl$_2$ m/z=337.0987. found m/z=337.0980.

Endo-3-(4-(1-Benzothiophen-5-yl)-1H-1,2,3-triazol-1-yl)tropane (25)

The product was isolated in the form of a white solid with a yield of 34% by following the general procedure B. R$_f$: 0.25 (CH$_2$Cl$_2$/MeOH/NH$_4$OH 90/10/0.1); Mp: 163° C. IR (ATR, Diamond): ν (cm$^{-1}$): 818, 896, 1018, 1079, 1114, 1218, 1338, 1394, 1439, 1552, 2100, 2929, 3036; $^1$H NMR (400 MHz, CDCl$_3$): δ (ppm) 1.54-1.62 (m, 2H), 1.93-2.02 (m, 2H), 2.30 (s, 3H), 2.54-2.61 (m, 4H), 3.20-3.28 (m, 2H), 4.64 (quint, 1H, J=5.0 Hz), 7.37 (d, 1H, J=5.4 Hz), 7.47 (d, 1H, J=5.4 Hz), 7.81 (dd, 1H, J=8.4 Hz and 1.2 Hz), 7.91 (s, 1H), 7.92 (d, 1H, J=8.4 Hz), 8.33 (d, 1H, J=1.2 Hz); $^{13}$C NMR (100 MHz, CDCl$_3$): δ (ppm) 25.8 (2CH$_2$), 35.8 (2CH$_2$), 40.5 (CH$_3$), 52.3 (CH), 59.6 (2CH), 119.0 ($_{aromatic}$CH), 120.7 ($_{aromatic}$CH), 122.3 ($_{aromatic}$CH), 123.0 ($_{aromatic}$CH), 124.2 ($_{aromatic}$CH), 127.3 (C$_q$), 127.4 ($_{aromatic}$CH), 139.5 (C$_q$), 140.2 (C$_q$), 147.9 (C$_q$); HRMS (EI-MS): calculated for C$_{18}$H$_{21}$N$_4$S m/z=325.1487. found m/z=325.1488.

Endo-3-(4-(1-benzofuran-5-yl)-1H-1,2,3-triazol-1-yl)topane (26)

The product was isolated in the form of a white solid with a yield of 35% by following the general procedure B. R$_f$: 0.23 (CH$_2$Cl$_2$/MeOH/NH$_4$OH 90/10/0.1); Mp: 104° C. IR (ATR, Diamond): ν (cm$^{-1}$): 988, 1030, 1067, 1108, 1224, 1338, 1443, 1457, 1496, 1518, 2361, 2873, 2929, 3115, 3351; $^1$H NMR (400 MHz, CDCl$_3$): δ (ppm) 1.55-1.60 (m, 2H), 1.94-1.99 (m, 2H), 2.30 (s, 3H), 2.55-2.60 (m, 4H), 3.22-3.27 (m, 2H), 4.64 (quint, 1H, J=5.0 Hz), 6.77-6.83 (m, 1H), 7.54 (d, 1H, J=8.6 Hz), 7.64 (d, 1H, J=2.1 Hz), 7.76 (dd, 1H, J=8.6 Hz, 1.5 Hz), 7.85 (s, 1H), 8.10 (d, 1H, J=1.5 Hz); $^{13}$C NMR (100 MHz, CDCl$_3$): δ (ppm) 25.8 (2CH$_2$), 35.8 (2CH$_2$), 40.6 (CH$_3$), 52.2 (CH), 59.6 (2CH), 107.0 ($_{aromatic}$CH), 111.9 ($_{aromatic}$CH), 118.6 ($_{aromatic}$CH), 118.7 ($_{aromatic}$CH), 122.6 ($_{aromatic}$CH), 126.0 (C$_q$), 128.1 (C$_q$), 145.8 ($_{aromatic}$CH), 148.1 (C$_q$), 155.0 (C$_q$); HRMS (EI-MS): calculated for C$_{18}$H$_{21}$N$_4$O m/z=309.1715. found m/z=309.1709.

Endo-3-(4-(5-bromothiophen-2-yl)-1H-1,2,3-triazol-1-yl)tropane (27)

The product was isolated in the form of a white solid with a yield of 29% by following the general procedure B. R$_f$: 0.32 (CH$_2$Cl$_2$/MeOH/NH$_4$OH: 90/10/0.1); Mp: 138° C. IR (ATR, Diamond): ν (cm$^{-1}$): 969, 1016, 1066, 1104, 1132, 1228, 1331, 1407, 1435, 2913, 2940, 2966, 3274; $^1$H NMR (400 MHz, CDCl$_3$): δ (ppm) 1.56-1.66 (m, 2H), 1.96-2.01 (m, 2H), 2.35 (s, 3H), 2.50-2.57 (m, 2H), 2.63-2.73 (m, 2H), 3.28-3.33 (m, 2H), 4.58-4.67 (m, 1H), 7.01 (d, 1H, J=3.8 Hz), 7.10 (d, 1H, J=3.8 Hz), 7.73 (s, 1H); $^{13}$C NMR (100 MHz, CDCl$_3$): δ (ppm) 25.8 (2CH$_2$), 35.4 (2CH$_2$), 40.3 (CH$_3$), 52.2 (CH), 59.8 (2CH), 112.2 (C$_q$), 118.5 ($_{aromatic}$CH), 124.3 ($_{aromatic}$CH), 130.6 ($_{aromatic}$CH), 134.8 (C$_q$), 142.3 (C$_q$); HRMS (EI-MS): calculated for C$_{14}$H$_{18}$N$_4$SBr m/z=353.0436. found m/z=353.0447.

Preparation of a Precursor of Octahydro Quinolizine Type Compounds (Formula (II-3))

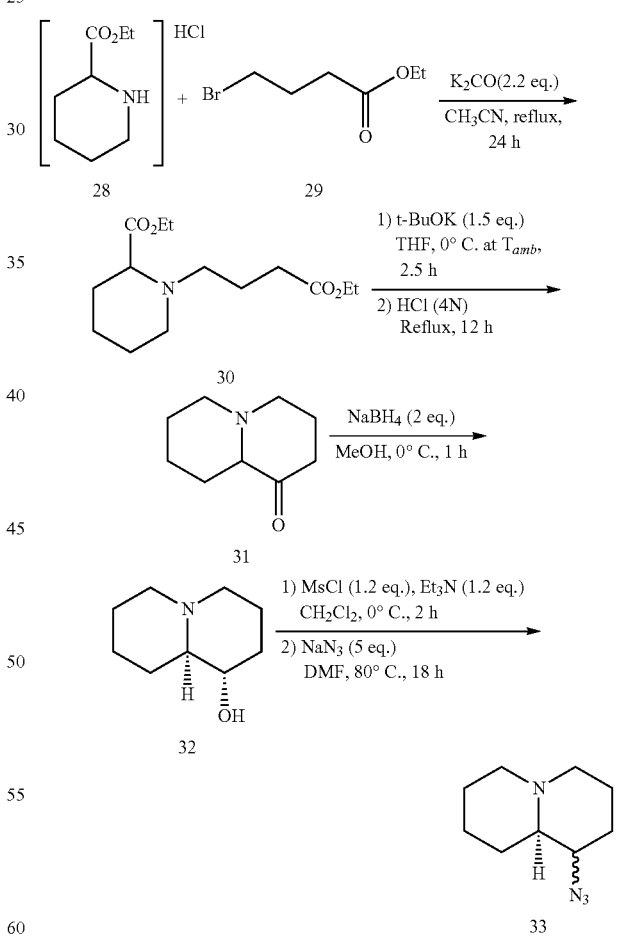

2-(4-Ethoxy-4-oxobutyl)piperidine-1-ethyl carboxylate (30)

To a solution of Ethyl Pipecolinate Hydrochloride 28 (12.4 g, 64.0 mmol) in 300 mL of acetonitrile, the following were added: ethyl 4-bromobutanoate 29 (11.0 mL, 76.8 mmol) and K$_2$CO$_3$ (19.5 g, 140.8 mmol). The reaction medium was then heated to reflux for a period of 24 hours. At the end of the reaction time, the solvent was evaporated under reduced pressure and then the residue was taken up again in ethyl acetate. The organic phase was washed with water, dried over anhydrous MgSO$_4$ and concentrated under vacuum. The crude product was purified by column chromatography on silica gel with the eluent used being a mixture of petroleum ether/ethyl acetate (4/1). The diester 30 was isolated in the form of a colourless liquid with a yield of 80%. R$_f$: 0.29 (PE/EtOAc: 3/1); IR (ATR, Diamond): ν (cm$^{-1}$): 1027, 1123, 1158, 1372, 1446, 1730, 2936; $^1$H NMR (400 MHz, CDCl$_3$): δ (ppm) 1.22 (t, 3H, J=7.1 Hz), 1.24 (t, 3H, J=7.1 Hz), 1.31-1.40 (m, 1H), 1.55-1.61 (m, 3H), 1.73-1.80 (m, 4H), 2.14-2.21 (m, 1H), 2.24-2.40 (m, 3H), 2.50-2.57 (m, 1H), 3.00-3.09 (m, 2H), 4.11 (q, 2H, J=7.1 Hz), 4.17 (q, 2H, J=7.1 Hz); $^{13}$C NMR (100 MHz, CDCl$_3$): δ (ppm) 14.5 (2CH$_3$), 22.3 (CH$_2$), 22.8 (CH$_2$), 25.5 (CH$_2$), 29.8 (CH$_2$), 32.4 (CH$_2$), 50.5 (CH$_2$), 55.8 (CH$_2$), 60.4 (CH$_2$), 60.5 (CH$_2$), 65.3 (CH), 173.8 (C=O), 174.0 (C=O); MS (IS): m/z=272.3 [MH]$^+$.

Hexahydro-2H-quinolizin-1(6H)-one (31)

A solution of 2-(4-ethoxy-4-oxobutyl)piperidine-1-ethyl carboxylate 30 (5.00 g, 18 4 mmol) in 100 mL of anhydrous Tetrahydrofuran (THF) was cooled to 0° C. to which t-BuOK (3.10 g, 27.6 mmol) was then added by portion. The reaction medium was stirred at 0° C. for a period of 30 minutes and then for a period of 2 hours at ambient temperature. Thereafter, the THF was evaporated under reduced pressure and the residue was diluted with ethyl acetate. The organic phase was washed with water, dried over anhydrous MgSO$_4$ and concentrated under vacuum. The residue was taken up again in 60 mL of diluted hydrochloric acid (4N) and then heated to reflux for a period of 12 hours. Upon completion of the reaction, the reaction medium was neutralised by the addition of solid NaHCO$_3$ and then the aqueous phase was extracted with CH$_2$Cl$_2$. The organic phase was then dried over anhydrous MgSO$_4$ and concentrated under reduced pressure. The ketone 31 was isolated in the form of a red liquid with a yield of 74%. R$_f$: 0.20 (EtOAc); IR (ATR, Diamond): ν (cm$^{-1}$): 1076, 1145, 1174, 1281, 1319, 1344, 1443, 1718, 2933; $^1$H NMR (250 MHz, CDCl$_3$): δ (ppm) 1.10-1.65 (m, 4H), 1.75-1.87 (m, 1H), 1.90-2.05 (m, 3H), 2.08-2.32 (m, 2H), 2.33-2.55 (m, 3H), 2.87-3.00 (m, 2H); $^{13}$C NMR (100 MHz, CDCl$_3$): δ (ppm) 24.0 (CH$_2$), 24.4 (CH$_2$), 25.6 (CH$_2$), 25.8 (CH$_2$), 39.4 (CH$_2$), 55.0 (CH$_2$), 57.1 (CH$_2$), 71.2 (CH), 207.5 (C=O); MS (IS): m/z=154.1 [MH]$^+$.

Octahydro-2H-1-quinolizin-ol (32)

To a solution of hexahydro-2H-quinolizin-1(6H)-one 31 (1.70 g, 11.1 mmol) in 100 mL of methanol at 0° C., NaBH$_4$ (840 mg, 22.2 mmol) was added by portion and the reaction medium was stirred at this temperature for a period of 1 hour. After evaporation of the solvent, the residue was taken up again in dichloromethane and then the organic phase was washed with water, dried over anhydrous MgSO$_4$ and concentrated under reduced pressure. The alcohol 32 was purified by column chromatography on silica gel with the eluent used being a mixture of CH$_2$Cl$_2$/MeOH/NH$_4$OH (90/10/0.1). It was isolated in the form of a white solid with a yield of 78%. R$_f$: 0.32 (CH$_2$Cl$_2$/MeOH: 4/1); Mp: 70° C. IR (ATR, Diamond): ν (cm$^{-1}$): 968, 1020, 1046, 1085, 1107, 1179, 1276, 1346, 1442, 1469, 2761, 2804, 2856, 2925, 2943, 3130; $^1$H NMR (250 MHz, CDCl$_3$): δ (ppm) 1.06-1.34 (m, 3H), 1.51-1.72 (m, 5H), 1.75-1.85 (m, 2H), 1.93-2.08 (m, 3H), 2.09-2.18 (m, 1H), 2.67-2.76 (m, 1H), 2.79-2.88 (m, 1H), 3.28 (ddd, 1H, J=11.1 Hz, 8.8 Hz and 4.6 Hz); $^{13}$C NMR (100 MHz, CDCl$_3$): δ (ppm) 23.5 (CH$_2$), 24.3 (CH$_2$), 25.9 (CH$_2$), 28.9 (CH$_2$), 34.2 (CH$_2$), 56.1 (CH$_2$), 53.3 (CH$_2$), 69.0 (CH), 72.8 (CH); MS (IS): m/z=156.1 [MH]$^+$.

1-Azidooctahydro-2-H-quinolizine (33)

To a solution of octahydro-2H-quinolizin-1-ol 32 (700 mg, 4.51 mmol) in 40 mL of CH$_2$Cl$_2$ at 0° C., the following were added: triethylamine (760 μL, 5.41 mmol) and mesyl chloride (420 μL, 5.41 mmol), for a period of 30 minutes. The reaction medium was stirred at 0° C. for a period of 2 hours. The reaction mixture was hydrolysed with the addition of a saturated NaHCO$_3$ solution. The organic phase was separated, dried over anhydrous MgSO$_4$ and evaporated under reduced pressure. The mesyl derivative prepared (1.05 g, 4.51 mmol) was heated at 80° C. in 30 mL of DMF (dimethyl formamide) for a period of 18 hours in the presence of sodium azide (1.46 g, 22.6 mmol). Upon completion of the reaction, the solvent was evaporated and then the residue was taken up again in CH$_2$Cl$_2$. The organic phase was washed twice with water, dried over anhydrous MgSO$_4$ and concentrated under reduced pressure. The azide 33 was purified by column chromatography on silica gel with the eluent used being ethyl acetate. It was isolated in the form of a yellow oil with a yield of 71% in the form of two inseparable diastereoisomers in the proportions of (3/2). R$_f$: 0.15 (EtOAc); IR (ATR, Diamond): ν (cm$^{-1}$): 980, 1024, 1113, 1133, 1155, 1254, 1444, 2090, 2799, 2930; $^1$H NMR (250 MHz, CDCl$_3$): δ (ppm) Majority Diastereoisomer d 1.11-1.30 (m, 2H), 1.56-1.82 (m, 6H), 1.95-2.17 (m, 3H), 2.30-2.46 (m, 2H), 2.70-2.79 (m, 1H), 2.94-3.07 (m, 2H). Minority Diastereoisomer d 1.30-1.50 (m, 2H), 1.56-1.82 (m, 6H), 1.95-2.17 (m, 3H), 2.30-2.46 (m, 2H), 2.79-2.88 (m, 1H), 2.98-3.07 (m, 1H), 3.17-3.27 (m, 1H); $^{13}$C NMR (100 MHz, CDCl$_3$): δ (ppm) Diastereoisomer Majority d 21.8 (CH$_2$), 23.5 (CH$_2$), 29.7 (CH$_2$), 31.8 (CH$_2$), 33.0 (CH$_2$), 55.8 (CH$_2$), 58.1 (CH$_2$), 68.1 (CH), 68.4 (CH). Minority Diastereoisomer d 23.8 (CH$_2$), 24.3 (CH$_2$), 25.8 (CH$_2$), 29.8 (CH$_2$), 30.3 (CH$_2$), 55.8 (CH$_2$), 56.4 (CH$_2$), 63.8 (CH), 66.5 (CH); MS (IS): m/z=181.4 [MH]$^+$.

Preparation of Octahydro Quinolizine Type Compounds 34-35 (Formula II-3))

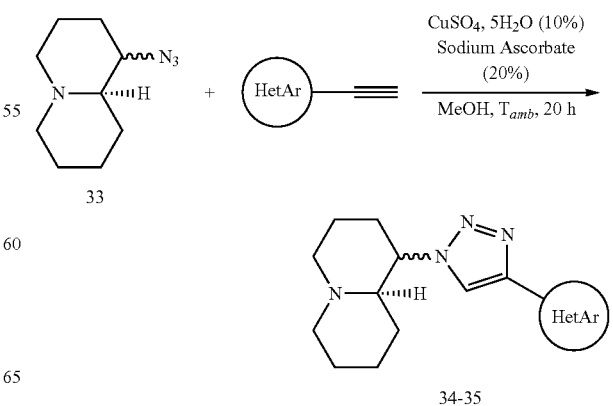

34-35

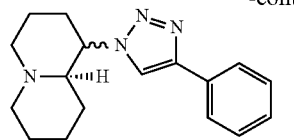

34

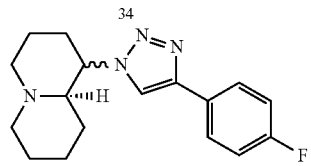

35

General Procedure C:

Under argon atmosphere, the azide 33 (180 mg, 1.00 mmol) was dissolved in 6 mL of methanol and then, the following were added successively: the alkyne (1.00 mmol), $CuSO_4 5H_2O$ (25 mg, 0.100 mmol) and sodium ascorbate (40 mg, 0.200 mmol). The reaction medium was stirred at ambient temperature for a period of 12 hours. At the end of the reaction time, the methanol was evaporated under reduced pressure and the residue was taken up again in dichloromethane. The organic phase was washed with a saturated $NaHCO_3$ solution, dried over anhydrous $MgSO_4$ and concentrated under reduced pressure. The products 34 and 35 were chromatographed by column chromatography on silica gel with the eluent used being a mixture of $CH_2Cl_2/MeOH/NH_4OH$ (99/1/0.1).

1-(4-Phenyl-1H-1,2,3-triazol-1-yl)-octahydro-2H-quinolizine (34)

By following the general procedure C, the product was isolated in the form of a white solid with a yield of 94% in the form of two separable diastereoisomers in the proportions of 3/2.

Minor Diastereoisomer:

$R_f$: 0.46 ($CH_2Cl_2/MeOH/NH_4OH$: 99/1/0.1); Mp: 150° C. IR (ATR, Diamond): ν ($cm^{-1}$): 977, 1023, 1113, 1219, 1294, 1349, 1372, 1434, 1460, 1482, 2754, 2804, 2852, 2925, 3081; $^1H$ NMR (250 MHz, $CDCl_3$): δ (ppm) 1.04-1.28 (m, 3H), 1.50-1.74 (m, 3H), 1.81-1.91 (m, 2H), 1.92-2.15 (m, 2H), 2.16-2.30 (m, 3H), 2.81-3.04 (m, 2H), 4.23-4.35 (m, 1H), 7.28-7.36 (m, 1H), 7.38-7.46 (m, 2H), 7.72 (s, 1H), 7.80-7.88 (m, 2H); $^{13}C$ NMR (100 MHz, $CDCl_3$): δ (ppm) 24.0 ($CH_2$), 24.3 ($CH_2$), 25.7 ($CH_2$), 29.0 ($CH_2$), 32.4 ($CH_2$), 56.0 ($CH_2$), 56.5 ($CH_2$), 64.0 (CH), 66.5 (CH), 118.8 ($_{aromatic}$CH), 125.9 (2$CH_{aromatic}$), 128.3 ($_{aromatic}$CH), 129.0 (2$CH_{aromatic}$), 130.9 ($C_q$), 147.6 ($C_q$); HRMS (EI-MS): calculated for $C_{17}H_{23}N_4$ m/z=283.1923. found m/z=283.19281.

Majority Diastereoisomer:

$R_f$: 0.52 ($CH_2Cl_2/MeOH/NH_4OH$: 99/1/0.1); Mp: 140° C. IR (ATR, Diamond): ν ($cm^{-1}$): 974, 1049, 1077, 1134, 1196, 1222, 1267, 1433, 1460, 1482, 2780, 2862, 2928; $^1H$ NMR (250 MHz, $CDCl_3$): δ (ppm) 1.39-1.56 (m, 1H), 1.60-1.93 (m, 7H), 1.95-2.08 (m, 1H), 2.20-2.35 (m, 1H), 2.41-2.66 (m, 2H), 3.02-3.22 (m, 3H), 4.36-4.53 (m, 1H), 7.28-7.36 (m, 1H), 7.38-7.46 (m, 2H), 7.74 (s, 1H), 7.80-7.89 (m, 2H); $^{13}C$ NMR (100 MHz, $CDCl_3$): δ (ppm) 22.7 ($CH_2$), 23.4 ($CH_2$), 29.5 ($CH_2$), 30.7 ($CH_2$), 35.7 ($CH_2$), 55.3 ($CH_2$), 58.2 ($CH_2$), 67.4 (CH), 67.9 (CH), 118.3 ($_{aromatic}$CH), 125.8 (2$CH_{aromatic}$), 128.2 ($_{aromatic}$CH), 129.0 (2$CH_{aromatic}$), 131.0 ($CO_3$ 147.6 ($C_q$); HRMS (EI-MS): calculated for $C_{17}H_{23}N_4$ m/z=283.1923. found m/z=283.1928.

1-[4-(4-Fluorophenyl)-1H-1,2,3-triazol-1-yl]-octahydro-2H-quinolizine (35)

By following the general procedure C, the product was isolated in the form of a white solid with a yield of 94% in the form of two separable diastereoisomers in the proportions of 3/2.

Minority Diastereoisomer:

$R_f$: 0.39 ($CH_2Cl_2/MeOH/NH_4OH$: 99/1/0.1); Mp: 142° C. IR (ATR, Diamond): ν ($cm^{-1}$): 1048, 1113, 1158, 1222, 1297, 1347, 1449, 1494, 1557, 1611, 2754, 2798, 2926, 3104; $^1H$ NMR (250 MHz, $CDCl_3$): δ (ppm) 1.02-1.30 (m, 3H), 1.49-1.74 (m, 3H), 1.81-2.05 (m, 3H), 2.07-2.30 (m, 4H), 2.81-3.02 (m, 2H), 4.20-4.38 (m, 1H), 7.11 (t, 2H, J=8.8 Hz), 7.68 (s, 1H), 7.80 (dd, 2H, J=8.8 Hz and 5.3 Hz); $^{13}C$ NMR (100 MHz, $CDCl_3$): δ (ppm) 24.0 ($CH_2$), 24.3 ($CH_2$), 25.7 ($CH_2$), 29.0 ($CH_2$), 32.4 ($CH_2$), 55.9 ($CH_2$), 56.5 ($CH_2$), 64.0 (CH), 66.5 (CH), 116.0 (d, 2$CH_{aromatic}$, J=22 Hz), 118.6 ($_{aromatic}$CH), 127.1 (d, $C_q$, J=3 Hz), 127.6 (d, 2$CH_{aromatic}$, J=8 Hz), 146.7 ($C_q$), 162.8 (d, $C_q$, J=247 Hz); HRMS (EI-MS): calculated for $C_{17}H_{22}FN_4$ m/z=301.1829. found m/z=301.1826.

Majority Diastereoisomer:

$R_f$: 0.50 ($CH_2Cl_2/MeOH/NH_4OH$: 99/1/0.1); Mp: 136° C. IR (ATR, Diamond): ν ($cm^{-1}$): 1050, 1159, 1223, 1346, 1448, 1493, 1557, 1612, 2794, 2927, 3104; $^1H$ NMR (250 MHz, $CDCl_3$): δ (ppm) 1.39-1.57 (m, 1H), 1.60-1.95 (m, 7H), 1.96-2.09 (m, 1H), 2.18-2.38 (m, 1H), 2.42-2.66 (m, 2H), 3.02-3.23 (m, 3H), 4.36-4.53 (m, 1H), 7.11 (t, 2H, J=8.7 Hz), 7.70 (s, 1H), 7.80 (d, 2H, J=8.6 Hz and 5.4 Hz); $^{13}C$ NMR (100 MHz, $CDCl_3$): δ (ppm) 22.7 ($CH_2$), 23.4 ($CH_2$), 29.5 ($CH_2$), 30.7 ($CH_2$), 35.7 ($CH_2$), 55.3 ($CH_2$), 58.2 ($CH_2$), 67.4 (CH), 67.9 (CH), 116.0 (d, 2$CH_{aromatic}$, J=22 Hz), 118.1 ($_{aromatic}$CH), 127.2 (d, $C_q$, J=3 Hz), 127.6 (d, 2$CH_{aromatic}$, J=8 Hz), 146.8 ($C_q$), 162.8 (d, $C_q$, J=247 Hz); HRMS (EI-MS): calculated for $C_{17}H_{22}FN_4$ m/z=301.1829. found m/z=301.1831.

Preparation of Quinuclidine Type Compounds 37-57 and 80-83 (Formula (II-2))

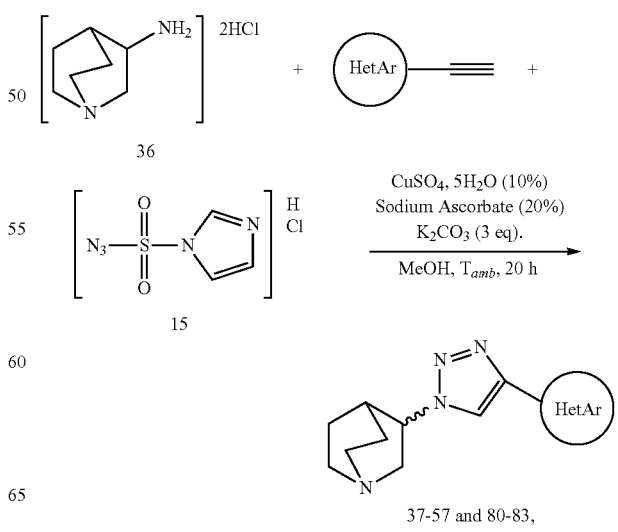

37-57 and 80-83,

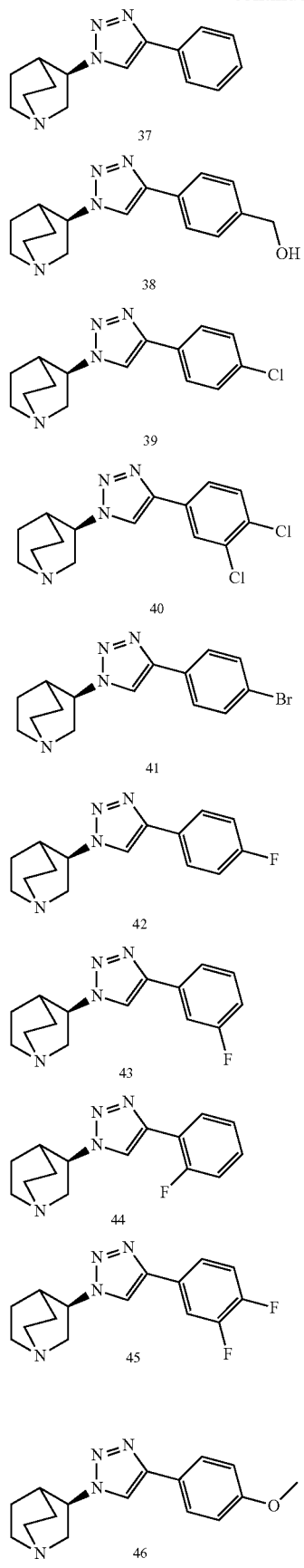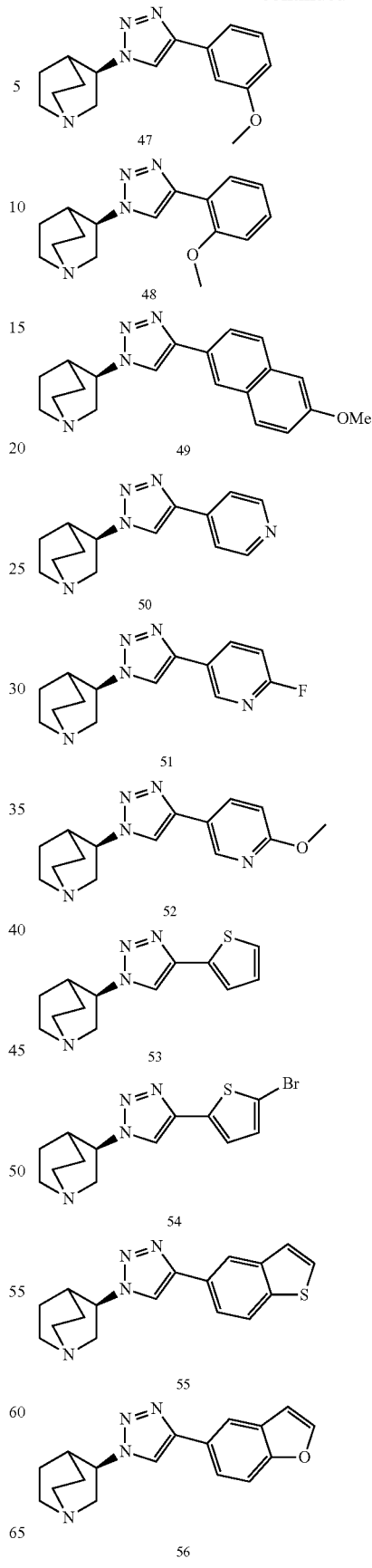

-continued

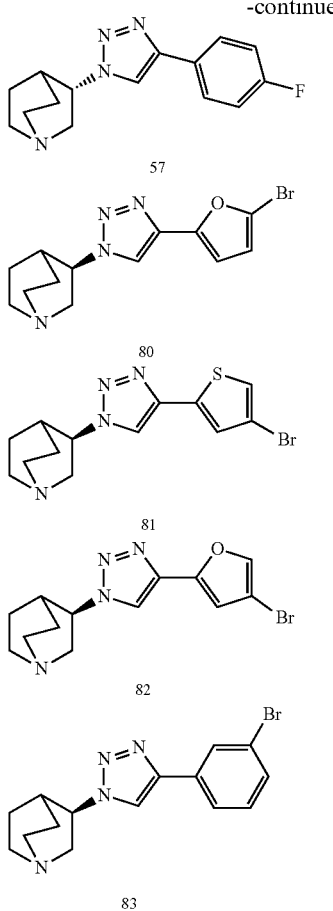

General Procedure D:

Under argon atmosphere, the 3-aminoquinuclidine 36 (212 mg, 1.00 mmol) and 1H-imidazole-1-sulfonyl azide 15 (232 mg, 1.10 mmol) were dissolved in 6 mL of methanol, to which the following were then added successively: $K_2CO_3$ (415 mg, 3.00 mmol) and a catalytic amount of $CuSO_4 5H_2O$ (25 mg, 0.100 mmol). The reaction medium was stirred at ambient temperature for a period of 6 hours and then concentrated under reduced pressure. The resulting solid obtained was then taken up again in 10 mL of ethyl ether, vacuum filtered and washed two times with 10 mL of ethyl ether. Finally, the filtrate was evaporated under reduced pressure and the resulting azide thus obtained was engaged in the subsequent step without any further purification.

The latter was dissolved in 6 mL of methanol to which the following were then added successively: the desired alkyne (1.00 mmol), $CuSO_4 5H_2O$ (25 mg, 0.100 mmol) and sodium ascorbate (40 mg, 0.200 mmol). The reaction medium was stirred at ambient temperature for a period of 12 hours. At the end of the reaction time, the methanol was evaporated under reduced pressure and then the residue was chromatographed by column chromatography on silica gel with the eluent used being a mixture of $CH_2Cl_2$/MeOH/$NH_4OH$ that enables good separation. In order to remove the traces of imidazole that are often present in the chromatographed triazole products, the mixture was dissolved in ethyl acetate, washed two times with water, dried over anhydrous $MgSO_4$ and evaporated to dryness.

(R)-3-(4-Phenyl-1H-1,2,3-triazol-1-yl)quinuclidine (37)

The product was isolated in the form of a white solid with a yield of 33% by following the general procedure D. $R_f$: 0.29 ($CH_2Cl_2$/MeOH/$NH_4OH$: 80/20/0.1); Mp: 132° C. IR (ATR, Diamond): ν ($cm^{-1}$): 973, 1023, 1043, 10.60, 1072, 1211, 1227, 1411, 1453, 1482, 2870, 2937; $^1H$ NMR (250 MHz, $CDCl_3$): δ (ppm) 1.45-1.61 (m, 1H), 1.68-1.79 (m, 1H), 1.82-1.92 (m, 1H), 2.32 (q, 1H, J=3.1 Hz), 2.90-3.10 (m, 3H), 3.15-3.35 (m, 1H), 3.56 (dd, 1H, J=9.9 Hz and 2.2 Hz), 3.62 (dd, 1H, J=9.9 Hz and 2.2 Hz), 3.81 (dd, 1H, J=14.4 Hz and 5.2 Hz), 4.69-4.79 (m, 1H), 7.29-7.37 (m, 1H), 7.39-7.47 (m, 2H), 7.81-7.86 (m, 2H), 7.85 (s, 1H); $^{13}C$ NMR (100 MHz, $CDCl_3$): δ (ppm) 19.9 ($CH_2$), 25.6 ($CH_2$), 28.3 (CH), 47.0 ($CH_2$), 47.4 ($CH_2$), 52.4 ($CH_2$), 58.0 (CH), 119.4 ($_{aromatic}$CH), 125.9 ($2CH_{aromatic}$), 128.4 ($_{aromatic}$CH), 129.1 ($2CH_{aromatic}$), 130.7 ($C_q$), 147.9 ($C_q$); HRMS (EI-MS): calculated for $C_{16}H_{19}N_4$ m/z=255.1610. found m/z=255.1613.

(R)-(4-(1-(Quinuclidin-3-yl)-1H-1,2,3-triazol-4-yl)phenyl)methanol (38)

The product was isolated in the form of a white solid with a yield of 32% by following the general procedure D. $R_f$: 0.11 ($CH_2Cl_2$/MeOH/$NH_4OH$: 80/20/0.1); Mp: 200° C. IR (ATR, Diamond): ν ($cm^{-1}$): 978, 1017, 1041, 1059, 1221, 1337, 1428, 1450, 1610, 2878, 2939, 3127, 3353; $^1H$ NMR (250 MHz, DMSO-$d_6$): δ (ppm) 1.39-1.56 (m, 2H), 1.71-1.82 (m, 2H), 2.22 (q, 1H, J=3.0 Hz), 2.77-2.87 (m, 3H), 2.95-3.08 (m, 1H), 3.34-3.55 (m, 3H), 4.56 (d, 1H, J=4.4 Hz), 4.74-4.83 (m, 1H), 5.25 (t, 1H, J=4.4 Hz), 7.42 (d, 2H, J=8.3 Hz), 7.87 (d, 2H, J=8.3 Hz), 8.74 (s, 1H); $^{13}C$ NMR (100 MHz, DMSO-$d_6$): δ (ppm) 19.6 ($CH_2$), 25.3 ($CH_2$), 27.6 (CH), 46.3 ($CH_2$), 46.6 ($CH_2$), 51.9 ($CH_2$), 57.4 (CH), 62.6 ($CH_2$), 120.6 ($_{aromatic}$CH), 124.9 ($2CH_{aromatic}$), 126.8 ($2CH_{aromatic}$), 129.3 ($C_q$), 142.1 ($C_q$), 146.1 ($C_q$); HRMS (EI-MS): calculated for $C_{16}H_{21}N_4O$ m/z=285.1715. found m/z=285.1702.

(R)-3-(4-(4-Chlorophenyl)-1H-1,2,3-triazol-1-yl)quinuclidine (39)

The product was isolated in the form of a white solid with a yield of 28% by following the general procedure D. $R_f$: 0.41 ($CH_2Cl_2$/MeOH/$NH_4OH$: 80/20/0.1); Mp: 144° C. IR (ATR, Diamond): ν ($cm^{-1}$): 971, 1014, 1060, 1092, 1190, 1202, 1324, 1401, 1433, 1452, 1468, 1484, 2868, 2939, 3110; $^1H$ NMR (250 MHz, $CDCl_3$): δ (ppm) 1.40-1.50 (m, 1H), 1.60-1.73 (m, 1H), 1.73-1.87 (m, 2H), 2.28 (sext, 1H, J=3.1 Hz), 2.84-3.00 (m, 3H), 3.08-3.22 (m, 1H), 3.49 (ddd, 1H, J=14.3 Hz, 9.9 Hz and 2.2 Hz), 3 70 (dd, 1H, J=14.3 Hz and 5.0 Hz), 4.55-4.71 (m, 1H), 7.40 (d, 2H, J=8.7 Hz), 7.77 (d, 2H, J=8.7 Hz), 7.80 (s, 1H); $^{13}C$ NMR (100 MHz, $CDCl_3$): δ (ppm) 20.2 ($CH_2$), 26.2 ($CH_2$), 28.4 (CH), 47.1 ($CH_2$), 47.5 ($CH_2$), 52.9 ($CH_2$), 58.7 (CH), 119.2 ($_{aromatic}$CH), 127.1 ($2CH_{aromatic}$), 129.3 ($2CH_{aromatic}$), 129.4 ($C_q$), 134.1 ($C_q$), 146.7 ($C_q$); HRMS (EI-MS): calculated for $C_{15}H_{18}N_4Cl$ m/z=289.1220. found m/z=289.1211.

(R)-3-(4-(3,4-Dichlorophenyl)-1H-1,2,3-triazol-1-yl)quinuclidine (40)

The product was isolated in the form of a white solid with a yield of 17% by following the general procedure D. $R_f$: 0.33 ($CH_2Cl_2$/MeOH/$NH_4OH$: 80/20/0.1); Mp: 108° C. IR (ATR, Diamond): ν (cm⁻¹): 986, 1029, 1044, 1133, 1231, 1324, 1457, 1561, 1606, 2871, 2942, 3385; ¹H NMR (250 MHz, CDCl₃): δ (ppm) 1.41-1.57 (m, 1H), 1.59-1.74 (m, 1H), 1.76-1.87 (m, 2H), 2.28 (q, 1H, J=3.0 Hz), 2.86-3.00 (m, 3H), 3.08-3.22 (m, 1H), 3.44-3.57 (m, 1H), 3.70 (dd, 1H, J=14.4 Hz and 5.0 Hz), 4.61-4.71 (m, 1H), 7.48 (d, 1H, J=8.4 Hz), 7.65 (dd, 1H, J=8.4 Hz and 1.9 Hz), 7.84 (s, 1H), 7.91 (d, 1H, J=1.9 Hz); ¹³C NMR (100 MHz, CDCl₃): δ (ppm) 20.1 (CH₂) 26.0 (CH₂), 28.3 (CH), 47.1 (CH₂), 47.4 (CH₂), 52.7 (CH₂), 58.7 (CH), 119.7 ($_{aromatic}$CH), 125.0 ($_{aromatic}$CH), 127.6 ($_{aromatic}$CH), 130.9 (C$_q$), 131.0 ($_{aromatic}$CH), 132.1 (C$_q$), 133.2 (C$_q$), 145.6 (C$_q$); HRMS (EI-MS): calculated for C₁₅H₁₇N₄Cl₂ m/z=323.0830. found m/z=323.0827.

(R)-3-(4-(4-Bromophenyl)-1H-1,2,3-triazol-1-yl) quinuclidine (41)

The product was isolated in the form of a white solid with a yield of 23% by following the general procedure D. R$_f$: 0.32 (CH₂Cl₂/MeOH/NH₄OH: 80/20/0.1); Mp: 158° C. IR (ATR, Diamond): ν (cm⁻¹): 972, 1009, 1043, 1060, 1070, 1186, 1218, 1315, 1424, 1451, 1479, 2867, 2936; ¹H NMR (250 MHz, CDCl₃): δ (ppm) 1.40-1.57 (m, 1H), 1.60-1.72 (m, 1H), 1.72-1.86 (m, 2H), 2.28 (q, 1H, J=3.1 Hz), 2.86-3.00 (m, 3H), 3.07-3.22 (m, 1H), 3.49 (ddd, 1H, J=14.5 Hz, 9.8 Hz and 2.2 Hz), 3.69 (dd, 1H, J=14.4 Hz and 5.0 Hz), 4.58-4.71 (m, 1H), 7.54 (d, 2H, J=8.6 Hz), 7.71 (d, 2H, J=8.6 Hz), 7.81 (s, 1H); ¹³C NMR (100 MHz, CDCl₃): δ (ppm) 20.2 (CH₂), 26.2 (CH₂), 28.4 (CH), 47.1 (CH₂), 47.5 (CH₂), 52.9 (CH₂), 58.7 (CH), 119.3 ($_{aromatic}$ CH), 122.2 (C$_q$), 127.4 (2CH$_{aromatic}$), 129.8 (C$_q$), 132.2 (2CH$_{aromatic}$), 146.8 (C$_q$); HRMS (EI-MS): calculated for C₁₅H₁₈N₄Br m/z=333.0715. found m/z=333.0722.

(R)-3-(4-(4-Fluorophenyl)-1H-1,2,3-triazol-1-yl) quinuclidine (42)

The product was isolated in the form of a white solid with a yield of 29% by following the general procedure D. R$_f$: 0.37 (CH₂Cl₂/MeOH/NH₄OH: 80/20/0.1); Mp: 180° C. IR (ATR, Diamond): ν (cm⁻¹): 973, 1014, 1044, 1060, 1160, 1225, 1453, 1495, 1560, 2375, 2869, 2936; ¹H NMR (250 MHz, DMSO-d₆): g (ppm) 1.49-1.62 (m, 2H), 1.81-1.94 (m, 2H), 2.31-2.36 (m, 1H), 2.94-3.08 (m, 3H), 3.12-3.26 (m, 1H), 3.57-3.71 (m, 2H), 3.91-5.02 (m, 1H), 7.34 (t, 2H, J=8.6 Hz), 7.94 (dd, 2H, J=8.6 Hz and 5.3 Hz), 8.83 (s, 1H); ¹³C NMR (100 MHz, DMSO-d₆): δ (ppm) 19.7 (CH₂), 23.8 (CH₂), 27.1 (CH), 45.9 (CH₂), 46.1 (CH₂), 50.8 (CH₂), 56.3 (CH), 115.8 (d, 2CH$_{aromatic}$, J=22 Hz), 121.0 ($_{aromatic}$CH), 127.1 (d, 2CH$_{aromatic}$, J=8 Hz), 127.3 (d, C$_q$, J=3 Hz), 145.4 (C$_q$), 161.7 (d, C$_q$, J=244 Hz), HRMS (EI-MS): calculated for C₁₅H₁₈FN₄ m/z=273.1516. found m/z=273.1508.

(R)-3-(4-(3-Fluorophenyl)-1H-1,2,3-triazol-1-yl) quinuclidine (43)

The product was isolated in the form of a solid white with a 29% by following the general procedure D. R$_f$: 0.31 (CH₂Cl₂/MeOH/NH₄OH: 80/20/0.1); Mp: 120° C. IR (ATR, Diamond): ν (cm⁻¹): 1041, 1061, 1148, 1214, 1266, 1315, 1345, 1449, 1487, 1589, 1620, 2869, 2936; ¹H NMR (250 MHz, CDCl₃): g (ppm) 1.40-1.55 (m, 1H), 1.60-1.72 (m, 1H), 1.72-1.86 (m, 2H), 2.28 (q, 1H, J=3.1 Hz), 2.84-3.00 (m, 3H), 3.08-3.22 (m, 1H), 3.50 (ddd, 1H, J=14.5 Hz, 9.8 Hz and 2.0 Hz), 3.70 (dd, 1H, J=14.5 Hz and 5.0 Hz), 4.60-4.70 (m, 1H), 7.03 (td, 1H, J=8.3 Hz and 2.3 Hz), 7.33-7.44 (m, 1H), 7.52-7.63 (m, 1H), 7.59 (s, 1H), 7.82 (s, 1H); ¹³C NMR (100 MHz, CDCl₃): δ (ppm) 20.2 (CH₂), 26.2 (CH₂), 28.4 (CH), 47.1 (CH₂), 47.5 (CH₂), 52.9 (CH₂), 58.8 (CH), 112.8 (d, $_{aromatic}$CH, J=22 Hz), 115.1 (d, $_{aromatic}$CH, J=22 Hz), 119.6 ($_{aromatic}$ CH), 121.5 (d, $_{aromatic}$CH, J=3 Hz), 130.6 (d, $_{aromatic}$CH, J=8 Hz), 133.0 (d, C$_q$, J=8 Hz), 146.8 (d, C$_q$, J=3 Hz), 163.4 (d, C q, J=246 Hz); HRMS (EI-MS): calculated for C₁₅H₁₈FN₄ m/z=273.1516. found m/z=273.1516.

(R)-3-(4-(2-Fluorophenyl)-1H-1,2,3-triazol-1-yl) quinuclidine (44)

The product is isolated in the form of a white solid with a yield of 22% by following the general procedure D. R$_f$: 0.42 (CH₂Cl₂/MeOH/NH₄OH: 80/20/0.1); Mp: 94° C. IR (ATR, Diamond): ν (cm⁻¹): 970, 1045, 1068, 1227, 1328, 1452, 1487, 1644, 2932, 3142, 3352; ¹H NMR (250 MHz, CDCl₃): δ (ppm) 1.41-1.55 (m, 1H), 1.63-1.74 (m, 1H), 1.76-1.88 (m, 2H), 2.30 (q, 1H, J=3.1 Hz), 2.87-3.00 (m, 3H), 3.10-3.24 (m, 1H), 3.50 (ddd, 1H, J=14.4 Hz, 9.8 Hz and 2.2 Hz), 3.75 (dd, 1H, J=14.4 Hz and 4.7 Hz), 4.63-4.72 (m, 1H), 7.09-7.18 (m, 1H), 7.22-7.34 (m, 2H), 7.98 (d, 1H, J=3.7 Hz), 8.32 (dd, 1H, J=7.5 Hz and 2.2 Hz); ¹³C NMR (100 MHz, CDCl₃): δ (ppm) 20.2 (CH₂), 26.2 (CH₂), 28.4 (CH), 47.1 (CH₂), 47.5 (CH₂), 52.8 (CH₂) 58.6 (CH), 115.8 (d, $_{aromatic}$CH, J=22 Hz), 118.8 (d, C$_q$, J=13 Hz), 122.4 (d, $_{aromatic}$CH, J=13 Hz), 124.8 (d, $_{aromatic}$CH, J=3 Hz), 128.0 (d, $_{aromatic}$CH, J=3 Hz), 129.5 (d, $_{aromatic}$CH, J=8 Hz), 141.2 (CO₃159.4 (d, C$_q$, J=248 Hz); HRMS (EI-MS): calculated for C₁₆H₁₈FN₄ m/z=273.1516. found m/z=273.1529.

(R)-3-(4-(3,4-difluorophenyl)-1H-1,2,3-triazol-1-yl) quinuclidine (45)

The product was isolated in the form of a white solid with a yield of 24% by following the general procedure D. R$_f$: 0.33 (CH₂Cl₂/MeOH/NH₄OH: 80/20/0.1); Mp: 122° C. IR (ATR, Diamond): ν (cm⁻¹): 969, 989, 1025, 1045, 1059, 1207, 1281, 1449, 1508, 1606, 2869, 2942; ¹H NMR (250 MHz, CDCl₃): δ (ppm) 1.40-1.55 (m, 1H), 1.59-1.74 (m, 1H), 1.74-1.88 (m, 2H), 2.26 (sext, 1H, J=3.1 Hz), 2.85-2.99 (m, 3H), 3.07-3.20 (m, 1H), 3.48 (ddd, 1H, J=14.4 Hz, 9.7 Hz and 2.1 Hz), 3.69 (dd, 1H, J=14.4 Hz and 4.8 Hz), 4.59-4.68 (m, 1H), 7.14-7.26 (m, 1H), 7.50-7.57 (m, 1H), 7.66 (ddd, 1H, J=11.2 Hz, 7.6 Hz and 2.1 Hz), 7.78 (s, 1H); ¹³C NMR (100 MHz, CDCl₃): δ (ppm) 20.2 (CH₂), 26.2 (CH₂), 28.4 (CH), 47.1 (CH₂), 47.5 (CH₂), 52.8 (CH₂) 58.8 (CH), 114.9 (d, $_{aromatic}$CH, J=18 Hz), 117.9 (d, $_{aromatic}$CH, J=18 Hz), 119.4 ($_{aromatic}$CH), 121.9 (q, $_{aromatic}$CH, J=6 Hz and 4 Hz), 128.0 (q, C$_q$, J=6 Hz and 4 Hz), 146.0 (C$_q$), 150.3 (q, C$_q$, J=248 Hz and 13 Hz), 150.8 (q, C$_q$, J=248 Hz and 13 Hz); HRMS (EI-MS): calculated for C₁₆H₁₇F₂N₄ m/z=291.1421. found m/z=291.1423.

(R)-3-(4-(4-Methoxyphenyl)-1H-1,2,3-triazol-1-yl) quinuclidine (46)

The product was isolated in the form of a white solid with a yield of 21% by following the general procedure D. R$_f$: 0.33 (CH₂Cl₂/MeOH/NH₄OH: 80/20/0.1); Mp: 122° C. IR (ATR, Diamond): ν (cm⁻¹): 1029, 1060, 1106, 1177, 1249, 1307, 1454, 1497, 1561, 1618, 2870, 2937, 3399; ¹H NMR (250 MHz, DMSO-d₆): δ (ppm) 1.38-1.50 (m, 2H), 1.72-1.82 (m, 2H), 2.19-2.26 (m, 1H), 2.74-2.92 (m, 3H), 2.96-3.17 (m, 1H), 3.33-3.62 (m, 2H), 3.83 (s, 3H), 4.74-4.83 (m, 1H), 7.05 (d, 2H, J=8.5 Hz), 7.83 (d, 2H, J=8.6 Hz), 8.66 (s, 1H); ¹³C NMR (100 MHz, DMSO-d₆): δ (ppm) 19.6 (CH₂), 25.2 (CH₂), 27.6 (CH), 46.3 (CH₂), 46.6 (CH₂), 51.8 (CH₂), 55.1 (CH₃), 57.2 (CH), 114.2 (2CH$_{aromatic}$), 119.9 ($_{aromatic}$CH), 123.5 (C$_q$), 126.5 (2CH$_{aromatic}$), 146.1 (C$_q$), 158.9 (C$_q$); HRMS (EI-MS): calculated for C₁₆H₂₁N₄O m/z=285.1715. found m/z=285.1726.

(R)-3-(4-(3-Methoxyphenyl)-1H-1,2,3-triazol-1-yl)quinuclidine (47)

The product was isolated in the form of a yellowish oil with a yield of 32% by following the general procedure D. R$_f$: 0.45 (CH₂Cl₂/MeOH/NH₄OH: 80/20/0.1); IR (ATR, Diamond): ν (cm⁻¹): 1040, 1158, 1243, 1282, 1321, 1455, 1483, 1584, 1610, 2872, 2942; ¹H NMR (250 MHz, CDCl₃): δ (ppm) 1.39-1.54 (m, 1H), 1.61-1.72 (m, 1H), 1.72-1.85 (m, 2H), 2.27 (sext, 1H, J=3.1 Hz), 2.84-2.98 (m, 3H), 3.08-3.22 (m, 1H), 3.48 (ddd, 1H, J=14.5 Hz, 9.8 Hz and 2.2 Hz), 3.71 (dd, 1H, J=14.5 Hz and 4.8 Hz), 3.85 (s, 3H), 4.59-4.68 (m, 1H), 6.85-6.90 (m, 1H) 7.28-7.38 (m, 2H), 7.44-7.47 (m, 1H), 7.80 (s, 1H); ¹³C NMR (100 MHz, CDCl₃): δ (ppm) 20.2 (CH₂) 26.2 (CH₂), 28.3 (CH), 47.1 (CH₂), 47.5 (CH₂), 52.8 (CH₂), 55.6 (CH₃), 58.6 (CH), 110.9 ($_{aromatic}$CH), 114.4 ($_{aromatic}$CH), 118.2 ($_{aromatic}$CH), 119.4 ($_{aromatic}$CH), 130.1 ($_{aromatic}$ CH), 132.1 (C$_q$), 147.6 (C$_q$), 160.2 (C$_q$); HRMS (EI-MS): calculated for C₁₆H₂₁N₄O m/z=285.1715. found m/z=285.1719.

(R)-3-(4-(2-Methoxyphenyl)-1H-1,2,3-triazol-1-yl)quinuclidine (48)

The product was isolated in the form of a white solid with a yield of 28% following the general procedure D. R$_f$: 0.50 (CH₂Cl₂/MeOH/NH₄OH: 80/20/0.1); Mp: 120° C. IR (ATR, Diamond): ν (cm⁻¹): 969, 1017, 1043, 1067, 1120, 1240, 1322, 1434, 1488, 1583, 2864, 2927; ¹H NMR (250 MHz, CDCl₃): δ (ppm) 1.37-1.52 (m, 1H), 1.63-1.74 (m, 1H), 1.74-1.85 (m, 2H), 2.28 (sext, 1H, J=3.1 Hz), 2.85-2.99 (m, 3H), 3.10-3.24 (m, 1H), 3.46 (ddd, 1H, J=14.3 Hz, 9.8 Hz and 2.2 Hz), 3.75 (dd, 1H, J=14.3 Hz and 5.2 Hz), 3.94 (s, 3H), 4.59-4.68 (m, 1H), 6.97 (d, 1H, J=8.3 Hz), 7.08 (td, 1H, J=7.6 Hz and 1.1 Hz), 7.31 (ddd, 1H, J=8.3 Hz, 7.6 Hz and 1.8 Hz), 8.08 (s, 1H), 8.35 (dd, 1H, J=7.6 Hz and 1.8 Hz); ¹³C NMR (100 MHz, CDCl₃): δ (ppm) 20.3 (CH₂), 26.2 (CH₂), 28.4 (CH), 47.2 (CH₂), 47.5 (CH₂), 52.8 (CH₂), 55.6 (CH₃), 58.4 (CH), 111.0 ($_{aromatic}$CH), 120.0 (C$_q$), 121.3 ($_{aromatic}$CH), 122.7 ($_{aromatic}$CH), 127.8 ($_{aromatic}$CH), 129.0 ($_{aromatic}$CH), 143.1 (C$_q$), 155.8 (C$_q$); HRMS (EI-MS): calculated for C₁₆H₂₁N₄O m/z=285.1723. found m/z=285.1715.

(R)-3-(4-(6-Methoxynaphthalen-2-yl)-1H-1,2,3-triazol-1-yl)quinuclidine (49)

The product was isolated in the form of a white solid with a yield of 21% by following the general procedure D. R$_f$: 0.29 (CH₂Cl₂/MeOH/NH₄OH: 80/20/0.1); Mp: 186° C. IR (ATR, Diamond): ν (cm⁻¹): 906, 1025, 1123, 1162, 1210, 1262, 1344, 1394, 1454, 1479, 1612, 1630, 2869, 2932; ¹H NMR (250 MHz, CDCl₃): δ (ppm) 1.42-1.56 (m, 1H), 1.65-1.76 (m, 1H), 1.76-1.88 (m, 2H), 2.31 (q, 1H, J=3.1 Hz), 2.86-3 02 (m, 3H), 3.10-3.24 (m, 1H), 3.52 (ddd, 1H, J=14.4 Hz, 9.7 Hz and 2.1 Hz), 3.73 (dd, 1H, J=14.4 Hz and 5.2 Hz), 3.93 (s, 3H), 4.58-4.75 (m, 1H), 7.15 (s, 1H), 7.14-7.20 (m, 1H), 7.79 (d, 2H, J=9.2 Hz), 7.89 (s, 1H), 7.91 (dd, 1H, J=8.6 Hz and 1.7 Hz), 8.26 (s, 1H); ¹³C NMR (100 MHz, CDCl₃): δ (ppm) 20.3 (CH₂), 26.2 (CH₂) 28.4 (CH), 47.2 (CH₂), 47.5 (CH₂), 52.9 (CH₂), 55.6 (CH₃), 58.7 (CH), 106.0 (CH$_{aro}$), 119.0 ($_{aromatic}$CH), 119.5 ($_{aromatic}$CH), 124.5 ($_{aromatic}$CH), 124.6 ($_{aromatic}$ CH), 126.1 (C$_q$), 127.6 ($_{aromatic}$CH), 129.2 (C$_q$), 129.9 ($_{aromatic}$ CH), 134.6 (C$_q$), 148.0 (C$_q$), 158.1 (C$_q$); HRMS (EI-MS): calculated for C₂₀H₂₃N₄O m/z=335.1872. found m/z=335.1866.

(R)-3-(4-(Pyridin-4-yl)-1H-1,2,3-triazole-1-yl)quinuclidine (50)

The product was isolated in the form of a brown solid with a yield of 30% by following the general procedure D. R$_f$: 0.21 (CH₂Cl₂/MeOH/NH₄OH: 80/20/0.1); Mp: 150° C. IR (ATR, Diamond): ν (cm⁻¹): 991, 1041, 1058, 1073, 1208, 1227, 1325, 1413, 1430, 1562, 1613, 2869, 2935; ¹H NMR (250 MHz, CDCl₃): δ (ppm) 1.42-1.56 (m, 1H), 1.60-1.76 (m, 1H), 1.76-1.88 (m, 2H), 2.29 (q, 1H, J=3.1 Hz), 2.86-3.00 (m, 3H), 3.07-3.25 (m, 1H), 3.50 (ddd, 1H, J=14.5 Hz, 9.7 Hz and 2.1 Hz), 3.71 (dd, 1H, J=14.4 Hz and 5.0 Hz), 4.63-4.72 (m, 1H), 7.73 (d, 2H, J=6.0 Hz), 7.95 (s, 1H), 8.66 (d, 2H, J=6.0 Hz); ¹³C NMR (100 MHz, CDCl₃): δ (ppm) 20.2 (CH₂), 26.2 (CH₂), 28.4 (CH), 47.1 (CH₂), 47.5 (CH₂), 52.9 (CH₂), 59.0 (CH), 120.1 (2CH$_{aromatic}$), 120.7 ($_{aromatic}$ CH), 138.2 (C$_q$), 145.3 (C$_q$), 150.7 (2CH aromatic); HRMS (EI-MS): calculated for C₁₄H₁₈N₅ m/z=256.1562. found m/z=256.1550.

(R)-3-(4-(6-fluoropyridin-3-yl)-1H-1,2,3-triazol-1-yl) quinuclidine (51)

The product was isolated in the form of a white solid with a yield of 18% by following the general procedure D. R$_f$: 0.32 (CH₂Cl₂/MeOH/NH₄OH: 80/20/0.1); Mp: 147° C. IR (ATR, Diamond): ν (cm⁻¹): 976, 1024, 1044, 1060, 1237, 1316, 1429, 1471, 1552, 1593, 2870, 2935; ¹H NMR (400 MHz, CDCl₃): δ (ppm) 1.45-1.54 (m, 1H), 1.63-1.72 (m, 1H), 1.74-1.90 (m, 2H), 2.29 (q, 1H, J=3.1 Hz), 2.87-3.02 (m, 3H), 3.11-3.20 (m, 1H), 3.51 (ddd, 1H, J=14.4 Hz, 9.8 Hz and 2.0 Hz), 3.71 (dd, 1H, J=14.4 Hz and 5.1 Hz), 4.63-4.69 (m, 1H), 7.02 (dd, 1H, J=8.5 Hz and 2.9 Hz), 7.87 (s, 1H), 8.28-8.37 (m, 1H), 8.60 (d, 1H, J=2.5 Hz); ¹³C NMR (100 MHz, CDCl₃): δ (ppm) 20.2 (CH₂), 26.2 (CH₂), 28.4 (CH), 47.1 (CH₂), 47.5 (CH₂), 52.9 (CH₂), 58.9 (CH), 110.1 (d, $_{aromatic}$CH, J=38 Hz), 119.4 ($_{aromatic}$CH), 125.3 (d, C$_q$, J=5 Hz), 138.7 (d, $_{aromatic}$CH, J=8 Hz), 143.8 (CO₃144.9 (d, $_{aromatic}$CH, J=15 Hz), 163.5 (d, C$_q$, J=240 Hz); HRMS (EI-MS): calculated for C₁₄H₁₇N₅F m/z=274.1468. found m/z=274.1465.

(R)-3-(4-(6-Methoxypyridin-3-yl)-1H-1,2,3-triazol-1-yl)quinuclidine (52)

The product was isolated in the form of a white solid with a yield of 28% by following the general procedure D. R$_f$: 0.28 (CH₂Cl₂/MeOH/NH₄OH: 80/20/0.1); Mp: 155° C. IR (ATR, Diamond): ν (cm⁻¹): 973, 1027, 1215, 1254, 1282, 1325, 1420, 1481, 1555, 1614, 1729, 2869, 2938; ¹H NMR (250 MHz, CDCl₃): δ (ppm) 1.40-1.55 (m, 1H), 1.62-1.74 (m, 1H), 1.74-1.88 (m, 2H), 2.27 (q, 1H, J=3.0 Hz), 2.84-3.00 (m, 3H), 3.08-3.22 (m, 1H), 3.42-3.56 (m, 1H), 3.72 (dd, 1H, J=14.3 Hz and 4.3 Hz), 3.97 (s, 3H), 4.58-4.69 (m, 1H), 6.81 (d, 1H, J=8.6 Hz), 7.77 (s, 1H), 8.07 (dd, 1H, J=8.6 Hz and 2.2 Hz), 8.56 (d, 1H, J=2.2 Hz); ¹³C NMR (100 MHz, CDCl₃): δ (ppm) 20.3 (CH₂), 26.2 (CH₂), 28.4 (CH), 47.2 (CH₂), 47.5 (CH₂), 52.9 (CH₂), 53.8 (CH₃), 58.8 (CH), 111.3 ($_{aromatic}$CH), 118.7 ($_{aromatic}$CH), 120.5 (C$_q$), 136.5

(R)-3-(4-(Thiophen-2-yl)-1H-1,2,3-triazol-1-yl)quinuclidine (53)

The product was isolated in the form of a brown solid with a yield of 38% following the general procedure D. $R_f$: 0.42 (CH$_2$Cl$_2$/MeOH/NH$_4$OH: 80/20/0.1); Mp: 137° C. IR (ATR, Diamond): ν (cm$^{-1}$): 931, 973, 1027, 1042, 1062, 1159, 1212, 1295, 1316, 1432, 1451, 2867, 2937, 3074; $^1$H NMR (250 MHz, CDCl$_3$): δ (ppm) 1.38-1.53 (m, 1H), 1.59-1.72 (m, 1H), 1.72-1.85 (m, 2H), 2.26 (q, 1H, J=3.1 Hz), 2.83-2.98 (m, 3H), 3.06-3.20 (m, 1H), 3.47 (ddd, 1H, J=14.5 Hz, 9.7 Hz and 2.0 Hz), 3.68 (dd, 1H, J=14.5 Hz and 5.0 Hz), 4.57-4.66 (m, 1H), 7.07 (dd, 1H, J=5.1 Hz and 3.6 Hz), 7.25-7.30 (m, 1H), 7.38 (dd, 1H, J=3.6 Hz and 1.1 Hz), 7.73 (s, 1H); $^{13}$C NMR (100 MHz, CDCl$_3$): δ (ppm) 20.2 (CH$_2$), 26.2 (CH$_2$), 28.3 (CH), 47.1 (CH$_2$), 47.4 (CH$_2$), 52.8 (CH$_2$), 58.7 (CH), 118.7 ($_{aromatic}$CH), 124.3 ($_{aromatic}$CH), 125.2 ($_{aromatic}$CH), 127.8 ($_{aromatic}$ CH), 133.2 (C$_q$), 142.9 (C$_q$); HRMS (EI-MS): calculated for C$_{13}$H$_{17}$N$_4$S m/z=261.1174. found m/z=261.1185.

(R)-3-(4-(5-Bromothiophen-2-yl)-1H-1,2,3-triazol-1-yl) quinuclidine (54)

The product was isolated in the form of a white solid with a yield of 42% by following the general procedure D. $R_f$: 0.46 (CH$_2$Cl$_2$/MeOH/NH$_4$OH: 80/20/0.1); Mp: 146° C. IR (ATR, Diamond): ν (cm$^{-1}$): 972, 1041, 1057, 1215, 1322, 1433, 1496, 1645, 2867, 2934, 3356; $^1$H NMR (400 MHz, CDCl$_3$): δ (ppm) 1.44-1.51 (m, 1H), 1.59-1.69 (m, 1H), 1.71-1.87 (m, 2H), 2.25 (q, 1H, J=3.0 Hz), 2.83-2.99 (m, 3H), 3.07-3.16 (m, 1H), 3.47 (ddd, 1H, J=14.4 Hz, 9.8 Hz and 2.2 Hz), 3.66 (ddd, 1H, J=14.4 Hz, 5.1 Hz and 1.6 Hz), 4.57-4.63 (m, 1H), 7.00 (d, 1H, J=3.8 Hz), 7.08 (d, 1H, J=3.8 Hz), 7.69 (s, 1H); $^{13}$C NMR (100 MHz, CDCl$_3$): δ (ppm) 20.1 (CH$_2$), 26.1 (CH$_2$), 28.3 (CH), 47.0 (CH$_2$), 47.4 (CH$_2$), 52.7 (CH$_2$), 58.7 (CH), 112.1 (C$_q$), 118.7 ($_{aromatic}$CH), 124.3 ($_{aromatic}$CH), 130.6 ($_{aromatic}$CH), 134.8 (C$_q$), 142.1 (C$_q$); HRMS (EI-MS): calculated for C$_{13}$H$_{16}$N$_4$SBr m/z=339.0279. found m/z=339.0283.

(R)-3-(4 Benzo[b](thiophen-5-yl)-1H-1,2,3-triazol-1-yl) quinuclidine (55)

The product was isolated in the form of a white solid with a yield of 32% by following the general procedure D. $R_f$: 0.32 (CH$_2$Cl$_2$/MeOH/NH$_4$OH: 80/20/0.1); Mp: 178° C. IR (ATR, Diamond): ν (cm$^{-1}$): 1023, 1047, 1202, 1223, 1323, 1440, 2866, 2933; $^1$H NMR (250 MHz, CDCl$_3$): δ (ppm) 1.44-1.53 (m, 1H), 1.66-1.76 (m, 1H), 1.76-1.88 (m, 2H), 2.30 (q, 1H, J=3.0 Hz), 2.86-3.00 (m, 3H), 3.11-3.21 (m, 1H), 3.50 (ddd, 1H, J=14.5 Hz, 9.8 Hz and 2.1 Hz), 3.70 (dd, 1H, J=14.5 Hz and 5.0 Hz), 4.62-4.69 (m, 1H), 7.37 (d, 1H, J=5.4 Hz), 7.47 (d, 1H, J=5.4 Hz), 7.80 (dd, 1H, J=8.4 Hz and 1.1 Hz), 7.86 (s, 1H), 7.92 (d, 1H, J=8.4 Hz), 8.33 (d, 1H, J=1.1 Hz); $^{13}$C NMR (100 MHz, CDCl$_3$): δ (ppm) 20.3 (CH$_2$), 26.2 (CH$_2$), 28.4 (CH), 47.2 (CH$_2$), 47.5 (CH$_2$), 52.9 (CH$_2$), 58.6 (CH), 119.1 ($_{aromatic}$CH), 120.8 ($_{aromatic}$CH), 122.4 (CH$_{aromatic}$), 123.1 ($_{aromatic}$CH), 124.2 ($_{aromatic}$CH), 127.2 (C$_q$), 127.4 ($_{aromatic}$CH), 139.6 (C$_q$), 140.2 (C$_q$), 147.9 (C$_q$); HRMS (EI-MS): calculated for C$_{17}$H$_{19}$N$_4$S m/z=311.1330. found m/z=311.1322.

(R)-3-(4-(Benzofuran-5-yl)-1H-1,2,3-triazol-1-yl) quinuclidine (56)

The product was isolated in the form of a white solid with a yield of 34% by following the general procedure D. $R_f$: 0.34 (CH$_2$Cl$_2$/MeOH/NH$_4$OH: 80/20/0.1); Mp: 178° C. IR (ATR, Diamond): ν (cm$^{-1}$): 989, 1029, 1042, 1062, 1109, 1194, 1221, 1321, 1455, 1497, 2870, 2935; $^1$H NMR (250 MHz, CDCl$_3$): δ (ppm) 1.44-1.53 (m, 1H), 1.67-1.77 (m, 1H), 1.77-1.89 (m, 2H), 2.30 (q, 1H, J=3.0 Hz), 2.88-3.00 (m, 3H), 3.12-3.22 (m, 1H), 3.46-3.55 (m, 1H), 3.73 (dd, 1H, J=14.3 Hz and 4.3 Hz), 4.63-4.69 (m, 1H), 6.81 (d, 1H, J=2.1 Hz), 7.54 (d, 1H, J=8.6 Hz), 7.64 (d, 1H, J=2.1 Hz), 7.76 (dd, 1H, J=8.6 Hz and 1.6 Hz), 7.82 (s, 1H), 8.10 (d, 1H, J=1.6 Hz); $^{13}$C NMR (100 MHz, CDCl$_3$): δ (ppm) 20.3 (CH$_2$), 26.2 (CH$_2$), 28.4 (CH), 47.2 (CH$_2$), 47.5 (CH$_2$), 52.9 (CH$_2$), 58.6 (CH), 107.0 ($_{aromatic}$CH), 111.9 ($_{aromatic}$CH), 118.6 ($_{aromatic}$CH), 118.8 ($_{aromatic}$CH), 122.6 ($_{aromatic}$CH), 125.9 (C$_q$), 128.2 (C$_q$), 145.9 ($_{aromatic}$CH), 148.2 (C$_q$), 155.1 (C$_q$); HRMS (EI-MS): calculated for C$_{17}$H$_{19}$N$_4$O m/z=295.1559. found m/z=295.1557.

(S)-3-(4-(4-Fluorophenyl)-1H-1,2,3-triazol-1-yl) quinuclidine (57)

The product was isolated in the form of a white solid with a yield of 33% by following the general procedure D. $R_f$: 0.37 (CH$_2$Cl$_2$/MeOH/NH$_4$OH: 80/20/0.1); Mp: 139° C. IR (ATR, Diamond): ν (cm$^{-1}$): 974, 1022, 1042, 1060, 1160, 1225, 1330, 1400, 1452, 1494, 1560, 1612, 2869, 2936; $^1$H NMR (250 MHz, CDCl$_3$): δ (ppm) 1.39-1.54 (m, 1H), 1.60-1.74 (m, 1H), 1.74-1.88 (m, 2H), 2.26 (sext, 1H, J=3.1 Hz), 2.84-2.98 (m, 3H), 3.07-3.21 (m, 1H), 3.48 (ddd, 1H, J=14.4 Hz, 9.8 Hz and 2.3 Hz), 3.70 (dd, 1H, J=14.4 Hz and 5.1 Hz), 4.59-4.68 (m, 1H), 7.11 (t, 2H, J=8.6 Hz), 7.77 (s, 1H), 7.77-7.84 (m, 2H); $^{13}$C NMR (100 MHz, CDCl$_3$): δ (ppm) 20.3 (CH$_2$), 26.2 (CH$_2$), 28.4 (CH), 47.2 (CH$_2$), 47.5 (CH$_2$), 52.9 (CH$_2$), 58.7 (CH), 116.0 (d, 2CH$_{aro}$, J=22 Hz), 118.9 ($_{aromatic}$CH), 127.1 (d, C$_q$, J=3 Hz), 127.6 (d, 2CH$_{aro}$, J=8 Hz), 146.9 (C$_q$), 162.8 (d, C$_q$, J=247 Hz); HRMS (EI-MS): calculated for C$_{15}$H$_{18}$N$_4$F m/z=273.1516. found m/z=273.1509.

(R)-3-[4-(5-Bromo-2-furyl)-1H-1,2,3-triazol-1-yl] quinuclidine (80)

The product was isolated in the form of a white solid with a yield of 38% by following the general procedure D. $R_f$: 0.26 (CH$_2$Cl$_2$/MeOH/NH$_4$OH: 95/5/1); Mp: 144° C.; IR (ATR, Diamond): ν (cm$^{-1}$): 972, 1047, 1057, 1228, 1343, 1476, 1530, 1624, 2869, 2937, 3126; $^1$H NMR (400 MHz, CDCl$_3$): δ (ppm) 1.44-1.51 (m, 1H), 1.59-1.67 (m, 1H), 1.73-1.87 (m, 2H), 2.25 (q, 1H, J=3.2 Hz), 2.85-3.00 (m, 3H), 3.07-3.15 (m, 1H), 3.49 (ddd, 1H, J=14.4 Hz, 10.0 Hz and 2.4 Hz), 3.64 (dd, 1H, J=14.4 Hz, 4.0 Hz), 4.63-4.66 (m, 1H), 6.40 (d, 1H, J=3.6 Hz), 6.82 (d, 1H, J=3.6 Hz), 7.8 (s, 1H); $^{13}$C NMR (100 MHz, CDCl$_3$): δ (ppm) 19.9 (CH$_2$), 25.9 (CH$_2$), 28.0 (CH), 46.9 (CH$_2$), 47.2 (CH$_2$), 52.6 (CH$_2$), 58.5 (CH), 108.8 (CH), 113.2 (CH), 118.6 (CH), 121.4 (C$_q$), 139.4 (C$_q$), 148.3 (C$_q$); HRMS (EI-MS): calculated for C$_{13}$H$_{16}$N$_4$OBr m/z=323.05020. found m/z=323.05015.

(R)-3-[4-(4-bromo-2-thienyl)-1H-1,2,3-triazol-1-yl] quinuclidine (81)

The product was isolated in the form of a white solid with a yield of 50% by following the general procedure D. $R_f$:

0.24 (CH$_2$Cl$_2$/MeOH/NH$_4$OH: 98/2/1); Mp: 106° C.; IR (ATR, Diamond): ν (cm$^{-1}$): 786, 988, 1054, 1226, 1326, 1452, 1497, 2870, 2938, 3107; $^1$H NMR (400 MHz, CDCl$_3$): δ (ppm) 1.45-1.52 (m, 1H), 1.61-1.69 (m, 1H), 1.76-1.85 (m, 2H), 2.26 (q, 1H, J=3.2 Hz), 2.85-3.00 (m, 3H), 3.09-3.16 (m, 1H), 3.49 (ddd, 1H, J=14.4 Hz, 10.0 Hz and 2.1 Hz), 3.66 (dd, 1H, J=14.4 Hz and 5.2 Hz), 4.60-4.65 (m, 1H), 7.19 (s, 1H), 7.26 (s, 1H), 7.74 (s, 1H); $^{13}$C NMR (100 MHz, CDCl$_3$): δ (ppm) 19.9 (CH$_2$), 25.9 (CH$_2$), 28.1 (CH), 46.9 (CH$_2$), 47.2 (CH$_2$), 52.6 (CH$_2$), 58.6 (CH), 110.2 (C$_q$), 118.7 (CH), 122.1 (CH), 126.4 (CH), 134.3 (C$_q$), 141.5 (C$_q$); HRMS (EI-MS): calculated for C$_{13}$H$_{16}$N$_4$SBr m/z=339.02766. found m/z=339.02736.

(R)-3-[4-(4-bromo-2-furyl)-1H-1,2,3-triazol-1-yl]quinuclidine (82)

The product was isolated in the form of a white solid with a yield of 43% by following the general procedure D. R$_f$: 0.22 (CH$_2$Cl$_2$/MeOH/NH$_4$OH: 98/2/1); Mp: 129° C.; IR (ATR, Diamond): ν (cm$^{-1}$): 785, 980, 1042, 1210, 1325, 1452, 1534, 2869, 2940, 3115; $^1$H NMR (400 MHz, CDCl$_3$): δ (ppm) 1.43-1.50 (m, 1H), 1.58-1.67 (m, 1H), 1.72-1.87 (m, 2H), 2.26 (q, 1H, J=2.8 Hz), 2.85-2.99 (m, 3H), 3.07-3.14 (m, 1H), 3.48 (ddd, 1H, J=14.4 Hz, 10.0 Hz and 2.2 Hz), 3.65 (dd, 1H, J=14.4 Hz and 3.6 Hz), 4.62-4.65 (m, 1H), 6.87 (s, 1H), 7.44 (s, 1H), 7.78 (s, 1H); $^{13}$C NMR (100 MHz, CDCl$_3$): δ (ppm) 19.9 (CH$_2$), 25.9 (CH$_2$), 28.0 (CH), 46.8 (CH$_2$), 47.2 (CH$_2$), 52.6 (CH$_2$), 58.5 (CH), 101.3 (C$_q$), 109.7 (CH), 119.0 (CH), 139.3 (C$_q$), 140.1 (CH), 147.2 (C$_q$); HRMS (EI-MS): calculated for C$_{13}$H$_{16}$N$_4$OBr m/z=323.05045. found m/z=323.05020.

(R)-3-[4-(3-bromophenyl)-1H-1,2,3-triazol-1-yl]quinuclidine (83)

The product was isolated in the form of a white solid with a yield of 50% by following the general procedure D. R$_f$: 0.18 (CH$_2$Cl$_2$/MeOH/NH$_4$OH: 97/3/1); Mp: 188° C. IR (ATR, Diamond): ν (cm$^{-1}$): 970, 1020, 1041, 1060, 1069, 1233, 1341, 14237 1455, 1470, 1603, 2868, 2938; $^1$H NMR (400 MHz, CDCl$_3$): δ (ppm) 1.44-1.50 (m, 1H), 1.61-1.65 (m, 1H), 1.73-1.87 (m, 2H), 2.27 (q, 1H, J=3.2 Hz), 2.86-3.00 (m, 3H), 3.09-3.17 (m, 1H), 3.49 (ddd, 1H, J=14.4 Hz, 9.8 Hz and 2.2 Hz), 3.68 (dd, 1H, J=14.4 Hz and 3.6 Hz), 4.63-4.65 (m, 1H), 7.29 (t, 1H, J=7.6 Hz), 7.45 (d, 1H, J=8.0 Hz), 7.78 (d, 1H, J=8.0 Hz), 7.83 (s, 1H), 7.98 (s, 1H); $^{13}$C NMR (100 MHz, CDCl$_3$) δ (ppm) 20.0 (CH$_2$), 26.0 (CH$_2$), 28.1 (CH), 46.9 (CH$_2$), 47.2 (CH$_2$), 52.6 (CH$_2$), 58.5 (CH), 119.3 (CH), 122.9 (C$_q$), 124.1 (CH), 128.6 (CH), 130.4 (CH), 131.0 (CH), 132.6 (C$_q$), 146.1 (C$_q$); HRMS (EI-MS): calculated for C$_{15}$H$_{18}$N$_4$.Br m/z=333.07111. found m/z=333.07094.

Fluorination of Alcohol 38

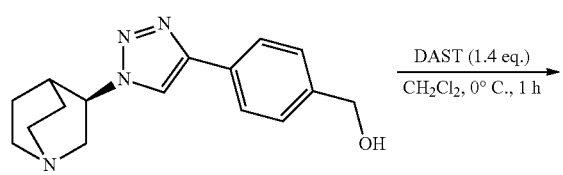

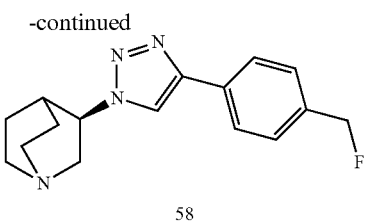

(R)-3-(4-(4-(Fluoromethyl)phenyl)-1H-1,2,3-triazol-1-yl)quinuclidine (58)

The alcohol 38 (140 mg, 0.500 mmol) was dissolved in 10 mL of dichloromethane and then at 0° C., diethylaminosulfur trifluoride (92 μL, 0.700 mmol) was added to it drop by drop. The reaction mixture was stirred at 0° C. for a period of one hour and then hydrolysed with the addition of a saturated NaHCO$_3$ solution. The organic phase was dried over anhydrous MgSO$_4$, and filtered and concentrated under reduced pressure. The fluorinated compound 58 was purified by column chromatography on silica gel with the eluent used being a mixture of CH$_2$Cl$_2$/MeOH/NH$_4$OH (90/10/0.1). The product 58 was isolated in the form of a white solid with a yield of 51%. R$_f$: 0.41 (CH$_2$Cl$_2$/MeOH/NH$_4$OH: 80/20/0.1); Mp: 138° C.; IR (ATR, Diamond): ν (cm$^{-1}$): 974, 1010, 1043, 1060, 1212, 1317, 1382, 1407, 1453, 1500, 2870, 2940; $^1$H NMR (250 MHz, CDCl$_3$): δ (ppm) 1.41-1.56 (m, 1H), 1.62-1.74 (m, 1H), 1.74-1.94 (m, 2H), 2.30 (q, 1H, J=3.1 Hz), 2.86-3.00 (m, 3H), 3.09-3.24 (m, 1H), 3.50 (ddd, 1H, J=14.6 Hz, 9.6 Hz and 2.0 Hz), 3.72 (dd, 1H, J=14.5 Hz and 5.1 Hz), 4.61-4.70 (m, 1H), 5.41 (d, 2H, J=47.8 Hz), 7.44 (dd, 2H, J=8.6 Hz and 1.6 Hz), 7.84 (s, 1H), 7.88 (dd, 2H, J=8.6 Hz and 1.0 Hz); $^{13}$C NMR (100 MHz, CDCl$_3$): δ (ppm) 20.3 (CH$_2$), 26.2 (CH$_2$), 28.4 (CH), 47.1 (CH$_2$), 47.5 (CH$_2$), 52.9 (CH$_2$), 58.7 (CH), 84.5 (d, CH$_2$, J=166 Hz), 119.4 ($_{aromatic}$CH), 126.1 (2CH$_{aromatic}$), 128.2 (d, 2CH$_{aro}$, J=6 Hz), 131.4 (d, C$_q$, J=3 Hz), 136.2 (d, C$_q$, J=17 Hz), 147.3 (C$_q$); HRMS (EI-MS): calculated for C$_{16}$H$_{20}$N$_4$F m/z=287.1672. found m/z=287.1660.

Preparation of the Quinuclidine Type Compound 60 Comprising a Triazole Ring Substituted in Position 4 and 5

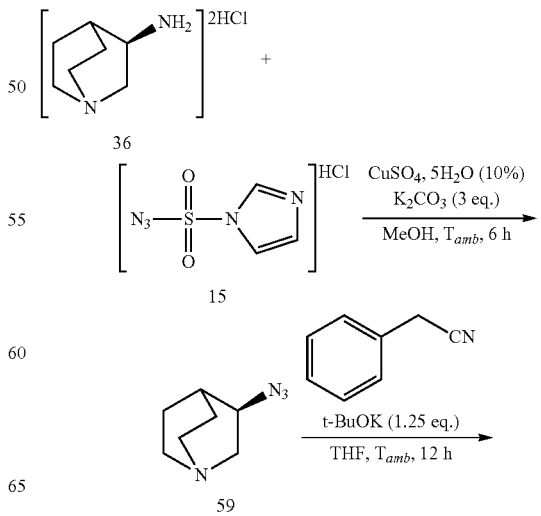

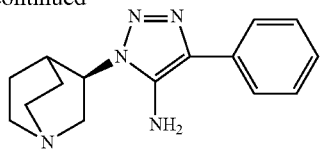

60

(R)-4-Phenyl-1-(quinuclidin-3-yl)-1H-1,2,3-triazol-5-amine (60)

Under argon atmosphere, 3(R)-aminoquinuclidine 36 (400 mg, 2.00 mmol) and the and 1H-imidazole-1-sulfonyl azide 15 (464 mg, 2.20 mmol) were dissolved in 12 mL of methanol, to which the following were then added successively: $K_2CO_3$ (830 mg, 6.00 mmol) and a catalytic amount of $CuSO_4 5H_2O$ (50 mg, 0.200 mmol). The reaction medium was stirred at ambient temperature for a period of 6 hours and then concentrated under reduced pressure. The resulting solid obtained was then taken up again in 20 mL of ethyl ether, vacuum filtered and then washed two times with 20 mL of ethyl ether. After evaporation of the filtrate under reduced pressure, the azide 59 was engaged in the subsequent step without any further purification. To a solution of azide 59 (2.00 mmol) in 10 mL of anhydrous THF, the following were added at ambient temperature: phenyl acetonitrile (0.28 mL, 2.40 mmol) and t-BuOK (337 mg, 3.00 mmol). The reaction medium was stirred at ambient temperature under argon atmosphere for a period of 12 hours. Thereafter the solvent was evaporated and then the residue was taken up again in dichloromethane and washed with water. The organic phase was dried over anhydrous $MgSO_4$, and filtered and evaporated under reduced pressure. The product was purified by column chromatography on silica gel with the eluent used being a mixture of $CH_2Cl_2$/MeOH/$NH_4OH$ (90/10/0.1) and then (70/30/0.1). The amine 60 was isolated in the form of a white solid with a yield of 43%. $R_f$: 0.11 ($CH_2Cl_2$/MeOH/$NH_4OH$: 70/30/0.1); mp: 120° C. IR (ATR, Diamond): $\nu$ (cm$^{-1}$): 982, 1007, 1056, 1266, 1323, 1360, 1445, 1510, 1585, 1607, 1633, 2870, 2940, 3175, 3307; $^1$H NMR (250 MHz, CDCl$_3$): $\delta$ (ppm) 1.33-1.48 (m, 1H), 1.72-2.00 (m, 3H), 2.12 (q, 1H, J=3.1 Hz), 2.82-3.01 (m, 3H), 3.26-3.40 (m, 2H), 3.71-3.80 (m, 2H), 4.01 (dd, 1H, J=14.2 Hz, 4.8 Hz), 4.23-4.32 (m, 1H), 7.27-7.35 (m, 1H), 7.41-7.49 (m, 2H), 7.67-7.72 (m, 2H); $^{13}$C NMR (100 MHz, CDCl$_3$): $\delta$ (ppm) 19.9 (CH$_2$), 26.1 (CH$_2$), 26.9 (CH), 47.2 (CH$_2$), 47.4 (CH$_2$) 51.5 (CH$_2$), 54.7 (CH), 125.9 (2CH$_{aromatic}$), 127.2 ($_{aromatic}$ CH), 129.2 (2CH$_{aromatic}$), 131.7 (C$_q$), 131.9 (C$_q$), 137.3 (C$_q$); HRMS (EI-MS): calculated for C$_{13}$H$_{20}$N$_3$ m/z=270.1719. found m/z=270.1732.

Preparation of Quinuclidine Type Compounds 61-63 and 84-111

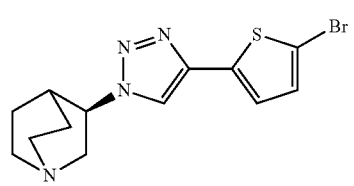

54

+

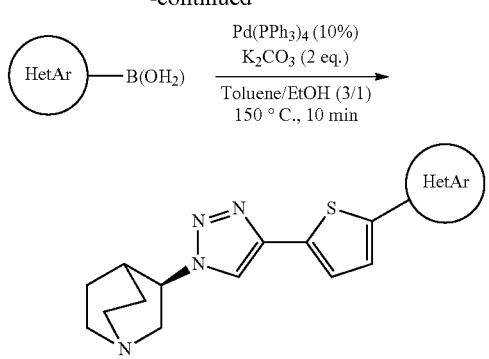

61-63 or 41, 80-83 +

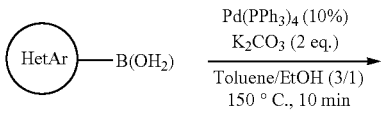

84-95, 98-100 and 106

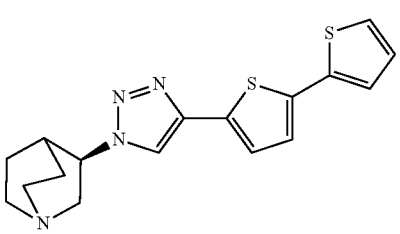

61

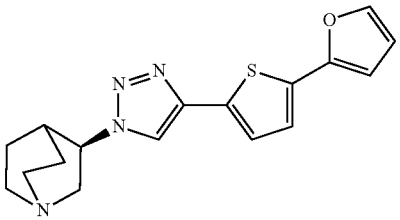

62

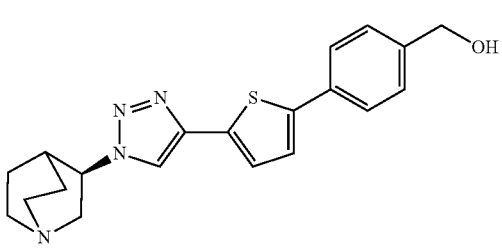

63

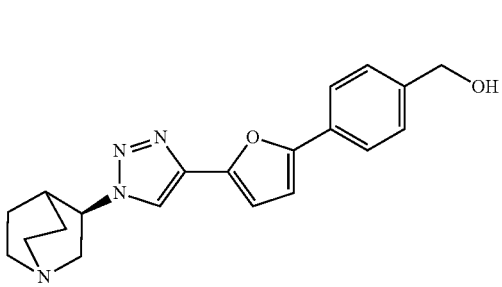

84

85
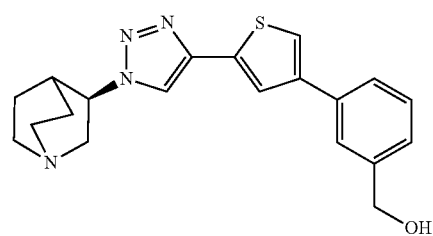
86
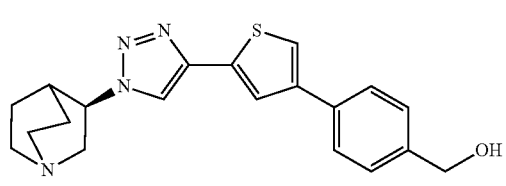
87
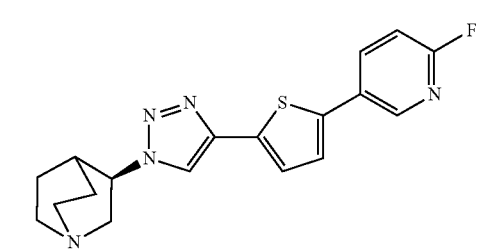
88
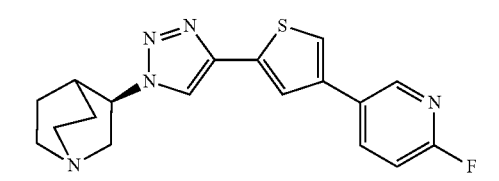
89
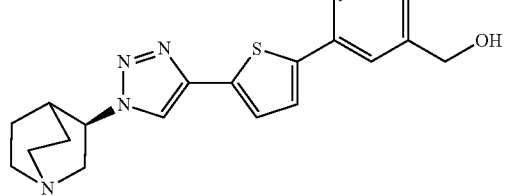
90
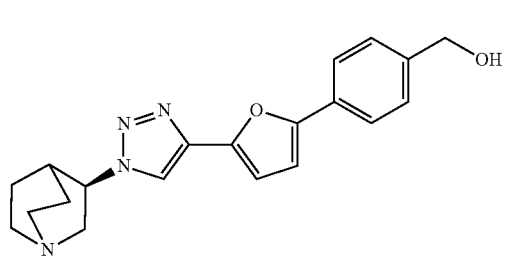
91
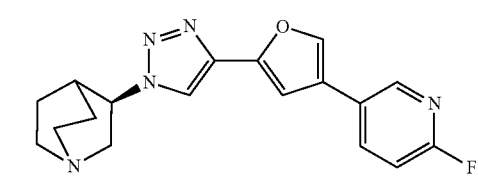
92
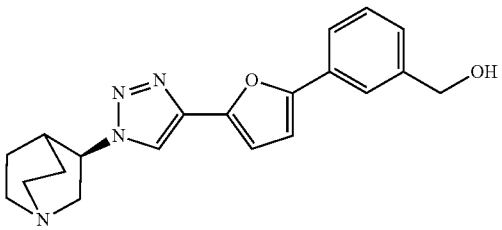
93
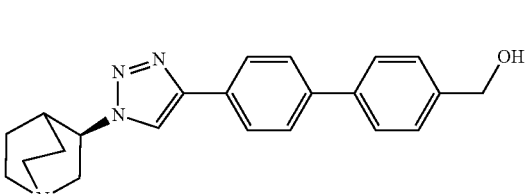
94
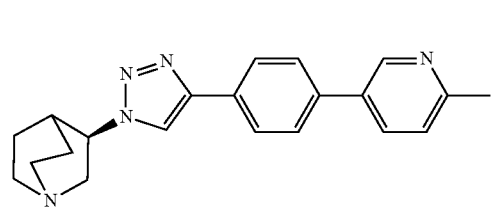
95
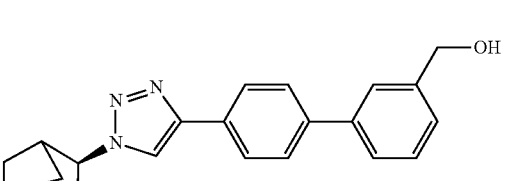
98
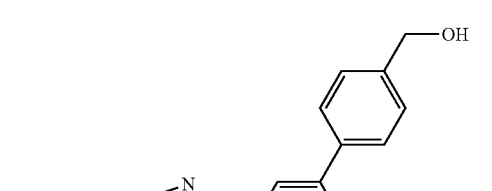
99
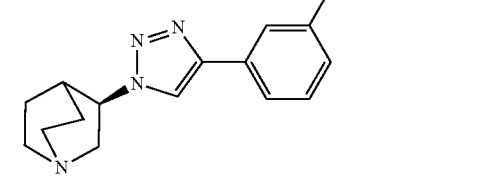

-continued

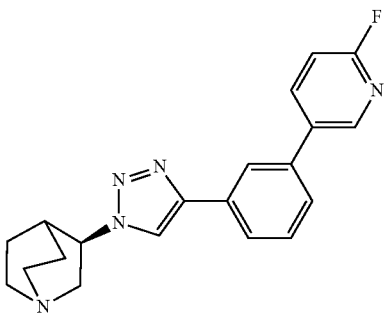

100

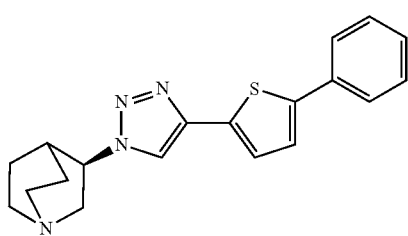

106

General Procedure E1:

To a solution of a brominated derivative selected from among the compounds 54, 41 and 80-83 (50 mg, 0.147 mmol) in a mixture of 1.5 mL of toluene and 0.5 ml of ethanol, the following were added: the desired boronic acid (0.176 mmol), $K_2CO_3$ (41 mg, 0.294 mmol) and tetrakis (triphenylphosphine)palladium (17 mg, 0.0147 mmol). After degassing, the reaction mixture was irradiated with microwave at 150° C. for a period of 10 minutes. The solvent was then evaporated and the residue was purified by column chromatography on silica gel with the eluent used being a mixture of $CH_2Cl_2/MeOH/NH_4OH$ (80/20/0.1).

(R)-3-(4-(2,7-Bithiophen-5-yl)-1H-1,2,3-triazol-1-yl)quinuclidine (61)

The product was isolated in the form of a brown solid with a yield of 73% by following the general procedure E1. $R_f$: 0.25 ($CH_2Cl_2$/MeOH/$NH_4OH$: 80/20/0.1); Mp: 182° C. IR (ATR, Diamond): ν ($cm^{-1}$): 1042, 1067, 1210, 1340, 1425, 1454, 1503, 1584, 2867, 2937; $^1$H NMR (400 MHz, CDCl$_3$): δ (ppm) 1.44-1.54 (m, 1H), 1.63-1.74 (m, 1H), 1.76-1.88 (m, 2H), 2.26-2.30 (m, 1H), 2.86-3.00 (m, 3H), 3.10-3.20 (m, 1H), 3.45-3.54 (m, 1H), 3.70 (dd, 1H, J=14.3 Hz and 4.6 Hz) 4.60-4 67 (m, 1H), 7.03 (dd, 1H, J=4.9 Hz and 3.8 Hz), 7.14 (d, 1H, J=3.6 Hz), 7.19-7.24 (m, 2H), 7.28 (d, 1H, J=3.6 Hz), 7.73 (s, 1H); $^{13}$C NMR (100 MHz, CDCl$_3$): δ (ppm) 20.1 (CH$_2$), 26.1 (CH$_2$), 28.3 (CH), 47.1 (CH$_2$), 47.4 (CH$_2$), 52.7 (CH$_2$), 58.7 (CH), 118.6 ($_{aromatic}$CH), 124.0 ($_{aromatic}$CH), 124.3 ($_{aromatic}$CH), 124.7 ($_{aromatic}$CH), 124.8 ($_{aromatic}$CH), 128.1 ($_{aromatic}$CH), 131.8 (C$_q$), 137.1 (C$_q$), 137.3 (C$_q$), 142.6 (C$_q$); HRMS (EI-MS): calculated for $C_{17}H_{19}N_4O_2$ m/z=343.1051. found m/z=343.1055.

(R)-3-(4-(5-(Furan-2-yl)thiophen-2-yl)-1H-1,2,3-triazol-1-yl)quinuclidine (62)

The product was isolated in the form of a white solid with a yield of 83% by following the general procedure E1. $R_f$: 0.27 ($CH_2Cl_2$/MeOH/$NH_4OH$: 80/20/0.1); Mp: 180° C. IR (ATR, Diamond): ν ($cm^{-1}$): 977, 1070, 1442, 1647, 2939, 3243; $^1$H NMR (400 MHz, CDCl$_3$): (ppm) 1.44-1.53 (m, 1H), 1.64-1.73 (m, 1H), 1.76-1.88 (m, 2H), 2.28 (q, 1H, J=3.0 Hz), 2.87-3.01 (m, 3H), 3.10-3.20 (m, 1H), 3.49 (ddd, 1H, J=14.4 Hz, 9.8 Hz and 2.1 Hz), 3.68 (ddd, 1H, J=14.4 Hz, 5.0 Hz and 1.5 Hz), 4.61-4.66 (m, 1H), 6.46 (dd, 1H, J=3.4 Hz and 1.8 Hz), 6.54 (d, 1H, J=3.4 Hz), 7.21 (d, 1H, J=3.8 Hz), 7.31 (d, 1H, J=3.8 Hz), 7.41-7.42 (m, 1H), 7.73 (s, 1H); $^{13}$C NMR (100 MHz, CDCl$_3$): δ (ppm) 20.1 (CH$_2$), 26.1 (CH$_2$), 28.3 (CH), 47.1 (CH$_2$), 47.4 (CH$_2$), 52.8 (CH$_2$), 58.7 (CH), 105.6 ($_{aromatic}$CH), 112.0 ($_{aromatic}$CH), 118.6 (CH$_{aromatic}$), 123.1 ($_{aromatic}$CH), 124.8 ($_{aromatic}$CH), 131.8 (C$_q$), 133.4 (C$_q$), 142.0 ($_{aromatic}$CH), 142.6 (C$_q$), 149.3 (C$_q$); HRMS (EI-MS): calculated for $C_{17}H_{19}N_4OS$ m/z=327.1280. found m/z=327.1284.

(R)-(4-(5-(1-(quinuclidin-3-yl)-1H-1,2,3-triazol-4-yl)thiophen-2-yl)phenyl)methanol (63)

The product was isolated in the form of a white solid with a yield of 72% by following the general procedure E1. $R_f$: 0.17 ($CH_2Cl_2$/MeOH/$NH_4OH$: 80/20/0.1); Mp: 253° C. IR (ATR, Diamond): ν ($cm^{-1}$): 983, 1041, 1214, 1306, 1355, 1416, 1454, 1502, 2823, 2872, 2941, 3110; $^1$H NMR (400 MHz, DMSO-d$_6$): δ (ppm) 1.38-1.52 (m, 2H), 1.72-1.80 (m, 2H), 2.20-2.26 (m, 1H), 2.76-2.85 (m, 3H), 2.96-3.05 (m, 1H), 3.34-3.51 (m, 2H), 4.56 (d, 2H, J=4.8 Hz), 4.76-7.82 (m, 1H), 5.27 (t, 1H, J=4.8 Hz), 7.41 (d, 2H, J=7.8 Hz), 7.47 (d, 1H, J=3.1 Hz), 7.54 (d, 1H, J=3.1 Hz), 7.69 (d, 2H, J=7.8 Hz), 8.72 (s, 1H); $^{13}$C NMR (100 MHz, DMSO-d$_6$): δ (ppm) 19.6 (CH$_2$), 25.3 (CH$_2$), 27.6 (CH), 46.3 (CH$_2$), 46.6 (CH$_2$), 51.9 (CH$_2$), 57.6 (CH), 62.5 (CH$_2$), 120.3 ($_{aromatic}$CH), 123.9 ($_{aromatic}$CH), 124.9 (2CH$_{aromatic}$), 125.1 ($_{aromatic}$CH), 127.1 (2CH$_{aromatic}$), 131.9 (C$_q$), 132.1 (C$_q$), 141.4 (C$_q$), 142.2 (2C$_q$); HRMS (EI-MS): calculated for $C_{20}H_{23}N_4OS$ m/z=367.1593. found m/z=367.1609.

(R)-[4-[5-[1-[quinuclidin-3-yl]-1H-1,2,3-triazol-4-yl]-2-furyl]-phenyl]-methanol (84)

The product was isolated in the form of a white solid with a yield of 72% by following the general procedure E1. $R_f$: 0.17 ($CH_2Cl_2$/MeOH/$NH_4OH$: 96/4/1); Mp: 209° C.; IR (ATR, Diamond): ν ($cm^{-1}$): 792, 980, 1042, 1201, 1327, 1413, 1457, 1502, 2879, 2946, 3116; $^1$H NMR (400 MHz, DMSO-d$_6$): δ (ppm) 1.31-1.46 (m, 2H), 1.65-1.77 (m, 2H), 2.20-2.22 (m, 1H), 2.71-2.78 (m, 3H), 2.93-3.01 (m, 1H), 3.34-3.50 (m, 2H), 4.51 (d, 2H, J=5.5 Hz), 4.72-4.81 (m, 1H), 5.23 (t, 1H, J=5.5 Hz), 6.88 (d, 2H, J=3.2 Hz), 7.02 (d, 1H, J=3.2 Hz), 7.38 (d, 1H, J=8.2 Hz), 7.74 (d, 2H, J=8.2 Hz), 8.67 (s, 1H); $^{13}$C NMR (100 MHz, DMSO-d$_6$): δ (ppm) 20.0 (CH$_2$), 25.7 (CH$_2$), 28.1 (CH), 46.8 (CH$_2$), 47.0 (CH$_2$), 52.1 (CH$_2$), 57.9 (CH), 63.0 (CH$_2$), 107.6 (CH), 108.7 (CH), 121.0 (CH), 123.6 (2CH), 127.3 (2CH), 128.9 (C$_q$), 139.3 (C$_q$), 142.5 (C$_q$), 146.0 (C$_q$), 152.9 (C$_q$); HRMS (EI-MS): calculated for $C_{20}H_{23}N_4O_2$ m/z=351.18155. found m/z=351.18154.

(R)-[3-[5-[1-[quinuclidin-3-yl]-1H2,3-triazol-4-yl]-2-thienyl]phenyl]methanol (85)

The product was isolated in the form of a white solid with a yield of 75% by following the general procedure E1. $R_f$: 0.17 ($CH_2Cl_2$/MeOH/$NH_4OH$: 98/2/1); Mp: 181° C.; IR (ATR, Diamond): ν ($cm^{-1}$): 796, 988, 1040, 1226, 1323, 1452, 1488, 2870, 2938, 3108; $^1$H NMR (400 MHz, DMSO-d$_6$): δ (ppm) 1.35-1.50 (m, 2H), 1.66-1.81 (m, 2H), 2.20-2.22 (m, 1H), 2.72-2.87 (m, 3H), 2.93-3.05 (m, 1H), 3.34-3.51 (m, 2H), 4.57 (s, 2H), 4.74-4.81 (m, 1H), 5.33 (bl, 1H), 7.28 (d, 1H, J=12.0 Hz), 7.39 (t, 1H, J=12.0 Hz), 7.46 (d, 1H, J=6.0 Hz), 7.53 (d, 1H, J=6.0 Hz), 7.58 (d, 1H, J=12.0 Hz), 7.65 (s, 1H), 8.70 (s, 1H); $^{13}$C NMR (100 MHz, DMSO-d$_6$): δ (ppm) 20.0 (CH$_2$), 25.7 (CH$_2$), 28.0 (CH), 46.7 (CH$_2$), 47.0 (CH$_2$), 52.2 (CH$_2$), 57.9 (CH), 63.0 (CH$_2$), 120.8 (CH), 123.5 (CH), 123.9 (CH), 124.6 (CH), 125.6 (CH), 126.2 (CH), 129.3 (CH), 132.8 (C$_q$), 133.6 (C$_q$), 141.8 (Cq), 142.8 (C$_q$), 144.0 (C$_q$); HRMS (EI-MS): calculated for C$_{20}$H$_{23}$N$_4$OS m/z=367.15871. found m/z=367.15904.

(R)-[4-[5-[1-[quinuclidin-3-yl]-1H-1,2,3-triazol-4-yl]-3-thienyl]phenyl]methanol (86)

The product was isolated in the form of a white solid with a yield of 72% by following the general procedure E1. R$_f$: 0.18 (CH$_2$Cl$_2$/MeOH/NH$_4$OH: 98/2/1); Mp: 196° C.; IR (ATR, Diamond): ν (cm$^{-1}$): 749, 785, 981, 1042, 1061, 1211, 1325, 1413, 1452, 1534, 2870, 2941, 3116; $^1$H NMR (400 MHz, DMSO-d$_6$) δ (ppm) 1.34-1.50 (m, 2H), 1.66-1.78 (m, 2H), 2.19 (q, 1H, J=2.8 Hz), 2.74-2.83 (m, 3H), 2.94-3.01 (m, 1H), 3.40 (d, 2H, J=7.2 Hz), 4.51 (s, 2H), 4.75-4.79 (m, 1H), 5.20 (bl, 1H), 7.35 (d, 2H, J=8.2 Hz), 7.68 (d, 2H, J=8.2 Hz), 7.80 (d, 1H, J=0.8 Hz), 7.89 (d, 1H, J=0.8 Hz), 8.70 (s, 1H); $^{13}$C NMR (100 MHz, DMSO-d$_6$): δ (ppm) 19.9 (CH$_2$), 25.6 (CH$_2$), 28.0 (CH), 46.7 (CH$_2$), 47.0 (CH$_2$), 52.3 (CH$_2$), 57.8 (CH), 63.0 (CH$_2$), 120.1 (CH), 120.7 (CH), 123.3 (CH), 126.0 (2CH), 127.4 (2CH), 133.7 (C$_q$), 134.3 (C$_q$), 142.0 (C$_q$), 142.1 (C$_q$), 142.2 (C$_q$); HRMS (EI-MS): calculated for C$_{20}$H$_{23}$N$_4$OS m/z=367.15871. found m/z=367.15889.

(R)-3-[4-[5-(6-fluoro-3-pyridyl)-2-thienyl]-1H,1,2,3-triazol-1-yl]quinuclidine (87)

The product was isolated in the form of a white solid with a yield of 80% by following the general procedure E1. R$_f$: 0.20 (CH$_2$Cl$_2$/MeOH/NH$_4$OH: 98/2/1); Mp: 163° C.; IR (ATR, Diamond): ν (cm$^{-1}$): 784, 801, 986, 1077, 1241, 1320, 1387, 1447, 1526, 1581, 2871, 2939, 3127; $^1$H NMR (400 MHz, CDCl$_3$): δ (ppm) 1.46-1.52 (m, 1H), 1.64-1.71 (m, 1H), 1.74-1.87 (m, 2H), 2.28 (q, 1H, J=2.8 Hz), 2.86-3.00 (m, 3H), 3.10-3.14 (m, 1H), 3.46 (ddd, 1H, J=14.4 Hz, 10.0 Hz and 2.0 Hz), 3.66 (dd, 1H, J=14.4 Hz, 4.0 Hz), 4.63-4.65 (m, 1H), 6.96 (dd, 1H, J=8.4 Hz and 2.4 Hz), 7.26 (d, 1H, J=3.8 Hz), 7.35 (d, 1H, J=3.8 Hz), 7.78 (s, 1H), 7.97 (td, 1H, J=8.4 Hz and 2.2 Hz), 8.46 (d, 1H, J=2.2 Hz); $^{13}$C NMR (100 MHz, CDCl$_3$): (ppm) 20.0 (CH$_2$), 25.9 (CH$_2$), 28.1 (CH), 46.9 (CH$_2$), 47.2 (CH$_2$), 52.6 (CH$_2$), 58.6 (CH), 109.7 (d, CH, J=38 Hz), 118.6 (CH), 124.7 (CH), 124.9 (CH), 128.4 (d, C$_q$, J=5 Hz), 133.6 (C$_q$), 138.2 (d, CH, J=8 Hz), 138.3 (C$_q$), 142.1 (C$_q$), 144.3 (d, CH, J=14 Hz), 162.8 (d, C$_q$, J=239 Hz); HRMS (EI-MS): calculated for C$_{18}$H$_{19}$N$_5$S m/z=356.13397. found m/z=356.13432.

(R)-3-[4-[4-(6-fluoro-3-pyridyl)-2-thienyl]-1H-1,2,3-triazol-1-yl]quinuclidine (88)

The product was isolated in the form of a white solid with a yield of 79% by following the general procedure E1. R$_f$: 0.20 (CH$_2$Cl$_2$/MeOH/NH$_4$OH: 98/2/1); Mp: 136° C.; IR (ATR, Diamond): ν (cm$^{-1}$): 793, 972, 1055, 1219, 1310, 1402, 1459, 1589, 2868, 2938, 3115; $^1$H NMR (400 MHz, CDCl$_3$): δ (ppm) 1.46-1.53 (m, 1H), 1.65-1.73 (m, 1H), 1.77-1.87 (m, 2H), 2.30 (q, 1H, J=2.8 Hz), 2.87-3.01 (m, 3H), 3.11-3.18 (m, 1H), 3.51 (ddd, 1H, J=14.4 Hz, 10.0 Hz and 2.0 Hz), 3.70 (dd, 1H, J=14.4 Hz and 4.0 Hz), 4.65-4.68 (m, 1H), 6.98 (dd, 1H, J=8.4 Hz and 2.8 Hz), 7.41 (s, 1H), 7.63 (s, 1H), 7.81 (s, 1H), 7.98 (td, 1H, J=8.4 Hz and 2.8 Hz), 8.46 (d, 1H, J=1.6 Hz); $^{13}$C NMR (100 MHz, CDCl$_3$): δ (ppm) 19.9 (CH$_2$), 25.9 (CH$_2$), 28.1 (CH), 46.9 (CH$_2$), 47.2 (CH$_2$), 52.6 (CH$_2$), 58.6 (CH), 109.6 (d, CH, J=38 Hz), 118.7 (CH), 120.7 (CH), 122.5 (CH), 129.5 (d, C$_q$, J=5 Hz), 134.7 (C$_q$), 138.0 (C$_q$), 138.8 (d, CH, J=7 Hz), 142.1 (C$_q$), 145.0 (d, CH, J=15 Hz) 162.8 (d, C$_q$, J=238 Hz); HRMS (EI-MS): calculated for C$_{18}$H$_{19}$N$_5$SF m/z=356.13397. found m/z=356.13430.

(R)-[3-[5-[1-[quinuclidin-3-yl]-1H-1,2,3-triazol-4-yl]-3-thienyl]phenyl]methanol (89)

The product was isolated in the form of a white solid with a yield of 77% by following the general procedure E1. R$_f$: 0.21 (CH$_2$Cl$_2$/MeOH/NH$_4$OH: 98/2/1); Mp: 211° C.; IR (ATR, Diamond): ν (cm$^{-1}$): 787, 996, 1041, 1162, 1233, 1324, 1437, 1455, 1603, 2868, 2937, 3367; $^1$H NMR (400 MHz, CDCl$_3$): δ (ppm) 1.43-1.58 (m, 1H), 1.62-1.90 (m, 3H), 2.26-2.32 (m, 1H), 2.47 (bl, 1H), 2.83-3.01 (m, 3H), 3.09-3.19 (m, 1H), 3.46 (ddd, 1H, J=15.6 Hz, 12.0 Hz and 3.6 Hz), 3.66 (dd, 1H, J=15.6 Hz and 7.6 Hz), 4.60-4.69 (m, 1H), 4.76 (s, 2H), 7.32 (d, 1H, J=12.2 Hz), 7.38-7.44 (m, 2H), 7.56 (dd, 1H, J=12.2 Hz and 2.2 Hz), 7.66 (s, 1H), 7.70 (d, 1H, J=2.2 Hz), 7.78 (s, 1H); $^{13}$C NMR (100 MHz, CDCl$_3$): δ (ppm) 19.9 (CH$_2$), 25.8 (CH$_2$), 28.0 (CH), 46.8 (CH$_2$), 47.1 (CH$_2$), 52.5 (CH$_2$), 58.4 (CH), 65.0 (CH$_2$), 118.5 (CH), 119.9 (CH), 123.2 (CH), 124.8 (CH), 125.3 (CH), 125.8 (CH), 129.0 (CH), 133.7 (C$_q$), 135.7 (C$_q$), 141.8 (C$_q$), 142.5 (2C$_q$); HRMS (EI-MS): calculated for C$_{20}$H$_{23}$N$_4$OS m/z=367.15871. found m/z=367.15909.

(R)-[4-[5-[1-[quinuclidin-3-yl]-1H-1,2,3-triazol-4-yl]-3-furyl]phenyl]methanol (90)

The product was isolated in the form of a white solid with a yield of 71% by following the general procedure E1. R$_f$: 0.2 (CH$_2$Cl$_2$/MeOH/NH$_4$OH: 96/4/1); Mp: 202° C.; IR (ATR, Diamond): ν (cm$^{-1}$): 795, 986, 1039, 1163, 1273, 1351, 1462, 1528, 1579, 2185, 2946; $^1$H NMR (400 MHz, DMSO-d$_6$): δ (ppm) 1.34-1.46 (m, 2H), 1.69-1.73 (m, 2H), 2.19 (q, 1H, J=2.8 Hz), 2.74-2.83 (m, 3H), 2.94-3.01 (m, 1H), 3.35-3.51 (m, 3H), 4.49 (s, 2H), 4.76-4.80 (m, 1H), 7.250 (s, 1H), 7.33 (d, 2H, J=8.2 Hz), 7.62 (d, 2H, J=8.2 Hz), 7.24 (s, 1H), 8.59 (s, 1H); $^{13}$C NMR (100 MHz, DMSO-d$_6$): δ (ppm) 19.9 (CH$_2$), 25.5 (CH$_2$), 28.0 (CH), 46.7 (CH$_2$), 46.9 (CH$_2$), 52.0 (CH$_2$), 57.8 (CH), 63.1 (CH$_2$), 105.2 (CH), 121.3 (CH), 125.7 (2CH), 127.3 (2CH), 127.7 (C$_q$), 130.3 (C$_q$), 139.1 (CH), 139.2 (C$_q$), 141.9 (C$_q$), 147.5 (C$_q$); HRMS (EI-MS): calculated for C$_{20}$H$_{23}$N$_4$O$_2$ m/z=351.18155. found m/z=351.18173.

(R)-3-[4-[4-(6-fluoro-3-pyridyl)-2-furyl]-1H-1,2,3-triazol-1-yl]quinuclidine (91)

The product was isolated in the form of a white solid with a yield of 73% by following the general procedure E1. R$_f$: 0.22 (CH$_2$Cl$_2$/MeOH/NH$_4$OH: 96/4/1); Mp: 210° C.; IR (ATR, Diamond): ν (cm$^{-1}$): 791, 986, 1058, 1247, 1310, 1418, 1491, 1564, 2872, 2944, 3091; $^1$H NMR (400 MHz, CDCl$_3$): δ (ppm) 1.45-1.53 (m, 1H), 1.62-1.68 (m, 1H), 1.76-1.89 (m, 2H), 2.29 (q, 1H, J=3.2 Hz), 2.87-3.01 (m, 3H), 3.10-3.18 (m, 1H), 3.51 (ddd, 1H, J=14.4 Hz, 10.0 Hz and 3.2 Hz), 3.70 (dd, 1H, J=14.4 Hz and 4.8 Hz), 4.66-4.69 (m, 1H), 6.98 (dd, 1H, J=8.4 Hz and 2.8 Hz), 7.13 (s, 1H), 7.74 (s, 1H), 7.85 (s, 1H), 7.90 (td, 1H, J=8.4 Hz and 2.4 Hz), 8.40 (d, 1H, J=2.4 Hz); $^{13}$C NMR (100 MHz, CDCl$_3$):

δ (ppm) 19.9 (CH$_2$), 25.9 (CH$_2$), 28.1 (CH), 46.9 (CH$_2$), 47.2 (CH$_2$), 52.7 (CH$_2$), 58.6 (CH), 105.0 (CH), 109.7 (d, CH, J=38 Hz), 118.9 (CH), 124.0 (C$_q$), 126.1 (d, C$_q$, J=4 Hz), 137.8 (CH), 138.4 (d, CH, J=8 Hz), 139.7 (C$_q$), 144.6 (d, CH, J=15 Hz), 148.0 (C$_q$), 162.8 (d, C$_q$, J=238 Hz); HRMS (EI-MS): calculated for C$_{18}$H$_{19}$N$_5$FO m/z=340.15681. found m/z=340.15696.

(R)-[3-[5-[1-[quinuclidin-3-yl]-1H-1,2,3-triazol-4-yl]-3-furyl]phenyl]methanol (92)

The product was isolated in the form of a white solid with a yield of 72% by following the general procedure E1. R$_f$: 0.19 (CH$_2$Cl$_2$/MeOH/NH$_4$OH: 96/4/1); Mp: 212° C.; IR (ATR, Diamond): ν (cm$^{-1}$): 798, 970, 1041, 1205, 1343, 1438, 1455, 1567, 2868, 2939, 3397; $^1$H NMR (400 MHz, CDCl$_3$): δ (ppm) 1.40-1.53 (m, 1H), 1.60-1.66 (m, 1H), 1.74-1.84 (m, 2H), 2.26 (q, 1H, J=2.8 Hz), 2.82-2.96 (m, 3H), 3.03-3.10 (m, 2H), 3.44 (ddd, 1H, J=15.6 Hz, 12.0 Hz and 3.6 Hz), 3.58 (dd, 1H, J=15.6 Hz and 7.6 Hz), 4.62-4.64 (m, 1H), 4.71 (s, 2H), 7.15 (s, 1H), 7.28 (d, 1H, J=7.6 Hz), 7.56 (t, 1H, J=7.6 Hz), 7.43 (d, 1H, J=7.6 Hz), 7.54 (s, 1H), 7.73 (s, 1H), 7.78 (s, 1H); $^{13}$C NMR (100 MHz, CDCl$_3$): δ (ppm) 19.8 (CH$_2$), 25.8 (CH$_2$), 27.9 (CH), 46.7 (CH$_2$), 47.0 (CH$_2$), 52.4 (CH$_2$), 58.3 (CH), 64.8 (CH$_2$), 105.5 (CH), 118.7 (CH), 124.3 (CH), 124.8 (CH), 125.8 (CH), 128.0 (C$_q$), 129.0 (CH), 132.1 (C$_q$), 137.9 (CH), 140.0 (C$_q$), 142.0 (C$_q$), 147.2 (C$_q$); HRMS (EI-MS): calculated for C$_{20}$H$_{23}$N$_4$O$_2$ m/z=351.18155. found m/z=351.18165.

(R)-[4-[4-[1-[quinuclidin-3-yl]-1H-1,2,3-triazol-4-yl]phenyl]phenyl]methanol (93)

The product was isolated in the form of a white solid with a yield of 81% by following the general procedure E1. R$_f$: 0.18 (CH$_2$Cl$_2$/MeOH/NH$_4$OH: 97/3/1); Mp: 250° C.; IR (ATR, Diamond): ν (cm$^{-1}$): 798, 973, 1042, 1223, 1344, 1429, 1451, 1661, 2869, 2938, 3119; $^1$H NMR (400 MHz, DMSO-d$_6$): δ (ppm) 1.36-1.49 (m, 2H), 1.69-1.75 (m, 2H), 2.20 (q, 1H, J=2.8 Hz), 2.73-2.80 (m, 3H), 2.96-3.03 (m, 1H), 3.35-3.49 (m, 2H), 4.54 (d, 2H, J=3.2 Hz), 4.75-4.77 (m, 1H), 5.21 (bl, 1H), 7.40 (d, 2H, J=8.2 Hz), 7.68 (d, 2H, J=8.2 Hz), 7.76 (d, 2H, J=8.4 Hz), 7.96 (d, 2H, J=8.4 Hz), 8.78 (s, 1H); $^{13}$C NMR (100 MHz, DMSO-d$_6$): δ (ppm) 20.0 (CH$_2$) 25.7 (CH$_2$), 28.1 (CH), 46.8 (CH$_2$), 47.0 (CH$_2$), 52.3 (CH$_2$), 57.8 (CH), 63.0 (CH$_2$), 121.3 (CH), 126.1 (2CH), 126.6 (2CH), 127.3 (2CH), 127.4 (2CH), 130.2 (C$_q$), 138.3 (C$_q$), 139.7 (C$_q$), 142.3 (C$_q$), 146.2 (C$_q$); HRMS (EI-MS): calculated for C$_{22}$H$_{25}$N$_4$O m/z=361.20229. found m/z=361.20277.

(R)-3-[4-[4-(6-fluoro-3-pyridyl)phenyl]-1H-1,2,3-triazol-1-yl]quinuclidine (94)

The product was isolated in the form of a yellow solid with a yield of 85% by following the general procedure E1. R$_f$: 0.22 (CH$_2$Cl$_2$/MeOH/NH$_4$OH: 97/3/1); Mp: 181° C.; IR (ATR, Diamond): ν (cm$^{-1}$): 811, 987, 1039, 1253, 1372, 1474, 1590, 2871, 2942, 3115; $^1$H NMR (400 MHz, CDCl$_3$): δ (ppm) 1.47-1.53 (m, 1H), 1.67-1.85 (m, 3H), 2.30 (q, 1H, J=3.2 Hz), 2.88-3.02 (m, 3H), 3.13-3.20 (m, 1H), 3.51 (ddd, 1H, J=14.2 Hz, 9.8 Hz and 2.2 Hz), 3.72 (dd, 1H, J=14.2 Hz and 4.0 Hz), 4.66-4.69 (m, 1H), 7.01 (dd, 1H, J=8.4 Hz and 2.8 Hz), 7.61 (d, 2H, J=8.2 Hz), 7.88 (s, 1H), 7.95 (d, 2H, J=8.4 Hz), 8.01 (td, 1H, J=8.2 Hz and 2.4 Hz), 8.45 (d, 1H, J=2.4 Hz); $^{13}$C NMR (100 MHz, CDCl$_3$): δ (ppm) 20.0 (CH$_2$), 26.0 (CH$_2$), 28.1 (CH), 46.9 (CH$_2$) 47.3 (CH$_2$), 52.7 (CH$_2$), 58.5 (CH), 109.5 (d, CH, J=37 Hz), 119.2 (CH), 126.3 (2CH), 127.4 (2CH), 130.6 (C$_q$), 134.2 (d, C$_q$, J=4 Hz), 136.2 (C$_q$), 139.5 (d, CH, J=8 Hz), 145.6 (d, CH, J=15 Hz), 146.8 (C$_q$), 163.1 (d, C$_q$, J=238 Hz); HRMS (EI-MS): calculated for C$_{20}$H$_{21}$N$_5$F m/z=350.17755. found m/z=350.17782.

(R)-[3-[4-[1-[quinuclidin-3-yl]-1H-1,2,3-triazol-4-yl]phenyl]phenyl]methanol (95)

The product was isolated in the form of a white solid with a yield of 80% by following the general procedure E1. R$_f$: 0.18 (CH$_2$Cl$_2$/MeOH/NH$_4$OH: 97/3/1); Mp: 207° C.; IR (ATR, Diamond): ν (cm$^{-1}$): 792, 982, 1038, 1225, 1324, 1437, 1455, 1603, 2874, 2941, 3367; $^1$H NMR (400 MHz, DMSO-d$_6$): δ (ppm) 1.32-1.52 (m, 2H), 1.67-1.74 (m, 2H), 2.20 (q, 1H, J=2.8 Hz), 2.73-2.80 (m, 3H), 2.96-3.05 (m, 1H), 3.36-3.50 (m, 2H), 4.58 (s, 2H), 4.76-4.78 (m, 1H), 5.25 (bl, 1H), 7.32 (d, 1H, J=7.2 Hz), 7.43 (t, 1H, J=7.6 Hz), 7.58 (d, 1H, J=7.6 Hz), 7.67 (s, 1H), 7.75 (d, 2H, J=8.2 Hz), 7.97 (d, 2H, J=8.2 Hz), 8.79 (s, 1H); $^{13}$C NMR (100 MHz, DMSO-d$_6$): δ (ppm) 20.0 (CH$_2$), 25.7 (CH$_2$), 28.1 (CH), 46.8 (CH$_2$), 47.0 (CH$_2$), 52.2 (CH$_2$), 57.8 (CH), 63.3 (CH$_2$), 121.4 (CH), 124.9 (CH), 125.2 (CH), 126.1 (3CH), 127.4 (2CH), 129.1 (CH), 130.4 (C$_q$), 139.8 (C$_q$), 139.9 (C$_q$), 143.7 (C$_q$), 146.2 (C$_q$); HRMS (EI-MS): calculated for C$_{22}$H$_{26}$N$_4$O m/z=361.20229. found m/z=361.20262.

(R)-[4-[3-[1-[quinuclidin-3-yl]-1H-1,2,3-triazol-4-yl]phenyl]phenyl]methanol (98)

The product was isolated in the form of a white solid with a yield of 87% by following the general procedure E1. R$_f$: 0.18 (CH$_2$Cl$_2$/MeOH/NH$_4$OH: 97/3/1); Mp: 214° C.; IR (ATR, Diamond): ν (cm$^{-1}$): 793, 972, 1041, 1222, 1320, 1451, 1481, 1660, 2868, 2939, 3077; $^1$H NMR (400 MHz, DMSO-d$_6$): δ (ppm) 1.31-1.49 (m, 2H), 1.70-1.74 (m, 2H), 2.20 (q, 1H, J=2.8 Hz), 2.74-2.78 (m, 3H), 2.94-3.01 (m, 1H), 3.38-3.46 (m, 2H), 4.55 (s, 2H), 4.74-4.78 (m, 1H), 5.23 (bl, 1H), 7.42 (d, 2H, J=7.6 Hz), 7.51 (t, 1H, J=7.6 Hz), 7.61 (d, 1H, J=7.6 Hz), 7.69 (d, 2H, J=7.6 Hz), 7.87 (d, 1H, J=7.6 Hz), 8.14 (s, 1H), 8.85 (s, 1H); $^{13}$C NMR (100 MHz, DMSO-d$_6$): δ (ppm) 20.0 (CH$_2$), 25.7 (CH$_2$), 28.1 (CH), 46.8 (CH$_2$), 47.0 (CH$_2$), 52.3 (CH$_2$), 57.8 (CH), 63.0 (CH$_2$), 121.5 (CH), 123.7 (CH), 124.3 (CH), 126.3 (CH), 126.8 (2CH), 127.4 (2CH) 129.9 (CH), 131.9 (C$_q$), 138.6 (C$_q$), 141.0 (C$_q$), 142.5 (C$_q$), 146.5 (C$_q$); HRMS (EI-MS): calculated for C$_{22}$H$_{26}$N$_4$O m/z=361.20229. found m/z=361.20237.

(R)-[3-[3-[1-[quinuclidin-3-yl]-1H-1,2,3-triazol-4-yl]phenyl]phenyl]methanol (99)

The product was isolated in the form of a white solid with a yield of 80% by following the general procedure E1. R$_f$: 0.18 (CH$_2$Cl$_2$/MeOH/NH$_4$OH: 97/3/1); Mp: 201° C.; IR (ATR, Diamond): ν (cm$^{-1}$): 793, 984, 1042, 1262, 1326, 1423, 1436, 1612, 1697, 1719, 2870, 2943, 3133; $^1$H NMR (400 MHz, DMSO-d$_6$) δ (ppm) 1.34-1.48 (m, 2H), 1.69-1.75 (m, 2H), 2.20 (q, 1H, J=2.8 Hz), 2.75-2.79 (m, 3H), 2.94-3.01 (m, 1H), 3.35-3.48 (m, 2H), 4.58 (d, 2H, J=5.6 Hz), 4.72-4.79 (m, 1H), 5.25 (d, 1H, J=5.6 Hz), 7.34 (d, 1H, J=7.6 Hz), 7.44 (t, 1H, J=7.6 Hz), 7.51-7.63 (m, 3H), 7.66 (s, 1H), 7.87 (d, 1H, J=7.6 Hz), 8.14 (s, 1H), 8.85 (s, 1H); $^{13}$C NMR (100 MHz, DMSO-d$_6$): δ (ppm) 20.0 (CH$_2$), 25.7 (CH$_2$), 28.1 (CH), 46.8 (CH$_2$), 47.0 (CH$_2$), 52.2 (CH$_2$), 57.8 (CH), 63.3 (CH$_2$), 121.5 (CH), 123.8 (CH), 124.5 (CH), 125.2

(CH), 125.5 (CH), 126.2 (CH), 126.5 (CH), 129.1 (CH), 129.9 (CH), 131.9 ($C_q$), 140.1 ($C_q$), 141.3 ($C_q$), 143.7 ($C_q$), 146.5 ($C_q$); HRMS (EI-MS): calculated for $C_{22}H_{25}N_4O$ m/z=361.20229. found m/z=361.20245.

(R)-3-[4-[3-(6-fluoro-3-pyridyl)phenyl]-1H-1,2,3-triazol-1-yl]quinuclidine (100)

The product was isolated in the form of a white solid with a yield of 82% following the general procedure E1. $R_f$: 0.23 (CH$_2$Cl$_2$/MeOH/NH$_4$OH: 97/3/1); Mp: 164° C.; IR (ATR, Diamond): ν (cm$^{-1}$): 789, 980, 1061, 1208, 1344, 1454, 1473, 1590, 2865, 2940, 3059; $^1$H NMR (400 MHz, CDCl$_3$): δ (ppm) 1.42-1.55 (m, 1H), 1.65-1.70 (m, 1H), 1.75-1.87 (m, 2H), 2.30 (q, 1H, J=3.2 Hz), 2.88-2.97 (m, 3H), 3.12-3.19 (m, 1H), 3.51 (ddd, 1H, J=14.4 Hz, 9.8 Hz and 2.2 Hz), 3.72 (dd, 1H, J=14.4 Hz and 4.0 Hz), 4.66-4.68 (m, 1H), 7.01 (dd, 1H, J=8.4 Hz and 2.8 Hz), 7.48-7.54 (m, 2H), 7.82 (d, 1H, J=7.2 Hz), 7.89 (s, 1H), 8.01-8.06 (m, 2H), 8.46 (d, 1H, J=2.0 Hz); $^{13}$C NMR (100 MHz, CDCl$_3$): δ (ppm) 20.0 (CH$_2$), 25.9 (CH$_2$), 28.1 (CH), 46.9 (CH$_2$), 47.2 (CH$_2$), 52.6 (CH$_2$), 58.5 (CH), 109.4 (d, CH, J=37 Hz), 119.2 (CH), 124.3 (CH), 125.3 (CH), 126.7 (CH), 129.6 (CH), 131.6 ($C_q$), 134.5 (d, $C_q$, J=4 Hz), 137.4 ($C_q$), 139.8 (d, CH, J=8 Hz), 145.8 (d, CH, J=15 Hz), 147.0 ($C_q$), 163.2 (d, $C_q$, J=238 Hz); HRMS (EI-MS): calculated for $C_{20}H_{21}N_5F$ m/z=350.17755. found m/z=350.17766.

(R)-3-[4-(5-phenyl-2-thienyl)-1H-1,2,3-triazol-1-yl]quinuclidine (106)

The product was isolated in the form of a white solid with a yield of 80% by following the general procedure E1. $R_f$: 0.25 (CH$_2$Cl$_2$/MeOH/NH$_4$OH: 98/2/1); Mp: 184° C.; IR (ATR, Diamond): ν (cm$^{-1}$): 789, 982, 1060, 1209, 1323, 1404, 1455, 1498, 1590, 2866, 2940, 3059; $^1$H NMR (400 MHz, CDCl$_3$): δ (ppm) 1.43-1.55 (m, 1H), 1.62-1.80 (m, 3H), 2.28 (q, 1H, J=2.8 Hz), 2.85-3.03 (m, 3H), 3.12-3.19 (m, 1H), 3.50 (ddd, 1H, J=14.4 Hz, 10.0 Hz and 2.8 Hz), 4.70 (dd, 1H, J=14.4 Hz and 4.0 Hz), 4.62-4.65 (m, 1H), 7.27-7.32 (m, 2H), 7.35-7.41 (m, 3H), 7.63 (t, 2H, J=7.6 Hz), 7.75 (s, 1H); $^{13}$C NMR (100 MHz, CDCl$_3$): δ (ppm) 20.0 (CH$_2$), 26.0 (CH$_2$), 28.1 (CH), 46.9 (CH$_2$), 47.2 (CH$_2$), 52.6 (CH$_2$), 58.3 (CH), 118.4 (CH), 123.5 (CH), 124.9 (CH), 125.6 (2CH), 127.6 (CH), 128.9 (2CH), 132.2 ($C_q$), 134.0 ($C_q$), 142.6 ($C_q$), 143.8 ($C_q$); HRMS (EI-MS): calculated for $C_{19}H_{21}N_4S$ m/z=337.148144. found m/z=337.148472.

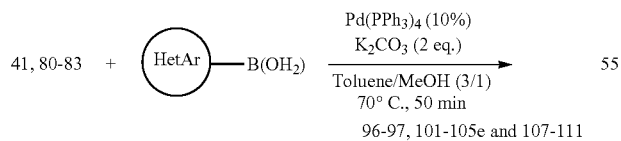

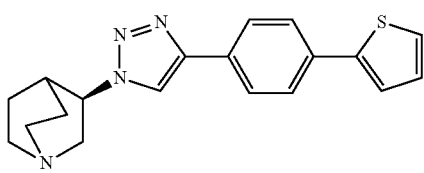

96

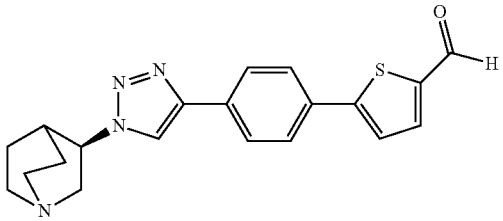

97

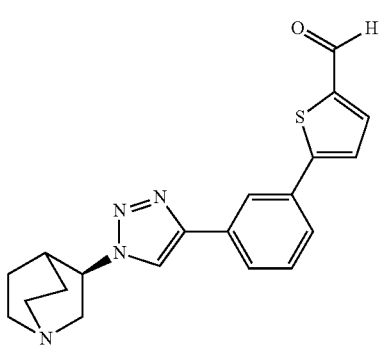

101

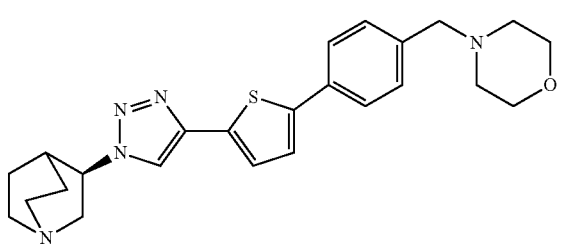

102

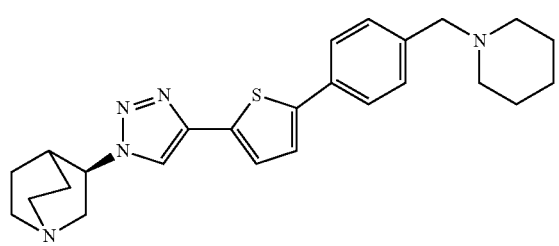

103

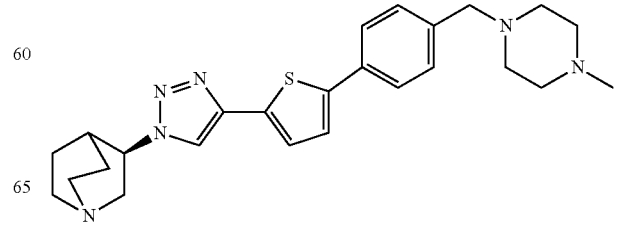

104

83

-continued

105

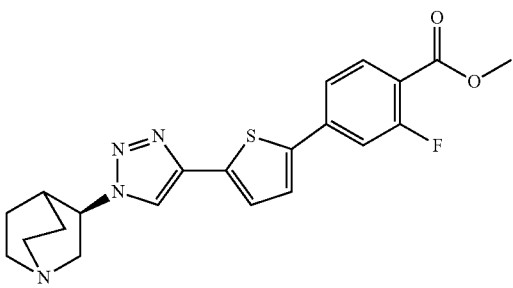

107

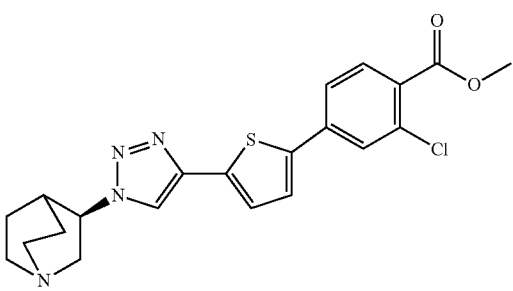

108

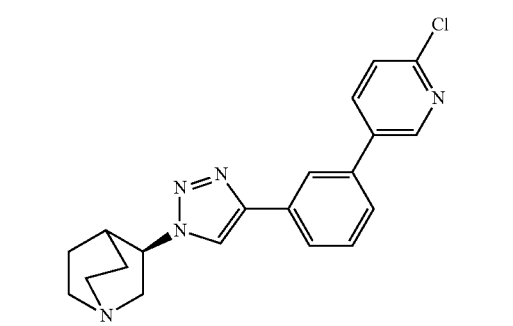

109

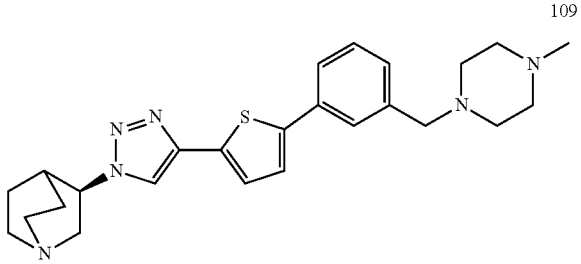

110

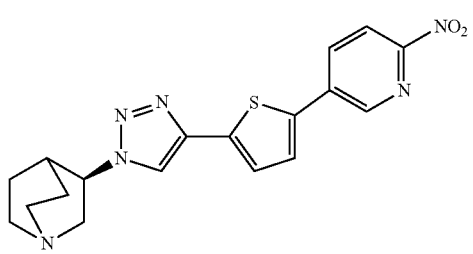

84

-continued

111

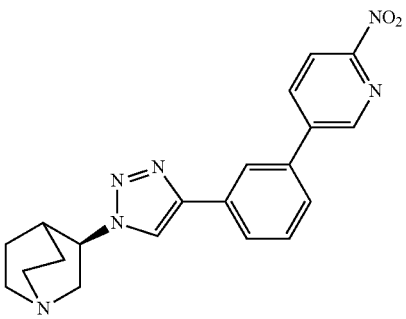

General Procedure E2:

To a solution of a brominated derivative (compound 41, 54, 80, 81, 82 or 83) (1.0 mmol) in a mixture of 3 mL of toluene and 1 mL of methanol, the following were added: the desired boronic acid (1.2 mmol), $K_2CO_3$ (2.0 mmol) and [1,1-bis(diphenylphosphino)ferrocene]dichloropalladium (II) $PdCl_2(dppf)$ (0.01 mmol). After degassing, the reaction mixture was irradiated by microwave at 70° C. for a period of 50 minutes. The solvent was evaporated and then the residue was purified by column chromatography on silica gel with the eluent used being a mixture of $CH_2Cl_2$/MeOH/ $NH_4OH$.

(R)-3-[4-[4-(2-thienyl)phenyl]-1H-1,2,3-triazol-1-yl] quinuclidine (96)

The product was isolated in the form of a white solid with a yield of 86% by following the general procedure E2. $R_f$: 0.17 ($CH_2Cl_2$/MeOH/$NH_4OH$: 97/3/1); Mp: 214° C.; IR (ATR, Diamond): ν ($cm^{-1}$): 791, 988, 1042, 1222, 1314, 1404, 1450, 1493, 2867, 2937, 3120; $^1$H NMR (400 MHz, $CDCl_3$): δ (ppm) 1.45-1.54 (m, 1H), 1.65-1.83 (m, 3H), 2.29 (q, 1H, J=2.8 Hz), 2.87-3.01 (m, 3H), 3.12-3.20 (m, 1H), 3.50 (ddd, 1H, J=14.4 Hz, 10.0 Hz and 3.2 Hz), 3.72 (dd, 1H, J=14.4 Hz and 3.2 Hz), 4.64-4.66 (m, 1H), 7.10 (dd, 1H, J=5.0 Hz and 3.6 Hz), 7.29 (dd, 1H, J=5.0 Hz and 1.2 Hz), 7.33-7.37 (m, 1H), 7.68 (d, 2H, J=8.4 Hz), 7.83-7.87 (m, 3H); $^{13}$C NMR (100 MHz, $CDCl_3$): δ (ppm) 20.0 ($CH_2$) 26.0 ($CH_2$), 28.1 (CH), 46.9 ($CH_2$), 47.3 ($CH_2$), 52.6 ($CH_2$), 58.4 (CH), 118.9 (CH), 123.2 (CH), 124.9 (CH), 126.0 (2CH), 126.2 (2CH), 128.1 (CH), 129.6 ($C_q$), 134.1 ($C_q$), 143.9 ($C_q$), 147.1 ($C_q$); HRMS (EI-MS): calculated for $C_{19}H_{21}N_4S$ m/z=337.14814. found m/z=337.14848.

(R)-5-[4-[1-[quinuclidin-3-yl]-1H-1,2,3-triazol-4-yl] phenyl]thiophene-2-carbaldehyde (97)

The product was isolated in the form of a white solid with a yield of 83% by following the general procedure E2. $R_f$: 0.19 ($CH_2Cl_2$/MeOH/$NH_4OH$: 97/3/1); Mp: 228° C.; IR (ATR, Diamond): ν ($cm^{-1}$): 806, 972, 1041, 1223, 1315, 1404, 1450, 1660, 2868, 2938, 3117; $^1$H NMR (400 MHz, $CDCl_3$): δ (ppm) 1.42-1.54 (m, 1H), 1.65-1.74 (m, 1H), 1.77-1.88 (m, 2H), 2.29 (q, 1H, J=3.2 Hz), 2.86-3.00 (m, 3H), 3.11-3.18 (m, 1H), 3.50 (ddd, 1H, J=14.4 Hz, 10.0 Hz and 3.6 Hz), 3.71 (dd, 1H, J=14.4 Hz and 3.6 Hz), 4.64-4.67 (m, 1H), 7.42 (d, 1H, J=4.0 Hz), 7.71-7.74 (m, 3H), 7.88-7.91 (m, 3H), 9.88 (s, 1H); $^{13}$C NMR (100 MHz, $CDCl_3$): δ (ppm) 20.0 ($CH_2$), 26.0 ($CH_2$), 28.1 (CH), 46.9 ($CH_2$), 47.2 ($CH_2$), 52.6 ($CH_2$), 58.5 (CH), 119.4 (CH), 124.1 (CH), 126.2 (2CH), 126.8 (2CH), 131.7 ($C_q$), 132.6 ($C_q$), 137.4 (CH), 142.4 ($C_q$), 146.6 ($C_q$), 153.6 ($C_q$), 182.7 (CH);

HRMS (EI-MS): calculated for $C_{20}H_{21}N_4SO$ m/z=365.14306. found m/z=365.14334.

(R)-5-[3-[1-[quinuclidin-3-yl]-1H-1,2,3-triazol-4-yl]phenyl]thiophene-2-carbaldehyde (101)

The product was isolated in the form of a white solid with a yield of 80% by following the general procedure E2. $R_f$: 0.24 ($CH_2Cl_2$/MeOH/$NH_4$OH: 97/3/1); Mp: 150° C.; IR (ATR, Diamond): ν ($cm^{-1}$): 792, 986, 1070, 1223, 1316, 1405, 1450, 1659, 2868, 2938, 3120; $^1$H NMR (400 MHz, CDCl$_3$): δ (ppm)) 1.46-1.56 (m, 1H), 1.66-1.90 (m, 3H), 2.29 (q, 1H, J=2.8 Hz), 2.88-3.02 (m, 3H), 3.13-3.20 (m, 1H), 3.50 (ddd, 1H, J=14.4 Hz, 10.0 Hz and 3.6 Hz), 3.71 (dd, 1H, J=14.4 Hz and 4.2 Hz), 4.67-4.69 (m, 1H), 7.47-7.51 (m, 2H), 7.63 (d, 1H, J=7.2 Hz), 7.76 (d, 1H, J=4.2 Hz), 7.85 (d, 1H, J=8.0 Hz), 7.91 (s, 1H), 8.17 (s, 1H), 9.91 (s, 1H); $^{13}$C NMR (100 MHz, CDCl$_3$): δ (ppm) 20.0 ($CH_2$), 25.9 ($CH_2$), 28.1 (CH), 46.9 ($CH_2$), 47.2 ($CH_2$), 52.6 ($CH_2$), 58.5 (CH), 119.4 (CH), 123.5 (CH), 124.5 (CH), 126.0 (CH), 126.5 (CH), 129.7 (CH), 131.7 ($C_q$), 133.6 ($C_q$), 137.3 (CH), 142.6 ($C_q$), 146.7 ($C_q$), 153.7 ($C_q$), 182.7 (CH); HRMS (EI-MS): calculated for $C_{20}H_{21}N_4SO$ m/z=365.14306. found m/z=365.14324.

(R)-4-[4-[5-[1-[quinuclidin-3-yl]-1H-1,2,3-triazol-4-yl]-2-thienyl]phenyl]methyl]morpholine (102)

The product was isolated in the form of a white solid with a yield of 83% by following the general procedure E2. $R_f$: 0.21 ($CH_2Cl_2$/MeOH/$NH_4$OH: 97/3/1); Mp: 222° C.; IR (ATR, Diamond): ν ($cm^{-1}$): 791, 987, 1040, 1220, 1345, 1451, 1498, 1662, 2803, 2868, 2938; $^1$H NMR (400 MHz, CDCl$_3$): δ (ppm) 1.41-1.53 (m, 1H), 1.62-1.86 (m, 3H), 2.27 (q, 1H, J=2.8 Hz), 2.45-2.28 (m, 4H), 2.28-3.00 (m, 3H), 3.10-3.19 (m, 1H), 3.46-3.50 (m, 3H), 3.66-3.72 (m, 5H), 4.61-4.64 (m, 1H), 7.27 (d, 1H, J=8.0 Hz), 7.33-7.36 (m, 3H), 7.57 (d, 2H, J=8.0 Hz), 7.73 (s, 1H); $^{13}$C NMR (100 MHz, CDCl$_3$): δ (ppm) 20.0 ($CH_2$), 26.0 ($CH_2$), 28.1 (CH), 46.9 ($CH_2$), 47.2 ($CH_2$), 52.6 ($CH_2$), 53.6 (2$CH_2$), 58.5 (CH), 63.0 ($CH_2$), 37.0 (2$CH_2$), 118.3 (CH), 123.4 (CH), 124.9 (CH), 125.5 (2CH), 129.7 (2CH), 132.0 ($C_q$), 133.0 ($C_q$), 137.4 ($C_q$), 142.6 (Cq), 143.6 ($C_q$); HRMS (EI-MS): calculated for $C_{24}H_{30}N_5OS$ m/z=436.216558. found m/z=436.216563.

(R)-3-[4-[5-[4-(1-piperidylmethyl)phenyl]-2-thienyl]-1H-1,2,3-triazol-1-yl]quinuclidine (103)

The product was isolated in the form of a white solid with a yield of 80% by following the general procedure E2. $R_f$: 0.21 ($CH_2Cl_2$/MeOH/$NH_4$OH: 97/3/1); Mp: 230° C.; IR (ATR, Diamond): ν ($cm^{-1}$): 792, 995, 1103, 1215, 1366, 1415, 1451, 1662, 2866, 2934, 3120; $^1$H NMR (400 MHz, CDCl$_3$): δ (ppm) 1.38-1.52 (m, 3H), 1.56-1.62 (m, 4H), 1.64-1.88 (m, 3H), 2.28 (q, 1H, J=2.8 Hz), 2.32-2.49 (m, 4H), 2.86-3.01 (m, 3H), 3.11-3.18 (m, 1H), 3.45-3.52 (m, 3H), 3.69 (dd, 1H, J=14.4 Hz and 5.2 Hz), 4.62-4.64 (m, 1H), 7.27 (d, 1H, J=8.0 Hz), 7.33-7.35 (m, 3H), 7.57 (d, 2H, J=8.0 Hz), 7.74 (s, 1H); $^{13}$C NMR (100 MHz, CDCl$_3$): δ (ppm) 20.0 ($CH_2$), 24.3 ($CH_2$), 25.9 (2$CH_2$), 26.0 ($CH_2$), 28.1 (CH), 46.9 ($CH_2$), 47.2 ($CH_2$), 52.6 ($CH_2$), 54.5 (2$CH_2$), 58.5 (CH), 63.4 ($CH_2$), 118.3 (CH), 123.2 (CH), 124.9 (CH), 125.4 (2CH), 129.7 (2CH), 131.8 ($C_q$), 132.6 ($C_q$), 138.3 ($C_q$), 142.6 ($C_q$), 143.8 ($C_q$); HRMS (EI-MS): calculated for $C_{25}H_{32}N_5S$ m/z=434.237293. found m/z=434.237451.

(R)-3-[4-[5-[4-[(4-methylpiperazin-1-yl)methyl]phenyl]-2-thienyl]-1H-1,2,3-triazol-1-yl]quinuclidine (104)

The product was isolated in the form of a white solid with a yield of 75% by following the general procedure E2. $R_f$: 0.20 ($CH_2Cl_2$/MeOH/$NH_4$OH: 97/3/1); Mp: 214° C.; IR (ATR, Diamond): ν ($cm^{-1}$): 792, 973, 1040, 1222, 1347, 1450, 1661, 2869, 2939, 3120; $^1$H NMR (400 MHz, CDCl$_3$): δ (ppm) 1.42-1.53 (m, 1H), 1.62-1.85 (m, 3H), 2.27-2.70 (m, 12H), 2.84-3.00 (m, 3H), 3.10-3.18 (m, 1H), 3.45-3.52 (m, 3H), 3.69 (dd, 1H, J=14.4 Hz and 5.2 Hz), 4.61-4.64 (m, 1H), 7.27 (d, 1H, J=8.0 Hz), 7.33-7.35 (m, 3H), 7.57 (d, 2H, J=8.0 Hz), 7.74 (s, 1H); $^{13}$C NMR (100 MHz, CDCl$_3$): δ (ppm) 20.0 ($CH_2$), 26.0 ($CH_2$), 28.1 (CH), 46.0 ($CH_3$), 46.9 ($CH_2$), 47.2 ($CH_2$), 52.6 (2$CH_2$), 53.1 (2$CH_2$), 55.1 ($CH_2$), 58.5 (CH), 62.6 ($CH_2$), 118.3 (CH), 123.3 (CH), 124.9 (CH), 125.5 (2CH), 129.7 (2CH), 131.9 ($C_q$), 132.8 ($C_q$), 137.9 ($C_q$), 142.6 (Cq), 143.7 ($C_q$); HRMS (EI-MS): calculated for $C_{25}H_{33}N_6S$ m/z=449.248193. found m/z=449.248404.

Methyl-2-fluoro-4-[5-[1-[(3R)-quinuclidin-3-yl]-1H-1,2,3-triazol-4-yl]-2-thienyl]benzoate (105)

The product was isolated in the form of a white solid with a yield of 85% by following the general procedure E2. $R_f$: 0.20 ($CH_2Cl_2$/MeOH/$NH_4$OH: 97/3/1); Mp: 250° C.; IR (ATR, Diamond): ν ($cm^{-1}$): 785, 926, 1090, 1262, 1326, 1422, 1472, 1612, 1703, 1718, 2870, 2943, 3133; $^1$H NMR (250 MHz, CDCl$_3$): δ (ppm) 1.30-1.52 (m, 2H), 1.63-1.81 (m, 2H), 2.20 (q, 1H, J=2.8 Hz), 2.71-3.03 (m, 4H), 3.33-3.50 (m, 2H), 3.87 (s, 3H), 4.71-4.83 (m, 1H), 7.51 (d, 1H, J=3.5 Hz), 7.62 (d, 1H, J=8.0 Hz), 7.70-7.81 (m, 2H), 7.93 (t, 1H, J=8.0 Hz), 8.76 (s, 1H); $^{13}$C NMR (62.5 MHz, CDCl$_3$): δ (ppm) 19.6 ($CH_2$), 25.4 ($CH_2$), 27.9 CH), 46.5 ($CH_2$), 46.8 ($CH_2$), 51.8 ($CH_2$), 52.3 ($CH_3$), 58.3 (CH), 113.2 (d, CH, J=38 Hz), 116.7 (d, $C_q$, J=10 Hz), 119.5 (CH), 120.9 (d, CH, J=6 Hz), 125.5 (CH), 125.9 (CH), 132.8 (CH), 134.1 ($C_q$), 140.4 (d, $C_q$, J=15 Hz), 140.9 (d, $C_q$, J=3 Hz), 142.2 ($C_q$), 162.3 (d, $C_q$, J=258 Hz), 164.7 (d, $C_q$, J=4 Hz); HRMS (EI-MS): calculated for $C_{21}H_{22}N_4O_2FS$ m/z=413.144202. found m/z=413.144364.

Methyl-2-chloro-4-[5-[1-[(3R)-quinuclidin-3-yl]-1H-1,2,3-triazol-4-yl]-2-thienyl]benzoate (107)

The product was isolated in the form of a white solid with a yield of 79% by following the general procedure E2. $R_f$: 0.20 ($CH_2Cl_2$/MeOH/$NH_4$OH: 97/3/1); Mp: 200° C.; IR (ATR, Diamond): ν ($cm^{-1}$): 792, 988, 1028, 1131, 1283, 1433, 1446, 1594, 1701, 2867, 2936, 3134; $^1$H NMR (400 MHz, CDCl$_3$): δ (ppm) 1.43-1.55 (m, 1H), 1.62-1.88 (m, 3H), 2.28 (q, 1H, J=2.8 Hz), 2.87-3.00 (m, 3H), 3.08-3.20 (m, 1H), 3.48 (ddd, 1H, J=14.4 Hz, 10.0 Hz and 2.8 Hz), 3.69 (dd, 1H, J=14.4 Hz and 4.2 Hz), 3.92 (s, 3H), 4.64-4.67 (m, 1H), 7.36 (s, 2H), 7.51 (dd, 1H, J=8.0 Hz and 1.2 Hz), 7.67 (s, 1H), 7.78 (s, 1H), 7.87 (d, 1H, J=8.0 Hz); $^{13}$C NMR (100 MHz, CDCl$_3$): δ (ppm) 19.9 ($CH_2$), 25.8 ($CH_2$), 28.1 (CH), 46.9 ($CH_2$), 47.2 ($CH_2$), 52.4 ($CH_3$), 52.5 ($CH_2$), 58.5 (CH), 118.8 (CH), 123.3 (CH), 125.1 (CH), 125.6 (CH), 127.6 (CH), 127.8 ($C_q$), 132.3 (CH), 134.4 ($C_q$), 134.7 ($C_q$), 138.4 ($C_q$), 140.5 ($C_q$), 142.1 ($C_q$), 165.5 ($C_q$); HRMS (EI-MS): calculated for $C_{21}H_{22}N_4ClO_2S$ M z 429.114651. found m/z=429.114907.

(R)-3-[4-[3-(6-chloro-3-pyridyl) phenyl]-1H-1,2,3-triazol-1-yl]quinuclidine (108)

The product was isolated in the form of a white solid with a yield of 20% by following the general procedure E2. $R_f$:

0.17 (CH$_2$Cl$_2$/MeOH/NH$_4$OH: 98/2/1); Mp (decom): 80° C.; IR (ATR, Diamond): ν (cm$^{-1}$): 831, 987, 1039, 1233, 1343, 1403, 1455, 1581, 2865, 2938, 3053; $^1$H NMR (400 MHz, CDCl$_3$): δ (ppm) 1.43-1.56 (m, 1H), 1.66-1.70 (m, 1H), 1.77-1.90 (m, 2H), 2.31 (q, 1H, J=3.0 Hz), 2.88-3.02 (m, 3H), 3.11-3.21 (m, 1H), 3.51 (ddd, 1H, J=14.4 Hz, 9.8 Hz and 2.2 Hz), 3.72 (dd, 1H, J=14.4 Hz and 3.6 Hz), 4.67-4.69 (m, 1H), 7.42 (d, 1H, J=8.4 Hz), 7.52-7.56 (m, 2H), 7.82 (dt, 1H, J=8.4 Hz and 1.2 Hz), 7.90-7.93 (m, 2H), 8.08 (s, 1H), 8.66 (d, 1H, J=2.4 Hz); $^{13}$C NMR (100 MHz, CDCl$_3$): δ (ppm) 20.0 (CH$_2$), 25.9 (CH$_2$), 28.1 (CH), 46.9 (CH$_2$), 47.2 (CH$_2$), 52.6 (CH$_2$), 58.5 (CH), 119.3 (CH), 124.2 (CH), 124.3 (CH), 125.6 (CH), 126.7 (CH), 129.7 (CH), 131.6 (C$_q$), 135.3 (C$_q$), 137.1 (Cq), 137.2 (CH), 146.9 (C$_q$), 147.9 (CH), 150.5 (C$_q$); HRMS (EI-MS): calculated for C$_{20}$H$_{21}$N$_5$Cl m/z=366.1480. found m/z=366.148142.

(R)-3-[4-[5-[3-[(4-methylpiperazin-1-yl)methyl]phenyl]-2-thienyl]-1H-1,2,3-triazol-1-yl]quinuclidine (109)

The product was isolated in the form of a white solid with a yield of 83% by following the general procedure E2. R$_f$: 0.20 (CH$_2$Cl$_2$/MeOH/NH$_4$OH: 97/3/1); Mp: 155° C.; IR (ATR, Diamond): ν (cm$^{-1}$): 788, 923, 1013, 1279, 1347, 1453, 1506, 2793, 2870, 2938, 3306; $^1$H NMR (400 MHz, CDCl$_3$): δ (ppm) 1.42-1.60 (m, 1H), 1.65-1.92 (m, 3H), 2.24-2.32 (m, 4H), 2.37-2.73 (m, 8H), 2.86-2.99 (m, 3H), 3.08-3.22 (m, 1H), 3.45-3.56 (m, 3H), 3.70 (dd, 1H, J=14.5 Hz and 5.2 Hz), 4.60-4.70 (m, 1H), 7.26-7.38 (m, 4H), 7.54 (d, 1H, J=7.5 Hz), 7.61 (m, 1H), 7.76 (s, 1H); $^{13}$C NMR (100 MHz, CDCl$_3$): δ (ppm) 20.0 (CH$_2$), 26.0 (CH$_2$) 28.1 (CH), 46.0 (CH$_3$), 46.9 (CH$_2$), 47.2 (CH$_2$), 52.6 (CH$_2$), 53.1 (2CH$_2$), 55.1 (2CH), 58.5 (CH), 62.8 (CH$_2$), 118.3 (CH), 123.6 (CH), 124.4 (CH), 124.8 (CH), 126.3 (CH), 128.4 (CH), 128.8 (CH), 132.1 (C$_q$), 133.9 (C$_q$), 139.1 (C$_q$), 142.6 (C$_q$), 143.8 (C$_q$); HRMS (EI-MS): calculated for C$_{25}$H$_{33}$N$_6$S m/z=449.248193. found m/z=449.247898.

(R)-3-[4-[5-(6-nitro-3-pyridyl)-2-thienyl]-1H-1,2,3-triazol-1-yl]quinuclidine (110)

The product was isolated as a white solid with a yield of 77% by following the general procedure E2. R$_f$: 0.19 (CH$_2$Cl$_2$/MeOH/NH$_4$OH: 98/2/1); Mp: 160° C.; IR (ATR, Diamond): ν (cm$^{-1}$): 788, 987, 1013, 1216, 1278, 1347, 1413, 1453, 1528, 2794, 2938, 3307; $^1$H NMR (250 MHz, CDCl$_3$): δ (ppm) 1.48-1.57 (m, 1H), 1.65-1.69 (m, 1H), 1.73-1.90 (m, 2H), 2.30 (q, 1H, J=2.8 Hz), 2.85-3.02 (m, 3H), 3.09-3.19 (m, 1H), 3.49 (ddd, 1H, J=14.4 Hz, 10.0 Hz and 2.8 Hz), 3.70 (dd, 1H, J=14.4 Hz and 4.4 Hz), 4.63-4.71 (m, 1H), 7.45 (d, 1H, J=3.2 Hz), 7.54 (d, 1H, J=3.2 Hz), 7.84 (s, 1H), 8.17 (d, 1H, J=8.2 Hz), 8.31 (d, 1H, J=8.2 Hz), 8.88 (s, 1H); $^{13}$C NMR (100 MHz, CDCl$_3$): δ (ppm) 20.0 (CH$_2$), 26.0 (CH$_2$), 28.1 (CH), 46.9 (CH$_2$), 47.2 (CH$_2$), 52.6 (CH$_2$), 58.3 (CH), 118.5 (CH), 119.0 (CH), 125.4 (CH), 127.3 (CH), 135.2 (CH), 135.7 (C$_q$), 136.6 (C$_q$), 136.7 (C$_q$), 141.6 (C$_q$), 145.0 (CH), 155.0 (C$_q$); HRMS (EI-MS): calculated for C$_{18}$H$_{19}$N$_6$O$_2$S m/z=383.128471. found m/z=383.128544.

(R)-3-[4-[3-(6-nitro-3-pyridyl) phenyl]-1H-1,2,3-triazol-1-yl]quinuclidine (111)

The product was isolated in the form of a white solid with a yield of 80% by following the general procedure E2. R$_f$: 0.23 (CH$_2$Cl$_2$/MeOH/NH$_4$OH: 98/2/1); Mp: 180° C.; IR (ATR, Diamond): ν (cm$^{-1}$): 793, 984, 1016, 1159, 1346, 1455, 1526, 2795, 2870, 2938; $^1$H NMR (250 MHz, CDCl$_3$): δ (ppm) 1.45-1.64 (m, 1H), 1.67-1.94 (m, 3H), 2.33 (q, 1H, J=2.8 Hz), 2.88-3.02 (m, 3H), 3.12-3.22 (m, 1H), 3.55 (ddd, 1H, J=14.5 Hz, 10.0 Hz and 2.8 Hz), 3.76 (dd, 1H, J=14.5 Hz and 4.4 Hz), 4.65-4.77 (m, 1H), 7.63 (d, 2H, J=4.5 Hz), 7.95 (s, 2H), 8.22-8.40 (m, 3H), 8.92 (s, 1H); $^{13}$C NMR (100 MHz, CDCl$_3$): δ (ppm) 20.0 (CH$_2$), 26.0 (CH$_2$) 28.2 (CH), 46.9 (CH$_2$), 47.2 (CH$_2$), 52.6 (CH$_2$), 58.6 (CH), 118.2 (CH), 119.4 (CH), 124.6 (CH), 126.7 (CH), 127.0 (CH), 130.0 (CH), 132.0 (C$_q$), 136.0 (C$_q$), 137.9 (CH), 142.1 (C$_q$), 146.5 (C$_q$), 147.2 (CH), 155.8 (C$_q$); HRMS (EI-MS): calculated for C$_{20}$H$_{21}$N$_6$O$_2$ m/z=377.172050. found m/z=377.172021.

Fluorination of Alcohols 63 and 85

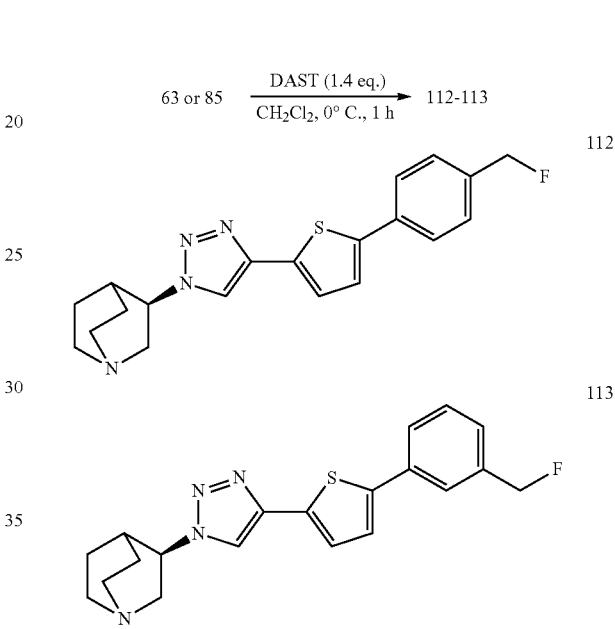

General Procedure H:

The alcohol derivative 63 or 85 (0.500 mmol) was dissolved in 10 mL of dichloromethane and then at 0° C., diethylaminosulfur trifluoride (0.700 mmol) was added therein drop by drop. The reaction mixture was stirred at 0° C. for a period of one hour and then hydrolysed by the addition of a saturated NaHCO$_3$ solution. The organic phase was dried over anhydrous MgSO$_4$, filtered and then concentrated under reduced pressure. The corresponding fluorinated compound (112 or 113) was purified by column chromatography on silica gel with the eluent used being a mixture of CH$_2$Cl$_2$/MeOH/NH$_4$OH.

(R)-3-[4-[5-[4-(fluoromethyl)phenyl]-2-thienyl]-1H-1,2,3-triazol-1-yl]quinuclidine (112)

The product was isolated in the form of a white solid with a yield of 45% by following the general procedure H. R$_f$: 0.25 (CH$_2$Cl$_2$/MeOH/NH$_4$OH: 98/2/1); Mp: 199° C.; IR (ATR, Diamond): ν (cm$^{-1}$): 962, 1042, 1060, 1219, 1376, 1414, 1454, 1502, 1601, 2163, 2321, 2937; $^1$H NMR (400 MHz, CDCl$_3$): δ (ppm) 1.45-1.54 (m, 1H), 1.66-1.70 (m, 1H), 1.77-1.90 (m, 2H), 2.30 (q, 1H, J=3.2 Hz), 2.88-2.98 (m, 3H), 3.12-3.19 (m, 1H), 3.50 (ddd, 1H, J=14.4 Hz, 9.6 Hz and 2.0 Hz), 3.71 (dd, 1H, J=14.4 Hz and 3.6 Hz), 4.64-4.67 (m, 1H), 5.40 (d, 2H, J=47.6 Hz), 7.31 (d, 1H, J=3.6 Hz), 7.36 (d, 1H, J=3.6 Hz), 7.40 (dd, 2H, J=8.0 Hz and 1.2 Hz), 7.64 (d, 2H, J=8.0 Hz), 7.75 (s, 1H); $^{13}$C NMR (100 MHz, CDCl$_3$): δ (ppm) 20.0 (CH$_2$), 25.9 (CH$_2$), 28.1 (CH), 46.9 (CH$_2$), 47.2 (CH$_2$), 52.6 (CH$_2$), 58.5 (CH), 84.2 (d, CH$_2$, J=166 Hz), 118.4 (CH), 123.9 (CH), 124.9 (CH), 125.8 (2CH), 128.2 (d, 2 CH, J=6 Hz), 132.6 (C$_q$), 134.5 (d, C$_q$, J=4 Hz), 135.4 (d, C$_q$, J=17 Hz), 142.5 (C$_q$), 143.1 (C$_q$); HRMS (EI-MS): calculated for C$_{20}$H$_{22}$N$_4$FS m/z=369.15437. found m/z=369.15433.

(R)-3-[4-[5-[3-(fluoromethyl)phenyl]-2-thienyl]-1H-1,2,3-triazol-1-yl]quinuclidine (113)

The product was isolated in the form of a white solid with a yield of 39% by following the general procedure H. R$_f$: 0.25 (CH$_2$Cl$_2$/MeOH/NH$_4$OH: 98/2/1); Mp: 144° C.; IR (ATR, Diamond): ν (cm$^{-1}$): 792, 971, 1041, 1211, 1364, 1452, 1588, 1606, 2165, 2869, 2939; $^1$H NMR (400 MHz, CDCl$_3$): δ (ppm) 1.46-1.54 (m, 1H), 1.65-1.80 (m, 3H), 2.27-2.31 (m, 1H), 2.88-2.98 (m, 3H), 3.11-3.18 (m, 1H), 3.50 (ddd, 1H, J=14.4 Hz, 9.6 Hz and 2.0 Hz), 3.71 (dd, 1H, J=14.4 Hz and 3.6 Hz), 4.62-4.66 (m, 1H), 5.43 (d, 2H, J=47.6 Hz), 7.29-7.31 (m, 2H), 7.36 (d, 1H, J=3.6 Hz), 7.42 (t, 1H, J=7.6 Hz), 7.61-7.63 (m, 2H), 7.76 (s, 1H); $^{13}$C NMR (100 MHz, GPM): δ (ppm) 20.0 (CH$_2$), 26.0 (CH$_2$), 28.1 (CH), 46.9 (CH$_2$), 47.2 (CH$_2$), 52.6 (CH$_2$), 58.5 (CH), 84.3 (d, CH$_2$, J=166 Hz), 118.5 (CH), 123.9 (CH), 124.5 (d, CH, J=6 Hz), 124.9 (CH), 125.9 (d, CH, J=3 Hz), 126.4 (d, CH, J=6 Hz), 129.2 (CH), 132.6 (C$_q$), 134.4 (C$_q$), 137.0 (d, C$_q$, J=17 Hz), 142.5 (C$_q$), 143.1 (C$_q$); HRMS (EI-MS): calculated for C$_{20}$H$_{22}$N$_4$FS m/z=369.154372. found m/z=369.154471.

Reduction of Aldehydes 97 or 101

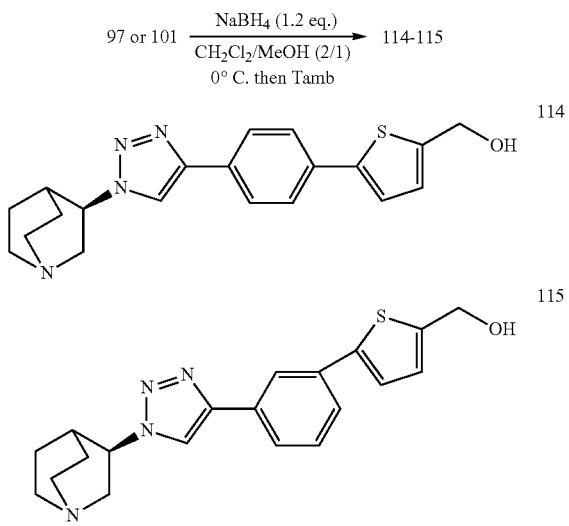

General Procedure I:

To a solution of the aldehyde derivative (1.0 mmol) in a mixture of 4 mL of dichloromethane and 2 mL of methanol, sodium borohydride (1.2 mmol) was slowly added at 0° C. The reaction mixture was then stirred at ambient temperature for a period of 15 minutes and then hydrolysed with the addition of 5 mL of water. 10 mL of dichloromethane was then added to the medium and the two phases were separated. The aqueous phase was extracted with 2×5 mL of dichloromethane. The organic phases were combined, dried over anhydrous MgSO$_4$, and filtered and evaporated under reduced pressure. The residue thus obtained was purified by column chromatography on silica gel with the eluent used being a mixture of CH$_2$Cl$_2$/MeOH/NH$_4$OH.

(R)-[5-[4-[1-[quinuclidin-3-yl]-1H-1,2,3-triazol-4-yl]phenyl]-2-thienyl]methanol (114)

The product was isolated in the form of a white solid with a yield of 85% by following the general procedure I. R$_f$: 0.12 (CH$_2$Cl$_2$/MeOH/NH$_4$OH: 97/3/1); Mp: 234° C.; IR (ATR, Diamond): ν (cm$^{-1}$): 791, 979, 1032, 1204, 1328, 1447, 1500, 1661, 2871, 2939, 3124; $^1$H NMR (400 MHz, CDCl$_3$): δ (ppm) 1.34-1.47 (m, 2H), 1.68-1.74 (m, 2H), 2.29 (q, 1H, J=2.8 Hz), 2.71-2.78 (m, 3H), 2.93-3.02 (m, 1H), 3.38 (m, 2H), 4.62 (d, 2H, J=5.2 Hz), 4.72-4.75 (m, 1H), 5.51 (t, 1H, J=5.2 Hz), 6.95 (d, 1H, J=3.6 Hz), 7.38 (d, 1H, J=3.6 Hz), 7.69 (d, 2H, J=8.4 Hz), 7.89 (d, 2H, J=8.4 Hz), 8.75 (m, 1H); $^{13}$C NMR (100 MHz, CDCl$_3$): δ (ppm) 20.0 (CH$_2$), 25.8 (CH$_2$), 28.1 (CH), 46.8 (CH$_2$), 47.0 (CH$_2$), 52.3 (CH$_2$), 57.9 (CH), 58.8 (CH$_2$), 121.3 (CH), 123.6 (CH), 125.7 (CH), 125.9 (2CH), 126.1 (2CH), 130.2 (C$_q$), 133.7 (C$_q$), 142.1 (C$_q$), 146.1 (C$_q$), 146.6 (C$_q$); HRMS (EI-MS): calculated for C$_{20}$H$_{23}$N$_4$SO m/z=367.15871. found m/z=367.15900.

(R)-[5-[3-[1-[quinuclidin-3-yl]-1H-1,2,3-triazol-4-yl]phenyl]-2-thienyl]-methanol (115)

The product was isolated in the form of a white solid with a yield of 82% by following the general procedure I. R$_f$: 0.16 (CH$_2$Cl$_2$/MeOH/NH$_4$OH: 97/3/1); Mp: 176° C.; IR (ATR, Diamond): ν (cm$^{-1}$): 795, 981, 1029, 1206, 1373, 1416, 1450, 1608, 2877, 2942, 3070; $^1$H NMR (400 MHz, CDCl$_3$): δ (ppm) 1.32-1.51 (m, 2H), 1.65-1.82 (m, 2H), 2.29 (q, 1H, J=2.8 Hz), 2.73-2.80 (m, 3H), 2.95-3.02 (m, 1H), 3.39-3.49 (m, 2H), 4.65 (s, 2H), 4.72-4.81 (m, 1H), 5.54 (bl, 1H), 6.98 (d, 1H, J=3.6 Hz), 7.42 (d, 1H, J=3.6 Hz), 7.47 (t, 1H, J=7.8 Hz), 7.57 (d, 1H, J=7.8 Hz), 7.80 (d, 1H, J=7.8 Hz), 8.11 (s, 1H), 8.85 (s, 1H); $^{13}$C NMR (100 MHz, CDCl$_3$): δ (ppm) 20.0 (CH$_2$), 25.7 (CH$_2$), 28.1 (CH), 46.8 (CH$_2$), 47.0 (CH$_2$), 52.3 (CH$_2$), 57.8 (CH), 58.8 (CH$_2$), 121.6 (CH), 122.0 (CH), 123.8 (CH), 124.4 (CH), 124.8 (CH), 125.6 (CH), 130.1 (CH), 132.0 (C$_q$), 135.0 (C$_q$), 142.1 (C$_q$), 146.1 (C$_q$), 146.8 (C$_q$); HRMS (EI-MS): calculated for C$_{20}$H$_{23}$N$_4$SO m/z=367.15871. found m/z=367.15892.

Chlorination of Alcohols 63 and 38

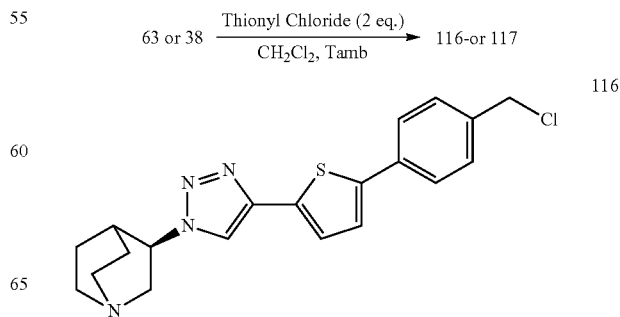

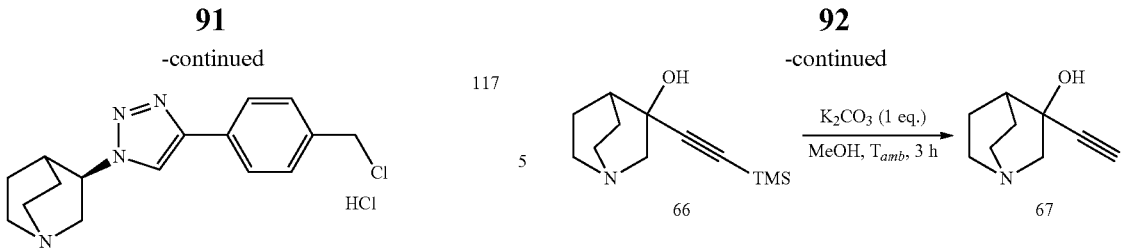

General Procedure J:

The alcohol derivative 63 or 38 (0.500 mmol) was dissolved in 10 mL of dichloromethane and then at 0° C., thionyl chloride (1.0 mmol) was added therein drop by drop, followed by a catalytic amount of dimethylformamide. The reaction mixture was then stirred at ambient temperature over a one night period. After evaporation of the solvent, the reaction mixture was washed with diethyl ether (5×10 mL). The precipitate thus formed was filtered and then dried under vacuum.

(R)-3-[4-[5-[4-(chloromethyl)phenyl]-2-thienyl]-1H-1,2,3-triazol-1-yl]quinuclidine, hydrochloride (116)

The product was isolated in the form of a beige solid with a yield of 96% by following the general procedure J. $R_f$: 0.3 ($CH_2Cl_2$/MeOH/$NH_4OH$: 98/2/1); Mp: 255° C.; IR (ATR, Diamond): ν ($cm^{-1}$): 797, 973, 1042, 1229, 1319, 1455, 1600, 1694, 2880, 3392; $^1H$ NMR (400 MHz, DMSO-$d_6$): (ppm) 1.56-1.87 (m, 2H), 1.95-2.14 (m, 2H), 2.52-2.55 (m, 1H), 3.20-3.50 (m, 4H), 3.87-3.06 (m, 2H), 4.80 (s, 2H), 5.16-5.32 (m, 1H), 7.42-7.60 (m, 4H), 7.67-7.78 (m, 2H), 8.87 (s, 1H), 11.20 (bl, 1H); $^{13}C$ NMR (100 MHz, DMSO-$d_6$): δ (ppm) 17.5 ($CH_2$), 21.6 ($CH_2$), 26.7 (CH), 45.6 ($CH_2$), 45.8 ($CH_2$), 46.3 ($CH_2$), 49.3 ($CH_2$), 55.1 (CH), 121.5 (CH), 125.3 (CH), 125.9 (2CH), 126.0 (CH), 130.2 (2CH), 132.8 ($C_q$), 133.8 ($C_q$), 137.5 ($C_q$), 142.2 ($C_q$), 142.3 ($C_q$); HRMS (EI-MS): calculated for $C_{20}H_{22}N_4SCl$ m/z=385.124822. found m/z=385.124944.

(R)-3-[4-[4-(chloromethyl)phenyl]-1H-1,2,3-triazol-1-yl]quinuclidine, hydrochloride (117)

The product was isolated in the form of a beige solid with a yield of 90% by following the general procedure J. $R_f$: 0.3 ($CH_2Cl_2$/MeOH/$NH_4OH$: 98/2/1); Mp: 240° C.; IR (ATR, Diamond): ν ($cm^{-1}$): 807, 973, 1040, 1210, 1319, 1455, 1613, 2560, 2956, 3398; $^1H$ NMR (400 MHz, DMSO-$d_6$): δ (ppm) 1.56-1.88 (m, 2H), 1.99-2.11 (m, 2H), 2.54-2.55 (m, 1H), 3.28-3.46 (m, 4H), 3.87-3.05 (m, 2H), 4.81 (s, 2H), 5.19-5.30 (m, 1H), 7.54 (d, 2H, J=8.2 Hz), 7.98 (d, 2H, J=8.2 Hz), 8.94 (s, 1H), 11.24 (bl, 1H); $^{13}C$ NMR (100 MHz, DMSO-$d_6$) δ (ppm) 17.5 ($CH_2$), 21.6 ($CH_2$), 26.7 (CH), 45.6 ($CH_2$), 45.8 ($CH_2$), 46.4 ($CH_2$), 49.3 ($CH_2$), 54.9 (CH), 122.2 (CH), 125.8 (2CH), 129.9 (2CH), 130.9 ($C_q$), 137.8 ($C_q$), 146.6 ($C_q$); HRMS (EI-MS): calculated for $C_{16}H_{20}N_4Cl$ m/z=303.137101. found m/z=303.1373213.

Preparation of a Precursor of Quinuclidine Type Compounds (Formula (III-1))

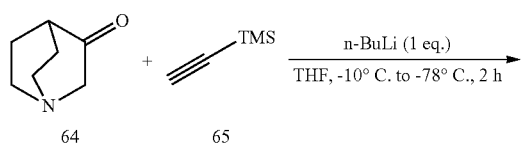

3-Ethynyl-3-hydroxyquinuclidine (67)

A solution of ethynyl(trimethyl)silane 65 (4.44 mL, 31.4 mmol) in 30 mL of THF was cooled to −10° C. and then 12.6 mL of a solution of n-BuLi (2.5 M in hexane) was added therein drop by drop. After 10 minutes of stirring at −10° C., the reaction medium was cooled to −78° C. and a solution of 3-quinuclidone 64 (3.74 g, 29.9 mmol) in 70 mL of THF was added therein. Upon completion of the addition, the cold bath was removed and the reaction mixture was allowed to return to ambient temperature. After an additional hour of reaction, it was hydrolysed with a saturated NaCl solution. The two phases were separated and the aqueous phase was extracted with ethyl acetate. The organic phases were combined, dried over anhydrous $MgSO_4$, and filtered and evaporated under reduced pressure.

The silyl derivative 66 (28.1 mmol) thus prepared was directly engaged in the deprotection reaction by means of stirring for a period of 3 hours in 60 ml of methanol in the presence $K_2CO_3$ (3.89 g, 28.1 mmol). The reaction medium was evaporated under reduced pressure and the residue was purified by column chromatography on silica gel with the eluent used being a mixture of $CH_2Cl_2$/MeOH/$NH_4OH$ (80/20/0.1). The product 67 was isolated in the form of a white solid with a yield of 43%. $R_f$: 0.35 ($CH_2Cl_2$/MeOH/$NH_4OH$: 80/20/0.1); Mp: 201° C.; IR (ATR, Diamond): ν ($cm^{-1}$): 989, 1024, 1048, 1071, 1138, 1154, 1317, 1455, 2596, 2754, 2873, 2934, 2950, 2965, 3216; $^1H$ NMR (250 MHz, MeOD): δ (ppm) 1.38-1.53 (m, 1H), 1.61-1.75 (m, 1H), 1.93-2.10 (m, 3H), 2.73-2.84 (m, 4H), 2.88 (d, 1H, J=13.8 Hz), 2.89 (s, 1H), 3.13 (d, 1H, J=13.8 Hz); $^{13}C$ NMR (100 MHz, MeOD): δ (ppm) 20 3 ($CH_2$), 24.2 ($CH_2$), 34.2 (CH), 46.9 ($CH_2$), 47.0 ($CH_2$), 65.0 ($CH_2$), 67.4 ($C_q$); MS (IS): m/z=152.8 $[MH]^+$.

Preparation of Quinuclidine Type Compounds 68-69 (Formula (III-1))

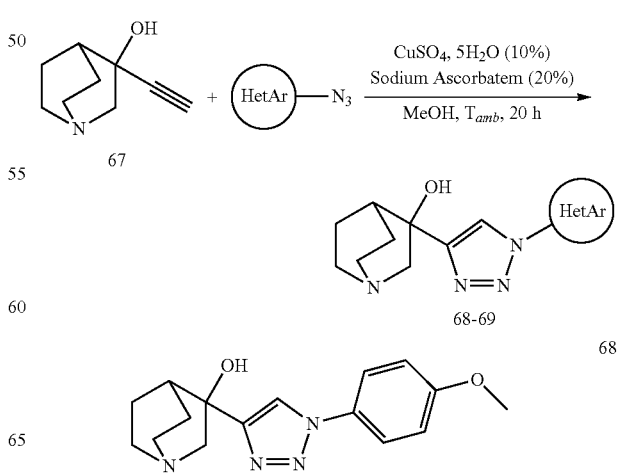

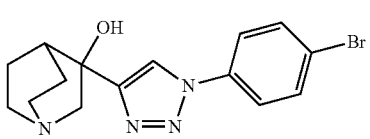

General Procedure F:

The alkyne 67 (151 mg, 1.00 mmol) was dissolved in 6 mL of methanol to which the following were then added successively: the desired azide (1.00 mmol), CuSO$_4$5H$_2$O (25 mg, 0.100 mmol) and sodium ascorbate (40 mg, 0.200 mmol). The reaction medium was stirred at ambient temperature for a period of 12 hours. At the end of the reaction time, the methanol was evaporated under reduced pressure and the residue was chromatographed by column chromatography on silica gel with the eluent used being a mixture of CH$_2$Cl$_2$/MeOH/NH$_4$OH (80/20/01).

3-(1-(4-Methoxyphenyl)-1H-1,2,3-triazol-4-yl)quinuclidin-3-ol (68)

The product was isolated in the form of a white solid with a yield of 87% by following the general procedure F. R$_f$: 0.22 (CH$_2$Cl$_2$/MeOH/NH$_4$OH: 80/20/0.1); Mp: 174° C.; IR (ATR, Diamond): ν (cm$^{-1}$): 992, 1049, 1133, 1231, 1251, 1305, 1439, 1517, 2873, 2928, 2998, 3112, 3348; $^1$H NMR (250 MHz, CDCl$_3$): δ (ppm) 1.42-1.58 (m, 3H), 2.17-2.31 (m, 2H), 2.76-2.95 (m, 3H), 2.95-3.14 (m, 2H), 3.20-3.43 (m, 1H), 6.61 (dd, 1H, J=14.4 Hz and 1.6 Hz), 3.86 (s, 3H), 7.00 (d, 2H, J=8.9 Hz), 7.62 (d, 2H, J=8.9 Hz), 7.89 (s, 1H); $^{13}$C NMR (100 MHz, CDCl$_3$): δ (ppm) 21.2 (CH$_2$), 23.3 (CH$_2$), 33.7 (CH), 46.5 (CH$_2$), 47.1 (CH$_2$), 55.8 (CH$_3$), 62.4 (CH$_2$), 69.7 (C$_q$), 115.0 (2CH$_{aromatic}$), 119.2 ($_{aromatic}$CH), 122.4 (2CH$_{aromatic}$), 130.7 (C$_q$), 154.5 (C$_q$), 160.0 (C$_q$); HRMS (EI-MS): calculated for C$_{16}$H$_{20}$N$_4$O$_2$ m/z=301.1665. found m/z=301.1669.

3-(1-(4-Bromophenyl)-1H-1,2,3-triazol-4-yl)quinuclidin-3-ol (69)

The product was isolated in the form of a white solid with a yield of 91% by following the general procedure F. R$_f$: 0.22 (CH$_2$Cl$_2$/MeOH/NH$_4$OH: 80/20/0.1); Mp: 214° C.; IR (ATR, Diamond): ν (cm$^{-1}$): 994, 1040, 1214, 1320, 1445, 1496, 2871, 2927, 3112; $^1$H NMR (250 MHz, CDCl$_3$): δ (ppm) 1.42-1.58 (m, 3H), 2.15-2.31 (m, 2H), 2.72-3.04 (m, 4H), 3.08 (d, 1H, J=14.3 Hz), 3.32 (s, 1H), 3.62 (dd, 1H, J=14.3 Hz and 1.3 Hz), 7.59-7.68 (m, 4H), 7.99 (s, 1H); $^{13}$C NMR (100 MHz, CDCl$_3$): δ (ppm) 21.8 (CH$_2$), 23.1 (CH$_2$), 33.7 (CH), 46.4 (CH$_2$), 47.1 (CH$_2$), 62.3 (CH$_2$) 69.7 (C$_q$), 119.0 ($_{aromatic}$CH), 122.1 (2CH$_{aromatic}$), 122.7 (C$_q$), 133.1 (2CH$_{aromatic}$), 136.1 (C$_q$), 155.1 (C$_q$); HRMS (EI-MS): calculated for C$_{15}$H$_{17}$BrN$_4$O m/z=349.0664. found m/z=349.0657.

Preparation of Quinuclidine Type Compounds 70-71 (Formula (III-1))

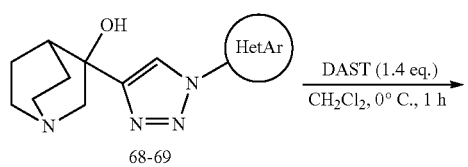

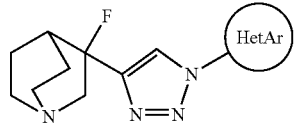

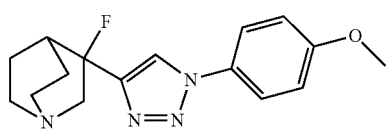

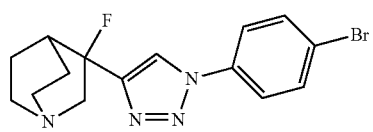

General Procedure G:

The alcohols 68-69 (0.500 mmol) were dissolved in 10 mL of dichloromethane and then at 0° C., diethylaminosulfur trifluoride (92 μL, 0.700 mmol) was added therein drop by drop. The reaction mixture was stirred at 0° C. for a period of one hour and hydrolysed with the addition of a saturated NaHCO$_3$ solution. The organic phase was dried over anhydrous MgSO$_4$, and filtered and concentrated under reduced pressure. The fluorinated compounds 70-71 were purified by column chromatography on silica gel with the eluent used being a mixture of CH$_2$Cl$_2$/MeOH/NH$_4$OH (80/20/0.1).

3-Fluoro-3-(1-(4-methoxyphenyl)-1H-1,2,3-triazol-4-yl)quinuclidine (70)

The product was isolated in the form of a yellowish oil with a yield of 64% by following the general procedure G. R$_f$: 0.54 (CH$_2$Cl$_2$/MeOH/NH$_4$OH: 80/20/0.1); IR (ATR, Diamond): ν (cm$^{-1}$): 992, 1043, 1110, 1175, 1254, 1306, 1462, 1518, 1611, 2961, 3392; $^1$H NMR (250 MHz, CDCl$_3$): δ (ppm) 1.45-1.64 (m, 2H), 1.62-1.82 (m, 1H), 2.02-2.19 (m, 1H), 2.28-2.36 (m, 1H), 2.74-2.90 (m, 1H), 2.90-3.04 (m, 3H), 3.28 (dd, 1H, J=30.5 Hz and 15.2 Hz), 3.75-3.93 (m, 1H), 3.85 (s, 3H), 7.01 (d, 2H, J=8.9 Hz), 7.62 (d, 2H, J=8.9 Hz), 7.93 (s, 1H); $^{13}$C NMR (100 MHz, CDCl$_3$): δ (ppm) 20.7 (d, CH$_2$, J=8 Hz), 22.4 (d, CH$_2$, J=8 Hz), 32.9 (d, CH, J=24 Hz), 46.5 (CH$_2$), 47.0 (CH$_2$), 55.8 (CH$_3$), 59.7 (d, CH$_2$, J=24 Hz), 93.4 (d, C$_q$, J=175 Hz), 115.0 (2CH$_{aromatic}$), 119.9 (d, CH, J=4 Hz), 122.4 (2CH$_{aromatic}$), 130.6 (C$_q$), 150.4 (d, C$_q$, J=32 Hz), 160.1 (C$_q$); $^{19}$F NMR (376 MHz, CDCl$_3$): δ (ppm)-136.59 (s, 1F); HRMS (EI-MS): calculated for C$_{16}$H$_{19}$FN$_4$O m/z=303.1621. found m/z=303.1623.

3-Fluoro-3-(1-(4-bromophenyl)-1H-1,2,3-triazol-4-yl)quinuclidine (71)

The product was isolated in the form of a white solid with a yield of 64% by following the general procedure G. R$_f$: 0.52 (CH$_2$Cl$_2$/MeOH/NH$_4$OH: 80/20/0.1); Mp: 127° C.; IR (ATR, Diamond): ν (cm$^{-1}$): 991, 1018, 1038, 1075, 1222, 1246, 1321, 1453, 1497, 2869, 2933; $^1$H NMR (250 MHz, CDCl$_3$): δ (ppm) 1.46-1.68 (m, 2H), 1.68-1.84 (m, 1H), 2.05-1.19 (m, 1H), 2.28-2.35 (m, 1H), 2.76-2.92 (m, 1H), 2.92-3.06 (m, 3H), 3.29 (dd, 1H, J=30.5 Hz and 15.2 Hz), 3.82 (dd, 1H, J=24.8 Hz and 15.2 Hz), 7.59-7.69 (m, 4H), 8.01 (s, 1H); $^{13}$C NMR (100 MHz, CDCl$_3$): δ (ppm) 20.6 (d, CH$_2$, J=8 Hz), 22.3 (d, CH$_2$, J=6 Hz), 32.9 (d, CH, J=24 Hz), 46.5 (CH$_2$), 47.0 (CH$_2$), 59.7 (d, CH$_2$, J=24 Hz), 93.4 (d, C$_q$, J=177 Hz), 119.6 (d, $_{aromatic}$CH, J=5 Hz), 122.1 (2CH$_{aromatic}$), 122.8 (C$_q$), 133.1 (2CH$_{aromatic}$), 136.0 (C$_q$), 151.0 (d, C$_q$, J=32 Hz), $^{19}$F NMR (376 MHz, CDCl$_3$): δ (ppm)-136.65 (s, 1F); HRMS (EI-MS): calculated for C$_{15}$H$_{17}$BRFN$_4$ m/z=351.0621. found m/z=351.0637.

Preparation of Quinuclidine Type Compound 79 (Formula (II-2))

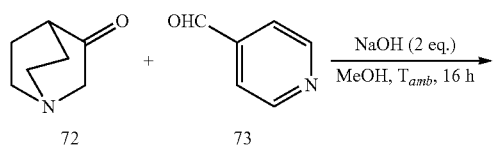

72    73

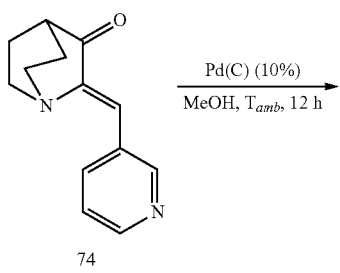

74

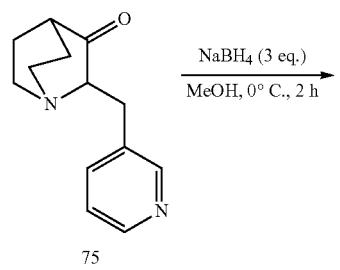

75

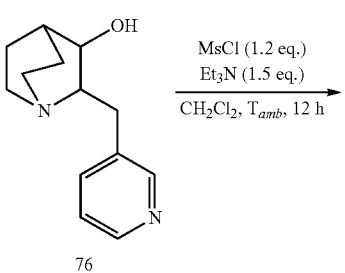

76

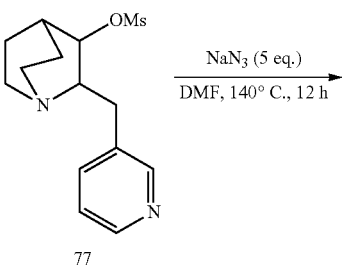

77

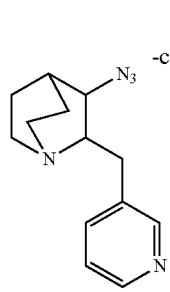

78

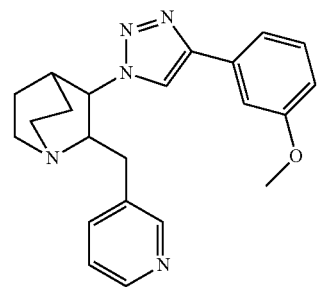

79

2-(Pyridin-3-ylmethylene)quinuclidin-3-one (74)

To a solution of quinuclidone 72 (2.00 g, 12.4 mmol) in 20 mL of methanol, NaOH (1.04 g, 26.0 mmol) was added. After stirring for 30 minutes at ambient temperature, the 3-pyridinecarboxaldehyde 73 (1.28 mL, 13.6 mmol) was added therein drop by drop and the reaction mixture was stirred for a period of 16 hours. The reaction was hydrolysed with the addition of a minimal amount of water until the complete dissolution of the salts present in the medium. The reaction medium was placed in the refrigerator until total precipitation was obtained and then the suspension was filtered under vacuum. The ketone 74 was isolated in the form of a yellow solid with a yield of 79%. R$_f$: 0.72 (CH$_2$Cl$_2$/MeOH/NH$_4$OH: 90/10/0.1); Mp: 113° C.; IR (ATR, Diamond): ν (cm$^{-1}$): 972, 1031, 1095, 1168, 1186, 1218, 1244, 1332, 1409, 1451, 1627, 1704, 2869, 2937, 2957; $^1$H NMR (250 MHz, CDCl$_3$): δ (ppm) 1.99 (td, 4H, J=7.9 Hz and 2.8 Hz), 2.60 (p, 1H, J=3.0 Hz), 2.87-3.02 (m, 2H), 3.07-3.21 (m, 2H), 6.93 (s, 1H), 7.25 (dd, 1H, J=8.0 Hz and 4.8 Hz), 8.45 (dt, 1H, J=8. Hz and 1.8 Hz), 8.50 (dd, 1H, J=4.8 Hz and 1.8 Hz), 8.99 (d, 1H, J=2.1 Hz); $^{13}$C NMR (100 MHz, CDCl$_3$): δ (ppm) 25.8 (2CH$_2$), 40.2 (CH), 47.5 (2CH$_2$), 121.5 ($_{aromatic}$CH), 123.4 ($_{aromatic}$CH), 130.1 (C$_q$), 138.6 ($_{aromatic}$CH), 146.6 (C$_q$), 150.0 ($_{aromatic}$CH), 153.0 ($_{aromatic}$CH), 205.7 (C=O); HRMS (EI-MS): calculated for C$_{13}$H$_{15}$N$_2$O m/z=215.1184. found m/z=215.1192.

2-(Pyridin-3-ylmethyl)quinuclidin-3-one (75)

Under hydrogen atmosphere, the ketone 73 (500 mg, 2.33 mmol) in 20 mL of methanol was reduced by the addition of a catalytic amount of Pd/C 10% (124 mg, 0.117 mmol) and stirred at ambient temperature for a period of 12 hours. Upon completion of the reaction, the reaction medium was filtered through Celite and the filtrate was evaporated under reduced pressure. The product was purified by column chromatography on silica gel with the eluent used being a mixture of CH$_2$Cl$_2$MeOH (9/1). The compound 75 was isolated in the form of a white solid with a yield of 63%. R$_f$: 0.23 (CH$_2$Cl$_2$/MeOH: 9/1); Mp: 95° C.; IR (ATR, Diamond): ν

(cm$^{-1}$): 984, 1028, 1053, 1071, 1096, 1185, 1328, 1422, 1459, 1477, 1576, 1715, 2869, 2962; $^1$H NMR (250 MHz, CDCl$_3$): δ (ppm) 1.93-2.07 (m, 4H), 2.47 (p, 1H, J=3.0 Hz), 2.75 (dd, 1H, J=14.9 Hz and 10.8 Hz), 2.82-2.93 (m, 2H), 3.03-3.24 (m, 3H), 3.31 (dd, 1H, J=10.8 Hz and 4.0 Hz), 7.20 (dd, 1H, J=7.8 Hz and 4.8 Hz), 7.59 (dt, 1H, J=7.8 Hz and 1.7 Hz), 8.45 (d, 1H, J=3.8 Hz), 8.51 (s, 1H); $^{13}$C NMR (100 MHz, CDCl$_3$): δ (ppm) 25.1 (CH$_2$), 27.1 (CH$_2$), 30.8 (CH$_2$), 40.2 (CH), 41.2 (CH$_2$), 49.0 (CH$_2$), 71.0 (CH), 123.5 ($_{aromatic}$CH), 134.7 (C$_q$), 136.4 ($_{aromatic}$CH), 148.0 ($_{aromatic}$CH), 150.4 ($_{aromatic}$CH and C$_q$); HRMS (EI-MS): calculated for C$_{13}$H$_{17}$N$_2$O m/z=217.1341. found m/z=217.1350.

2-(Pyridin-3-ylmethyl)quinuclidin-3-ol (76)

To a solution of the ketone 75 (450 mg, 2.08 mmol) in 40 mL of methanol cooled to 0° C. with the use of an ice bath, an excess of NaBH$_4$ (236 mg, 6.24 mmol) was added by portion. After two hours of stirring, the methanol was evaporated and the residue was taken up again in dichloromethane. The organic phase was washed with water, dried over anhydrous MgSO$_4$ and filtered and evaporated under reduced pressure. The alcohol 76 was isolated in the form of a white solid with a yield of 93% in the form of two inseparable diastereoisomers in the proportions of 1/1. R$_f$: 0.26 (CH$_2$Cl$_2$/MeOH/NH$_4$OH: 80/20/0.1); IR (ATR, Diamond): ν (cm$^{-1}$): 981, 1025, 1042, 1066, 1093, 1130, 1168, 1193, 1311, 1344, 1422, 1454, 1480, 1575, 2364, 2871, 2940, 3143; $^1$H NMR (250 MHz, CDCl$_3$): δ (ppm) 1.26-1.40 (m, 2H), 1.42-1.56 (m, 2H), 1.58-1.72 (m, 2H), 1.77-2.01 (m, 4H), 2.58-2.92 (m, 10H), 2.95-3.25 (m, 6H), 3.47-3.53 (m, 1H), 3.83-3.91 (m, 1H), 7.14-7.23 (m, 2H), 7.57-7.65 (m, 2H), 8.30-8.55 (m, 4H); $^{13}$C NMR (100 MHz, CDCl$_3$): δ (ppm) 18.7 (CH$_2$), 19.1 (CH$_2$), 24.7 (CH$_2$), 25.7 (CH$_2$), 29.5 (CH), 30.5 (CH), 31.0 (CH$_2$), 36.5 (CH$_2$), 41.0 (CH$_2$), 41.8 (CH$_2$), 48.9 (CH$_2$), 50.0 (CH$_2$), 62.2 (CH), 67.3 (CH), 68.4 (CH), 74.1 (CH), 123.5 ($_{aromatic}$CH), 123.6 ($_{aromatic}$CH), 135.2 (C$_q$), 136.5 (C$_q$), 137.0 (2CH$_{aromatic}$), 147.2 ($_{aromatic}$CH), 147.6 ($_{aromatic}$CH), 150.3 ($_{aromatic}$CH), 150.6 ($_{aromatic}$CH) HRMS (EI-MS): calculated for C$_{13}$H$_{19}$N$_2$O m/z=219.1497. found m/z=219.1491.

2-(Pyridin-3-ylmethyl)quinuclidin-3-yl methane sulfonate (77)

To a solution of the alcohol 76 (360 mg, 1.65 mmol) in 15 mL of dichloromethane at ambient temperature, the following were added: mesyl chloride (150 μL, 1.98 mmol) and triethylamine (350 μL, 2.48 mmol). The reaction medium was stirred at ambient temperature for a period of 12 hours and then the reaction was hydrolysed with the addition of a saturated NaHCO$_3$ solution. The organic phase was separated, dried over anhydrous MgSO$_4$ and filtered and evaporated under reduced pressure. The product was purified by column chromatography on silica gel with the eluent used being a mixture of CH$_2$Cl$_2$/MeOH/NH$_4$OH (90/10/0.1). The mesylated compound 77 was isolated in the form of a yellow solid with a yield of 70% in the form of two inseparable diastereoisomers in the proportions of 1/1. R$_f$: 0.35 (CH$_2$Cl$_2$/MeOH/NH$_4$OH: 90/10/0.1); IR (ATR, Diamond): ν (cm$^{-1}$): 890, 937, 989, 1027, 1166, 1321, 1342, 1428, 1461, 1479, 2873, 2943; $^1$H NMR (250 MHz, CDCl$_3$): δ (ppm) 1.35-1.95 (m, 8H), 2.19-2.31 (m, 2H), 2.62-3.15 (m, 13H), 2.74 (s, 3H), 2.91 (s, 3H), 3.23-3.33 (m, 1H), 4.44-4.49 (m, 1H), 4.89-4.95 (m, 1H), 7.17-7.26 (m, 2H), 7.52-7.62 (m, 2H), 8.41-8.53 (m, 4H); $^{13}$C NMR (100 MHz, CDCl$_3$): δ (ppm) 18.3 (CH$_2$), 19.2 (CH$_2$), 24.1 (CH$_2$), 25.1 (CH$_2$), 28.0 (CH), 28.5 (CH), 30.7 (CH$_2$) 35.7 (CH$_2$), 38.4 (CH$_3$), 38.5 (CH$_3$), 40.6 (CH$_2$), 41.3 (CH$_2$), 48.7 (CH$_2$), 49.8 (CH$_2$), 60.2 (CH), 64.3 (CH), 80.7 (CH), 84.1 (CH), 123.4 ($_{aromatic}$CH), 123.6 ($_{aromatic}$CH), 134.1 (C$_q$), 135.0 (C$_q$), 136.5 ($_{aromatic}$CH), 136.8 ($_{aromatic}$CH), 147.8 ($_{aromatic}$CH), 148.1 ($_{aromatic}$CH), 150.6 ($_{aromatic}$CH), 150.7 ($_{aromatic}$CH); HRMS (EI-MS): calculated for C$_{14}$H$_{21}$N$_2$O$_3$S m/z=297.1273. found m/z=297.1281.

3-(4-(3-Methoxyphenyl)-1H-1,2,3-triazol-1-yl)-2-(pyridin-3-ylmethyl)quinuclidine (79)

The mesyl derivative 77 (300 mg, 1.01 mmol) and the sodium azide (330 mg, 5.05 mmol) were heated to 140° C. in 10 mL of DMF (dimethylformamide) for a period of 12 hours. Upon completion of the reaction, the solvent was evaporated and then the residue was taken up again in CH$_2$Cl$_2$. The organic phase was washed two times with water, dried over anhydrous MgSO$_4$ and concentrated under reduced pressure. The azide 78 was purified by column chromatography on silica gel with the eluent used being a mixture of CH$_2$Cl$_2$/MeOH/NH$_4$OH (90/10/0.1).

The azide 78 (110 mg, 0.452 mmol) was dissolved in 4 mL of methanol to which the following were then added successively: 3-ethynylanisole (60 μL, 0.452 mmol), CuSO$_4$5H$_2$O (11 mg, 0.045 mmol) and sodium ascorbate (18 mg, 0.090 mmol). The reaction medium was stirred at ambient temperature for a period of 12 hours. Upon completion of the reaction time period, the methanol was evaporated under reduced pressure and then the residue was chromatographed by column chromatography on silica gel with the eluent used being a mixture of CH$_2$Cl$_2$/MeOH/NH$_4$OH (90/10/0.1). The product 79 was isolated in the form of a yellow oil with a yield of 48% in the form of a single diastereoisomer. R$_f$: 0.24 (CH$_2$Cl$_2$/MeOH/NH$_4$OH: 90/10/0.1); IR (ATR, Diamond): ν (cm$^{-1}$): 986, 1037, 1074, 1157, 1244, 1282, 1320, 1424, 1458, 1479, 1583, 1609, 2872, 2943; $^1$H NMR (250 MHz, DMSO-d$_6$, 80° C.): δ (ppm) 1.36-1.51 (m, 1H), 1.62-1.96 (m, 3H), 2.21 (q, 1H, J=2.8 Hz), 2.67-3.25 (m, 6H), 3.75-3.84 (m, 1H), 3.87 (s, 3H), 4.48 (d, 1H, J=7.0 Hz), 6.89-7.01 (m, 1H), 7.22 (dd, 1H, J=7.8 Hz and 4.8 Hz), 7.35-7.48 (m, 3H), 7.64 (dt, 1H, J=7.8 Hz and 1.9 Hz), 8.34 (d, 1H, J=3.4 Hz), 8.49 (s, 1H), 8.54 (s, 1H); $^{13}$C NMR (100 MHz, DMSO-d$_6$, 80° C.): δ (ppm) 19.1 (CH$_2$), 25.8 (CH$_2$), 29.2 (CH), 34.9 (CH$_2$), 40.0 (CH$_2$), 48.5 (CH$_2$), 54.8 (CH$_3$), 61.2 (CH), 63.7 (CH), 110.5 ($_{aromatic}$CH), 113.1 ($_{aromatic}$CH), 117.3 ($_{aromatic}$CH), 120.4 ($_{aromatic}$CH), 122.5 ($_{aromatic}$CH), 129.4 ($_{aromatic}$CH), 132.0 (C$_q$), 134.1 (C$_q$), 135.8 ($_{aromatic}$CH), 145.6 (C$_q$), 146.7 ($_{aromatic}$CH), 149.7 ($_{aromatic}$CH), 159.4 (C$_q$); HRMS (EI-MS): calculated for C$_{22}$H$_{25}$N$_5$O m/z=375.2059. found m/z=376.21334.

Biochemical Activity of the Compounds of the Invention
Determination of the Affinity of the Compounds of the Invention for the Nicotinic Receptors Rα7

The compounds of the present invention have been tested for their affinity with the Rα7s in competition with a reference ligand, the [$^{125}$I]α-bungarotoxin, on rat brain membrane preparation, in accordance with the protocol described by Davies et al. (1999) with slight modification.

Membrane Preparation

Male rats of the Wistar strain (Centre d'Olevage R. Janvier/R. Janvier breeding centre, Saint Berthevin) weighing 250 g were used in accordance with the rules related to animal experimentation currently in effect. After decapitation (2 animals per experiment), the brains were quickly removed, collected on ice, and the frontal cortex was dissected and weighed. The tissue was ground (Janke & Kunkel Ultra Turrax T25, 9500 rev/min.) in 2 ml of cold buffer (HEPES buffer [4-(2-hydroxyethyl)-1-piperazineethanesulfonic acid] 15 mM, containing 120 mM NaCl, 5.4 mM KCl, 0.8 mM $MgCl_2$ and 1.8 mM $CaCl_2$, pH 7.4) and then centrifuged (Beckman J2-21 M/E centrifuge) at 45 000×g at 4° C. for 10 minutes. The supernatant was removed, the pellet was taken up again in 2 ml of the same buffer and then resuspended. The assay of the proteins was carried out in accordance with the method developed by Bradford (1976) on the dregs (Spectronic 20®-Genesys™). It was then diluted in the buffer in a manner so as to obtain 0.25 g/ml of protein.

Binding Study

The reference ligand used was [$^{125}$I]α-bungarotoxin (Perkin Elmer, specific activity 81.4 TBq/mmol). The tubes were prepared in duplicate.

In each tube (BD Vacutainer, AES Chemunex) containing 0.4 ml of 50 mM Tris-HCl buffer containing 120 mM NaCl, 5 mM KCl, 1 mM $MgCl_2$, 2.5 mM CaCl2, pH 7.4, the following were added: 0.2 ml of the protein suspension, 0.2 ml of a solution of [$^{125}$I]α-bungarotoxin (that is a concentration of 2 nM) diluted in the Tris buffer, and 0.2 ml of a solution containing the compound to be tested at various concentrations ranging from $10^{-6}$ to $10^{-10}$ M. Non-specific binding was determined in the presence of $10^{-6}$ M of α-bungarotoxin (Tocris). The tubes were incubated in an oven at 22° C. for a period of 3 hours.

The content of the tubes was thereafter diluted in 3 ml of Tris buffer at 4° C. supplemented with 0.1% BSA (bovine serum albumin), filtered (Hoefer™ FH225V Filter Manifold, Fisher Scientific) on GF/C filters (Whatman), presoaked in cold Tris buffer supplemented with 0.05% polyethyleneimine and then rinsed three times with 2 ml of cold buffer.

The residual radioactivity of the filters was measured by counting (Cobra 5020, Beckman), the $IC_{50}$ was determined graphically and the Ki calculated ($Ki=IC_{50}/(1+[L^*]/Kd)$ (Cheng and Prussof 1973).

| Compound No. | Structure | Molar Mass Empirical Formula Solubility | Activity on Rα7 |
|---|---|---|---|
| 16 | 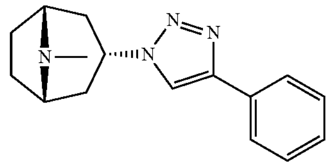 [SMILES: CN1[C@@H]2CC[C@H]1C[C@@H](n1cc(-c3ccccc3)nn1)C2] | M = 268.36 g/mol $C_{16}H_{20}N_4$ $CHCl_3$ – DMSO | 168 ± 68 nM |
| 17 | 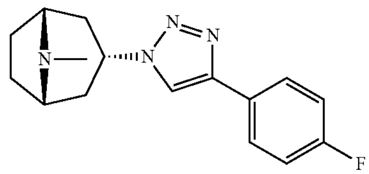 [SMILES: CN1[C@@H]2CC[C@H]1C[C@@H](n1cc(-c3ccc(F)cc3)nn1)C2] | M = 286.35 g/mol $C_{16}H_{19}FN_4$ $CHCl_3$ – DMSO | 210 ± 31 nM |
| 19 | 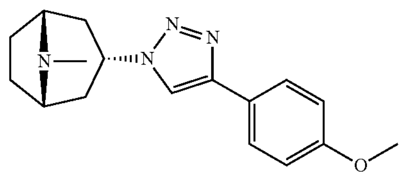 [SMILES: COc1ccc(-c2cn([C@H]3C[C@H]4CC[C@@H](C3)N4C)nn2)cc1] | M = 298.38 g/mol $C_{17}H_{22}N_4O$ CHCl3 – DMSO | 283 ± 76 nM |
| 22 | 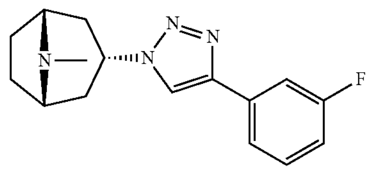 [SMILES: CN1[C@@H]2CC[C@H]1C[C@@H](n1cc(-c3cccc(F)c3)nn1)C2] | M = 286.35 g/mol $C_{16}H_{19}FN_4$ $CHCl_3$ – DMSO | 16 ± 9 nM |
| 24 | 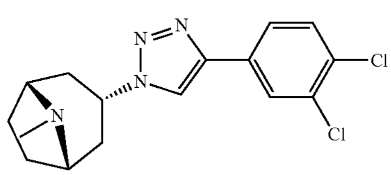 [SMILES: CN1[C@@H]2CC[C@H]1C[C@@H](n1cc(-c3ccc(Cl)c(Cl)c3)nn1)C2] | M = 337.25 g/mol $C_{16}H_{18}Cl_2N_4$ $CHCl_3$ – DMSO | 110 ± 36 nM |

-continued

| Compound No. | Structure | Molar Mass Empirical Formula Solubility | Activity on Rα7 |
|---|---|---|---|
| 25 | 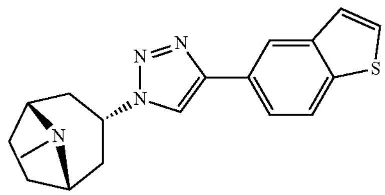 | M = 324.44 g/mol<br>$C_{18}H_{20}N_4S$<br>$CHCl_3$ – DMSO | 14 ± 4 nM |
| 26 | 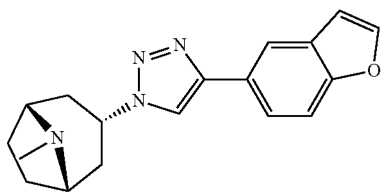 [SMILES: CN1[C@@H]2CC[C@H]1C[C@@H](n1cc(-c3ccc4sccc4c3)nn1)C2] | M = 308.38 g/mol<br>$C_{18}H_{20}N_4O$<br>$CHCl_3$ – DMSO | 13 ± 5 nM |
| 27 | 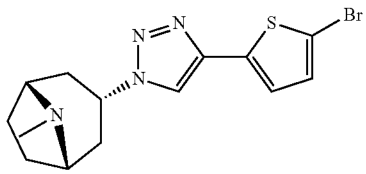 [SMILES: CN1[C@@H]2CC[C@H]1C[C@@H](n1cc(-c3ccc(Br)s3)nn1)C2] | M = 353.28 g/mol<br>$C_{14}H_{17}BrN_4S$<br>$CHCl_3$ – DMSO | 275 ± 43 nM |
| 37 | 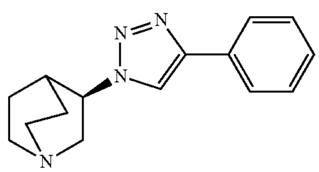 [SMILES: c1ccc(-c2cn([C@H]3CN4CCC3CC4)nn2)cc1] | M = 254.33 g/mol<br>$C_{15}H_{18}N_4$<br>$CHCl_3$ – DMSO | 8 ± 4 nM |
| 42 | 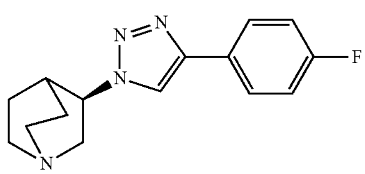 [SMILES: Fc1ccc(-c2cn([C@H]3CN4CCC3CC4)nn2)cc1] | M = 272.32 g/mol<br>$C_{15}H_{17}FN_4$<br>DMSO | 15 ± 4 nM |
| 46 | 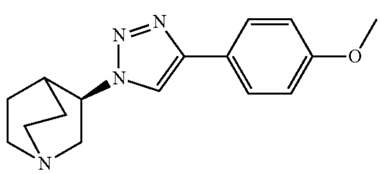 [SMILES: COc1ccc(-c2cn([C@H]3CN4CCC3CC4)nn2)cc1] | M = 284.36 g/mol<br>$C_{16}H_{20}N_4O$<br>DMSO | 11 ± 1 nM |
| 39 | 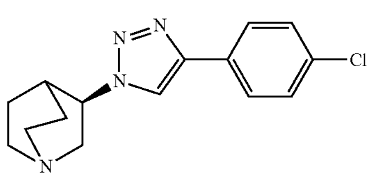 [SMILES: Clc1ccc(-c2cn([C@H]3CN4CCC3CC4)nn2)cc1] | M = 288.78 g/mol<br>$C_{15}H_{17}ClN_4$<br>$CHCl_3$ – DMSO | 8 ± 3 nM |
| 49 | 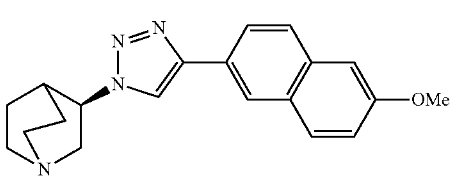 [SMILES: COc1ccc2cc(-c3cn([C@H]4CN5CCC4CC5)nn3)ccc2c1] | M = 334.41 g/mol<br>$C_{20}H_{22}N_4O$<br>$CHCl_3$ – DMSO | 196 ± 21 nM |

-continued

| Compound No. | Structure | Molar Mass Empirical Formula Solubility | Activity on Rα7 |
|---|---|---|---|
| 41 | 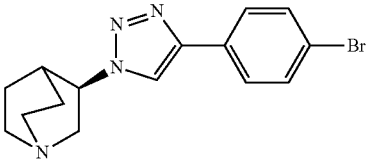 [SMILES: Brc1ccc(-c2cn([C@H]3CN4CCC3CC4)nn2)cc1] | M = 333.23 g/mol<br>$C_{15}H_{17}BrN_4$<br>$CHCl_3$ – DMSO | 6 ± 3 nM |
| 38 | 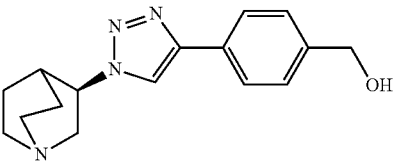 [SMILES: OCc1ccc(-c2cn([C@H]3CN4CCC3CC4)nn2)cc1] | M = 284.36 g/mol<br>$C_{16}H_{20}N_4O$<br>DMSO | 10 ± 3 nM |
| 43 | 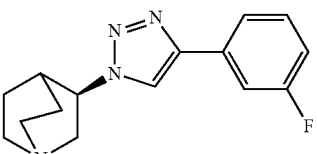 | M = 272.32 g/mol<br>$C_{15}H_{17}FN_4$<br>$CHCl_3$ – DMSO | 10 ± 1 nM |
| 50 | 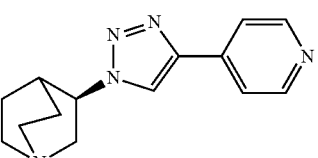 | M = 255.32 g/mol<br>$C_{15}H_{17}N_5$<br>$CHCl_3$ – DMSO | 141 ± 41 nM |
| 58 | 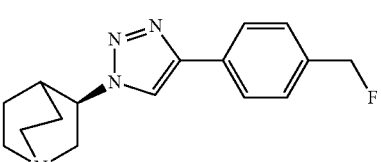 | M = 286.35 g/mol<br>$C_{16}H_{19}FN_5$<br>$CHCl_3$ – DMSO | 21 ± 7 nM |
| 40 | 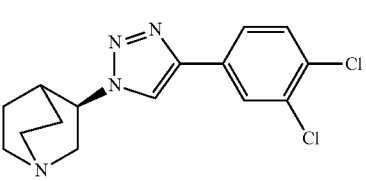 [SMILES: Clc1ccc(-c2cn([C@H]3CN4CCC3CC4)nn2)cc1Cl] | M = 323.22 g/mol<br>$C_{15}H_{16}Cl_2N_4$<br>$CHCl_3$ – DMSO | 19 ± 6 nM |
| 55 | 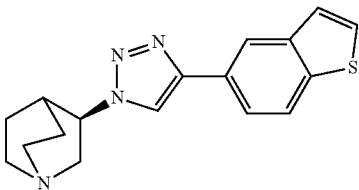 [SMILES: c1cc2cc(-c3cn([C@H]4CN5CCC4CC5)nn3)ccc2s1] | M = 310.42 g/mol<br>$C_{17}H_{18}N_4S$<br>$CHCl_3$ – DMSO | 19 ± 1 nM |
| 56 | 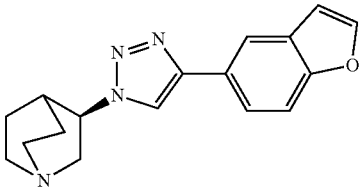 [SMILES: c1cc2cc(-c3cn([C@H]4CN5CCC4CC5)nn3)ccc2o1] | M = 294.35 g/mol<br>$C_{17}H_{18}N_4O$<br>$CHCl_3$ – DMSO | 3 ± 1 nM |

-continued

| Compound No. | Structure | Molar Mass Empirical Formula Solubility | Activity on Rα7 |
|---|---|---|---|
| 54 | 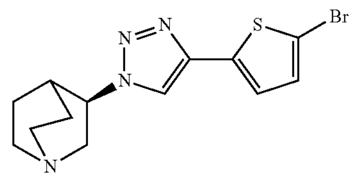 [SMILES: Brc1ccc(-c2cn([C@H]3CN4CCC3CC4)nn2)s1] | M = 339.25 g/mol<br>C₁₃H₁₅BrN₄S<br>CHCl₃ – DMSO | 13 ± 4 nM |
| 61 | 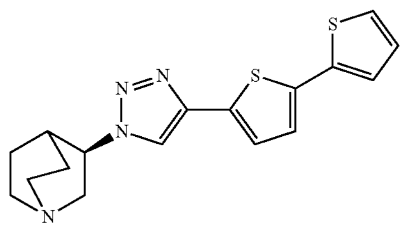 [SMILES: c1csc(-c2ccc(-c3cn([C@H]4CN5CCC4CC5)nn3)s2)c1] | M = 342.48 g/mol<br>C₁₇H₁₈N₄S₂<br>CHCl₃ – DMSO | 20 ± 2 nM |
| 62 | 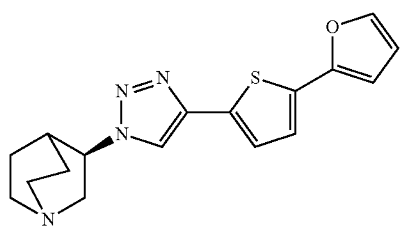 [SMILES: c1coc(-c2ccc(-c3cn([C@H]4CN5CCC4CC5)nn3)s2)c1] | M = 326.42 g/mol<br>C₁₇H₁₈N₄OS<br>CHCl₃ – DMSO | 10 ± 1 nM |
| 44 | 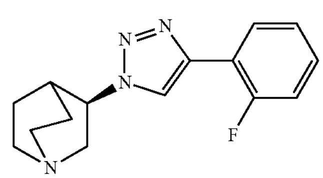 [SMILES: Fc1ccccc1-c1cn([C@H]2CN3CCC2CC3)nn1] | M = 272.32 g/mol<br>C₁₅H₁₇FN₄<br>CHCl₃ – DMSO | 13 ± 3 nM |
| 48 | 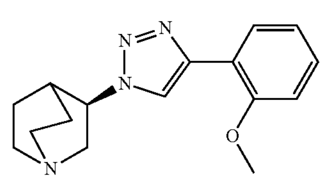 [SMILES: COc1ccccc1-c1cn([C@H]2CN3CCC2CC3)nn1] | M = 284.36 g/mol<br>C₁₆H₂₀N₄O<br>CDCl₃ – DMSO | 112 ± 26 nM |
| 47 | 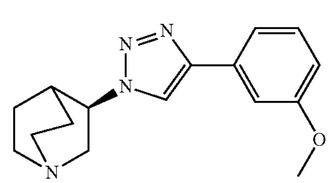 [SMILES: COc1cccc(-c2cn([C@H]3CN4CCC3CC4)nn2)c1] | M = 284.36 g/mol<br>C₁₆H₂₀N₄O<br>CDCl₃ – DMSO | 2.3 ± 1 nM |
| 51 | 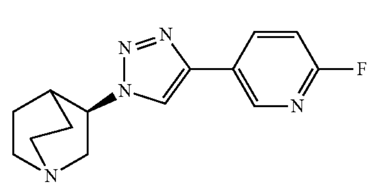 [SMILES: Fc1ccc(-c2cn([C@H]3CN4CCC3CC4)nn2)cn1] | M = 273.31 g/mol<br>C₁₄H₁₆FN₅<br>CDCl₃ – DMSO | 469 ± 6 nM |

-continued

| Compound No. | Structure | Molar Mass Empirical Formula Solubility | Activity on Rα7 |
|---|---|---|---|
| 52 | 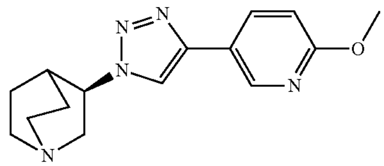 [SMILES: COc1ccc(-c2cn([C@H]3CN4CCC3CC4)nn2)cn1] | M = 285.34 g/mol<br>$C_{15}H_{19}N_5O$<br>$CDCl_3$ – DMSO | 105 ± 29 nM |
| 57 | 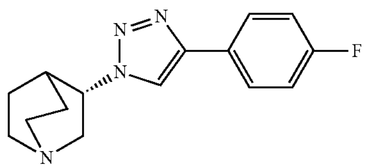 [SMILES: Fc1ccc(-c2cn([C@@H]3CN4CCC3CC4)nn2)cc1] | M = 272.32 g/mol<br>$C_{15}H_{17}FN_4$<br>$CDCl_3$ – DMSO | 114 ± 38 nM |
| 45 | 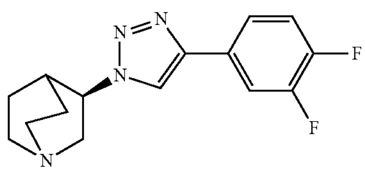 [SMILES: Fc1ccc(-c2cn([C@H]3CN4CCC3CC4)nn2)cc1F] | M = 290.31 g/mol<br>$C_{15}H_{16}F_2N_4$<br>$CDCl_3$ – DMSO | 10 ± 4 nM |
| 53 | 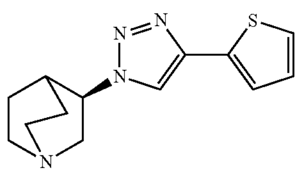 [SMILES: c1csc(-c2cn([C@H]3CN4CCC3CC4)nn2)c1] | M = 260.36 g/mol<br>$C_{13}H_{16}N_4S$<br>$CDCl_3$ – DMSO | 9.5 ± 3 nM |
| 60 | 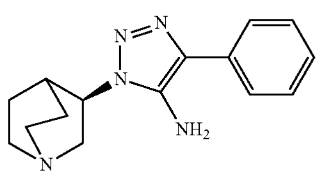 [SMILES: Nc1c(-c2ccccc2)nnn1[C@H]1CN2CCC1CC2] | M = 269.34 g/mol<br>$C_{15}H_{19}N_5$<br>$CDCl_3$ – DMSO | 11 ± 4 nM |
| 63 | 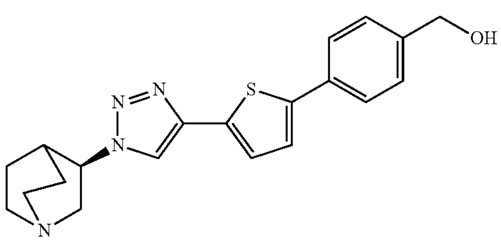 [SMILES: OCc1ccc(-c2ccc(-c3cn([C@H]4CN5CCC4CC5)nn3)s2)cc1] | M = 366.48 g/mol<br>$C_{20}H_{22}N_4OS$<br>$CDCl_3$ – DMSO | 0.6 ± 0.2 nM |
| 71 | 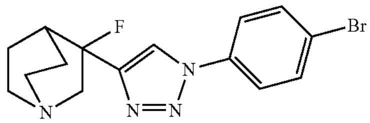 [SMILES: FC1(c2cn(-c3ccc(Br)cc3)nn2)CN2CCC1CC2] | M = 351.22 g/mol<br>$C_{15}H_{16}BrFN_4$<br>$CHCl_3$ – DMSO | 150 ± 10 nM |

| Compound No. | Structure | Molar Mass Empirical Formula Solubility | Activity on Rα7 |
|---|---|---|---|
| 79 | 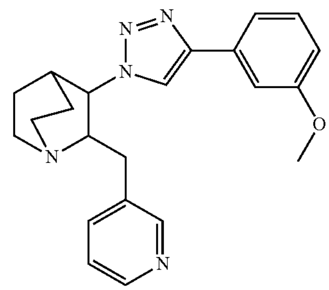 [SMILES: COc1cccc(-c2cn(C3C4CCN(CC4)C3Cc3cccnc3)nn2)c1] | M = 375.47 g/mol<br>C$_{22}$H$_{25}$N$_5$O<br>CHCl$_3$ – DMSO | ND |
| 83 | 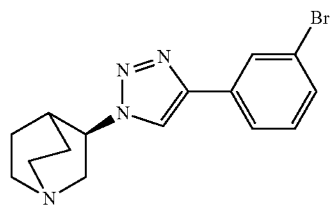 [SMILES: Brc1cccc(-c2cn([C@H]3CN4CCC3CC4)nn2)c1] | M = 333.23 g/mol<br>C15H17N4Br<br>CH$_2$Cl$_2$/MeOH-DMSO | 11+/−2 nM |
| 84 | 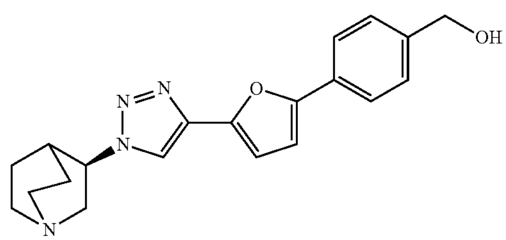 | M = 350.42 g/mol<br>C$_2$H$_{22}$N$_4$O$_2$<br>DMSO | 6+/−3 nM |
| 85 | 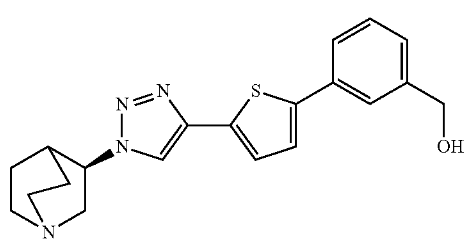 [SMILES: OCc1cccc(-c2ccc(-c3cn([C@H]4CN5CCC4CC5)nn3)s2)c1] | M = 366.49 g/mol<br>C$_{20}$H$_{22}$N$_4$OS<br>DMSO | 0.7+/−0.3 nM |
| 86 | 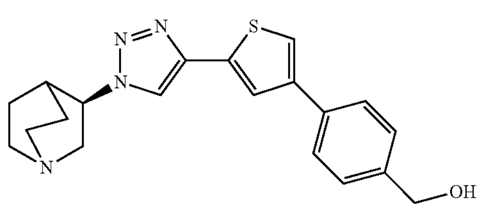 [SMILES: OCc1ccc(-c2csc(-c3cn([C@H]4CN5CCC4CC5)nn3)c2)cc1] | M = 366.49 g/mol<br>C$_{20}$H$_{22}$N$_4$OS<br>DMSO | 1.5+/−0.6 nM |
| 87 | 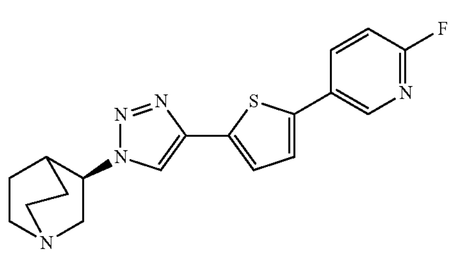 [SMILES: Fc1ccc(-c2ccc(-c3cn([C@H]4CN5CCC4CC5)nn3)s2)cn1] | M = 355.44 g/mol<br>C$_{18}$H$_{18}$FN$_3$S<br>CH$_2$Cl$_2$—CHCl3 – DMSO | 13+/−2 nM |

-continued

| Compound No. | Structure | Molar Mass Empirical Formula Solubility | Activity on Rα7 |
|---|---|---|---|
| 88 | 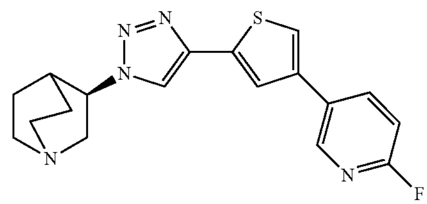 | M = 355.54 g/mol<br>C18H18N5F2<br>CH₂Cl₂/MeOH-DMSO | 31+/−4 nM |
| 89 | 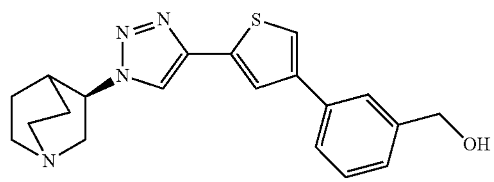 [SMILES: OCc1cccc(-c2csc(-c3cn([C@H]4CN5CCC4CC5)nn3)c2)c1] | M = 366.49 g/mol<br>C20H22N4OS<br>CH₂Cl₂/MeOH-DMSO | 13+/−3 nM |
| 90 | 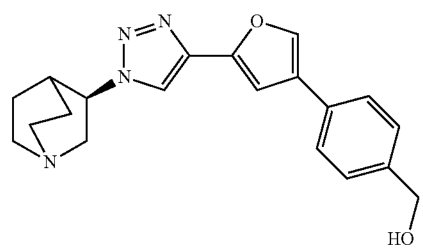 [SMILES: OCc1ccc(-c2coc(-c3cn([C@H]4CN5CCC4CC5)nn3)c2)cc1] | M = 350.42 g/mol<br>C20H22N4O2<br>CH₂Cl₂—CHCl₃ – DMSO | 9+/−2 nM |
| 91 | 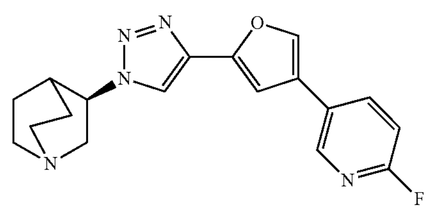 | M = 339.38 g/mol<br>C18H18N5OF<br>CH2Cl2—CHCl3 – DMSO | 117+/−26 nM |
| 92 | 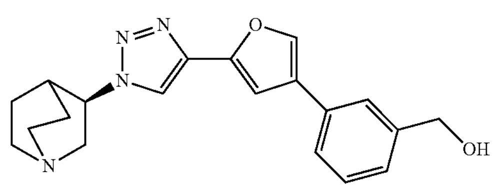 [SMILES: OCc1cccc(-c2coc(-c3cn([C@H]4CN5CCC4CC5)nn3)c2)c1] | M = 350.42 g/mol<br>C20H22N4O2<br>CH₂Cl₂—CHCl₃ – DMSO | 115+/−5 nM |
| 93 | 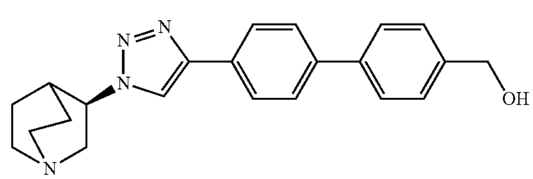 [SMILES: OCc1ccc(-c2ccc(-c3cn([C@H]4CN5CCC4CC5)nn3)cc2)cc1] | M = 360.46 g/mol<br>C22H24N4O<br>CH₂Cl₂/MeOH-DMSO | 137 nM (n = 2) |
| 95 | 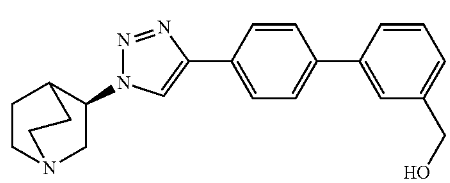 [SMILES: OCc1cccc(-c2ccc(-c3cn([C@H]4CN5CCC4CC5)nn3)cc2)c1] | M = 360.46 g/mol<br>C22H24N4O<br>CH₂Cl₂/MeOH-DMSO | 100+/−21 nM |

| Compound No. | Structure | Molar Mass<br>Empirical Formula<br>Solubility | Activity on Rα7 |
|---|---|---|---|
| 96 | 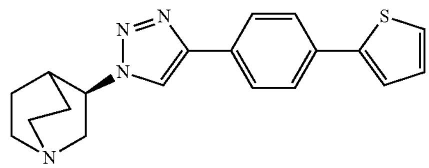 [SMILES: c1csc(-c2ccc(-c3cn([C@H]4CN5CCC4CC5)nn3)cc2)c1] | M = 336.46 g/mol<br>C19H20N4S<br>CH$_2$Cl$_2$/MeOH-DMSO | 135 nM (n = 2) |
| 97 | 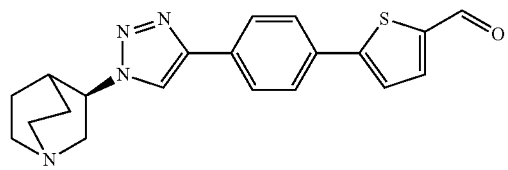 [SMILES: O=Cc1ccc(-c2ccc(-c3cn([C@H]4CN5CCC4CC5)nn3)cc2)s1] | M = 3664.47 g/mol<br>C20H20N4OS<br>CH$_2$Cl$_2$/MeOH-DMSO | 90-120 nM |
| 98 | 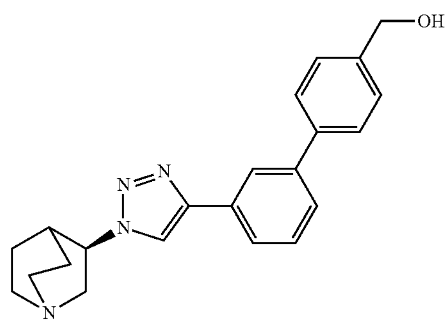 [SMILES: OCc1ccc(-c2cccc(-c3cn([C@H]4CN5CCC4CC5)nn3)c2)cc1] | M = 360.46 g/mol<br>C22H24N4O<br>CH$_2$Cl$_2$/MeOH-DMSO | 105 nM (n = 2) |
| 99 | 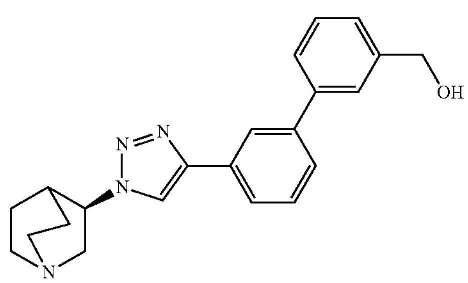 [SMILES: OCc1cccc(-c2cccc(-c3cn([C@H]4CN5CCC4CC5)nn3)c2)c1] | M = 360.46 g/mol<br>C22H24N4O<br>CH$_2$Cl$_2$/MeOH-DMSO | 1.4+/−0.6 nM |
| 100 | 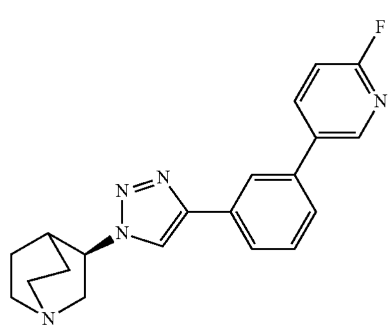 [SMILES: Fc1ccc(-c2cccc(-c3cn([C@H]4CN5CCC4CC5)nn3)c2)cn1] | M = 349.41 g/mol<br>C20H20N5F<br>CH2Cl2—CHCl3 − DMSO | 16+/−4 nM |

-continued

| Compound No. | Structure | Molar Mass Empirical Formula Solubility | Activity on Rα7 |
|---|---|---|---|
| 101 | 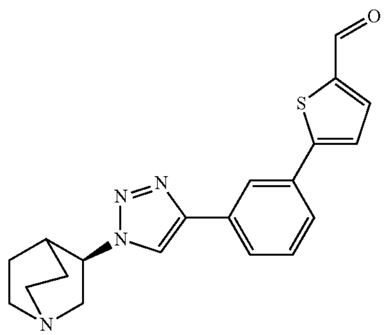 [SMILES: O=Cc1ccc(-c2cccc(-c3cn([C@H]4CN5CCC4CC5)nn3)c2)s1] | M = 364.47 g/mol<br>C20H20N4OS<br>CH$_2$Cl$_2$/MeOH-DMSO | 7+/−2 nM |
| 102 | 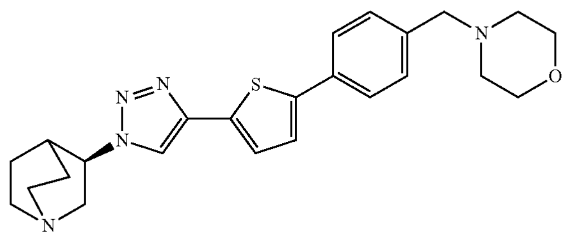 [SMILES: c1cc(-c2ccc(-c3cn([C@H]4CN5CCC4CC5)nn3)s2)ccc1CN1CCOCC1] | M = 435 g/mol<br>C24H29N5OS<br>CH$_2$Cl$_2$/MeOH-DMSO | 0.9+/−0.2 nM |
| 103 | 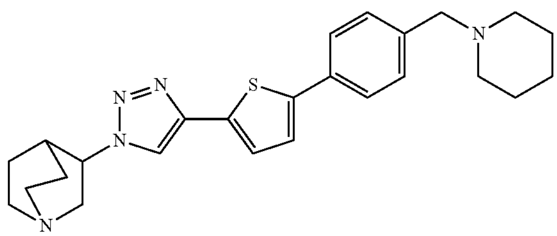 [SMILES: c1cc(-c2ccc(-c3cn(C4CN5CCC4CC5)nn3)s2)ccc1CN1CCCCC1] | M = 433 g/mol<br>C25H31N5S<br>CH$_2$Cl$_2$/MeOH-DMSO | 0.3+/−0.1 nM |
| 104 | 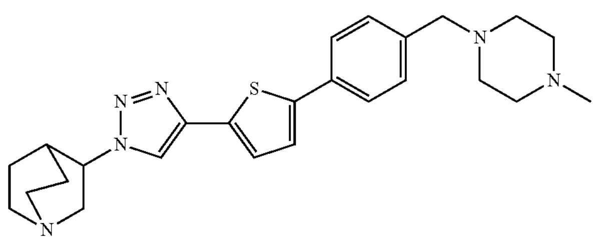 [SMILES: CN1CCN(Cc2ccc(-c3ccc(-c4cn(C5CN6CCC5CC6)nn4)s3)cc2)CC1] | M = 448 g/mol<br>C25H32N6S<br>CH$_2$Cl$_2$/MeOH-DMSO | 0.3+/−0.1 nM |
| 105 | 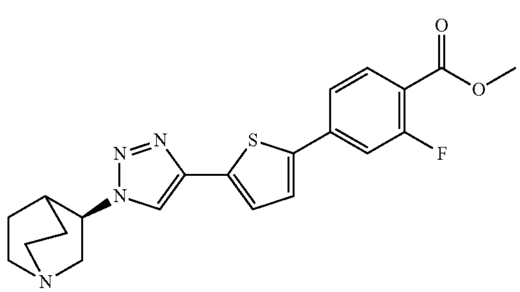 [SMILES: COC(=O)c1ccc(-c2ccc(-c3cn([C@H]4CN5CCC4CC5)nn3)s2)cc1F] | M = 412 g/mol<br>C21H21FN4O2S<br>CH$_2$Cl$_2$/MeOH-DMSO | 85 nM (n = 2) |

-continued

| Compound No. | Structure | Molar Mass Empirical Formula Solubility | Activity on Rα7 |
|---|---|---|---|
| 112 | 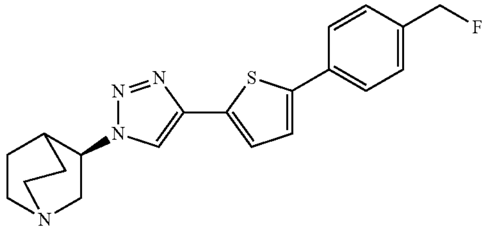 [SMILES: FCc1ccc(-c2ccc(-c3cn([C@H]4CN5CCC4CC5)nn3)s2)cc1] | M = 368.48 g/mol<br>C$_{20}$H$_{21}$FN$_4$S<br>CH$_2$Cl$_2$—CHCl$_3$ – DMSO | 5+/−2 nM |
| 114 | 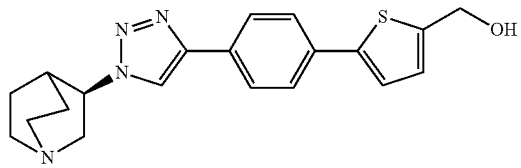 [SMILES: OCc1ccc(-c2ccc(-c3cn([C@H]4CN5CCC4CC5)nn3)cc2)s1] | M = 366.49 g/mol<br>C20H22N4OS<br>CH$_2$Cl$_2$/MeOH-DMSO | 160 nM (n = 2) |
| 115 | 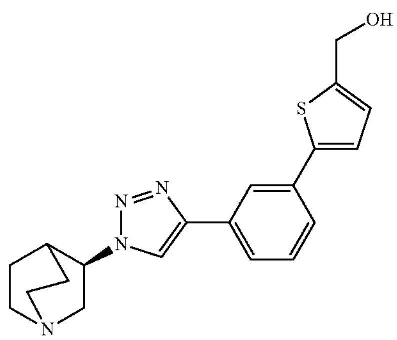 [SMILES: OCc1ccc(-c2cccc(-c3cn([C@H]4CN5CCC4CC5)nn3)c2)s1] | M = 366.49 g/mol<br>C20H22N4OS<br>CH$_2$Cl$_2$/MeOH-DMSO | 0.5+/−0.2 nM |

Determination of the Specificity of the Compounds of the Invention for the Nicotinic Receptors Rα7

The fluorinated compounds presenting a significant affinity for Rα7 (Ki relative to [$^{125}$I]α-bungarotoxin≤20 nM) were evaluated in vitro for their affinity relative to the α4β2 nicotinic receptors (reference tracer [$^3$H]cytisine, Pabreza et al. 1991), muscarinic receptors (reference tracer [$^3$H]QNB, Richards 1990) and serotonin 5-HT3 receptors (reference tracer [$^3$H]BRL-43694, Hope et al. 1996).

REFERENCES

Bradford et al. (1976) *Anal Biochem* 72: 248-254.
Cheng et al. (1973) *Biochem Pharmacol* 22: 3099-3108.
Davies et al. (1999) *Neuropharmacology* 38: 679-690.
Hope et al. (1996) *Br J Pharmacol* 118: 1237-1245.
Pabreza et al. (1991) *Mol Pharmacol* 39: 9-12.
Richards et al. (1990) *Br J Pharmacol* 99: 753-761.

The invention claimed is:
1. A compound having the general formula (I) as follows:

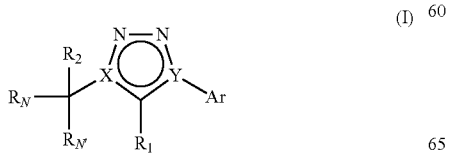

(I)

wherein:

X represents C and Y represents N; or

X represents N and Y represents C;

the Ar group is selected from among aryl groups comprising from 6 to 30 carbon atoms, optionally substituted by one or more groups selected from the group consisting of:

halogen atoms, a —OH group, linear or branched alkyl and alkoxy groups comprising from 1 to 10 carbon atoms, possibly substituted, and aryl groups comprising from 6 to 30 carbon atoms, optionally substituted by at least one —CH$_2$OH group, and heteroaryl groups comprising from 1 to 30 carbon atoms, optionally substituted by at least one substituent selected from the group consisting of: a halogen atom, —C(=O)H, —CH$_2$OH and NO$_2$, the R$_N$ and R$_{N'}$ groups, together with the carbon atoms to which they are bound, form a monocyclic or bicyclic azacycloalkane group comprising at least one trisubstituted endocyclic nitrogen atom, optionally in quaternary ammonium form, selected from the group consisting of:

said azacycloalkane group being optionally substituted by one or more groups selected from the group consisting of:
- halogen atoms,
- —OH group, and
- linear or branched alkyl and alkoxy groups comprising from 1 to 10 carbon atoms, optionally substituted, $R_1$ is a group selected from the group consisting of:
- halogen atoms,
- aryl groups comprising from 6 to 30 carbon atoms and heteroaryl groups comprising from 1 to 30 carbon atoms, optionally substituted,
- —R, —OR or —SiRR'R", R, R' and R" groups being independently selected from the group consisting of a hydrogen atom and linear or branched alkyl groups comprising from 1 to 10 carbon atoms, optionally substituted,
- —NR$_a$R$_b$, R$_a$ and R$_b$ groups being independently selected from the group consisting of hydrogen atom and alkyl and acyl groups comprising from 1 to 10 carbon atoms, optionally substituted, and
- —NHR$_c$ and R$_c$ groups being selected from among aryl groups comprising from 6 to 30 carbon atoms and the heteroaryl groups comprising from 1 to 30 carbon atoms; and $R_2$ is selected from the group consisting of: H when X is N, halogen atoms, —R, —OR, —C(O)Oalkyl, —OC(O)R, —OC(O)NHR, —O—(SO$_2$)—R and —O—(SO$_2$)—NHR groups, wherein R is as defined here above; and pharmaceutically acceptable salts thereof, hydrates or polymorphic crystalline structures, racemates, diastereoisomers or enantiomers thereof, wherein the following compounds are excluded:
- 3-(1-(2,3-difluorophenyl)-1H-tetrazol-5-yl)-5-(1-(8-methyl-8-azabicyclo[3.2.1]octan-3-yl)-1H-1,2,3-triazol-4-yl)pyridin-2-amine; and
- 3-(1-(2,3-difluorophenyl)-1H-tetrazol-5-yl)-5-(1-(quinuclidin-3-yl)-1H-1,2,3-triazol-4-yl)pyridin-2-amine.

2. The compound according to claim 1, wherein the R$_N$ and R$_{N'}$ groups, together with the carbon atoms to which they are bound, form a group selected from the group consisting of tropane, quinuclidine and octahydro-quinolizine groups.

3. The compound according to claim 1, having the general formula (II) as follows:

(II)

wherein:
- the Ar group is selected from the group consisting of phenyl and naphthalenyl groups, optionally substituted by one or more substituents selected from the group consisting of:
  - halogen atoms,
  - a —OH group,
  - linear or branched alkyl and alkoxy groups comprising from 1 to 10 carbon atoms, optionally substituted, and
  - aryl groups comprising from 6 to 30 carbon atoms, optionally substituted by at least one —CH$_2$OH group, and heteroaryl groups comprising from 1 to 30 carbon atoms, optionally substituted by at least one substituent selected from the group consisting of: a halogen atom, —C(=O)H, —CH$_2$OH and NO$_2$;
- the R$_N$ and R$_{N'}$ groups, together with the carbon atoms to which they are bound, form a group selected from the group consisting of tropane, quinuclidine and octahydro-quinolizine groups;
- $R_1$ is selected from the group consisting of:
  - a hydrogen atom,
  - halogen atoms,
  - aryl groups comprising from 6 to 30 carbon atoms and heteroaryl groups comprising from 1 to 30 carbon atoms, optionally substituted,
  - —NR$_a$R$_b$ groups, wherein R$_a$ and R$_b$ are as previously defined, and
  - —NHR$_c$ groups, wherein R$_c$ is as previously defined.

4. The compound according to claim 1, having the general formula (II-1) as follows:

(II-1)

wherein Ar is as previously defined.

5. The compound according to claim 1, having the general formula (II-2) as follows:

(II-2)

wherein
the $R_2$ group represents a linear or branched alkyl group comprising from 1 to 10 carbon atoms, optionally substituted by an aryl group comprising from 6 to 30 carbon atoms or by a heteroaryl group comprising from 1 to 30 carbon atoms, optionally substituted, and
the $R_1$ and Ar groups are as previously defined.

6. The compound according to claim 1, having the general formula (II-3) as follows:

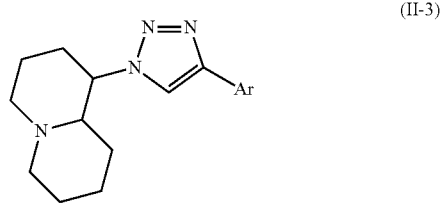

wherein Ar is as previously defined.

7. The compound according to claim 1, having the general formula (III) as follows:

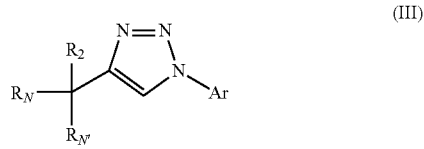

wherein:
the Ar group is selected from among phenyl and naphtalenyl groups, optionally substituted by one or more substituents selected from the group consisting of:
halogen atoms,
—R and —OR groups, wherein R is as previously defined, and
aryl groups comprising from 6 to 30 carbon atoms or heteroaryl groups comprising from 1 to 30 carbon atoms, optionally substituted;
$R_N$ and $R_{N'}$ groups, together with the carbon atoms to which they are bound, form a group selected from the group consisting of tropane, quinuclidine and octahydro-quinolizine groups; and
$R_2$ is —H, —F or —OH.

8. The compound according to claim 1, having the general formula (III-1) as follows:

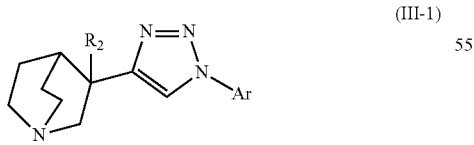

wherein the $R_2$ and Ar groups are as previously defined.

9. The compound according to claim 1, comprising at least one radioactive isotope selected from the group consisting of D, $^{18}F$, $^{11}C$ and $^{123}I$.

10. A drug comprising a compound according to claim 1.

11. An agonist or antagonist for the alpha 7 nicotinic receptor, comprising the compound of claim 1.

12. A radiopharmaceutical marker comprising a compound according to claim 9.

13. The compound according to claim 1, comprising at least one radioactive isotope selected from the group consisting of D, $^{18}F$, $^{11}C$ and $^{123}I$ as an $R_2$ group.

14. A method for treating diseases related to disruption of cholinergic systems and involving an alpha 7 nicotinic receptor, comprising administering a pharmaceutically acceptable amount of the compound of claim 1 to a patient in need thereof.

15. A compound having the general formula (I) as follows:

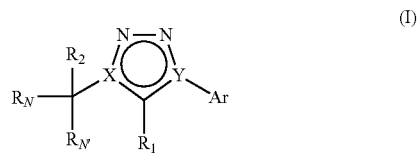

wherein:
X represents C and Y represents N; or
X represents N and Y represents C;
the Ar group is selected from among heteroaryl groups comprising from 1 to 30 carbon atoms, optionally substituted by one or more groups selected from the group consisting of:
halogen atoms,
a —OH group,
linear or branched alkyl and alkoxy groups comprising from 1 to 10 carbon atoms, optionally substituted, and
aryl groups comprising from 6 to 30 carbon atoms and heteroaryl groups comprising from 1 to 30 carbon atoms,
said aryl groups being optionally substituted by at least one substituent selected from the group consisting of:
—CH$_2$OH;
halogen;
—CH$_2$F, —CH$_2$Cl;
COOCH$_3$;

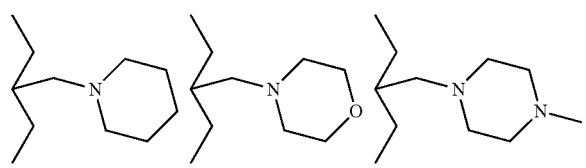

the $R_N$ and $R_{N'}$ groups, together with the carbon atoms to which they are bound, form a monocyclic or bicyclic azacycloalkane group comprising at least one trisubstituted endocyclic nitrogen atom, optionally in quaternary ammonium form, selected from the group consisting of:

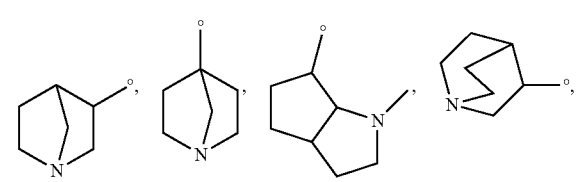

123

-continued

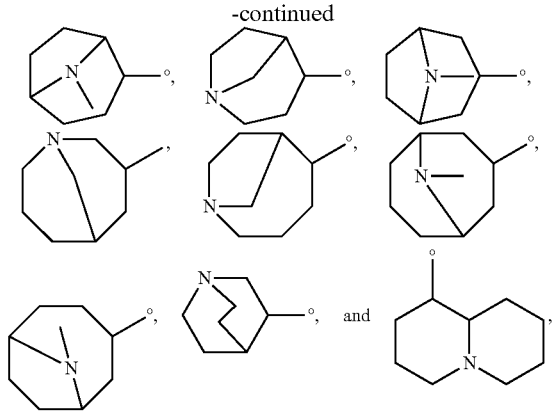

said azacycloalkane group being optionally substituted by one or more groups selected from the group consisting of:
halogen atoms,
—OH group, and
linear or branched alkyl and alkoxy groups comprising from 1 to 10 carbon atoms, optionally substituted,
$R_1$ is a group selected from the group consisting of:
halogen atoms,
aryl groups comprising from 6 to 30 carbon atoms and heteroaryl groups comprising from 1 to 30 carbon atoms, optionally substituted,
—R, —OR or —SiRR'R", R, R' and R" groups being independently selected from the group consisting of a hydrogen atom and linear or branched alkyl groups comprising from 1 to 10 carbon atoms, optionally substituted,
—$NR_aR_b$, $R_a$ and $R_b$ groups being independently selected from the group consisting of a hydrogen atom and alkyl and acyl groups comprising from 1 to 10 carbon atoms, optionally substituted, and
—$NHR_c$, $R_c$ groups being selected from among aryl groups comprising from 6 to 30 carbon atoms and heteroaryl groups comprising from 1 to 30 carbon atoms; and
$R_2$ is selected from the group consisting of: H when X is N, halogen atoms, —R, —OR, —C(O)Oalkyl, —OC(O)R, —OC(O)NHR, —O—($SO_2$)—R and —O—($SO_2$)—NHR groups, wherein R is as defined here above; and
pharmaceutically acceptable salts thereof, hydrates or polymorphic crystalline structures, racemates, diastereoisomers or enantiomers thereof,
wherein the following compounds are excluded:
3-(1-(2,3-difluorophenyl)-1H-tetrazol-5-yl)-5-(1-(8-methyl-8-azabicyclo[3.2.1]octan-3-yl)-1H-1,2,3-triazol-4-yl)pyridin-2-amine-; and
3-(1-(2,3-difluorophenyl)-1H-tetrazol-5-yl)-5-(1-(quinuclidin-3-yl)-1H-1,2,3-triazol-4-yl)pyridin-2-amine.

16. The compound according to claim 15, having the general formula (II) as follows:

124

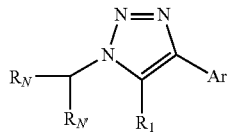 (II)

wherein:
the Ar group is selected from the group consisting of pyridyl, thiophenyl, furanyl, benzothiophenyl, and benzofuranyl groups, optionally substituted by one or more substituents selected from the group consisting of:
halogen atoms,
a —OH group,
linear or branched alkyl and alkoxy groups comprising from 1 to 10 carbon atoms, optionally substituted, and
aryl groups comprising from 6 to 30 carbon atoms and heteroaryl groups comprising from 1 to 30 carbon atoms, optionally substituted;
said aryl groups being optionally substituted by at least one substituent selected from the group consisting of:
—$CH_2OH$;
a halogen;
—$CH_2F$;
—$CH_2Cl$;
$COOCH_3$; and

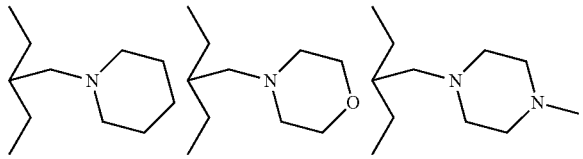

the $R_N$ and $R_{N'}$ groups, together with the carbon atoms to which they are bound, form a group selected from the group consisting of tropane, quinuclidine and octahydro-quinolizine groups;
$R_1$ is selected from the group consisting of:
a hydrogen atom,
halogen atoms,
aryl groups comprising from 6 to 30 carbon atoms and heteroaryl groups comprising from 1 to 30 carbon atoms, optionally substituted,
—$NR_aR_b$ groups, wherein $R_a$ and $R_b$ are as previously defined, and
—$NHR_c$ groups, wherein $R_c$ is as previously defined.

17. The compound according to claim 1, wherein Ar is an aryl group comprising from 6 to 30 carbon atoms, substituted by one or more heteroaryl groups comprising from 1 to 30 carbon atoms, substituted by at least one —$CH_2OH$ group.

* * * * *